US009068990B2

(12) United States Patent
Taylor et al.

(10) Patent No.: US 9,068,990 B2
(45) Date of Patent: Jun. 30, 2015

(54) METHODS OF PREDICTING AND DECREASING THE RISK OF PREGNANCY LOSS

(71) Applicant: University of Louisville Research Foundation, Inc., Louisville, KY (US)

(72) Inventors: Douglas D. Taylor, Louisville, KY (US); Cicek Gercel-Taylor, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 0 days.

(21) Appl. No.: 14/276,601

(22) Filed: May 13, 2014

(65) Prior Publication Data

US 2014/0356348 A1    Dec. 4, 2014

Related U.S. Application Data

(63) Continuation of application No. 13/583,981, filed as application No. PCT/US2011/028192 on Mar. 11, 2011, now abandoned.

(60) Provisional application No. 61/313,024, filed on Mar. 11, 2010.

(51) Int. Cl.
*G01N 33/68* (2006.01)

(52) U.S. Cl.
CPC ........ *G01N 33/689* (2013.01); *G01N 2333/775* (2013.01); *G01N 2333/78* (2013.01); *G01N 2800/50* (2013.01)

(58) Field of Classification Search
None
See application file for complete search history.

(56) References Cited

U.S. PATENT DOCUMENTS

| 5,223,440 | A | 6/1993 | Teng et al. |
|---|---|---|---|
| 2003/0129674 | A1 | 7/2003 | Martens et al. |
| 2006/0024725 | A1 | 2/2006 | Hussa et al. |
| 2006/0024757 | A1 | 2/2006 | Hussa et al. |
| 2007/0160997 | A1 | 7/2007 | Chen |
| 2009/0291889 | A1 | 11/2009 | Breit et al. |
| 2011/0047632 | A1 | 2/2011 | Robinson et al. |

FOREIGN PATENT DOCUMENTS

| EP | 1 722 225 | 11/2006 |
|---|---|---|
| JP | 07-500911 | 1/1995 |
| JP | 2006-524331 | 10/2006 |
| JP | 2008-514900 | 5/2008 |
| JP | 2010-517048 | 5/2010 |
| WO | 93/09438 | 5/1993 |
| WO | 2004/088324 | 10/2004 |
| WO | 2006/026020 | 3/2006 |
| WO | 2008/092164 | 7/2008 |

OTHER PUBLICATIONS

English translation of Office Action cited in JP 2012-557293 mailed Sep. 16, 2014 (5 pages).
Patent Examination Report Nos. 1 and 2 issued for Australian Patent Application No. 2011226687 mailed Dec. 11, 2013.
Communication received for European Patent Application No. 11754206.8 mailed May 14, 2014.
Benyo et al., "Noncoordinated expression of luteal cell messenger ribonucleic acids during human chorionic gonadotropin stimulation of the primate corpus luteum," Endocrinology, 133:699-704, 1993 (Abstract Only).
Cekmen et al., "Plasma lipid and lipoprotein concentrations in pregnancy induced hypertension," Clin. Biochem., 36:575-578, 2003.
Cereus et al., "Parental human leukocyte antigens and implantation failure after in-vitro fertilization," Hum. Reprod., 13:39-43, 1998.
Choudhury and Knapp, "Human reproductive failure I: immunological factors," Hum. Reprod. Update, 7(2):113-134, 2001.
Eblen et al., "Alterations in humoral immune responses associated with recurrent pregnancy loss," Fertil. Steril. 73:305-313, 2000.
Esadeg et al., "Alpha-2 Macroglobulin Controls Trophoblast Positioning in Mouse Implantation Sites," Placenta, 24:912-921, 2003.
Extended European Search Report in EP Application No. 11754206.8, Jul. 29, 2013, 8 pages.
Farese et al., "A novel function for apolipoprotein B: lipoprotein synthesis in the yolk sac is critical for maternal-fetal lipid transport in mice," J Lipid Res., 37:347-360, 1996.
Giacomini et al., "First-trimester human trophoblast is class II major histocompatibility complex mRNA+/antigen," Hum. Immunol, 39:281-289, 1994 (Abstract Only).
Gill, III "Mechanisms of action of major-histocompatibility-complex-linked genes affecting reproduction," Am. J Reprod. Immunol., 41:23-33, 1999 (Abstract Only).
Guller et al., "Fetal membranes: Anatomy and biochemistry," Up-To-Date, Sep. 2013, 11 pages.
Guller et al., "The role of placental Fas ligand in maintaining immune privilege at maternal-fetal interface," Semin. Reprod. Endocrinol., 17:39-44, 1999 (Abstract Only).

(Continued)

*Primary Examiner* — Jacob Cheu
(74) *Attorney, Agent, or Firm* — Fish & Richardson P.C.

(57) ABSTRACT

Described are methods for diagnosing and predicting the risk of pregnancy loss in a subject based on the presence of an aberrant humoral response to three proteins, Apolipoprotein B-100, alpha2macrogloblin (alpha2M), and fibronectin. The presence or a detectable level of maternal IgG antibodies to trophoblast-derived fibronectin and/or ApoB-100, and/or the absence or a non-detectable level of antibodies specifically binding to alpha2M is associated with a history of RPL and an increased risk of pregnancy loss. Also described are methods for identifying subjects at risk of pregnancy loss, selecting subjects for participation in a clinical study, and methods of decreasing the risk of pregnancy loss in a subject which include detecting the presence or absence of antibodies to one or more of trophoblast-derived ApoB-100, alpha2M, and fibronectin. Also provided are kits that contain ApoB-100, alpha2M, and fibronectin.

17 Claims, 7 Drawing Sheets

(56) References Cited

OTHER PUBLICATIONS

Hill et al., "T. helper 1 immunity to trophoblast antigens in women with recurrent spontaneous abortion," JAMA 273:1933-1936, 1995.
International Preliminary Report and Patentability in International Application No. PCT/US2011/028192, issued Sep. 11, 2012, 7 pages.
Jefferis et al., "Effector mechanisms activated by human IgG subclass antibodies: clinical and molecular aspects," Ann. Biol. Clin., 52:57-65, 1994 (Abstract Only).
Jenkins et al., "Evidence of a $T_H1$ type response associated with recurrent miscarriage," Fertil. Steril. 73:1206-1208, 2000 (Abstract Only).
Jensen et al., "Receptors for alpha 2-macroglobulin- and pregnancy zone protein-proteinase complexes in the human placental syncytiotrophoblast," Placenta, 9:463-477, 1988.
Karahan et al., "Serum anti-carbonic anhydrase I and II antibodies and idiopathic recurrent pregnancy loss," Reproductive Biomed., 19(6):859-863, Dec. 2009.
Konova et al., "Anti-Elastin Antibodies and Elastin Turnover in Normal Pregnancy and Recurrent Pregnancy Loss," Am J Reproductive Immunol., 61(2):167-174, Feb. 2009.
Mellor and Munn, "Immunology at the maternal-fetal interface: lessons for T cell tolerance and suppression," Ann. Rev. Immunol., 18:367-391, 2000.
Mercorio et al., "Cervical fetal fibronectin as a predictor of first trimester pregnancy outcome in unexplained recurrent miscarriage," Eur. J Gynecol. Reprod. Biol., 126:165-169, 2006.
PCT Examiner, Cho, Hyun Kyung, International Search Report and Written Opinion of International Patent Application No. PCT/US2011/028192, mailed Nov. 30, 2011, 13 pages.
Roman et al., "Regulation of IL-lb gene transcription by fibronectin in human monocytic cells. Role of protein kinase C and AP-$_1$," Cytokine, 12:1581-1596, 2000 (Abstract Only).
Sarandol et al., "Oxidizability of apolipoprotein B-containing lipoproteins, levels of lipid peroxidation products and antioxidants in normal pregnancy," Arch. Gynecol. Obstet., 270:157-160, 2004 (Abstract Only).
Sarandol et al., "Oxidizability of apolipoprotein B-containing lipoproteins and serum paraoxonase/arylesterase activities in preeclampsia," Clin. Biochem. 37:990-996, 2004 (Abstract Only).
Saunders et al., "Alterations in antibody immune responses and trophoblast antigens recognized in women with recurrent pregnancy loss," Fertil. Steril., 94(4):S48, abstract O-164, Sep. 2010, 1 page.
Saunders et al., Am. J. Reproductive Immunology, 68:438-449 (2012).
Shimizu et al., "Trans-placental transport of alpha-2 macroglobulin and inclusion of alpha-2 macroglobulin in maternal and neonatal rats with acute inflammation," Exp. Anim., 51:361-365, 2002.
Stirrat, "Recurrent miscarriage I: definition and epidemiology," Lancet, 336:673-675, 1990.
Szekeres-Bartho and Balasch, "Progestagen therapy for recurrent miscarriage," Hum. Reprod. Update, 14:27-35, 2008.
Thomas et al., "Plasma protein synthesis and secretion in the visceral yolk sac of the fetal rat: gene expression, protein synthesis and secretion," Placenta, 11:413-430, 1990 (Abstract Only).
Versalovic et al., Clinical & Experimental Immunology, 80:381-383 (1990).
Wilson et al., "Abnormal immunoglobulin subclass patterns in women with a history of recurrent miscarriage," Fertil Steril. 76:915-917, 2001 (Abstract Only).
Wozniak, S. et al. "Fibronectin levels in threatened abortion", Ginekol Pol., Dec. 1998, vol. 69, No. 12, pp. 949-955, Abstract only.
Yamada et al., "Stage-specific uptake of apolipoprotein-B in ovarian follicles and corpora lutea of the menstrual cycle and early pregnancy," Hum. Reprod. 13:944-952, 1998.
Zavazava et al., "Soluble HLA class I molecules: biological significance and clinical implications," Mol. Med. Today 4:116-121, 1998 (Abstract Only).
Examiner's Report mailed Mar. 19, 2015 in Australian Patent Application No. 2011226687, 4 pgs.
Arinola et al., "Bacteraemia and Acute Phase Proteins in Nigerian Women with Spontaneous Recurrent Abortion," *African J. Clin. Exp. Microbiol.* 6(3):203-207 (Sep. 2005).
Communication issued for European Patent Application No. 11754206.8-1402 mailed Feb. 25, 2015.

SEQUENCE LISTING

<160> NUMBER OF SEQ ID NOS: 18

<210> SEQ ID NO 1
<211> LENGTH: 14121
<212> TYPE: DNA
<213> ORGANISM: Homo sapiens

<400> SEQUENCE: 1

| | | | | | | |
|---|---|---|---|---|---|---|
| attcccaccg | ggacctgcgg | ggctgagtgc | ccttctcggt | tgctgccgct | gaggagcccg | 60 |
| cccagccagc | cagggccgcg | aggccgaggc | caggccgcag | cccaggagcc | gccccaccgc | 120 |
| agctggcgat | ggacccgccg | aggcccgcgc | tgctggcgct | gctggcgctg | cctgcgctgc | 180 |
| tgctgctgct | gctggcgggc | gccagggccg | aagaggaaat | gctggaaaat | gtcagcctgg | 240 |
| tctgtccaaa | agatgcgacc | cgattcaagc | acctccggaa | gtacacatac | aactatgagg | 300 |
| ctgagagttc | cagtgagtc  | cctgggactg | ctgattcaag | aagtgccacc | aggatcaact | 360 |
| gcaaggttga | gctggaggtt | ccccagctct | gcagcttcat | cctgaagacc | agccagtgca | 420 |
| ccctgaaaga | ggtgtatggc | ttcaaccctg | agggcaaagc | cttgctgaag | aaaaccaaga | 480 |
| actctgagga | gtttgctgca | gccatgtcca | ggtatgagct | caagctggcc | attccagaag | 540 |
| ggaagcaggt | tttcctttac | ccggagaaag | atgaacctac | ttacatcctg | aacatcaaga | 600 |
| ggggcatcat | ttctgccctc | ctggttcccc | cagagacaga | agaagccaag | caagtgttgt | 660 |
| ttctggatac | cgtgtatgga | aactgctcca | ctcactttac | cgtcaagacg | aggaagggca | 720 |
| atgtggcaac | agaaatatcc | actgaaagag | acctggggca | gtgtgatcgc | ttcaagccca | 780 |
| tccgcacagg | catcagccca | cttgctctca | tcaaaggcat | gacccgcccc | ttgtcaactc | 840 |
| tgatcagcag | cagccagtcc | tgtcagtaca | cactggacgc | taagaggaag | catgtggcag | 900 |
| aagccatctg | caaggagcaa | cacctcttcc | tgcctttctc | ctacaagaat | aagtatggga | 960 |
| tggtagcaca | agtgacacag | actttgaaac | ttgaagacac | accaaagatc | aacagccgct | 1020 |
| tctttggtga | aggtactaag | aagatgggcc | tcgcatttga | gagcaccaaa | tccacatcac | 1080 |
| ctccaaagca | ggccgaagct | gttttgaaga | ctctccagga | actgaaaaaa | ctaaccatct | 1140 |
| ctgagcaaaa | tatccagaga | gctaatctct | tcaataagct | ggttactgag | ctgagaggcc | 1200 |
| tcagtgatga | agcagtcaca | tctctcttgc | cacagctgat | tgaggtgtcc | agccccatca | 1260 |
| ctttacaagc | cttggttcag | tgtggacagc | ctcagtgctc | cactcacatc | ctccagtggc | 1320 |
| tgaaacgtgt | gcatgccaac | ccccttctga | tagatgtggt | cacctacctg | gtggccctga | 1380 |
| tccccgagcc | ctcagcacag | cagctgcgag | agatcttcaa | catggcgagg | gatcagcgca | 1440 |
| gccgagccac | cttgtatgcg | ctgagccacg | cggtcaacaa | ctatcataag | acaaacccta | 1500 |
| cagggaccca | ggagctgctg | acattgcta  | attacctgat | ggaacagatt | caagatgact | 1560 |
| gcactgggga | tgaagattac | acctatttga | ttctgcgggt | cattggaaat | atgggccaaa | 1620 |
| ccatggagca | gttaactcca | gaactcaagt | cttcaatcct | gaaatgtgtc | caaagtacaa | 1680 |
| agccatcact | gatgatccag | aaagctgcca | tccaggctct | gcggaaaatg | gagcctaaag | 1740 |
| acaaggacca | ggaggttctt | cttcagactt | tccttgatga | tgcttctccg | ggagataagc | 1800 |
| gactggctgc | ctatcttatg | ttgatgagga | gtccttcaca | ggcagatatt | aacaaaattg | 1860 |
| tccaaattct | accatgggaa | cagaatgagc | aagtgaagaa | ctttgtggct | tcccatattg | 1920 |
| ccaatatctt | gaactcagaa | gaattggata | tccaagatct | gaaaagtta  | gtgaagaag  | 1980 |
| ctctgaaaga | atctcaactt | ccaactgtca | tggacttcag | aaaattctct | cggaactatc | 2040 |
| aactctacaa | atctgtttct | cttccatcac | ttgacccagc | ctcagccaaa | atagaaggga | 2100 |

```
atcttatatt tgatccaaat aactaccttc ctaaagaaag catgctgaaa actaccctca   2160
ctgcctttgg atttgcttca gctgacctca tcgagattgg cttggaagga aaaggctttg   2220
agccaacatt ggaagctctt tttgggaagc aaggattttt cccagacagt gtcaacaaag   2280
ctttgtactg ggttaatggt caagttcctg atggtgtctc taaggtctta gtggaccact   2340
ttggctatac caaagatgat aaacatgagc aggatatggt aaatggaata atgctcagtg   2400
ttgagaagct gattaaagat ttgaaatcca agaagtccc ggaagccaga gcctacctcc    2460
gcatcttggg agaggagctt ggttttgcca gtctccatga cctccagctc ctgggaaagc   2520
tgcttctgat gggtgcccgc actctgcagg ggatccccca gatgattgga gaggtcatca   2580
ggaagggctc aaagaatgac tttttcttc actacatctt catggagaat gcctttgaac    2640
tccccactgg agctggatta cagttgcaaa tatcttcatc tggagtcatt gctcccggag   2700
ccaaggctgg agtaaaactg gaagtagcca acatgcaggc tgaactggtg caaaaccct    2760 ccgtgtctgt ggagtttgtg acaaatatgg gcatcatcat tccggacttc gctaggagtg   2820
gggtccagat gaacaccaac ttcttccacg agtcgggtct ggaggctcat gttgccctaa   2880
aagctgggaa gctgaagttt atcattcctt ccccaaagag accagtcaag ctgctcagtg   2940
gaggcaacac attacatttg gtctctacca ccaaaacgga ggtgatccca cctctcattg   3000
agaacaggca gtcctggtca gtttgcaagc aagtctttcc tggcctgaat tactgcacct   3060
caggcgctta ctccaacgcc agctccacag actccgcctc ctactatccg ctgaccgggg   3120
acaccagatt agagctggaa ctgaggccta caggagagat tgagcagtat tctgtcagcg   3180
caacctatga gctccagaga gaggacagag ccttggtgga taccctgaag tttgtaactc   3240
aagcagaagg tgcgaagcag actgaggcta ccatgacatt caaatataat cggcagagta   3300
tgaccttgtc cagtgaagtc caaattccgg attttgatgt tgacctcgga acaatcctca   3360
gagttaatga tgaatctact gagggcaaaa cgtcttacag actcacccctg gacattcaga   3420 acaagaaaat tactgaggtc gccctcatgg gccacctaag ttgtgacaca aaggaagaaa   3480
gaaaaatcaa gggtgttatt tccatacccc gtttgcaagc agaagccaga agtgagatcc   3540
tcgcccactg gtcgcctgcc aaactgcttc tccaaatgga ctcatctgct acagcttatg   3600
gctccacagt ttccaagagg gtggcatggc attatgatga agagaagatt gaatttgaat   3660
ggaacacagg caccaatgta gataccaaaa aaatgacttc caatttccct gtggatctct   3720
ccgattatcc taagagcttg catatgtatg ctaatagact cctggatcac agagtccctc   3780
aaacagacat gactttccgg cacgtgggtt ccaaattaat agttgcaatg agctcatggc   3840
ttcagaaggc atctgggagt cttccttata cccagacttt gcaagaccac ctcaatagcc   3900
tgaaggagtt caacctccag aacatgggat tgccagactt ccacatccca gaaaacctct   3960
tcttaaaaag cgatggccgg gtcaaatata ccttgaacaa gaacagtttg aaaattgaga   4020
ttcctttgcc ttttggtggc aaatcctcca gagatctaaa gatgttagag actgttagga   4080
caccagccct ccacttcaag tctgtgggat tccatctgcc atctcgagag ttccaagtcc   4140
ctacttttac cattcccaag ttgtatcaac tgcaagtgcc tctcctgggt gttctagacc   4200
tctccacgaa tgtctacagc aacttgtaca actggtccgc ctcctacagt ggtggcaaca   4260
ccagcacaga ccatttcagc cttcgggctc gttaccacat gaaggctgac tctgtggttg   4320
acctgctttc ctacaatgtg caaggatctg gagaaacaac atatgaccac aagaatacgt   4380
tcacactatc atgtgatggg tctctacgcc acaaatttct agattcgaat atcaaattca   4440
```

```
gtcatgtaga aaaacttgga aacaacccag tctcaaaagg tttactaata ttcgatgcat    4500
ctagttcctg gggaccacag atgtctgctt cagttcattt ggactccaaa aagaaacagc    4560
atttgtttgt caaagaagtc aagattgatg gcagttcag agtctcttcg ttctatgcta     4620
aaggcacata tggcctgtct tgtcagaggg atcctaacac tggccggctc aatggagagt    4680
ccaacctgag gtttaactcc tcctacctcc aaggcaccaa ccagataaca ggaagatatg    4740
aagatggaac cctctcccte acctccacct ctgatctgca aagtggcatc attaaaaata    4800
ctgcttccct aaagtatgag aactacgagc tgactttaaa atctgacacc aatgggaagt    4860
ataagaactt tgccacttct aacaagatgg atatgacctt ctctaagcaa aatgcactgc    4920
tgcgttctga atatcaggct gattacgagt cattgaggtt cttcagcctg ctttctggat    4980
cactaaattc ccatggtctt gagttaaatg ctgacatctt aggcactgac aaaattaata    5040
gtggtgctca caaggcgaca ctaaggattg gccaagatgg aatatctacc agtgcaacga    5100
ccaacttgaa gtgtagtctc ctggtgctgg agaatgagct gaatgcagag cttggcctct    5160
ctggggcatc tatgaaatta caacaaatg gccgcttcag ggaacacaat gcaaaattca     5220
gtctggatgg gaaagccgcc ctcacagagc tatcactggg aagtgcttat caggccatga    5280
ttctgggtgt cgacagcaaa aacattttca acttcaaggt cagtcaagaa ggacttaagc    5340
tctcaaatga catgatgggc tcatatgctg aaatgaaatt tgaccacaca aacagtctga    5400
acattgcagg cttatcactg gacttctctt caaaacttga caacatttac agctctgaca    5460
agttttataa gcaaactgtt aatttacagc tacagcccta ttctctggta actactttaa    5520
acagtgacct gaaatacaat gctctggatc tcaccaacaa tgggaaacta cggctagaac    5580
ccctgaagct gcatgtggct ggtaacctaa aggagcctaa ccaaaataat gaaataaaac    5640
acatctatgc catctcttct gctgccttat cagcaagcta taaagcagac actgttgcta    5700
aggttcaggg tgtggagttt agccatcggc tcaacacaga catcgctggg ctggcttcag    5760
ccattgacat gagcacaaac tataattcag actcactgca tttcagcaat gtcttccgtt    5820
ctgtaatggc cccgtttacc atgaccatcg atgcacatac aaatggcaat gggaaactcg    5880
ctctctgggg agaacatact gggcagctgt atagcaaatt cctgttgaaa gcagaacctc    5940
tggcatttac tttctctcat gattacaaag gctccacaag tcatcatctc gtgtctagga    6000
aaagcatcag tgcagctctt gaacacaaag tcagtgccct gcttactcca gctgagcaga    6060
caggcacctg gaaactcaag acccaattta caacaatga atacagccag gacttggatg     6120
cttacaacac taaagataaa attggcgtgg agcttactgg acgaactctg gctgacctaa    6180
ctctactaga ctccccaatt aaagtgccac ttttactcag tgagcccatc aatatcattg    6240
atgctttaga gatgagagat gccgttgaga agccccaaga atttacaatt gttgcttttg    6300
taaagtatga taaaaccaa gatgttcact ccattaacct cccatttttt gagaccttgc      6360
aagaatattt tgagaggaat cgacaaacca ttatagttgt actggaaaac gtacagagaa    6420
acctgaagca catcaatatt gatcaatttg taagaaaata cagagcagcc ctgggaaaac    6480
tcccacagca agctaatgat tatctgaatt cattcaattg ggagagacaa gtttcacatg    6540
ccaaggagaa actgactgct ctcacaaaaa agtatagaat tacagaaaat gatatacaaa    6600
ttgcattaga tgatgccaaa atcaactta atgaaaaact atctcaactg cagacatata     6660
tgatacaatt tgatcagtat attaaagata gttatgattt acatgatttg aaaatagcta    6720
ttgctaatat tattgatgaa atcattgaaa aattaaaaag tcttgatgag cactatcata    6780
tccgtgtaaa tttagtaaaa acaatccatg atctacattt gtttattgaa aatattgatt    6840
```

```
ttaacaaaag tggaagtagt actgcatcct ggattcaaaa tgtggatact aagtaccaaa   6900
tcagaatcca gatacaagaa aaactgcagc agcttaagag acacatacag aatatagaca   6960
tccagcacct agctggaaag ttaaaacaac acattgaggc tattgatgtt agagtgcttt   7020
tagatcaatt gggaactaca atttcatttg aaagaataaa tgacgttctt gagcatgtca   7080
aacactttgt tataaatctt attggggatt ttgaagtagc tgagaaaatc aatgccttca   7140
gagccaaagt ccatgagtta atcgagaggt atgaagtaga ccaacaaatc caggttttaa   7200
tggataaatt agtagagttg gcccaccaat acaagttgaa ggagactatt cagaagctaa   7260
gcaatgtcct acaacaagtt aagataaaag attactttga gaaattggtt ggatttattg   7320
atgatgctgt caagaagctt aatgaattat cttttaaaac attcattgaa gatgttaaca   7380
aattccttga catgttgata aagaaattaa agtcatttga ttaccaccag tttgtagatg   7440
aaaccaatga caaaatccgt gaggtgactc agagactcaa tggtgaaatt caggctctgg   7500
aactaccaca aaaagctgaa gcattaaaac tgttttttaga ggaaaccaag gccacagttg   7560
cagtgtatct ggaaagccta caggacacca aaataaccct aatcatcaat tggttacagg   7620
aggctttaag ttcagcatct ttggctcaca tgaaggccaa attccgagag accctagaag   7680
atacacgaga ccgaatgtat caaatggaca ttcagcagga acttcaacga tacctgtctc   7740
tggtaggcca ggtttatagc acacttgtca cctacatttc tgattggtgg actcttgctg   7800
ctaagaacct tactgacttt gcagagcaat attctatcca agattgggct aaacgtatga   7860
aagcattggt agagcaaggg ttcactgttc ctgaaatcaa gaccatcctt gggaccatgc   7920
ctgcctttga agtcagtctt caggctcttc agaaagctac cttccagaca cctgattta   7980 tagtccccct aacagatttg aggattccat cagttcagat aaacttcaaa gacttaaaaa   8040
atataaaaat cccatccagg ttttccacac cagaatttac catccttaac accttccaca   8100
ttccttcctt tacaattgac tttgtagaaa tgaaagtaaa gatcatcaga accattgacc   8160
agatgctgaa cagtgagctg cagtggcccg ttccagatat atatctcagg gatctgaagg   8220
tggaggacat tcctctagcg agaatcaccc tgccagactt ccgtttacca gaaatcgcaa   8280
ttccagaatt cataatccca actctcaacc ttaatgattt tcaagttcct gaccttcaca   8340
taccagaatt ccagcttccc cacatctcac acacaattga agtacctact tttggcaagc   8400
tatacagtat tctgaaaatc caatctcctc ttttcacatt agatgcaaat gctgacatag   8460
ggaatggaac cacctcagca aacgaagcag gtatcgcagc ttccatcact gccaaggag   8520 agtccaaatt agaagttctc aattttgatt ttcaagcaaa tgcacaactc tcaaacccta   8580
agattaatcc gctggctctg aaggagtcag tgaagttctc cagcaagtac ctgagaacgg   8640
agcatgggag tgaaatgctg tttttttggaa atgctattga gggaaaatca aacacagtgg   8700
caagtttaca cacagaaaaa aatacactgg agcttagtaa tggagtgatt gtcaagataa   8760
acaatcagct taccctggat agcaacacta aatacttcca caattgaac atccccaaac   8820 tggacttctc tagtcaggct gacctgcgca acgagatcaa gacactgttg aaagctggcc   8880
acatagcatg gacttcttct ggaaaagggt catggaaatg gcctgcccc agattctcag   8940 atgagggaac acatgaatca caaattagtt tcaccataga aggacccctc acttcctttg   9000
gactgtccaa taagatcaat agcaaacacc taagagtaaa ccaaaacttg gtttatgaat   9060
ctggctccct caacttttct aaacttgaaa ttcaatcaca agtcgattcc cagcatgtgg   9120
gccacagtgt tctaactgct aaaggcatgg cactgttttgg agaagggaag gcagagttta   9180
```

```
ctgggaggca tgatgctcat ttaaatggaa aggttattgg aactttgaaa aattctcttt      9240
tcttttcagc ccagccattt gagatcacgg catccacaaa caatgaaggg aatttgaaag      9300
ttcgttttcc attaaggtta acagggaaga tagacttcct gaataactat gcactgtttc      9360
tgagtcccag tgcccagcaa gcaagttggc aagtaagtgc taggttcaat cagtataagt      9420
acaaccaaaa tttctctgct ggaaacaacg agaacattat ggaggcccat gtaggaataa      9480
atggagaagc aaatctggat ttcttaaaca ttcctttaac aattcctgaa atgcgtctac      9540
cttacacaat aatcacaact cctccactga agatttctc tctatgggaa aaaacaggct       9600
tgaaggaatt cttgaaaacg acaaagcaat catttgattt aagtgtaaaa gctcagtata      9660
agaaaaacaa acacaggcat tccatcacaa atcctttggc tgtgctttgt gagtttatca      9720
gtcagagcat caaatccttt gacaggcatt ttgaaaaaaa cagaaacaat gcattagatt      9780
ttgtcaccaa atcctataat gaaacaaaaa ttaagtttga taagtacaaa gctgaaaaat      9840
ctcacgacga gctccccagg accttttcaaa ttcctggata cactgttcca gttgtcaatg     9900
ttgaagtgtc tccattcacc atagagatgt cggcattcgg ctatgtgttc ccaaaagcag      9960
tcagcatgcc tagtttctcc atcctaggtt ctgacgtccg tgtgccttca tacacattaa     10020
tcctgccatc attagagctg ccagtccttc atgtccctag aaatctcaag ctttctcttc     10080
cagatttcaa ggaattgtgt accataagcc atattttat tcctgccatg gcaatatta      10140 cctatgattt ctcctttaaa tcaagtgtca tcacactgaa taccaatgct gaactttta     10200 accagtcaga tattgttgct catctccttt cttcatcttc atctgtcatt gatgcactgc     10260
agtacaaatt agagggcacc acaagattga caagaaaaag gggattgaag ttagccacag     10320
ctctgtctct gagcaacaaa tttgtggagg gtagtcataa cagtactgtg agcttaacca     10380
cgaaaaatat ggaagtgtca gtggcaacaa ccacaaaagc ccaaattcca attttgagaa     10440
tgaatttcaa gcaagaactt aatggaaata ccaagtcaaa acctactgtc tcttcctcca     10500 tggaattta gtatgatttc aattcttcaa tgctgtactc taccgctaaa ggagcagttg     10560
accacaagct tagcttggaa agcctcacct cttactttc cattgagtca tctaccaaag     10620
gagatgtcaa gggttcggtt ctttctcggg aatattcagg aactattgct agtgaggcca     10680
acacttactt gaattccaag agcacacggt cttcagtgaa gctgcagggc acttccaaaa     10740
ttgatgatat ctggaacctt gaagtaaaag aaaattttgc tggagaagcc acactccaac     10800
gcatatattc cctctgggag cacagtacga aaaaccactt acagctagag ggcctctttt     10860
tcaccaacgg agaacataca agcaaagcca ccctggaact ctctccatgg caaatgtcag     10920
ctcttgttca ggtccatgca agtcagccca gttccttcca tgatttccct gaccttggcc     10980
aggaagtggc cctgaatgct aacactaaga accagaagat cagatggaaa aatgaagtcc     11040
ggattcattc tgggtctttc cagagccagg tcgagctttc caatgaccaa gaaaaggcac     11100
accttgacat tgcaggatcc ttagaaggac acctaaggtt cctcaaaaat atcatcctac     11160
cagtctatga caagagctta tgggatttcc taaagctgga tgtaaccacc agcattggta     11220
ggagacagca tcttcgtgtt tcaactgcct ttgtgtacac caaaaacccc aatggctatt     11280
cattctccat ccctgtaaaa gttttggctg ataaattcat tattcctggg ctgaaactaa     11340
atgatctaaa ttcagttctt gtcatgccta cgttccatgt cccatttaca gatcttcagg     11400
ttccatcgtg caaacttgac ttcagagaaa tacaaatcta taagaagctg agaacttcat     11460
catttgccct caacctacca acactccccg aggtaaaatt ccctgaagtt gatgtgttaa     11520
caaaatattc tcaaccagaa gactccttga ttcccttttt tgagataacc gtgcctgaat     11580
```

```
ctcagttaac tgtgtcccag ttcacgcttc caaaaagtgt ttcagatggc attgctgctt   11640
tggatctaaa tgcagtagcc aacaagatcg cagactttga gttgcccacc atcatcgtgc   11700
ctgagcagac cattgagatt ccctccatta agttctctgt acctgctgga attgtcattc   11760
cttcctttca agcactgact gcacgctttg aggtagactc tcccgtgtat aatgccactt   11820
ggagtgccag tttgaaaaac aaagcagatt atgttgaaac agtcctggat tccacatgca   11880
gctcaaccgt acagttccta gaatatgaac taaatgtttt gggaacacac aaaatcgaag   11940
atggtacgtt agcctctaag actaaaggaa catttgcaca ccgtgacttc agtgcagaat   12000
atgaagaaga tggcaaatat gaaggacttc aggaatggga aggaaaagcg cacctcaata   12060
tcaaaagccc agcgttcacc gatctccatc tgcgctacca gaaagacaag aaaggcatct   12120
ccacctcagc agcctcccca gccgtaggca ccgtgggcat ggatatggat gaagatgacg   12180
acttttctaa atggaacttc tactacagcc ctcagtcctc tccagataaa aaactcacca   12240
tattcaaaac tgagttgagg gtccgggaat ctgatgagga aactcagatc aaagttaatt   12300
gggaagaaga ggcagcttct ggcttgctaa cctctctgaa agacaacgtg cccaaggcca   12360
caggggtcct ttatgattat gtcaacaagt accactggga acacacaggg ctcaccctga   12420
gagaagtgtc ttcaaagctg agaagaaatc tgcagaacaa tgctgagtgg gtttatcaag   12480
gggccattag gcaaattgat gatatcgacg tgaggttcca gaaagcagcc agtggcacca   12540
ctgggaccta ccaagagtgg aaggacaagg cccagaatct gtaccaggaa ctgttgactc   12600
aggaaggcca agccagtttc cagggactca aggataacgt gtttgatggc ttggtacgag   12660
ttactcaaga attccatatg aaagtcaagc atctgattga ctcactcatt gatttttctga  12720 acttccccag attccagttt ccggggaaac ctgggatata cactagggag gaactttgca   12780
ctatgttcat aagggaggta gggacggtac tgtcccaggt atattcgaaa gtccataatg   12840
gttcagaaat actgttttcc tatttccaag acctagtgat tacacttcct ttcgagttaa   12900
ggaaacataa actaatagat gtaatctcga tgtataggga actgttgaaa gatttatcaa   12960
aagaagccca agaggtattt aaagccattc agtctctcaa gaccacagag gtgctacgta   13020
atcttcagga cctttttacaa ttcatttttcc aactaataga agataacatt aaacagctga   13080
aagagatgaa atttacttat cttattaatt atatccaaga tgagatcaac acaatcttca   13140
gtgattatat cccatatgtt tttaaattgt tgaaagaaaa cctatgcctt aatcttcata   13200
agttcaatga atttattcaa aacgagcttc aggaagcttc tcaagagtta cagcagatcc   13260
atcaatacat tatggcccttt cgtgaagaat attttgatcc aagtatagtt ggctggacag   13320
tgaaatatta tgaacttgaa gaaaagatag tcagtctgat caagaacctg ttagttgctc   13380
ttaaggactt ccattctgaa tatattgtca gtgcctctaa cttttacttcc caactctcaa   13440 gtcaagttga gcaatttctg cacagaaata ttcaggaata tcttagcatc cttaccgatc   13500
cagatggaaa agggaaagag aagattgcag agctttctgc cactgctcag gaataattaa   13560
aaagccaggc cattgcgacg aagaaaataa tttctgatta ccaccagcag tttagatata   13620
aactgcaaga ttttttcagac caactctctg attactatga aaaatttatt gctgaatcca   13680
aaagattgat tgacctgtcc attcaaaact accacacatt tctgatatac atcacggagt   13740
tactgaaaaa gctgcaatca accacagtca tgaacccctc catgaagctt gctccaggag   13800
aacttactat catcctctaa ttttttaaaa gaaatcttca tttattcttc ttttccaatt   13860
gaactttcac atagcacaga aaaaattcaa actgcctata ttgataaaac catacagtga   13920
```

-continued

```
gccagccttg cagtaggcag tagactataa gcagaagcac atatgaactg gacctgcacc    13980
aaagctggca ccagggctcg gaaggtctct gaactcagaa ggatggcatt ttttgcaagt    14040
taaagaaaat caggatctga gttattttgc taaacttggg ggaggaggaa caaataaatg    14100
gagtctttat tgtgtatcat a                                              14121
```

```
<210> SEQ ID NO 2
<211> LENGTH: 4563
<212> TYPE: PRT
<213> ORGANISM: Homo sapiens

<400> SEQUENCE: 2
```

| | | | | | | | | | | | | | | | |
|---|---|---|---|---|---|---|---|---|---|---|---|---|---|---|---|
| Met | Asp | Pro | Pro | Arg | Pro | Ala | Leu | Leu | Ala | Leu | Leu | Ala | Leu | Pro | Ala |
| 1 | | | | 5 | | | | | 10 | | | | | 15 | |
| Leu | Leu | Leu | Leu | Leu | Leu | Ala | Gly | Ala | Arg | Ala | Glu | Glu | Glu | Met | Leu |
| | | | 20 | | | | | 25 | | | | | 30 | | |
| Glu | Asn | Val | Ser | Leu | Val | Cys | Pro | Lys | Asp | Ala | Thr | Arg | Phe | Lys | His |
| | | | | 35 | | | | | 40 | | | | | 45 | |
| Leu | Arg | Lys | Tyr | Thr | Tyr | Asn | Tyr | Glu | Ala | Glu | Ser | Ser | Ser | Gly | Val |
| | 50 | | | | | 55 | | | | | 60 | | | | |
| Pro | Gly | Thr | Ala | Asp | Ser | Arg | Ser | Ala | Thr | Arg | Ile | Asn | Cys | Lys | Val |
| 65 | | | | | 70 | | | | | 75 | | | | | 80 |
| Glu | Leu | Glu | Val | Pro | Gln | Leu | Cys | Ser | Phe | Ile | Leu | Lys | Thr | Ser | Gln |
| | | | | 85 | | | | | 90 | | | | | 95 | |
| Cys | Thr | Leu | Lys | Glu | Val | Tyr | Gly | Phe | Asn | Pro | Glu | Gly | Lys | Ala | Leu |
| | | | 100 | | | | | 105 | | | | | 110 | | |
| Leu | Lys | Lys | Thr | Lys | Asn | Ser | Glu | Glu | Phe | Ala | Ala | Ala | Met | Ser | Arg |
| | | | | 115 | | | | | 120 | | | | | 125 | |
| Tyr | Glu | Leu | Lys | Leu | Ala | Ile | Pro | Glu | Gly | Lys | Gln | Val | Phe | Leu | Tyr |
| | 130 | | | | | 135 | | | | | 140 | | | | |
| Pro | Glu | Lys | Asp | Glu | Pro | Thr | Tyr | Ile | Leu | Asn | Ile | Lys | Arg | Gly | Ile |
| 145 | | | | | 150 | | | | | 155 | | | | | 160 |
| Ile | Ser | Ala | Leu | Leu | Val | Pro | Pro | Glu | Thr | Glu | Glu | Ala | Lys | Gln | Val |
| | | | | 165 | | | | | 170 | | | | | 175 | |
| Leu | Phe | Leu | Asp | Thr | Val | Tyr | Gly | Asn | Cys | Ser | Thr | His | Phe | Thr | Val |
| | | | 180 | | | | | 185 | | | | | 190 | | |
| Lys | Thr | Arg | Lys | Gly | Asn | Val | Ala | Thr | Glu | Ile | Ser | Thr | Glu | Arg | Asp |
| | | | | 195 | | | | | 200 | | | | | 205 | |
| Leu | Gly | Gln | Cys | Asp | Arg | Phe | Lys | Pro | Ile | Arg | Thr | Gly | Ile | Ser | Pro |
| | 210 | | | | | 215 | | | | | 220 | | | | |
| Leu | Ala | Leu | Ile | Lys | Gly | Met | Thr | Arg | Pro | Leu | Ser | Thr | Leu | Ile | Ser |
| 225 | | | | | 230 | | | | | 235 | | | | | 240 |
| Ser | Ser | Gln | Ser | Cys | Gln | Tyr | Thr | Leu | Asp | Ala | Lys | Arg | Lys | His | Val |
| | | | | 245 | | | | | 250 | | | | | 255 | |
| Ala | Glu | Ala | Ile | Cys | Lys | Glu | Gln | His | Leu | Phe | Leu | Pro | Phe | Ser | Tyr |
| | | | 260 | | | | | 265 | | | | | 270 | | |
| Lys | Asn | Lys | Tyr | Gly | Met | Val | Ala | Gln | Val | Thr | Gln | Thr | Leu | Lys | Leu |
| | | | | 275 | | | | | 280 | | | | | 285 | |
| Glu | Asp | Thr | Pro | Lys | Ile | Asn | Ser | Arg | Phe | Phe | Gly | Glu | Gly | Thr | Lys |
| | 290 | | | | | 295 | | | | | 300 | | | | |
| Lys | Met | Gly | Leu | Ala | Phe | Glu | Ser | Thr | Lys | Ser | Thr | Ser | Pro | Pro | Lys |
| 305 | | | | | 310 | | | | | 315 | | | | | 320 |
| Gln | Ala | Glu | Ala | Val | Leu | Lys | Thr | Leu | Gln | Glu | Leu | Lys | Lys | Leu | Thr |
| | | | | 325 | | | | | 330 | | | | | 335 | |

```
Ile Ser Glu Gln Asn Ile Gln Arg Ala Asn Leu Phe Asn Lys Leu Val
            340                 345                 350

Thr Glu Leu Arg Gly Leu Ser Asp Glu Ala Val Thr Ser Leu Leu Pro
            355                 360                 365

Gln Leu Ile Glu Val Ser Ser Pro Ile Thr Leu Gln Ala Leu Val Gln
            370                 375                 380

Cys Gly Gln Pro Gln Cys Ser Thr His Ile Leu Gln Trp Leu Lys Arg
385                 390                 395                 400

Val His Ala Asn Pro Leu Leu Ile Asp Val Val Thr Tyr Leu Val Ala
                405                 410                 415

Leu Ile Pro Glu Pro Ser Ala Gln Gln Leu Arg Glu Ile Phe Asn Met
            420                 425                 430

Ala Arg Asp Gln Arg Ser Arg Ala Thr Leu Tyr Ala Leu Ser His Ala
            435                 440                 445

Val Asn Asn Tyr His Lys Thr Asn Pro Thr Gly Thr Gln Glu Leu Leu
            450                 455                 460

Asp Ile Ala Asn Tyr Leu Met Glu Gln Ile Gln Asp Asp Cys Thr Gly
465                 470                 475                 480

Asp Glu Asp Tyr Thr Tyr Leu Ile Leu Arg Val Ile Gly Asn Met Gly
                485                 490                 495

Gln Thr Met Glu Gln Leu Thr Pro Glu Leu Lys Ser Ser Ile Leu Lys
            500                 505                 510

Cys Val Gln Ser Thr Lys Pro Ser Leu Met Ile Gln Lys Ala Ala Ile
            515                 520                 525

Gln Ala Leu Arg Lys Met Glu Pro Lys Asp Lys Asp Gln Glu Val Leu
            530                 535                 540

Leu Gln Thr Phe Leu Asp Asp Ala Ser Pro Gly Asp Lys Arg Leu Ala
545                 550                 555                 560

Ala Tyr Leu Met Leu Met Arg Ser Pro Ser Gln Ala Asp Ile Asn Lys
                565                 570                 575

Ile Val Gln Ile Leu Pro Trp Glu Gln Asn Glu Gln Val Lys Asn Phe
            580                 585                 590

Val Ala Ser His Ile Ala Asn Ile Leu Asn Ser Glu Glu Leu Asp Ile
            595                 600                 605

Gln Asp Leu Lys Lys Leu Val Lys Glu Ala Leu Lys Glu Ser Gln Leu
            610                 615                 620

Pro Thr Val Met Asp Phe Arg Lys Phe Ser Arg Asn Tyr Gln Leu Tyr
625                 630                 635                 640

Lys Ser Val Ser Leu Pro Ser Leu Asp Pro Ala Ser Ala Lys Ile Glu
                645                 650                 655

Gly Asn Leu Ile Phe Asp Pro Asn Asn Tyr Leu Pro Lys Glu Ser Met
            660                 665                 670

Leu Lys Thr Thr Leu Thr Ala Phe Gly Phe Ala Ser Ala Asp Leu Ile
            675                 680                 685

Glu Ile Gly Leu Glu Gly Lys Gly Phe Glu Pro Thr Leu Glu Ala Leu
            690                 695                 700

Phe Gly Lys Gln Gly Phe Phe Pro Asp Ser Val Asn Lys Ala Leu Tyr
705                 710                 715                 720

Trp Val Asn Gly Gln Val Pro Asp Gly Val Ser Lys Val Leu Val Asp
                725                 730                 735

His Phe Gly Tyr Thr Lys Asp Asp Lys His Glu Gln Asp Met Val Asn
            740                 745                 750

Gly Ile Met Leu Ser Val Glu Lys Leu Ile Lys Asp Leu Lys Ser Lys
```

-continued

```
                    755                 760                 765
Glu Val Pro Glu Ala Arg Ala Tyr Leu Arg Ile Leu Gly Glu Leu
770                 775                 780

Gly Phe Ala Ser Leu His Asp Leu Gln Leu Leu Gly Lys Leu Leu Leu
785                 790                 795                 800

Met Gly Ala Arg Thr Leu Gln Gly Ile Pro Gln Met Ile Gly Glu Val
                    805                 810                 815

Ile Arg Lys Gly Ser Lys Asn Asp Phe Phe Leu His Tyr Ile Phe Met
                    820                 825                 830

Glu Asn Ala Phe Glu Leu Pro Thr Gly Ala Gly Leu Gln Leu Gln Ile
                    835                 840                 845

Ser Ser Ser Gly Val Ile Ala Pro Gly Ala Lys Ala Gly Val Lys Leu
850                 855                 860

Glu Val Ala Asn Met Gln Ala Glu Leu Val Ala Lys Pro Ser Val Ser
865                 870                 875                 880

Val Glu Phe Val Thr Asn Met Gly Ile Ile Pro Asp Phe Ala Arg
                    885                 890                 895

Ser Gly Val Gln Met Asn Thr Asn Phe Phe His Glu Ser Gly Leu Glu
                    900                 905                 910

Ala His Val Ala Leu Lys Ala Gly Lys Leu Lys Phe Ile Ile Pro Ser
                    915                 920                 925

Pro Lys Arg Pro Val Lys Leu Leu Ser Gly Asn Thr Leu His Leu
930                 935                 940

Val Ser Thr Thr Lys Thr Glu Val Ile Pro Leu Ile Glu Asn Arg
945                 950                 955                 960

Gln Ser Trp Ser Val Cys Lys Gln Val Phe Pro Gly Leu Asn Tyr Cys
                    965                 970                 975

Thr Ser Gly Ala Tyr Ser Asn Ala Ser Ser Thr Asp Ser Ala Ser Tyr
                    980                 985                 990

Tyr Pro Leu Thr Gly Asp Thr Arg Leu Glu Leu Glu Leu Arg Pro Thr
                    995                 1000                1005

Gly Glu Ile Glu Gln Tyr Ser Val Ser Ala Thr Tyr Glu Leu Gln Arg
    1010                1015                1020

Glu Asp Arg Ala Leu Val Asp Thr Leu Lys Phe Val Thr Gln Ala Glu
1025                1030                1035                1040

Gly Ala Lys Gln Thr Glu Ala Thr Met Thr Phe Lys Tyr Asn Arg Gln
                    1045                1050                1055

Ser Met Thr Leu Ser Ser Glu Val Gln Ile Pro Asp Phe Asp Val Asp
                    1060                1065                1070

Leu Gly Thr Ile Leu Arg Val Asn Asp Glu Ser Thr Glu Gly Lys Thr
                    1075                1080                1085

Ser Tyr Arg Leu Thr Leu Asp Ile Gln Asn Lys Lys Ile Thr Glu Val
                    1090                1095                1100

Ala Leu Met Gly His Leu Ser Cys Asp Thr Lys Glu Glu Arg Lys Ile
1105                1110                1115                1120

Lys Gly Val Ile Ser Ile Pro Arg Leu Gln Ala Glu Ala Arg Ser Glu
                    1125                1130                1135

Ile Leu Ala His Trp Ser Pro Ala Lys Leu Leu Leu Gln Met Asp Ser
                    1140                1145                1150

Ser Ala Thr Ala Tyr Gly Ser Thr Val Ser Lys Arg Val Ala Trp His
                    1155                1160                1165

Tyr Asp Glu Glu Lys Ile Glu Phe Glu Trp Asn Thr Gly Thr Asn Val
                    1170                1175                1180
```

-continued

```
Asp Thr Lys Lys Met Thr Ser Asn Phe Pro Val Asp Leu Ser Asp Tyr
1185                1190                1195                1200

Pro Lys Ser Leu His Met Tyr Ala Asn Arg Leu Leu Asp His Arg Val
                1205                1210                1215

Pro Gln Thr Asp Met Thr Phe Arg His Val Gly Ser Lys Leu Ile Val
                1220                1225                1230

Ala Met Ser Ser Trp Leu Gln Lys Ala Ser Gly Ser Leu Pro Tyr Thr
                1235                1240                1245

Gln Thr Leu Gln Asp His Leu Asn Ser Leu Lys Glu Phe Asn Leu Gln
                1250                1255                1260

Asn Met Gly Leu Pro Asp Phe His Ile Pro Glu Asn Leu Phe Leu Lys
1265                1270                1275                1280

Ser Asp Gly Arg Val Lys Tyr Thr Leu Asn Lys Asn Ser Leu Lys Ile
                1285                1290                1295

Glu Ile Pro Leu Pro Phe Gly Gly Lys Ser Ser Arg Asp Leu Lys Met
                1300                1305                1310

Leu Glu Thr Val Arg Thr Pro Ala Leu His Phe Lys Ser Val Gly Phe
                1315                1320                1325

His Leu Pro Ser Arg Glu Phe Gln Val Pro Thr Phe Thr Ile Pro Lys
                1330                1335                1340

Leu Tyr Gln Leu Gln Val Pro Leu Leu Gly Val Leu Asp Leu Ser Thr
1345                1350                1355                1360

Asn Val Tyr Ser Asn Leu Tyr Asn Trp Ser Ala Ser Tyr Ser Gly Gly
                1365                1370                1375

Asn Thr Ser Thr Asp His Phe Ser Leu Arg Ala Arg Tyr His Met Lys
                1380                1385                1390

Ala Asp Ser Val Val Asp Leu Leu Ser Tyr Asn Val Gln Gly Ser Gly
                1395                1400                1405

Glu Thr Thr Tyr Asp His Lys Asn Thr Phe Thr Leu Ser Cys Asp Gly
                1410                1415                1420

Ser Leu Arg His Lys Phe Leu Asp Ser Asn Ile Lys Phe Ser His Val
1425                1430                1435                1440

Glu Lys Leu Gly Asn Asn Pro Val Ser Lys Gly Leu Leu Ile Phe Asp
                1445                1450                1455

Ala Ser Ser Ser Trp Gly Pro Gln Met Ser Ala Ser Val His Leu Asp
                1460                1465                1470

Ser Lys Lys Lys Gln His Leu Phe Val Lys Glu Val Lys Ile Asp Gly
                1475                1480                1485

Gln Phe Arg Val Ser Ser Phe Tyr Ala Lys Gly Thr Tyr Gly Leu Ser
                1490                1495                1500

Cys Gln Arg Asp Pro Asn Thr Gly Arg Leu Asn Gly Glu Ser Asn Leu
1505                1510                1515                1520

Arg Phe Asn Ser Ser Tyr Leu Gln Gly Thr Asn Gln Ile Thr Gly Arg
                1525                1530                1535

Tyr Glu Asp Gly Thr Leu Ser Leu Thr Ser Thr Ser Asp Leu Gln Ser
                1540                1545                1550

Gly Ile Ile Lys Asn Thr Ala Ser Leu Lys Tyr Glu Asn Tyr Glu Leu
                1555                1560                1565

Thr Leu Lys Ser Asp Thr Asn Gly Lys Tyr Lys Asn Phe Ala Thr Ser
                1570                1575                1580

Asn Lys Met Asp Met Thr Phe Ser Lys Gln Asn Ala Leu Leu Arg Ser
1585                1590                1595                1600
```

-continued

Glu Tyr Gln Ala Asp Tyr Glu Ser Leu Arg Phe Phe Ser Leu Leu Ser
                1605                1610                1615

Gly Ser Leu Asn Ser His Gly Leu Glu Leu Asn Ala Asp Ile Leu Gly
            1620                1625                1630

Thr Asp Lys Ile Asn Ser Gly Ala His Lys Ala Thr Leu Arg Ile Gly
            1635                1640                1645

Gln Asp Gly Ile Ser Thr Ser Ala Thr Thr Asn Leu Lys Cys Ser Leu
            1650                1655                1660

Leu Val Leu Glu Asn Glu Leu Asn Ala Glu Leu Gly Leu Ser Gly Ala
1665                1670                1675                1680

Ser Met Lys Leu Thr Thr Asn Gly Arg Phe Arg Glu His Asn Ala Lys
            1685                1690                1695

Phe Ser Leu Asp Gly Lys Ala Ala Leu Thr Glu Leu Ser Leu Gly Ser
            1700                1705                1710

Ala Tyr Gln Ala Met Ile Leu Gly Val Asp Ser Lys Asn Ile Phe Asn
            1715                1720                1725

Phe Lys Val Ser Gln Glu Gly Leu Lys Leu Ser Asn Asp Met Met Gly
            1730                1735                1740

Ser Tyr Ala Glu Met Lys Phe Asp His Thr Asn Ser Leu Asn Ile Ala
1745                1750                1755                1760

Gly Leu Ser Leu Asp Phe Ser Ser Lys Leu Asp Asn Ile Tyr Ser Ser
            1765                1770                1775

Asp Lys Phe Tyr Lys Gln Thr Val Asn Leu Gln Leu Gln Pro Tyr Ser
            1780                1785                1790

Leu Val Thr Thr Leu Asn Ser Asp Leu Lys Tyr Asn Ala Leu Asp Leu
            1795                1800                1805

Thr Asn Asn Gly Lys Leu Arg Leu Glu Pro Leu Lys Leu His Val Ala
            1810                1815                1820

Gly Asn Leu Lys Gly Ala Tyr Gln Asn Asn Glu Ile Lys His Ile Tyr
1825                1830                1835                1840

Ala Ile Ser Ser Ala Ala Leu Ser Ala Ser Tyr Lys Ala Asp Thr Val
            1845                1850                1855

Ala Lys Val Gln Gly Val Glu Phe Ser His Arg Leu Asn Thr Asp Ile
            1860                1865                1870

Ala Gly Leu Ala Ser Ala Ile Asp Met Ser Thr Asn Tyr Asn Ser Asp
            1875                1880                1885

Ser Leu His Phe Ser Asn Val Phe Arg Ser Val Met Ala Pro Phe Thr
            1890                1895                1900

Met Thr Ile Asp Ala His Thr Asn Gly Asn Gly Lys Leu Ala Leu Trp
1905                1910                1915                1920

Gly Glu His Thr Gly Gln Leu Tyr Ser Lys Phe Leu Leu Lys Ala Glu
            1925                1930                1935

Pro Leu Ala Phe Thr Phe Ser His Asp Tyr Lys Gly Ser Thr Ser His
            1940                1945                1950

His Leu Val Ser Arg Lys Ser Ile Ser Ala Ala Leu Glu His Lys Val
            1955                1960                1965

Ser Ala Leu Leu Thr Pro Ala Glu Gln Thr Gly Thr Trp Lys Leu Lys
            1970                1975                1980

Thr Gln Phe Asn Asn Asn Glu Tyr Ser Gln Asp Leu Asp Ala Tyr Asn
1985                1990                1995                2000

Thr Lys Asp Lys Ile Gly Val Glu Leu Thr Gly Arg Thr Leu Ala Asp
            2005                2010                2015

Leu Thr Leu Leu Asp Ser Pro Ile Lys Val Pro Leu Leu Leu Ser Glu

-continued

```
                2020                2025                2030
Pro Ile Asn Ile Ile Asp Ala Leu Glu Met Arg Asp Ala Val Glu Lys
        2035                2040                2045
Pro Gln Glu Phe Thr Ile Val Ala Phe Val Lys Tyr Asp Lys Asn Gln
        2050                2055                2060
Asp Val His Ser Ile Asn Leu Pro Phe Phe Glu Thr Leu Gln Glu Tyr
2065                2070                2075                2080
Phe Glu Arg Asn Arg Gln Thr Ile Ile Val Val Leu Glu Asn Val Gln
                2085                2090                2095
Arg Asn Leu Lys His Ile Asn Ile Asp Gln Phe Val Arg Lys Tyr Arg
        2100                2105                2110
Ala Ala Leu Gly Lys Leu Pro Gln Gln Ala Asn Asp Tyr Leu Asn Ser
        2115                2120                2125
Phe Asn Trp Glu Arg Gln Val Ser His Ala Lys Glu Lys Leu Thr Ala
        2130                2135                2140
Leu Thr Lys Lys Tyr Arg Ile Thr Glu Asn Asp Ile Gln Ile Ala Leu
2145                2150                2155                2160
Asp Asp Ala Lys Ile Asn Phe Asn Glu Lys Leu Ser Gln Leu Gln Thr
        2165                2170                2175
Tyr Met Ile Gln Phe Asp Gln Tyr Ile Lys Asp Ser Tyr Asp Leu His
        2180                2185                2190
Asp Leu Lys Ile Ala Ile Ala Asn Ile Ile Asp Glu Ile Ile Glu Lys
        2195                2200                2205
Leu Lys Ser Leu Asp Glu His Tyr His Ile Arg Val Asn Leu Val Lys
        2210                2215                2220
Thr Ile His Asp Leu His Leu Phe Ile Glu Asn Ile Asp Phe Asn Lys
2225                2230                2235                2240
Ser Gly Ser Ser Thr Ala Ser Trp Ile Gln Asn Val Asp Thr Lys Tyr
        2245                2250                2255
Gln Ile Arg Ile Gln Ile Gln Glu Lys Leu Gln Gln Leu Lys Arg His
        2260                2265                2270
Ile Gln Asn Ile Asp Ile Gln His Leu Ala Gly Lys Leu Lys Gln His
        2275                2280                2285
Ile Glu Ala Ile Asp Val Arg Val Leu Leu Asp Gln Leu Gly Thr Thr
        2290                2295                2300
Ile Ser Phe Glu Arg Ile Asn Asp Val Leu Glu His Val Lys His Phe
2305                2310                2315                2320
Val Ile Asn Leu Ile Gly Asp Phe Glu Val Ala Glu Lys Ile Asn Ala
        2325                2330                2335
Phe Arg Ala Lys Val His Glu Leu Ile Glu Arg Tyr Glu Val Asp Gln
        2340                2345                2350
Gln Ile Gln Val Leu Met Asp Lys Leu Val Glu Leu Ala His Gln Tyr
        2355                2360                2365
Lys Leu Lys Glu Thr Ile Gln Lys Leu Ser Asn Val Leu Gln Gln Val
        2370                2375                2380
Lys Ile Lys Asp Tyr Phe Glu Lys Leu Val Gly Phe Ile Asp Asp Ala
2385                2390                2395                2400
Val Lys Lys Leu Asn Glu Leu Ser Phe Lys Thr Phe Ile Glu Asp Val
        2405                2410                2415
Asn Lys Phe Leu Asp Met Leu Ile Lys Lys Leu Lys Ser Phe Asp Tyr
        2420                2425                2430
His Gln Phe Val Asp Glu Thr Asn Asp Lys Ile Arg Glu Val Thr Gln
        2435                2440                2445
```

```
Arg Leu Asn Gly Glu Ile Gln Ala Leu Glu Leu Pro Gln Lys Ala Glu
        2450                2455                2460

Ala Leu Lys Leu Phe Leu Glu Glu Thr Lys Ala Thr Val Ala Val Tyr
2465                2470                2475                2480

Leu Glu Ser Leu Gln Asp Thr Lys Ile Thr Leu Ile Ile Asn Trp Leu
            2485                2490                2495

Gln Glu Ala Leu Ser Ser Ala Ser Leu Ala His Met Lys Ala Lys Phe
        2500                2505                2510

Arg Glu Thr Leu Glu Asp Thr Arg Asp Arg Met Tyr Gln Met Asp Ile
        2515                2520                2525

Gln Gln Glu Leu Gln Arg Tyr Leu Ser Leu Val Gly Val Tyr Ser
        2530                2535                2540

Thr Leu Val Thr Tyr Ile Ser Asp Trp Trp Thr Leu Ala Ala Lys Asn
2545                2550                2555                2560

Leu Thr Asp Phe Ala Glu Gln Tyr Ser Ile Gln Asp Trp Ala Lys Arg
            2565                2570                2575

Met Lys Ala Leu Val Glu Gln Gly Phe Thr Val Pro Glu Ile Lys Thr
        2580                2585                2590

Ile Leu Gly Thr Met Pro Ala Phe Glu Val Ser Leu Gln Ala Leu Gln
        2595                2600                2605

Lys Ala Thr Phe Gln Thr Pro Asp Phe Ile Val Pro Leu Thr Asp Leu
        2610                2615                2620

Arg Ile Pro Ser Val Gln Ile Asn Phe Lys Asp Leu Lys Asn Ile Lys
2625                2630                2635                2640

Ile Pro Ser Arg Phe Ser Thr Pro Glu Phe Thr Ile Leu Asn Thr Phe
            2645                2650                2655

His Ile Pro Ser Phe Thr Ile Asp Phe Val Glu Met Lys Val Lys Ile
        2660                2665                2670

Ile Arg Thr Ile Asp Gln Met Leu Asn Ser Glu Leu Gln Trp Pro Val
        2675                2680                2685

Pro Asp Ile Tyr Leu Arg Asp Leu Lys Val Glu Asp Ile Pro Leu Ala
        2690                2695                2700

Arg Ile Thr Leu Pro Asp Phe Arg Leu Pro Glu Ile Ala Ile Pro Glu
2705                2710                2715                2720

Phe Ile Ile Pro Thr Leu Asn Leu Asn Asp Phe Gln Val Pro Asp Leu
            2725                2730                2735

His Ile Pro Glu Phe Gln Leu Pro His Ile Ser His Thr Ile Glu Val
        2740                2745                2750

Pro Thr Phe Gly Lys Leu Tyr Ser Ile Leu Lys Ile Gln Ser Pro Leu
        2755                2760                2765

Phe Thr Leu Asp Ala Asn Ala Asp Ile Gly Asn Gly Thr Thr Ser Ala
2770                2775                2780

Asn Glu Ala Gly Ile Ala Ala Ser Ile Thr Ala Lys Gly Glu Ser Lys
2785                2790                2795                2800

Leu Glu Val Leu Asn Phe Asp Phe Gln Ala Asn Ala Gln Leu Ser Asn
            2805                2810                2815

Pro Lys Ile Asn Pro Leu Ala Leu Lys Glu Ser Val Lys Phe Ser Ser
        2820                2825                2830

Lys Tyr Leu Arg Thr Glu His Gly Ser Glu Met Leu Phe Phe Gly Asn
        2835                2840                2845

Ala Ile Glu Gly Lys Ser Asn Thr Val Ala Ser Leu His Thr Glu Lys
        2850                2855                2860
```

```
Asn Thr Leu Glu Leu Ser Asn Gly Val Ile Val Lys Ile Asn Asn Gln
2865                2870                2875                2880

Leu Thr Leu Asp Ser Asn Thr Lys Tyr Phe His Lys Leu Asn Ile Pro
            2885                2890                2895

Lys Leu Asp Phe Ser Ser Gln Ala Asp Leu Arg Asn Glu Ile Lys Thr
        2900                2905                2910

Leu Leu Lys Ala Gly His Ile Ala Trp Thr Ser Ser Gly Lys Gly Ser
    2915                2920                2925

Trp Lys Trp Ala Cys Pro Arg Phe Ser Asp Glu Gly Thr His Glu Ser
2930                2935                2940

Gln Ile Ser Phe Thr Ile Glu Gly Pro Leu Thr Ser Phe Gly Leu Ser
2945                2950                2955                2960

Asn Lys Ile Asn Ser Lys His Leu Arg Val Asn Gln Asn Leu Val Tyr
            2965                2970                2975

Glu Ser Gly Ser Leu Asn Phe Ser Lys Leu Glu Ile Gln Ser Gln Val
        2980                2985                2990

Asp Ser Gln His Val Gly His Ser Val Leu Thr Ala Lys Gly Met Ala
    2995                3000                3005

Leu Phe Gly Glu Gly Lys Ala Glu Phe Thr Gly Arg His Asp Ala His
3010                3015                3020

Leu Asn Gly Lys Val Ile Gly Thr Leu Lys Asn Ser Leu Phe Phe Ser
3025                3030                3035                3040

Ala Gln Pro Phe Glu Ile Thr Ala Ser Thr Asn Asn Glu Gly Asn Leu
            3045                3050                3055

Lys Val Arg Phe Pro Leu Arg Leu Thr Gly Lys Ile Asp Phe Leu Asn
        3060                3065                3070

Asn Tyr Ala Leu Phe Leu Ser Pro Ser Ala Gln Gln Ala Ser Trp Gln
    3075                3080                3085

Val Ser Ala Arg Phe Asn Gln Tyr Lys Tyr Asn Gln Asn Phe Ser Ala
3090                3095                3100

Gly Asn Asn Glu Asn Ile Met Glu Ala His Val Gly Ile Asn Gly Glu
3105                3110                3115                3120

Ala Asn Leu Asp Phe Leu Asn Ile Pro Leu Thr Ile Pro Glu Met Arg
            3125                3130                3135

Leu Pro Tyr Thr Ile Ile Thr Thr Pro Pro Leu Lys Asp Phe Ser Leu
        3140                3145                3150

Trp Glu Lys Thr Gly Leu Lys Glu Phe Leu Lys Thr Thr Lys Gln Ser
    3155                3160                3165

Phe Asp Leu Ser Val Lys Ala Gln Tyr Lys Lys Asn Lys His Arg His
3170                3175                3180

Ser Ile Thr Asn Pro Leu Ala Val Leu Cys Glu Phe Ile Ser Gln Ser
3185                3190                3195                3200

Ile Lys Ser Phe Asp Arg His Phe Glu Lys Asn Arg Asn Asn Ala Leu
            3205                3210                3215

Asp Phe Val Thr Lys Ser Tyr Asn Glu Thr Lys Ile Lys Phe Asp Lys
        3220                3225                3230

Tyr Lys Ala Glu Lys Ser His Asp Glu Leu Pro Arg Thr Phe Gln Ile
    3235                3240                3245

Pro Gly Tyr Thr Val Pro Val Val Asn Val Glu Val Ser Pro Phe Thr
3250                3255                3260

Ile Glu Met Ser Ala Phe Gly Tyr Val Phe Pro Lys Ala Val Ser Met
3265                3270                3275                3280

Pro Ser Phe Ser Ile Leu Gly Ser Asp Val Arg Val Pro Ser Tyr Thr
```

```
                    3285             3290             3295
Leu Ile Leu Pro Ser Leu Glu Leu Pro Val Leu His Val Pro Arg Asn
            3300             3305             3310
Leu Lys Leu Ser Leu Pro Asp Phe Lys Glu Leu Cys Thr Ile Ser His
        3315             3320             3325
Ile Phe Ile Pro Ala Met Gly Asn Ile Thr Tyr Asp Phe Ser Phe Lys
        3330             3335             3340
Ser Ser Val Ile Thr Leu Asn Thr Asn Ala Glu Leu Phe Asn Gln Ser
3345             3350             3355             3360
Asp Ile Val Ala His Leu Leu Ser Ser Ser Ser Val Ile Asp Ala
            3365             3370             3375
Leu Gln Tyr Lys Leu Glu Gly Thr Thr Arg Leu Thr Arg Lys Arg Gly
        3380             3385             3390
Leu Lys Leu Ala Thr Ala Leu Ser Leu Ser Asn Lys Phe Val Glu Gly
        3395             3400             3405
Ser His Asn Ser Thr Val Ser Leu Thr Lys Asn Met Glu Val Ser
        3410             3415             3420
Val Ala Thr Thr Thr Lys Ala Gln Ile Pro Ile Leu Arg Met Asn Phe
3425             3430             3435             3440
Lys Gln Glu Leu Asn Gly Asn Thr Lys Ser Lys Pro Thr Val Ser Ser
            3445             3450             3455
Ser Met Glu Phe Lys Tyr Asp Phe Asn Ser Ser Met Leu Tyr Ser Thr
        3460             3465             3470
Ala Lys Gly Ala Val Asp His Lys Leu Ser Leu Glu Ser Leu Thr Ser
        3475             3480             3485
Tyr Phe Ser Ile Glu Ser Ser Thr Lys Gly Asp Val Lys Gly Ser Val
        3490             3495             3500
Leu Ser Arg Glu Tyr Ser Gly Thr Ile Ala Ser Glu Ala Asn Thr Tyr
3505             3510             3515             3520
Leu Asn Ser Lys Ser Thr Arg Ser Ser Val Lys Leu Gln Gly Thr Ser
            3525             3530             3535
Lys Ile Asp Asp Ile Trp Asn Leu Glu Val Lys Glu Asn Phe Ala Gly
        3540             3545             3550
Glu Ala Thr Leu Gln Arg Ile Tyr Ser Leu Trp Glu His Ser Thr Lys
        3555             3560             3565
Asn His Leu Gln Leu Glu Gly Leu Phe Phe Thr Asn Gly Glu His Thr
        3570             3575             3580
Ser Lys Ala Thr Leu Glu Leu Ser Pro Trp Gln Met Ser Ala Leu Val
3585             3590             3595             3600
Gln Val His Ala Ser Gln Pro Ser Ser Phe His Asp Phe Pro Asp Leu
            3605             3610             3615
Gly Gln Glu Val Ala Leu Asn Ala Asn Thr Lys Asn Gln Lys Ile Arg
        3620             3625             3630
Trp Lys Asn Glu Val Arg Ile His Ser Gly Ser Phe Gln Ser Gln Val
        3635             3640             3645
Glu Leu Ser Asn Asp Gln Glu Lys Ala His Leu Asp Ile Ala Gly Ser
        3650             3655             3660
Leu Glu Gly His Leu Arg Phe Leu Lys Asn Ile Ile Leu Pro Val Tyr
3665             3670             3675             3680
Asp Lys Ser Leu Trp Asp Phe Leu Lys Leu Asp Val Thr Thr Ser Ile
            3685             3690             3695
Gly Arg Arg Gln His Leu Arg Val Ser Thr Ala Phe Val Tyr Thr Lys
        3700             3705             3710
```

Asn Pro Asn Gly Tyr Ser Phe Ser Ile Pro Val Lys Val Leu Ala Asp
        3715                3720                3725

Lys Phe Ile Ile Pro Gly Leu Lys Leu Asn Asp Leu Asn Ser Val Leu
        3730                3735                3740

Val Met Pro Thr Phe His Val Pro Phe Thr Asp Leu Gln Val Pro Ser
3745                3750                3755                3760

Cys Lys Leu Asp Phe Arg Glu Ile Gln Ile Tyr Lys Lys Leu Arg Thr
            3765                3770                3775

Ser Ser Phe Ala Leu Asn Leu Pro Thr Leu Pro Glu Val Lys Phe Pro
            3780                3785                3790

Glu Val Asp Val Leu Thr Lys Tyr Ser Gln Pro Glu Asp Ser Leu Ile
        3795                3800                3805

Pro Phe Phe Glu Ile Thr Val Pro Glu Ser Gln Leu Thr Val Ser Gln
        3810                3815                3820

Phe Thr Leu Pro Lys Ser Val Ser Asp Gly Ile Ala Ala Leu Asp Leu
3825                3830                3835                3840

Asn Ala Val Ala Asn Lys Ile Ala Asp Phe Glu Leu Pro Thr Ile Ile
            3845                3850                3855

Val Pro Glu Gln Thr Ile Glu Ile Pro Ser Ile Lys Phe Ser Val Pro
        3860                3865                3870

Ala Gly Ile Val Ile Pro Ser Phe Gln Ala Leu Thr Ala Arg Phe Glu
        3875                3880                3885

Val Asp Ser Pro Val Tyr Asn Ala Thr Trp Ser Ala Ser Leu Lys Asn
        3890                3895                3900

Lys Ala Asp Tyr Val Glu Thr Val Leu Asp Ser Thr Cys Ser Ser Thr
3905                3910                3915                3920

Val Gln Phe Leu Glu Tyr Glu Leu Asn Val Leu Gly Thr His Lys Ile
            3925                3930                3935

Glu Asp Gly Thr Leu Ala Ser Lys Thr Lys Gly Thr Phe Ala His Arg
        3940                3945                3950

Asp Phe Ser Ala Glu Tyr Glu Glu Asp Gly Lys Tyr Glu Gly Leu Gln
        3955                3960                3965

Glu Trp Glu Gly Lys Ala His Leu Asn Ile Lys Ser Pro Ala Phe Thr
        3970                3975                3980

Asp Leu His Leu Arg Tyr Gln Lys Asp Lys Lys Gly Ile Ser Thr Ser
3985                3990                3995                4000

Ala Ala Ser Pro Ala Val Gly Thr Val Gly Met Asp Met Asp Glu Asp
            4005                4010                4015

Asp Asp Phe Ser Lys Trp Asn Phe Tyr Tyr Ser Pro Gln Ser Ser Pro
        4020                4025                4030

Asp Lys Lys Leu Thr Ile Phe Lys Thr Glu Leu Arg Val Arg Glu Ser
        4035                4040                4045

Asp Glu Glu Thr Gln Ile Lys Val Asn Trp Glu Glu Glu Ala Ala Ser
4050                4055                4060

Gly Leu Leu Thr Ser Leu Lys Asp Asn Val Pro Lys Ala Thr Gly Val
4065                4070                4075                4080

Leu Tyr Asp Tyr Val Asn Lys Tyr His Trp Glu His Thr Gly Leu Thr
            4085                4090                4095

Leu Arg Glu Val Ser Ser Lys Leu Arg Arg Asn Leu Gln Asn Asn Ala
            4100                4105                4110

Glu Trp Val Tyr Gln Gly Ala Ile Arg Gln Ile Asp Asp Ile Asp Val
        4115                4120                4125

-continued

```
Arg Phe Gln Lys Ala Ala Ser Gly Thr Thr Gly Thr Tyr Gln Glu Trp
    4130                4135                4140

Lys Asp Lys Ala Gln Asn Leu Tyr Gln Glu Leu Leu Thr Gln Glu Gly
4145                4150                4155                4160

Gln Ala Ser Phe Gln Gly Leu Lys Asp Asn Val Phe Asp Gly Leu Val
                4165                4170                4175

Arg Val Thr Gln Glu Phe His Met Lys Val Lys His Leu Ile Asp Ser
            4180                4185                4190

Leu Ile Asp Phe Leu Asn Phe Pro Arg Phe Gln Phe Pro Gly Lys Pro
        4195                4200                4205

Gly Ile Tyr Thr Arg Glu Glu Leu Cys Thr Met Phe Ile Arg Glu Val
    4210                4215                4220

Gly Thr Val Leu Ser Gln Val Tyr Ser Lys Val His Asn Gly Ser Glu
4225                4230                4235                4240

Ile Leu Phe Ser Tyr Phe Gln Asp Leu Val Ile Thr Leu Pro Phe Glu
                4245                4250                4255

Leu Arg Lys His Lys Leu Ile Asp Val Ile Ser Met Tyr Arg Glu Leu
            4260                4265                4270

Leu Lys Asp Leu Ser Lys Glu Ala Gln Glu Val Phe Lys Ala Ile Gln
        4275                4280                4285

Ser Leu Lys Thr Thr Glu Val Leu Arg Asn Leu Gln Asp Leu Leu Gln
    4290                4295                4300

Phe Ile Phe Gln Leu Ile Glu Asp Asn Ile Lys Gln Leu Lys Glu Met
4305                4310                4315                4320

Lys Phe Thr Tyr Leu Ile Asn Tyr Ile Gln Asp Glu Ile Asn Thr Ile
                4325                4330                4335

Phe Ser Asp Tyr Ile Pro Tyr Val Phe Lys Leu Leu Lys Glu Asn Leu
            4340                4345                4350

Cys Leu Asn Leu His Lys Phe Asn Glu Phe Ile Gln Asn Glu Leu Gln
        4355                4360                4365

Glu Ala Ser Gln Glu Leu Gln Gln Ile His Gln Tyr Ile Met Ala Leu
    4370                4375                4380

Arg Glu Glu Tyr Phe Asp Pro Ser Ile Val Gly Trp Thr Val Lys Tyr
4385                4390                4395                4400

Tyr Glu Leu Glu Glu Lys Ile Val Ser Leu Ile Lys Asn Leu Leu Val
                4405                4410                4415

Ala Leu Lys Asp Phe His Ser Glu Tyr Ile Val Ser Ala Ser Asn Phe
            4420                4425                4430

Thr Ser Gln Leu Ser Ser Gln Val Glu Gln Phe Leu His Arg Asn Ile
        4435                4440                4445

Gln Glu Tyr Leu Ser Ile Leu Thr Asp Pro Asp Gly Lys Gly Lys Glu
    4450                4455                4460

Lys Ile Ala Glu Leu Ser Ala Thr Ala Gln Glu Ile Ile Lys Ser Gln
4465                4470                4475                4480

Ala Ile Ala Thr Lys Lys Ile Ile Ser Asp Tyr His Gln Gln Phe Arg
                4485                4490                4495

Tyr Lys Leu Gln Asp Phe Ser Asp Gln Leu Ser Asp Tyr Tyr Glu Lys
            4500                4505                4510

Phe Ile Ala Glu Ser Lys Arg Leu Ile Asp Leu Ser Ile Gln Asn Tyr
        4515                4520                4525

His Thr Phe Leu Ile Tyr Ile Thr Glu Leu Leu Lys Lys Leu Gln Ser
    4530                4535                4540

Thr Thr Val Met Asn Pro Tyr Met Lys Leu Ala Pro Gly Glu Leu Thr
```

|   | 4545 | 4550 | 4555 | 4560 |
|---|---|---|---|---|

Ile Ile Leu

<210> SEQ ID NO 3
<211> LENGTH: 8449
<212> TYPE: DNA
<213> ORGANISM: Homo sapiens

<400> SEQUENCE: 3

| gcccgcgccg gctgtgctgc acaggggag gagagggaac cccaggcgcg agcgggaaga | 60 |
|---|---|
| ggggacctgc agccacaact tctctggtcc tctgcatccc ttctgtccct ccacccgtcc | 120 |
| ccttccccac cctctggccc ccaccttctt ggaggcgaca accccgggga ggcattagaa | 180 |
| gggatttttc ccgcaggttg cgaagggaag caaacttggt ggcaacttgc ctcccgtgc | 240 |
| gggcgtctct ccccaccgt ctcaacatgc ttaggggtcc ggggcccggg ctgctgctgc | 300 |
| tggccgtcca gtgcctgggg acagcggtgc cctccacggg agcctcgaag agcaagaggc | 360 |
| aggctcagca aatggttcag ccccagtccc cggtggctgt cagtcaaagc aagcccggtt | 420 |
| gttatgacaa tggaaaacac tatcagataa atcaacagtg ggagcggacc tacctaggca | 480 |
| atgcgttggt ttgtacttgt tatggaggaa gccgaggttt taactgcgag agtaaacctg | 540 |
| aagctgaaga acttgctttt gacaagtaca ctgggaacac ttaccgagtg ggtgacactt | 600 |
| atgagcgtcc taaagactcc atgatctggg actgtacctg catcggggct gggcgaggga | 660 |
| gaataagctg taccatcgca aaccgctgcc atgaagggg tcagtcctac aagattggtg | 720 |
| acacctggag gagaccacat gagactggtg gttacatgtt agagtgtgtg tgtcttggta | 780 |
| atggaaaagg agaatggacc tgcaagccca tagctgagaa gtgttttgat catgctgctg | 840 |
| ggacttccta tgtggtcgga gaaacgtggg agaagcccta ccaaggctgg atgatggtag | 900 |
| attgtacttg cctgggagaa ggcagcggac gcatcacttg cacttctaga aatagatgca | 960 |
| acgatcagga cacaaggaca tcctatagaa ttggagacac ctggagcaag aaggataatc | 1020 |
| gaggaaacct gctccagtgc atctgcacag gcaacggccg aggagagtgg aagtgtgaga | 1080 |
| ggcacacctc tgtgcagacc acatcgagcg gatctggccc cttcaccgat gttcgtgcag | 1140 |
| ctgtttacca accgcagcct caccccccagc ctcctcccta tggccactgt gtcacagaca | 1200 |
| gtggtgtggt ctactctgtg gggatgcagt ggctgaagac acaaggaaat aagcaaatgc | 1260 |
| tttgcacgtg cctgggcaac ggagtcagct gccaagagac agctgtaacc cagacttacg | 1320 |
| gtggcaactc aaatggagag ccatgtgtct taccattcac ctacaatggc aggacgttct | 1380 |
| actcctgcac cacagaaggg cgacaggacg acatctttg gtgcagcaca acttcgaatt | 1440 |
| atgagcagga ccagaaatac tctttctgca cagaccacac tgttttggtt cagactcgag | 1500 |
| gaggaaattc caatggtgcc ttgtgccact tccccttcct atacaacaac cacaattaca | 1560 |
| ctgattgcac ttctgagggc agaagagaca acatgaagtg gtgtgggacc acacagaact | 1620 |
| atgatgccga ccagaagttt gggttctgcc ccatggctgc ccacgaggaa atctgcacaa | 1680 |
| ccaatgaagg ggtcatgtac cgcattggag atcagtggga taagcagcat gacatgggtc | 1740 |
| acatgatgag gtgcacgtgt gttgggaatg gtcgtgggga atggacatgc attgcctact | 1800 |
| cgcagcttcg agatcagtgc attgttgatg acatcactta caatgtgaac gacacattcc | 1860 |
| acaagcgtca tgaagagggg cacatgctga actgtacatg cttcggtcag gtcggggca | 1920 |
| ggtgaagtg tgatcccgtc gaccaatgcc aggattcaga gactgggacg ttttatcaaa | 1980 |
| ttggagattc atgggagaag tatgtgcatg gtgtcagata ccagtgctac tgctatggcc | 2040 |

```
gtggcattgg ggagtggcat tgccaacctt tacagaccta tccaagctca agtggtcctg   2100
tcgaagtatt tatcactgag actccgagtc agcccaactc ccaccccatc cagtggaatg   2160
caccacagcc atctcacatt tccaagtaca ttctcaggtg gagacctaaa aattctgtag   2220
gccgttggaa ggaagctacc ataccaggcc acttaaactc ctacaccatc aaaggcctga   2280
agcctggtgt ggtatacgag ggccagctca tcagcatcca gcagtacggc caccaagaag   2340
tgactcgctt tgacttcacc accaccagca ccagcacacc tgtgaccagc aacaccgtga   2400
caggagagac gactcccttt tctcctcttg tggccacttc tgaatctgtg accgaaatca   2460
cagccagtag ctttgtggtc tcctgggtct cagcttccga caccgtgtcg ggattccggg   2520
tggaatatga gctgagtgag gagggagatg agccacagta cctggatctt ccaagcacag   2580
ccacttctgt gaacatccct gacctgcttc ctggccgaaa atacattgta aatgtctatc   2640
agatatctga ggatggggag cagagtttga tcctgtctac ttcacaaaca acagcgcctg   2700
atgcccctcc tgacccgact gtggaccaag ttgatgacac ctcaattgtt gttcgctgga   2760
gcagacccca ggctcccatc acagggtaca gaatagtcta ttcgccatca gtagaaggta   2820
gcagcacaga actcaacctt cctgaaactg caaactccgt caccctcagt gacttgcaac   2880
ctggtgttca gtataacatc actatctatg ctgtggaaga aaatcaagaa agtacacctg   2940
ttgtcattca acaagaaacc actggcaccc cacgctcaga tacagtgccc tctcccaggg   3000
acctgcagtt tgtggaagtg acagacgtga aggtcaccat catgtggaca ccgcctgaga   3060
gtgcagtgac cggctaccgt gtggatgtga tccccgtcaa cctgcctggc gagcacgggc   3120
agaggctgcc catcagcagg aacacctttg cagaagtcac cgggctgtcc cctggggtca   3180
cctattactt caaagtcttt gcagtgagcc atgggaggga gagcaagcct ctgactgctc   3240
aacagacaac caaactggat gctcccacta acctccagtt tgtcaatgaa actgattcta   3300
ctgtcctggt gagatggact ccacctcggg cccagataac aggataccga ctgaccgtgg   3360
gccttacccg aagaggacag cccaggcagt acaatgtggg tccctctgtc tccaagtacc   3420
cactgaggaa tctgcagcct gcatctgagt acaccgtatc cctcgtggcc ataaagggca   3480
accaagagag ccccaaagcc actggagtct ttaccacact gcagcctggg agctctattc   3540
caccttacaa caccgaggtg actgagacca ccattgtgat cacatggacg cctgctccaa   3600
gaattggttt taagctgggt gtacgaccaa gccaggagg agaggcacca cgagaagtga   3660
cttcagactc aggaagcatc gttgtgtccg gcttgactcc aggagtagaa tacgtctaca   3720
ccatccaagt cctgagagat ggacaggaaa gagatgcgcc aattgtaaac aaagtggtga   3780
caccattgtc tccaccaaca aacttgcatc tggaggcaaa ccctgacact ggagtgctca   3840
cagtctcctg ggagaggagc accaccccag acattactgg ttatagaatt accacaaccc   3900
ctacaaacgg ccagcaggga aattctttgg aagaagtggt ccatgctgat cagagctcct   3960
gcactttga taacctgagt cccggcctgg agtacaatgt cagtgtttac actgtcaagg   4020
atgacaagga aagtgtccct atctctgata ccatcatccc agctgttcct cctcccactg   4080
acctgcgatt caccaacatt ggtccagaca ccatgcgtgt cacctgggct ccaccccat   4140
ccattgattt aaccaacttc ctggtgcgtt actcacctgt gaaaaatgag gaagatgttg   4200
cagagttgtc aatttctcct tcagacaatg cagtggtctt aacaaatctc tgcctggta   4260
cagaatatgt agtgagtgtc tccagtgtct acgaacaaca tgagagcaca cctcttagag   4320
gaagacagaa aacaggtctt gattccccaa ctggcattga cttttctgat attactgcca   4380
```

```
actcttttac tgtgcactgg attgctcctc gagccaccat cactggctac aggatccgcc    4440
atcatcccga gcacttcagt gggagacctc gagaagatcg ggtgccccac tctcggaatt    4500
ccatcaccct caccaacctc actccaggca cagagtatgt ggtcagcatc gttgctctta    4560
atggcagaga ggaaagtccc ttattgattg gccaacaatc aacagtttct gatgttccga    4620
gggacctgga agttgttgct gcgacccca ccagcctact gatcagctgg gatgctcctg    4680
ctgtcacagt gagatattac aggatcactt acggagagac aggaggaaat agccctgtcc    4740
aggagttcac tgtgcctggg agcaagtcta cagctaccat cagcggcctt aaacctggag    4800
ttgattatac catcactgtg tatgctgtca ctggccgtgg agacagcccc gcaagcagca    4860
agccaatttc cattaattac cgaacagaaa ttgacaaacc atcccagatg caagtgaccg    4920
atgttcagga caacagcatt agtgtcaagt ggctgccttc aagttcccct gttactggtt    4980
acagagtaac caccactccc aaaaatggac caggaccaac aaaaactaaa actgcaggtc    5040
cagatcaaac agaaatgact attgaaggct gcagcccac agtggagtat gtggttagtg    5100
tctatgctca gaatccaagc ggagagagtc agcctctggt tcagactgca gtaaccaaca    5160
ttgatcgccc taaggactg gcattcactg atgtggatgt cgattccatc aaaattgctt    5220
gggaaagccc cagggggcaa gtttccaggt acagggtgac ctactcgagc cctgaggatg    5280
gaatccatga gctattccct gcacctgatg gtgaagaaga cactgcagag ctgcaaggcc    5340
tcagaccggg ttctgagtac acagtcagtg tggttgcctt gcacgatgat atggagagcc    5400 agccctgat tggaacccag tccacagcta ttcctgcacc aactgacctg aagttcactc    5460
aggtcacacc cacaagcctg agcgcccagt ggacaccacc caatgttcag ctcactggat    5520
atcgagtgcg ggtgacccc aaggagaaga ccggaccaat gaaagaaatc aaccttgctc    5580
ctgacagctc atccgtggtt gtatcaggac ttatggtggc caccaaatat gaagtgagtg    5640
tctatgctct taaggacact ttgacaagca gaccagctca gggagttgtc accactctgg    5700
agaatgtcag cccaccaaga agggctcgtg tgacagatgc tactgagacc accatcacca    5760
ttagctggag aaccaagact gagacgatca ctggcttcca agttgatgcc gttccagcca    5820
atggccagac tccaatccag agaaccatca agccagatgt cagaagctac accatcacag    5880
gtttacaacc aggcactgac tacaagatct acctgtacac cttgaatgac aatgctcgga    5940
gctcccctgt ggtcatcgac gcctccactg ccattgatgc accatccaac ctgcgtttcc    6000
tggccaccac acccaattcc ttgctggtat catggcagcc gccacgtgcc aggattaccg    6060
gctacatcat caagtatgag aagcctgggt ctcctcccag agaagtggtc cctcggcccc    6120
gccctggtgt cacagaggct actattactg gcctggaacc gggaaccgaa tatacaattt    6180
atgtcattgc cctgaagaat aatcagaaga gcgagcccct gattggaagg aaaaagacag    6240
acgagcttcc ccaactggta accttccac accccaatct tcatggacca gagatcttgg    6300
atgttccttc cacagttcaa aagacccctt tcgtcaccca ccctgggtat gacactggaa    6360
atggtattca gcttcctggc acttctggtc agcaacccag tgttgggcaa caaatgatct    6420
ttgaggaaca tggttttagg cggaccacac cgcccacaac ggccacccc ataaggcata    6480 ggccaagaca atacccgccg aatgtaggac aagaagctct ctctcagaca accatctcat    6540 gggcccccatt ccaggacact tctgagtaca tcatttcatg tcatcctgtt ggcactgatg    6600
aagaaccctt acagttcagg gttcctggaa cttctaccag tgccactctg acaggcctca    6660
ccagaggtgc cacctacaac atcatagtgg aggcactgaa agaccagcag aggcataagg    6720
ttcgggaaga ggttgttacc gtgggcaact ctgtcaacga aggcttgaac caacctacgg    6780
```

```
atgactcgtg ctttgacccc tacacagttt cccattatgc cgttggagat gagtgggaac    6840
gaatgtctga atcaggcttt aaactgttgt gccagtgctt aggctttgga agtggtcatt    6900
tcagatgtga ttcatctaga tggtgccatg acaatggtgt gaactacaag attggagaga    6960
agtgggaccg tcaggagaaa atggccagat gatgagctg cacatgtctt gggaacggaa     7020
aaggagaatt caagtgtgac cctcatgagg caacgtgtta tgatgatggg aagacatacc    7080
acgtaggaga acagtggcag aaggaatatc tcggtgccat ttgctcctgc acatgctttg    7140
gaggccagcg gggctggcgc tgtgacaact gccgcagacc tgggggtgaa cccagtcccg    7200
aaggcactac tggccagtcc tacaaccagt attctcagag ataccatcag agaacaaaca    7260
ctaatgttaa ttgcccaatt gagtgcttca tgcctttaga tgtacaggct gacagagaag    7320
attcccgaga gtaaatcatc tttccaatcc agaggaacaa gcatgtctct ctgccaagat    7380
ccatctaaac tggagtgatg ttagcagacc cagcttagag ttcttctttc tttcttaagc    7440
cctttgctct ggaggaagtt ctccagcttc agctcaactc acagcttctc caagcatcac    7500
cctgggagtt tcctgagggt tttctcataa atgagggctg cacattgcct gttctgcttc    7560
gaagtattca ataccgctca gtattttaaa tgaagtgatt ctaagatttg gtttgggatc    7620
aataggaaag catatgcagc caaccaagat gcaaatgttt tgaaatgata tgaccaaaat    7680
tttaagtagg aaagtcaccc aaacacttct gctttcactt aagtgtctgg cccgcaatac    7740
tgtaggaaca agcatgatct tgttactgtg atattttaaa tatccacagt actcactttt    7800
tccaaatgat cctagtaatt gcctagaaat atctttctct tacctgttat ttatcaattt    7860
ttcccagtat ttttatacgg aaaaaattgt attgaaaaca cttagtatgc agttgataag    7920
aggaatttgg tataattatg gtgggtgatt attttttata ctgtatgtgc caaagcttta    7980
ctactgtgga aagacaactg ttttaataaa agatttacat tccacaactt gaagttcatc    8040
tatttgatat aagacacctt cggggggaaat aattcctgtg aatattcttt ttcaattcag    8100
caaacatttg aaaatctatg atgtgcaagt ctaattgttg atttcagtac aagatttttct   8160 aaatcagttg ctacaaaaac tgattggttt ttgtcacttc atctcttcac taatggagat    8220
agctttacac tttctgcttt aatagattta agtggacccc aatatttatt aaaattgcta    8280
gtttaccgtt cagaagtata atagaaataa tctttagttg ctcttttcta accattgtaa    8340
ttcttccctt cttccctcca cctttccttc attgaataaa cctctgttca aagagattgc    8400
ctgcaaggga aataaaaatg actaagatat taaaaaaaaa aaaaaaaa                 8449
```

<210> SEQ ID NO 4
<211> LENGTH: 2355
<212> TYPE: PRT
<213> ORGANISM: Homo sapiens

<400> SEQUENCE: 4

Met Leu Arg Gly Pro Gly Pro Leu Leu Leu Ala Val Gln Cys
1               5                   10                  15

Leu Gly Thr Ala Val Pro Ser Thr Gly Ala Ser Lys Ser Lys Arg Gln
                20                  25                  30

Ala Gln Gln Met Val Gln Pro Gln Ser Pro Val Ala Val Ser Gln Ser
            35                  40                  45

Lys Pro Gly Cys Tyr Asp Asn Gly Lys His Tyr Gln Ile Asn Gln Gln
        50                  55                  60

Trp Glu Arg Thr Tyr Leu Gly Asn Ala Leu Val Cys Thr Cys Tyr Gly
65                  70                  75                  80

```
Gly Ser Arg Gly Phe Asn Cys Glu Ser Lys Pro Glu Ala Glu Thr
                85                  90                  95
Cys Phe Asp Lys Tyr Thr Gly Asn Thr Tyr Arg Val Gly Asp Thr Tyr
                100                 105                 110
Glu Arg Pro Lys Asp Ser Met Ile Trp Asp Cys Thr Cys Ile Gly Ala
                115                 120                 125
Gly Arg Gly Arg Ile Ser Cys Thr Ile Ala Asn Arg Cys His Glu Gly
        130                 135                 140
Gly Gln Ser Tyr Lys Ile Gly Asp Thr Trp Arg Arg Pro His Glu Thr
145                 150                 155                 160
Gly Gly Tyr Met Leu Glu Cys Val Cys Leu Gly Asn Gly Lys Gly Glu
                165                 170                 175
Trp Thr Cys Lys Pro Ile Ala Glu Lys Cys Phe Asp His Ala Ala Gly
                180                 185                 190
Thr Ser Tyr Val Val Gly Glu Thr Trp Glu Lys Pro Tyr Gln Gly Trp
        195                 200                 205
Met Met Val Asp Cys Thr Cys Leu Gly Glu Gly Ser Gly Arg Ile Thr
210                 215                 220
Cys Thr Ser Arg Asn Arg Cys Asn Asp Gln Asp Thr Arg Thr Ser Tyr
225                 230                 235                 240
Arg Ile Gly Asp Thr Trp Ser Lys Lys Asp Asn Arg Gly Asn Leu Leu
                245                 250                 255
Gln Cys Ile Cys Thr Gly Asn Gly Arg Gly Glu Trp Lys Cys Glu Arg
                260                 265                 270
His Thr Ser Val Gln Thr Thr Ser Ser Gly Ser Gly Pro Phe Thr Asp
        275                 280                 285
Val Arg Ala Ala Val Tyr Gln Pro Gln Pro His Pro Gln Pro Pro
290                 295                 300
Tyr Gly His Cys Val Thr Asp Ser Gly Val Val Tyr Ser Val Gly Met
305                 310                 315                 320
Gln Trp Leu Lys Thr Gln Gly Asn Lys Gln Met Leu Cys Thr Cys Leu
                325                 330                 335
Gly Asn Gly Val Ser Cys Gln Glu Thr Ala Val Thr Gln Thr Tyr Gly
                340                 345                 350
Gly Asn Ser Asn Gly Glu Pro Cys Val Leu Pro Phe Thr Tyr Asn Gly
        355                 360                 365
Arg Thr Phe Tyr Ser Cys Thr Thr Glu Gly Arg Gln Asp Gly His Leu
        370                 375                 380
Trp Cys Ser Thr Thr Ser Asn Tyr Glu Gln Asp Gln Lys Tyr Ser Phe
385                 390                 395                 400
Cys Thr Asp His Thr Val Leu Val Gln Thr Arg Gly Gly Asn Ser Asn
                405                 410                 415
Gly Ala Leu Cys His Phe Pro Phe Leu Tyr Asn Asn His Asn Tyr Thr
                420                 425                 430
Asp Cys Thr Ser Glu Gly Arg Arg Asp Asn Met Lys Trp Cys Gly Thr
        435                 440                 445
Thr Gln Asn Tyr Asp Ala Asp Gln Lys Phe Gly Phe Cys Pro Met Ala
450                 455                 460
Ala His Glu Glu Ile Cys Thr Thr Asn Glu Gly Val Met Tyr Arg Ile
465                 470                 475                 480
Gly Asp Gln Trp Asp Lys Gln His Asp Met Gly His Met Met Arg Cys
                485                 490                 495
```

-continued

Thr Cys Val Gly Asn Gly Arg Gly Glu Trp Thr Cys Ile Ala Tyr Ser
            500                 505                 510

Gln Leu Arg Asp Gln Cys Ile Val Asp Ile Thr Tyr Asn Val Asn
        515                 520                 525

Asp Thr Phe His Lys Arg His Glu Glu Gly His Met Leu Asn Cys Thr
        530                 535                 540

Cys Phe Gly Gln Gly Arg Gly Arg Trp Lys Cys Asp Pro Val Asp Gln
545                 550                 555                 560

Cys Gln Asp Ser Glu Thr Gly Thr Phe Tyr Gln Ile Gly Asp Ser Trp
            565                 570                 575

Glu Lys Tyr Val His Gly Val Arg Tyr Gln Cys Tyr Cys Tyr Gly Arg
            580                 585                 590

Gly Ile Gly Glu Trp His Cys Gln Pro Leu Gln Thr Tyr Pro Ser Ser
            595                 600                 605

Ser Gly Pro Val Glu Val Phe Ile Thr Glu Thr Pro Ser Gln Pro Asn
            610                 615                 620

Ser His Pro Ile Gln Trp Asn Ala Pro Gln Pro Ser His Ile Ser Lys
625                 630                 635                 640

Tyr Ile Leu Arg Trp Arg Pro Lys Asn Ser Val Gly Arg Trp Lys Glu
            645                 650                 655

Ala Thr Ile Pro Gly His Leu Asn Ser Tyr Thr Ile Lys Gly Leu Lys
            660                 665                 670

Pro Gly Val Val Tyr Glu Gly Gln Leu Ile Ser Ile Gln Gln Tyr Gly
            675                 680                 685

His Gln Glu Val Thr Arg Phe Asp Phe Thr Thr Thr Ser Thr Ser Thr
            690                 695                 700

Pro Val Thr Ser Asn Thr Val Thr Gly Glu Thr Thr Pro Phe Ser Pro
705                 710                 715                 720

Leu Val Ala Thr Ser Glu Ser Val Thr Glu Ile Thr Ala Ser Ser Phe
            725                 730                 735

Val Val Ser Trp Val Ser Ala Ser Asp Thr Val Ser Gly Phe Arg Val
            740                 745                 750

Glu Tyr Glu Leu Ser Glu Glu Gly Asp Glu Pro Gln Tyr Leu Asp Leu
            755                 760                 765

Pro Ser Thr Ala Thr Ser Val Asn Ile Pro Asp Leu Leu Pro Gly Arg
            770                 775                 780

Lys Tyr Ile Val Asn Val Tyr Gln Ile Ser Glu Asp Gly Glu Gln Ser
785                 790                 795                 800

Leu Ile Leu Ser Thr Ser Gln Thr Thr Ala Pro Asp Ala Pro Pro Asp
            805                 810                 815

Pro Thr Val Asp Gln Val Asp Asp Thr Ser Ile Val Val Arg Trp Ser
            820                 825                 830

Arg Pro Gln Ala Pro Ile Thr Gly Tyr Arg Ile Val Tyr Ser Pro Ser
            835                 840                 845

Val Glu Gly Ser Ser Thr Glu Leu Asn Leu Pro Glu Thr Ala Asn Ser
            850                 855                 860

Val Thr Leu Ser Asp Leu Gln Pro Gly Val Gln Tyr Asn Ile Thr Ile
865                 870                 875                 880

Tyr Ala Val Glu Glu Asn Gln Glu Ser Thr Pro Val Val Ile Gln Gln
            885                 890                 895

Glu Thr Thr Gly Thr Pro Arg Ser Asp Thr Val Pro Ser Pro Arg Asp
            900                 905                 910

Leu Gln Phe Val Glu Val Thr Asp Val Lys Val Thr Ile Met Trp Thr

-continued

```
              915                 920                 925
Pro Pro Glu Ser Ala Val Thr Gly Tyr Arg Val Asp Val Ile Pro Val
    930                 935                 940
Asn Leu Pro Gly Glu His Gly Gln Arg Leu Pro Ile Ser Arg Asn Thr
945                 950                 955                 960
Phe Ala Glu Val Thr Gly Leu Ser Pro Gly Val Thr Tyr Tyr Phe Lys
                965                 970                 975
Val Phe Ala Val Ser His Gly Arg Glu Ser Lys Pro Leu Thr Ala Gln
            980                 985                 990
Gln Thr Thr Lys Leu Asp Ala Pro Thr Asn Leu Gln Phe Val Asn Glu
        995                 1000                1005
Thr Asp Ser Thr Val Leu Val Arg Trp Thr Pro Pro Arg Ala Gln Ile
    1010                1015                1020
Thr Gly Tyr Arg Leu Thr Val Gly Leu Thr Arg Arg Gly Gln Pro Arg
1025                1030                1035                1040
Gln Tyr Asn Val Gly Pro Ser Val Ser Lys Tyr Pro Leu Arg Asn Leu
                1045                1050                1055
Gln Pro Ala Ser Glu Tyr Thr Val Ser Leu Val Ala Ile Lys Gly Asn
            1060                1065                1070
Gln Glu Ser Pro Lys Ala Thr Gly Val Phe Thr Thr Leu Gln Pro Gly
        1075                1080                1085
Ser Ser Ile Pro Pro Tyr Asn Thr Glu Val Thr Glu Thr Thr Ile Val
    1090                1095                1100
Ile Thr Trp Thr Pro Ala Pro Arg Ile Gly Phe Lys Leu Gly Val Arg
1105                1110                1115                1120
Pro Ser Gln Gly Gly Glu Ala Pro Arg Glu Val Thr Ser Asp Ser Gly
                1125                1130                1135
Ser Ile Val Val Ser Gly Leu Thr Pro Gly Val Glu Tyr Val Tyr Thr
            1140                1145                1150
Ile Gln Val Leu Arg Asp Gly Gln Glu Arg Asp Ala Pro Ile Val Asn
        1155                1160                1165
Lys Val Val Thr Pro Leu Ser Pro Pro Thr Asn Leu His Leu Glu Ala
    1170                1175                1180
Asn Pro Asp Thr Gly Val Leu Thr Val Ser Trp Glu Arg Ser Thr Thr
1185                1190                1195                1200
Pro Asp Ile Thr Gly Tyr Arg Ile Thr Thr Thr Pro Thr Asn Gly Gln
                1205                1210                1215
Gln Gly Asn Ser Leu Glu Glu Val Val His Ala Asp Gln Ser Ser Cys
            1220                1225                1230
Thr Phe Asp Asn Leu Ser Pro Gly Leu Glu Tyr Asn Val Ser Val Tyr
        1235                1240                1245
Thr Val Lys Asp Asp Lys Glu Ser Val Pro Ile Ser Asp Thr Ile Ile
    1250                1255                1260
Pro Ala Val Pro Pro Pro Thr Asp Leu Arg Phe Thr Asn Ile Gly Pro
1265                1270                1275                1280
Asp Thr Met Arg Val Thr Trp Ala Pro Pro Pro Ser Ile Asp Leu Thr
                1285                1290                1295
Asn Phe Leu Val Arg Tyr Ser Pro Val Lys Asn Glu Glu Asp Val Ala
            1300                1305                1310
Glu Leu Ser Ile Ser Pro Ser Asp Asn Ala Val Val Leu Thr Asn Leu
        1315                1320                1325
Leu Pro Gly Thr Glu Tyr Val Val Ser Val Ser Ser Val Tyr Glu Gln
    1330                1335                1340
```

```
His Glu Ser Thr Pro Leu Arg Gly Arg Gln Lys Thr Gly Leu Asp Ser
1345                1350                1355                1360

Pro Thr Gly Ile Asp Phe Ser Asp Ile Thr Ala Asn Ser Phe Thr Val
            1365                1370                1375

His Trp Ile Ala Pro Arg Ala Thr Ile Thr Gly Tyr Arg Ile Arg His
        1380                1385                1390

His Pro Glu His Phe Ser Gly Arg Pro Arg Glu Asp Arg Val Pro His
    1395                1400                1405

Ser Arg Asn Ser Ile Thr Leu Thr Asn Leu Thr Pro Gly Thr Glu Tyr
1410                1415                1420

Val Val Ser Ile Val Ala Leu Asn Gly Arg Glu Glu Ser Pro Leu Leu
1425                1430                1435                1440

Ile Gly Gln Gln Ser Thr Val Ser Asp Val Pro Arg Asp Leu Glu Val
                1445                1450                1455

Val Ala Ala Thr Pro Thr Ser Leu Leu Ile Ser Trp Asp Ala Pro Ala
            1460                1465                1470

Val Thr Val Arg Tyr Tyr Arg Ile Thr Tyr Gly Glu Thr Gly Gly Asn
        1475                1480                1485

Ser Pro Val Gln Glu Phe Thr Val Pro Gly Ser Lys Ser Thr Ala Thr
    1490                1495                1500

Ile Ser Gly Leu Lys Pro Gly Val Asp Tyr Thr Ile Thr Val Tyr Ala
1505                1510                1515                1520

Val Thr Gly Arg Gly Asp Ser Pro Ala Ser Ser Lys Pro Ile Ser Ile
                1525                1530                1535

Asn Tyr Arg Thr Glu Ile Asp Lys Pro Ser Gln Met Gln Val Thr Asp
            1540                1545                1550

Val Gln Asp Asn Ser Ile Ser Val Lys Trp Leu Pro Ser Ser Ser Pro
        1555                1560                1565

Val Thr Gly Tyr Arg Val Thr Thr Thr Pro Lys Asn Gly Pro Gly Pro
    1570                1575                1580

Thr Lys Thr Lys Thr Ala Gly Pro Asp Gln Thr Glu Met Thr Ile Glu
1585                1590                1595                1600

Gly Leu Gln Pro Thr Val Glu Tyr Val Val Ser Val Tyr Ala Gln Asn
                1605                1610                1615

Pro Ser Gly Glu Ser Gln Pro Leu Val Gln Thr Ala Val Thr Asn Ile
            1620                1625                1630

Asp Arg Pro Lys Gly Leu Ala Phe Thr Asp Val Asp Val Asp Ser Ile
        1635                1640                1645

Lys Ile Ala Trp Glu Ser Pro Gln Gly Gln Val Ser Arg Tyr Arg Val
    1650                1655                1660

Thr Tyr Ser Ser Pro Glu Asp Gly Ile His Glu Leu Phe Pro Ala Pro
1665                1670                1675                1680

Asp Gly Glu Glu Asp Thr Ala Glu Leu Gln Gly Leu Arg Pro Gly Ser
                1685                1690                1695

Glu Tyr Thr Val Ser Val Val Ala Leu His Asp Asp Met Glu Ser Gln
            1700                1705                1710

Pro Leu Ile Gly Thr Gln Ser Thr Ala Ile Pro Ala Pro Thr Asp Leu
        1715                1720                1725

Lys Phe Thr Gln Val Thr Pro Thr Ser Leu Ser Ala Gln Trp Thr Pro
    1730                1735                1740

Pro Asn Val Gln Leu Thr Gly Tyr Arg Val Arg Val Thr Pro Lys Glu
1745                1750                1755                1760
```

-continued

Lys Thr Gly Pro Met Lys Glu Ile Asn Leu Ala Pro Asp Ser Ser Ser
            1765            1770            1775

Val Val Val Ser Gly Leu Met Val Ala Thr Lys Tyr Glu Val Ser Val
            1780            1785            1790

Tyr Ala Leu Lys Asp Thr Leu Thr Ser Arg Pro Ala Gln Gly Val Val
            1795            1800            1805

Thr Thr Leu Glu Asn Val Ser Pro Arg Arg Ala Arg Val Thr Asp
1810            1815            1820

Ala Thr Glu Thr Thr Ile Thr Ile Ser Trp Arg Thr Lys Thr Glu Thr
1825            1830            1835            1840

Ile Thr Gly Phe Gln Val Asp Ala Val Pro Ala Asn Gly Gln Thr Pro
            1845            1850            1855

Ile Gln Arg Thr Ile Lys Pro Asp Val Arg Ser Tyr Thr Ile Thr Gly
            1860            1865            1870

Leu Gln Pro Gly Thr Asp Tyr Lys Ile Tyr Leu Tyr Thr Leu Asn Asp
            1875            1880            1885

Asn Ala Arg Ser Ser Pro Val Val Ile Asp Ala Ser Thr Ala Ile Asp
            1890            1895            1900

Ala Pro Ser Asn Leu Arg Phe Leu Ala Thr Thr Pro Asn Ser Leu Leu
1905            1910            1915            1920

Val Ser Trp Gln Pro Pro Arg Ala Arg Ile Thr Gly Tyr Ile Ile Lys
            1925            1930            1935

Tyr Glu Lys Pro Gly Ser Pro Arg Glu Val Val Pro Arg Pro Arg
            1940            1945            1950

Pro Gly Val Thr Glu Ala Thr Ile Thr Gly Leu Glu Pro Gly Thr Glu
            1955            1960            1965

Tyr Thr Ile Tyr Val Ile Ala Leu Lys Asn Asn Gln Lys Ser Glu Pro
            1970            1975            1980

Leu Ile Gly Arg Lys Lys Thr Asp Glu Leu Pro Gln Leu Val Thr Leu
1985            1990            1995            2000

Pro His Pro Asn Leu His Gly Pro Glu Ile Leu Asp Val Pro Ser Thr
            2005            2010            2015

Val Gln Lys Thr Pro Phe Val Thr His Pro Gly Tyr Asp Thr Gly Asn
            2020            2025            2030

Gly Ile Gln Leu Pro Gly Thr Ser Gly Gln Gln Pro Ser Val Gly Gln
            2035            2040            2045

Gln Met Ile Phe Glu Glu His Gly Phe Arg Arg Thr Thr Pro Pro Thr
            2050            2055            2060

Thr Ala Thr Pro Ile Arg His Arg Pro Arg Pro Tyr Pro Pro Asn Val
2065            2070            2075            2080

Gly Gln Glu Ala Leu Ser Gln Thr Thr Ile Ser Trp Ala Pro Phe Gln
            2085            2090            2095

Asp Thr Ser Glu Tyr Ile Ile Ser Cys His Pro Val Gly Thr Asp Glu
            2100            2105            2110

Glu Pro Leu Gln Phe Arg Val Pro Gly Thr Ser Thr Ser Ala Thr Leu
            2115            2120            2125

Thr Gly Leu Thr Arg Gly Ala Thr Tyr Asn Ile Ile Val Glu Ala Leu
            2130            2135            2140

Lys Asp Gln Gln Arg His Lys Val Arg Glu Val Val Thr Val Gly
2145            2150            2155            2160

Asn Ser Val Asn Glu Gly Leu Asn Gln Pro Thr Asp Asp Ser Cys Phe
            2165            2170            2175

Asp Pro Tyr Thr Val Ser His Tyr Ala Val Gly Asp Glu Trp Glu Arg

```
              2180              2185              2190
Met Ser Glu Ser Gly Phe Lys Leu Leu Cys Gln Cys Leu Gly Phe Gly
        2195              2200              2205

Ser Gly His Phe Arg Cys Asp Ser Ser Arg Trp Cys His Asp Asn Gly
        2210              2215              2220

Val Asn Tyr Lys Ile Gly Glu Lys Trp Asp Arg Gln Gly Glu Asn Gly
2225              2230              2235              2240

Gln Met Met Ser Cys Thr Cys Leu Gly Asn Gly Lys Gly Glu Phe Lys
            2245              2250              2255

Cys Asp Pro His Glu Ala Thr Cys Tyr Asp Asp Gly Lys Thr Tyr His
        2260              2265              2270

Val Gly Glu Gln Trp Gln Lys Glu Tyr Leu Gly Ala Ile Cys Ser Cys
        2275              2280              2285

Thr Cys Phe Gly Gly Gln Arg Gly Trp Arg Cys Asp Asn Cys Arg Arg
        2290              2295              2300

Pro Gly Gly Glu Pro Ser Pro Glu Gly Thr Thr Gly Gln Ser Tyr Asn
2305              2310              2315              2320

Gln Tyr Ser Gln Arg Tyr His Gln Arg Thr Asn Thr Asn Val Asn Cys
            2325              2330              2335

Pro Ile Glu Cys Phe Met Pro Leu Asp Val Gln Ala Asp Arg Glu Asp
        2340              2345              2350

Ser Arg Glu
        2355

<210> SEQ ID NO 5
<211> LENGTH: 2402
<212> TYPE: DNA
<213> ORGANISM: Homo sapiens

<400> SEQUENCE: 5
gcccgcgccg gctgtgctgc acaggggag gagagggaac cccaggcgcg agcgggaaga      60
ggggacctgc agccacaact tctctggtcc tctgcatccc ttctgtccct ccacccgtcc    120
ccttccccac cctctggccc ccaccttctt ggaggcgaca accccgggca ggcattagaa    180
gggatttttc ccgcaggttg cgaagggaag caaacttggt ggcaacttgc ctcccggtgc    240
gggcgtctct cccccaccgt ctcaacatgc ttaggggtcc ggggcccggg ctgctgctgc    300
tggccgtcca gtgcctgggg acagcggtgc cctccacggg agcctcgaag agcaagaggc    360
aggctcagca aatggttcag ccccagtccc cggtggctgt cagtcaaagc aagcccggtt    420
gttatgacaa tggaaaacac tatcagataa atcaacagtg ggagcggacc tacctaggca    480
atgcgttggt ttgtacttgt tatggaggaa gccgaggttt aactgcgag agtaaacctg     540 aagctgaaga gcttgctttg acaagtaca ctgggaacac ttaccgagtg ggtgacactt      600
atgagcgtcc taaagactcc atgatctggg actgtacctg catcgggct gggcgaggga     660 gaataagctg taccatcgca aaccgctgcc atgaagggg tcagtcctac aagattggtg     720
acacctggag gagaccacat gagactggtg gttacatgtt agagtgtgtg tgtcttggta    780
atggaaaagg agaatggacc tgcaagccca gctgagaa gtgttttgat catgctgctg      840
gacttcctta tgtggtcgga gaacgtgggg agaagcccta ccaaggctgg atgatggtag    900
attgtacttg cctgggagaa ggcagcggac gcatcacttg cacttctaga aatagatgca    960
acgatcagga cacaaggaca tcctataaa ttggagacac ctggagcaag aaggataatc     1020
gaggaaacct gctccagtgc atctgcacag gcaacggccg aggagagtgg aagtgtgaga   1080
```

```
ggcacacctc tgtgcagacc acatcgagcg atctggccc cttcaccgat gttcgtgcag    1140
ctgtttacca accgcagcct cacccccagc ctcctcccta tggccactgt gtcacagaca    1200
gtggtgtggt ctactctgtg gggatgcagt ggctgaagac acaaggaaat aagcaaatgc    1260
tttgcacgtg cctgggcaac ggagtcagct gccaagagac agctgtaacc cagacttacg    1320
gtggcaactc aaatggagag ccatgtgtct taccattcac ctacaatggc aggacgttct    1380
actcctgcac cacagaaggg cgacaggacg gacatctttg gtgcagcaca acttcgaatt    1440
atgagcagga ccagaaatac tctttctgca cagaccacac tgttttggtt cagactcgag    1500
gaggaaattc caatggtgcc ttgtgccact tccccttcct atacaacaac acaattaca    1560 ctgattgcac ttctgagggc agaagagaca acatgaagtg gtgtgggacc acacagaact    1620
atgatgccga ccagaagttt gggttctgcc ccatggctgc ccacgaggaa atctgcacaa    1680
ccaatgaagg ggtcatgtac cgcattggag atcagtggga taagcagcat gacatgggtc    1740
acatgatgag gtgcacgtgt gttgggaatg tcgtgggga atggacatgc attgcctact    1800
cgcagcttcg agatcagtgc attgttgatg acatcactta caatgtgaac gacacattcc    1860
acaagcgtca tgaagagggg cacatgctga actgtacatg cttcggtcag gtcggggca    1920 ggtggaagtg tgatcccgtc gaccaatgcc aggattcaga gactgggacg ttttatcaaa    1980
ttggagattc atgggagaag tatgtgcatg gtgtcagata ccagtgctac tgctatggcc    2040
gtggcattgg ggagtggcat tgccaacctt tacagaccta tccaagctca gtggtcctg    2100 tcgaagtatt tatcactgag actccgagtc agcccaactc ccaccccatc cagtggaatg    2160
caccacagcc atctcacatt tccaagtaca ttctcaggtg agacctgtg agtatcccac    2220 ccagaaacct tggatactga gtctcctaat cttatcaatt ctgatggttt cttttttcc    2280 cagcttttga gccaacaact ctgattaact attcctatag catttactat atttgtttag    2340
tgaacaaaca atatgtggtc aattaaattg acttgtagac tgaaaaaaaa aaaaaaaaa    2400 aa                                                                    2402
```

<210> SEQ ID NO 6
<211> LENGTH: 657
<212> TYPE: PRT
<213> ORGANISM: Homo sapiens

<400> SEQUENCE: 6

```
Met Leu Arg Gly Pro Gly Pro Gly Leu Leu Leu Leu Ala Val Gln Cys
 1               5                  10                  15

Leu Gly Thr Ala Val Pro Ser Thr Gly Ala Ser Lys Ser Lys Arg Gln
            20                  25                  30

Ala Gln Gln Met Val Gln Pro Gln Ser Pro Val Ala Val Ser Gln Ser
        35                  40                  45

Lys Pro Gly Cys Tyr Asp Asn Gly Lys His Tyr Gln Ile Asn Gln Gln
    50                  55                  60

Trp Glu Arg Thr Tyr Leu Gly Asn Ala Leu Val Cys Thr Cys Tyr Gly
65                  70                  75                  80

Gly Ser Arg Gly Phe Asn Cys Glu Ser Lys Pro Glu Ala Glu Glu Thr
                85                  90                  95

Cys Phe Asp Lys Tyr Thr Gly Asn Thr Tyr Arg Val Gly Asp Thr Tyr
            100                 105                 110

Glu Arg Pro Lys Asp Ser Met Ile Trp Asp Cys Thr Cys Ile Gly Ala
        115                 120                 125

Gly Arg Gly Arg Ile Ser Cys Thr Ile Ala Asn Arg Cys His Glu Gly
```

```
                130                 135                 140
Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
                165                 170                 175

Trp Thr Cys Lys Pro Ile Ala Glu Lys Cys Phe Asp His Ala Ala Gly
                180                 185                 190

Thr Ser Tyr Val Val Gly Glu Thr Trp Glu Lys Pro Tyr Gln Gly Trp
                195                 200                 205

Met Met Val Asp Cys Thr Cys Leu Gly Glu Gly Ser Gly Arg Ile Thr
210                 215                 220

Cys Thr Ser Arg Asn Arg Cys Asn Asp Gln Asp Thr Arg Thr Ser Tyr
225                 230                 235                 240

Arg Ile Gly Asp Thr Trp Ser Lys Lys Asp Asn Arg Gly Asn Leu Leu
                245                 250                 255

Gln Cys Ile Cys Thr Gly Asn Gly Arg Gly Glu Trp Lys Cys Glu Arg
                260                 265                 270

His Thr Ser Val Gln Thr Thr Ser Ser Gly Ser Gly Pro Phe Thr Asp
                275                 280                 285

Val Arg Ala Ala Val Tyr Gln Pro Gln Pro His Pro Gln Pro Pro Pro
290                 295                 300

Tyr Gly His Cys Val Thr Asp Ser Gly Val Val Tyr Ser Val Gly Met
305                 310                 315                 320

Gln Trp Leu Lys Thr Gln Gly Asn Lys Gln Met Leu Cys Thr Cys Leu
                325                 330                 335

Gly Asn Gly Val Ser Cys Gln Glu Thr Ala Val Thr Gln Thr Tyr Gly
                340                 345                 350

Gly Asn Ser Asn Gly Glu Pro Cys Val Leu Pro Phe Thr Tyr Asn Gly
                355                 360                 365

Arg Thr Phe Tyr Ser Cys Thr Thr Glu Gly Arg Gln Asp Gly His Leu
                370                 375                 380

Trp Cys Ser Thr Thr Ser Asn Tyr Glu Gln Asp Gln Lys Tyr Ser Phe
385                 390                 395                 400

Cys Thr Asp His Thr Val Leu Val Gln Thr Arg Gly Gly Asn Ser Asn
                405                 410                 415

Gly Ala Leu Cys His Phe Pro Phe Leu Tyr Asn Asn His Asn Tyr Thr
                420                 425                 430

Asp Cys Thr Ser Glu Gly Arg Arg Asp Asn Met Lys Trp Cys Gly Thr
                435                 440                 445

Thr Gln Asn Tyr Asp Ala Asp Gln Lys Phe Gly Phe Cys Pro Met Ala
                450                 455                 460

Ala His Glu Glu Ile Cys Thr Thr Asn Glu Gly Val Met Tyr Arg Ile
465                 470                 475                 480

Gly Asp Gln Trp Asp Lys Gln His Asp Met Gly His Met Met Arg Cys
                485                 490                 495

Thr Cys Val Gly Asn Gly Arg Gly Glu Trp Thr Cys Ile Ala Tyr Ser
                500                 505                 510

Gln Leu Arg Asp Gln Cys Ile Val Asp Asp Ile Thr Tyr Asn Val Asn
                515                 520                 525

Asp Thr Phe His Lys Arg His Glu Glu Gly His Met Leu Asn Cys Thr
                530                 535                 540

Cys Phe Gly Gln Gly Arg Gly Arg Trp Lys Cys Asp Pro Val Asp Gln
545                 550                 555                 560
```

```
Cys Gln Asp Ser Glu Thr Gly Thr Phe Tyr Gln Ile Gly Asp Ser Trp
                565                 570                 575
Glu Lys Tyr Val His Gly Val Arg Tyr Gln Cys Tyr Cys Tyr Gly Arg
            580                 585                 590
Gly Ile Gly Glu Trp His Cys Gln Pro Leu Gln Thr Tyr Pro Ser Ser
        595                 600                 605
Ser Gly Pro Val Glu Val Phe Ile Thr Glu Thr Pro Ser Gln Pro Asn
    610                 615                 620
Ser His Pro Ile Gln Trp Asn Ala Pro Gln Pro Ser His Ile Ser Lys
625                 630                 635                 640
Tyr Ile Leu Arg Trp Arg Pro Val Ser Ile Pro Arg Asn Leu Gly
                645                 650                 655
Tyr

<210> SEQ ID NO 7
<211> LENGTH: 7912
<212> TYPE: DNA
<213> ORGANISM: Homo sapiens

<400> SEQUENCE: 7
```

| | | | | | |
|---|---|---|---|---|---|
| gcccgcgccg | gctgtgctgc | acaggggag | gagagggaac | cccaggcgcg | agcgggaaga | 60 |
| ggggacctgc | agccacaact | tctctggtcc | tctgcatccc | ttctgtccct | ccacccgtcc | 120 |
| ccttccccac | cctctggccc | ccaccttctt | ggaggcgaca | accccgggaa | ggcattagaa | 180 |
| gggattttc | ccgcaggttg | cgaagggaag | caaacttggt | ggcaacttgc | ctcccgtgc | 240 |
| gggcgtctct | cccccaccgt | ctcaacatgc | ttaggggtcc | ggggcccggg | ctgctgctgc | 300 |
| tggccgtcca | gtgcctgggg | acagcggtgc | cctccacggg | agcctcgaag | agcaagaggc | 360 |
| aggctcagca | aatggttcag | ccccagtccc | cggtggctgt | cagtcaaagc | aagcccggtt | 420 |
| gttatgacaa | tggaaaacac | tatcagataa | atcaacagtg | ggagcggacc | tacctaggca | 480 |
| atgcgttggt | ttgtacttgt | tatggaggaa | gccgaggttt | taactgcgag | agtaaacctg | 540 |
| aagctgaaga | gacttgcttt | gacaagtaca | ctgggaacac | ttaccgagtg | ggtgacactt | 600 |
| atgagcgtcc | taaagactcc | atgatctggg | actgtacctg | catcggggct | gggcgaggga | 660 |
| gaataagctg | taccatcgca | aaccgctgcc | atgaagggg | tcagtcctac | aagattggtg | 720 |
| acacctggag | gagaccacat | gagactggtg | gttacatgtt | agagtgtgtg | tgtcttggta | 780 |
| atggaaaagg | agaatggacc | tgcaagccca | tagctgagaa | gtgttttgat | catgctgctg | 840 |
| ggacttccta | tgtggtcgga | gaaacgtggg | agaagcccta | ccaaggctgg | atgatggtag | 900 |
| attgtacttg | cctgggagaa | ggcagcggac | gcatcacttg | cacttctaga | aatagatgca | 960 |
| acgatcagga | cacaaggaca | tcctatagaa | ttggagacac | ctggagcaag | aaggataatc | 1020 |
| gaggaaacct | gctccagtgc | atctgcacag | gcaacggccg | aggagagtgg | aagtgtgaga | 1080 |
| ggcacacctc | tgtgcagacc | acatcgacg | gatctggccc | cttcaccgat | gttcgtgcag | 1140 |
| ctgtttacca | accgcagcct | cacccccagc | ctcctcccta | tggccactgt | gtcacagaca | 1200 |
| gtggtgtggt | ctactctgtg | gggatgcagt | ggctgaagac | acaaggaaat | aagcaaatgc | 1260 |
| tttgcacgtg | cctgggcaac | ggagtcagct | gccaagagac | agctgtaacc | cagacttacg | 1320 |
| gtggcaactc | aaatggagag | ccatgtgtct | taccattcac | ctacaatggc | aggacgttct | 1380 |
| actcctgcac | cacagaaggg | cgacaggacg | gacatctttg | gtgcagcaca | acttcgaatt | 1440 |
| atgagcagga | ccagaaatac | tctttctgca | cagaccacac | tgttttggtt | cagactcgag | 1500 |

```
gaggaaattc caatggtgcc ttgtgccact tccccttcct atacaacaac cacaattaca   1560
ctgattgcac ttctgagggc agaagagaca catgaagtg gtgtgggacc acacagaact    1620
atgatgccga ccagaagttt gggttctgcc ccatggctgc ccacgaggaa atctgcacaa   1680
ccaatgaagg ggtcatgtac cgcattggag atcagtggga taagcagcat gacatgggtc   1740
acatgatgag gtgcacgtgt gttgggaatg gtcgtgggga atggacatgc attgcctact   1800
cgcagcttcg agatcagtgc attgttgatg acatcactta caatgtgaac gacacattcc   1860
acaagcgtca tgaagagggg cacatgctga actgtacatg cttcggtcag ggtcgggggca   1920 ggtggaagtg tgatcccgtc gaccaatgcc aggattcaga gactgggacg ttttatcaaa   1980
ttggagattc atgggagaag tatgtgcatg gtgtcagata ccagtgctac tgctatggcc   2040
gtggcattgg ggagtggcat tgccaacctt tacagaccta tccaagctca agtggtcctg   2100
tcgaagtatt tatcactgag actccgagtc agcccaactc ccaccccatc cagtggaatg   2160
caccacagcc atctcacatt tccaagtaca ttctcaggtg gagacctaaa aattctgtag   2220
gccgttggaa ggaagctacc ataccaggcc acttaaactc ctacaccatc aaaggcctga   2280
agcctggtgt ggtatacgag ggccagctca tcagcatcca gcagtacggc caccaagaag   2340
tgactcgctt tgacttcacc accaccagca ccagcacacc tgtgaccagc aacaccgtga   2400
caggagagac gactcccttt tctcctcttg tggccacttc tgaatctgtg accgaaatca   2460
cagccagtag ctttgtggtc tcctgggtct cagcttccga caccgtgtcg ggattccggg   2520
tggaatatga gctgagtgag gagggagatg agccacagta cctggatctt ccaagcacag   2580
ccacttctgt gaacatccct gacctgcttc ctggccgaaa atacattgta aatgtctatc   2640
agatatctga ggatggggag cagagtttga tcctgtctac ttcacaaaca cagcgcctg   2700 atgcccctcc tgacccgact gtggaccaag ttgatgacac ctcaattgtt gttcgctgga   2760 gcagaccccca ggctcccatc acagggtaca gaatagtcta ttcgccatca gtagaaggta   2820
gcagcacaga actcaacctt cctgaaactg caaactccgt caccctcagt gacttgcaac   2880
ctggtgttca gtataacatc actatctatg ctgtggaaga aaatcaagaa gtacacctg   2940 ttgtcattca acaagaaacc actggcaccc cacgctcaga tacagtgccc tctcccaggg   3000
acctgcagtt tgtggaagtg acagacgtga aggtcaccat catgtggaca ccgcctgaga   3060
gtgcagtgac cggctaccgt gtggatgtga tccccgtcaa cctgcctggc gagcacgggc   3120
agaggctgcc catcagcagg aacacctttg cagaagtcac cgggctgtcc cctggggtca   3180
cctattactt caaagtcttt gcagtgagcc atggagggga gagcaagcct ctgactgctc   3240
aacagacaac caaactggat gctcccacta acctccagtt tgtcaatgaa actgattcta   3300
ctgtcctggt gagatggact ccacctcggg cccagataac aggataccga ctgaccgtgg   3360
gccttacccg aagaggacag cccaggcagt acaatgtggg tccctctgtc tccaagtacc   3420
cactgaggaa tctgcagcct gcatctgagt acaccgtatc cctcgtggcc ataaagggca   3480
accaagagag ccccaaagcc actggagtct ttaccacact gcagcctggg agctctattc   3540
caccttacaa caccgaggtg actgagacca ccattgtgat cacatggacg cctgctccaa   3600
gaattggttt taagctgggt gtacgaccaa gccaggagg agaggcacca cgagaagtga   3660
cttcagactc aggaagcatc gttgtgtccg gcttgactcc aggagtagaa tacgtctaca   3720
ccatccaagt cctgagagat ggacaggaaa gagatgcgcc aattgtaaac aaagtggtga   3780
caccattgtc tccaccaaca aacttgcatc tggaggcaaa ccctgacact ggagtgctca   3840
cagtctcctg ggagaggagc accaccccag acattactgg ttatagaatt accacaaccc   3900
```

```
ctacaaacgg ccagcaggga aattctttgg aagaagtggt ccatgctgat cagagctcct   3960
gcacttttga taacctgagt cccggcctgg agtacaatgt cagtgtttac actgtcaagg   4020
atgacaagga aagtgtccct atctctgata ccatcatccc agctgttcct cctcccactg   4080
acctgcgatt caccaacatt ggtccagaca ccatgcgtgt cacctgggct ccaccccat    4140 ccattgattt aaccaacttc ctggtgcgtt actcacctgt gaaaaatgag gaagatgttg   4200
cagagttgtc aatttctcct tcagacaatg cagtggtctt aacaaatctc ctgcctggta   4260
cagaatatgt agtgagtgtc tccagtgtct acgaacaaca tgagagcaca cctcttagag   4320
gaagacagaa aacaggtctt gattccccaa ctggcattga cttttctgat attactgcca   4380
actcttttac tgtgcactgg attgctcctc gagccaccat cactggctac aggatccgcc   4440
atcatcccga gcacttcagt gggagacctc gagaagatcg ggtgcccac tctcggaatt    4500 ccatcaccct caccaacctc actccaggca cagagtatgt ggtcagcatc gttgctctta   4560
atggcagaga ggaaagtccc ttattgattg ccaacaatc aacagtttct gatgttccga    4620
gggacctgga agttgttgct gcgaccccca ccagcctact gatcagctgg gatgctcctg   4680
ctgtcacagt gagatattac aggatcactt acggagagac aggaggaaat agccctgtcc   4740
aggagttcac tgtgcctggg agcaagtcta cagctaccat cagcggcctt aaacctggag   4800
ttgattatac catcactgtg tatgctgtca ctggccgtgg agacagcccc gcaagcagca   4860
agccaatttc cattaattac cgaacagaaa ttgacaaacc atcccagatg caagtgaccg   4920
atgttcagga caacagcatt agtgtcaagt ggctgccttc aagttcccct gttactggtt   4980
acagagtaac caccactccc aaaaatggac caggaccaac aaaaactaaa actgcaggtc   5040
cagatcaaac agaaatgact attgaaggct gcagcccac agtggagtat gtggttagtg    5100
tctatgctca gaatccaagc ggagagagtc agcctctggt tcagactgca gtaaccacta   5160
ttcctgcacc aactgacctg aagttcactc aggtcacacc cacaagcctg agcgcccagt   5220
ggacaccacc caatgttcag ctcactggat atcgagtgcg ggtgaccccc aaggagaaga   5280
ccggaccaat gaaagaaatc aaccttgctc ctgacagctc atccgtggtt gtatcaggac   5340
ttatggtggc caccaaatat gaagtgagtg tctatgctct taaggacact ttgacaagca   5400
gaccagctca gggagttgtc accactctgg agaatgtcag cccaccaaga agggctcgtg   5460
tgacagatgc tactgagacc accatcacca ttagctggag aaccaagact gagacgatca   5520
ctggcttcca agttgatgcc gttccagcca atggccagac tccaatccag agaaccatca   5580
agccagatgt cagaagctac accatcacag gtttacaacc aggcactgac tacaagatct   5640
acctgtacac cttgaatgac aatgctcgga gctcccctgt ggtcatcgac gcctccactg   5700
ccattgatgc accatccaac ctgcgtttcc tggccaccac acccaattcc ttgctggtat   5760
catggcagcc gccacgtgcc aggattaccg gctacatcat caagtatgag aagcctgggt   5820
ctcctcccag agaagtggtc cctcggcccc gccctggtgt cacagaggct actattactg   5880
gcctggaacc gggaaccgaa tatacaattt atgtcattgc cctgaagaat aatcagaaga   5940
gcgagcccct gattggaagg aaaaagacag acaagaagc tctctctcag acaaccatct   6000
catgggcccc attccaggac acttctgagt acatcatttc atgtcatcct gttggcactg   6060
atgaagaacc cttacagttc agggttcctg gaacttctac cagtgccact ctgacaggcc   6120
tcaccagagg tgccacctac aacatcatag tggaggcact gaaagaccag cagaggcata   6180
aggttcggga agaggttgtt accgtgggca actctgtcaa cgaaggcttg aaccaaccta   6240
```

```
cggatgactc gtgctttgac ccctacacag tttcccatta tgccgttgga gatgagtggg    6300
aacgaatgtc tgaatcaggc tttaaactgt tgtgccagtg cttaggcttt ggaagtggtc    6360
atttcagatg tgattcatct agatggtgcc atgacaatgg tgtgaactac aagattggag    6420
agaagtggga ccgtcaggga gaaaatggcc agatgatgag ctgcacatgt cttgggaacg    6480
gaaaaggaga attcaagtgt gaccctcatg aggcaacgtg ttatgatgat gggaagacat    6540
accacgtagg agaacagtgg cagaaggaat atctcggtgc catttgctcc tgcacatgct    6600
ttggaggcca gcggggctgg cgctgtgaca actgccgcag acctgggggt gaacccagtc    6660
ccgaaggcac tactgccag tcctacaacc agtattctca gagataccat cagagaacaa    6720
acactaatgt taattgccca attgagtgct tcatgccttt agatgtacag gctgacagag    6780
aagattcccg agagtaaatc atctttccaa tccagaggaa caagcatgtc tctctgccaa    6840
gatccatcta aactggagtg atgttagcag acccagctta gagttcttct ttctttctta    6900
agccctttgc tctggaggaa gttctccagc ttcagctcaa ctcacagctt ctccaagcat    6960
caccctggga gtttcctgag ggttttctca taaatgaggg ctgcacattg cctgttctgc    7020
ttcgaagtat tcaataccgc tcagtatttt aaatgaagtg attctaagat ttggtttggg    7080
atcaatagga aagcatatgc agccaaccaa gatgcaaatg ttttgaaatg atatgaccaa    7140
aattttaagt aggaaagtca cccaaacact tctgctttca cttaagtgtc tggcccgcaa    7200
tactgtagga acaagcatga tcttgttact gtgatatttt aaatatccac agtactcact    7260
ttttccaaat gatcctagta attgcctaga aatatctttc tcttacctgt tatttatcaa    7320 ttttttcccag tattttttata cggaaaaaat tgtattgaaa acacttagta tgcagttgat    7380
aagaggaatt tggtataatt atggtgggtg attatttttt atactgtatg tgccaaagct    7440
ttactactgt ggaaagacaa ctgtttttaat aaaagattta cattccacaa cttgaagttc    7500
atctatttga tataagacac cttcggggga ataattcct gtgaatattc tttttcaatt    7560
cagcaaacat ttgaaaatct atgatgtgca agtctaattg ttgatttcag tacaagattt    7620
tctaaatcag ttgctacaaa aactgattgg tttttgtcac ttcatctctt cactaatgga    7680 gatagctta cactttctgc tttaatagat ttaagtggac cccaatattt attaaaattg    7740
ctagtttacc gttcagaagt ataatagaaa taatctttag ttgctctttt ctaaccattg    7800
taattcttcc cttcttccct ccaccttttcc ttcattgaat aaacctctgt tcaaagagat    7860
tgcctgcaag ggaaataaaa atgactaaga tattaaaaaa aaaaaaaaaa aa    7912
```

<210> SEQ ID NO 8
<211> LENGTH: 2176
<212> TYPE: PRT
<213> ORGANISM: Homo sapiens

<400> SEQUENCE: 8

```
Met Leu Arg Gly Pro Gly Pro Gly Leu Leu Leu Leu Ala Val Gln Cys
  1               5                  10                  15

Leu Gly Thr Ala Val Pro Ser Thr Gly Ala Ser Lys Ser Lys Arg Gln
             20                  25                  30

Ala Gln Gln Met Val Gln Pro Gln Ser Pro Val Ala Val Ser Gln Ser
         35                  40                  45

Lys Pro Gly Cys Tyr Asp Asn Gly Lys His Tyr Gln Ile Asn Gln Gln
     50                  55                  60

Trp Glu Arg Thr Tyr Leu Gly Asn Ala Leu Val Cys Thr Cys Tyr Gly
 65                  70                  75                  80
```

-continued

```
Gly Ser Arg Gly Phe Asn Cys Glu Ser Lys Pro Glu Ala Glu Thr
                 85                  90                  95
Cys Phe Asp Lys Tyr Thr Gly Asn Thr Tyr Arg Val Gly Asp Thr Tyr
            100                 105                 110
Glu Arg Pro Lys Asp Ser Met Ile Trp Asp Cys Thr Cys Ile Gly Ala
        115                 120                 125
Gly Arg Gly Arg Ile Ser Cys Thr Ile Ala Asn Arg Cys His Glu Gly
    130                 135                 140
Gly Gln Ser Tyr Lys Ile Gly Asp Thr Trp Arg Pro His Glu Thr
145                 150                 155                 160
Gly Gly Tyr Met Leu Glu Cys Val Cys Leu Gly Asn Gly Lys Gly Glu
                165                 170                 175
Trp Thr Cys Lys Pro Ile Ala Glu Lys Cys Phe Asp His Ala Ala Gly
            180                 185                 190
Thr Ser Tyr Val Val Gly Glu Thr Trp Glu Lys Pro Tyr Gln Gly Trp
        195                 200                 205
Met Met Val Asp Cys Thr Cys Leu Gly Glu Gly Ser Gly Arg Ile Thr
    210                 215                 220
Cys Thr Ser Arg Asn Arg Cys Asn Asp Gln Asp Thr Arg Thr Ser Tyr
225                 230                 235                 240
Arg Ile Gly Asp Thr Trp Ser Lys Lys Asp Asn Arg Gly Asn Leu Leu
                245                 250                 255
Gln Cys Ile Cys Thr Gly Asn Gly Arg Gly Glu Trp Lys Cys Glu Arg
            260                 265                 270
His Thr Ser Val Gln Thr Thr Ser Ser Gly Ser Gly Pro Phe Thr Asp
        275                 280                 285
Val Arg Ala Ala Val Tyr Gln Pro Gln Pro His Pro Gln Pro Pro Pro
    290                 295                 300
Tyr Gly His Cys Val Thr Asp Ser Gly Val Val Tyr Ser Val Gly Met
305                 310                 315                 320
Gln Trp Leu Lys Thr Gln Gly Asn Lys Gln Met Leu Cys Thr Cys Leu
                325                 330                 335
Gly Asn Gly Val Ser Cys Gln Glu Thr Ala Val Thr Gln Thr Tyr Gly
            340                 345                 350
Gly Asn Ser Asn Gly Glu Pro Cys Val Leu Pro Phe Thr Tyr Asn Gly
        355                 360                 365
Arg Thr Phe Tyr Ser Cys Thr Thr Glu Gly Arg Gln Asp Gly His Leu
    370                 375                 380
Trp Cys Ser Thr Thr Ser Asn Tyr Glu Gln Asp Gln Lys Tyr Ser Phe
385                 390                 395                 400
Cys Thr Asp His Thr Val Leu Val Gln Thr Arg Gly Gly Asn Ser Asn
                405                 410                 415
Gly Ala Leu Cys His Phe Pro Phe Leu Tyr Asn Asn His Asn Tyr Thr
            420                 425                 430
Asp Cys Thr Ser Glu Gly Arg Arg Asp Asn Met Lys Trp Cys Gly Thr
        435                 440                 445
Thr Gln Asn Tyr Asp Ala Asp Gln Lys Phe Gly Phe Cys Pro Met Ala
    450                 455                 460
Ala His Glu Glu Ile Cys Thr Thr Asn Glu Gly Val Met Tyr Arg Ile
465                 470                 475                 480
Gly Asp Gln Trp Asp Lys Gln His Asp Met Gly His Met Met Arg Cys
                485                 490                 495
Thr Cys Val Gly Asn Gly Arg Gly Glu Trp Thr Cys Ile Ala Tyr Ser
```

```
                500               505                510
Gln Leu Arg Asp Gln Cys Ile Val Asp Asp Ile Thr Tyr Asn Val Asn
            515                 520                525
Asp Thr Phe His Lys Arg His Glu Glu Gly His Met Leu Asn Cys Thr
            530                 535                540
Cys Phe Gly Gln Gly Arg Gly Arg Trp Lys Cys Asp Pro Val Asp Gln
545                 550                 555                560
Cys Gln Asp Ser Glu Thr Gly Thr Phe Tyr Gln Ile Gly Asp Ser Trp
                565                 570                575
Glu Lys Tyr Val His Gly Val Arg Tyr Gln Cys Tyr Cys Tyr Gly Arg
            580                 585                590
Gly Ile Gly Glu Trp His Cys Gln Pro Leu Gln Thr Tyr Pro Ser Ser
            595                 600                605
Ser Gly Pro Val Glu Val Phe Ile Thr Glu Thr Pro Ser Gln Pro Asn
            610                 615                620
Ser His Pro Ile Gln Trp Asn Ala Pro Gln Pro Ser His Ile Ser Lys
625                 630                 635                640
Tyr Ile Leu Arg Trp Arg Pro Lys Asn Ser Val Gly Arg Trp Lys Glu
                645                 650                655
Ala Thr Ile Pro Gly His Leu Asn Ser Tyr Thr Ile Lys Gly Leu Lys
            660                 665                670
Pro Gly Val Val Tyr Glu Gly Gln Leu Ile Ser Ile Gln Gln Tyr Gly
            675                 680                685
His Gln Glu Val Thr Arg Phe Asp Phe Thr Thr Thr Ser Thr Ser Thr
            690                 695                700
Pro Val Thr Ser Asn Thr Val Thr Gly Glu Thr Thr Pro Phe Ser Pro
705                 710                 715                720
Leu Val Ala Thr Ser Glu Ser Val Thr Glu Ile Thr Ala Ser Ser Phe
                725                 730                735
Val Val Ser Trp Val Ser Ala Ser Asp Thr Val Ser Gly Phe Arg Val
                740                 745                750
Glu Tyr Glu Leu Ser Glu Glu Gly Asp Glu Pro Gln Tyr Leu Asp Leu
            755                 760                765
Pro Ser Thr Ala Thr Ser Val Asn Ile Pro Asp Leu Leu Pro Gly Arg
770                 775                 780
Lys Tyr Ile Val Asn Val Tyr Gln Ile Ser Glu Asp Gly Glu Gln Ser
785                 790                 795                800
Leu Ile Leu Ser Thr Ser Gln Thr Thr Ala Pro Asp Ala Pro Pro Asp
                805                 810                815
Pro Thr Val Asp Gln Val Asp Asp Thr Ser Ile Val Val Arg Trp Ser
            820                 825                830
Arg Pro Gln Ala Pro Ile Thr Gly Tyr Arg Ile Val Tyr Ser Pro Ser
            835                 840                845
Val Glu Gly Ser Ser Thr Glu Leu Asn Leu Pro Glu Thr Ala Asn Ser
            850                 855                860
Val Thr Leu Ser Asp Leu Gln Pro Gly Val Gln Tyr Asn Ile Thr Ile
865                 870                 875                880
Tyr Ala Val Glu Glu Asn Gln Glu Ser Thr Pro Val Val Ile Gln Gln
                885                 890                895
Glu Thr Thr Gly Thr Pro Arg Ser Asp Thr Val Pro Ser Pro Arg Asp
            900                 905                910
Leu Gln Phe Val Glu Val Thr Asp Val Lys Val Thr Ile Met Trp Thr
            915                 920                925
```

```
Pro Pro Glu Ser Ala Val Thr Gly Tyr Arg Val Asp Val Ile Pro Val
    930                 935                 940

Asn Leu Pro Gly Glu His Gly Gln Arg Leu Pro Ile Ser Arg Asn Thr
945                 950                 955                 960

Phe Ala Glu Val Thr Gly Leu Ser Pro Gly Val Thr Tyr Tyr Phe Lys
                965                 970                 975

Val Phe Ala Val Ser His Gly Arg Glu Ser Lys Pro Leu Thr Ala Gln
            980                 985                 990

Gln Thr Thr Lys Leu Asp Ala Pro Thr Asn Leu Gln Phe Val Asn Glu
        995                 1000                1005

Thr Asp Ser Thr Val Leu Val Arg Trp Thr Pro Arg Ala Gln Ile
    1010                1015                1020

Thr Gly Tyr Arg Leu Thr Val Gly Leu Thr Arg Arg Gly Gln Pro Arg
1025                1030                1035                1040

Gln Tyr Asn Val Gly Pro Ser Val Ser Lys Tyr Pro Leu Arg Asn Leu
                1045                1050                1055

Gln Pro Ala Ser Glu Tyr Thr Val Ser Leu Val Ala Ile Lys Gly Asn
            1060                1065                1070

Gln Glu Ser Pro Lys Ala Thr Gly Val Phe Thr Thr Leu Gln Pro Gly
        1075                1080                1085

Ser Ser Ile Pro Pro Tyr Asn Thr Glu Val Thr Glu Thr Thr Ile Val
    1090                1095                1100

Ile Thr Trp Thr Pro Ala Pro Arg Ile Gly Phe Lys Leu Gly Val Arg
1105                1110                1115                1120

Pro Ser Gln Gly Gly Glu Ala Pro Arg Glu Val Thr Ser Asp Ser Gly
                1125                1130                1135

Ser Ile Val Val Ser Gly Leu Thr Pro Gly Val Glu Tyr Val Tyr Thr
            1140                1145                1150

Ile Gln Val Leu Arg Asp Gly Gln Glu Arg Asp Ala Pro Ile Val Asn
        1155                1160                1165

Lys Val Val Thr Pro Leu Ser Pro Pro Thr Asn Leu His Leu Glu Ala
    1170                1175                1180

Asn Pro Asp Thr Gly Val Leu Thr Val Ser Trp Glu Arg Ser Thr Thr
1185                1190                1195                1200

Pro Asp Ile Thr Gly Tyr Arg Ile Thr Thr Thr Pro Thr Asn Gly Gln
                1205                1210                1215

Gln Gly Asn Ser Leu Glu Glu Val Val His Ala Asp Gln Ser Ser Cys
            1220                1225                1230

Thr Phe Asp Asn Leu Ser Pro Gly Leu Glu Tyr Asn Val Ser Val Tyr
        1235                1240                1245

Thr Val Lys Asp Asp Lys Glu Ser Val Pro Ile Ser Asp Thr Ile Ile
    1250                1255                1260

Pro Ala Val Pro Pro Pro Thr Asp Leu Arg Phe Thr Asn Ile Gly Pro
1265                1270                1275                1280

Asp Thr Met Arg Val Thr Trp Ala Pro Pro Ser Ile Asp Leu Thr
                1285                1290                1295

Asn Phe Leu Val Arg Tyr Ser Pro Val Lys Asn Glu Glu Asp Val Ala
            1300                1305                1310

Glu Leu Ser Ile Ser Pro Ser Asp Asn Ala Val Val Leu Thr Asn Leu
        1315                1320                1325

Leu Pro Gly Thr Glu Tyr Val Val Ser Val Ser Val Tyr Glu Gln
    1330                1335                1340
```

```
His Glu Ser Thr Pro Leu Arg Gly Arg Gln Lys Thr Gly Leu Asp Ser
1345                1350                1355                1360

Pro Thr Gly Ile Asp Phe Ser Asp Ile Thr Ala Asn Ser Phe Thr Val
            1365                1370                1375

His Trp Ile Ala Pro Arg Ala Thr Ile Thr Gly Tyr Arg Ile Arg His
        1380                1385                1390

His Pro Glu His Phe Ser Gly Arg Pro Arg Glu Asp Arg Val Pro His
    1395                1400                1405

Ser Arg Asn Ser Ile Thr Leu Thr Asn Leu Thr Pro Gly Thr Glu Tyr
1410                1415                1420

Val Val Ser Ile Val Ala Leu Asn Gly Arg Glu Glu Ser Pro Leu Leu
1425                1430                1435                1440

Ile Gly Gln Gln Ser Thr Val Ser Asp Val Pro Arg Asp Leu Glu Val
                1445                1450                1455

Val Ala Ala Thr Pro Thr Ser Leu Leu Ile Ser Trp Asp Ala Pro Ala
            1460                1465                1470

Val Thr Val Arg Tyr Tyr Arg Ile Thr Tyr Gly Glu Thr Gly Gly Asn
        1475                1480                1485

Ser Pro Val Gln Glu Phe Thr Val Pro Gly Ser Lys Ser Thr Ala Thr
    1490                1495                1500

Ile Ser Gly Leu Lys Pro Gly Val Asp Tyr Thr Ile Thr Val Tyr Ala
1505                1510                1515                1520

Val Thr Gly Arg Gly Asp Ser Pro Ala Ser Ser Lys Pro Ile Ser Ile
                1525                1530                1535

Asn Tyr Arg Thr Glu Ile Asp Lys Pro Ser Gln Met Gln Val Thr Asp
            1540                1545                1550

Val Gln Asp Asn Ser Ile Ser Val Lys Trp Leu Pro Ser Ser Ser Pro
        1555                1560                1565

Val Thr Gly Tyr Arg Val Thr Thr Thr Pro Lys Asn Gly Pro Gly Pro
    1570                1575                1580

Thr Lys Thr Lys Thr Ala Gly Pro Asp Gln Thr Glu Met Thr Ile Glu
1585                1590                1595                1600

Gly Leu Gln Pro Thr Val Glu Tyr Val Val Ser Val Tyr Ala Gln Asn
                1605                1610                1615

Pro Ser Gly Glu Ser Gln Pro Leu Val Gln Thr Ala Val Thr Thr Ile
            1620                1625                1630

Pro Ala Pro Thr Asp Leu Lys Phe Thr Gln Val Thr Pro Thr Ser Leu
        1635                1640                1645

Ser Ala Gln Trp Thr Pro Pro Asn Val Gln Leu Thr Gly Tyr Arg Val
    1650                1655                1660

Arg Val Thr Pro Lys Glu Lys Thr Gly Pro Met Lys Glu Ile Asn Leu
1665                1670                1675                1680

Ala Pro Asp Ser Ser Ser Val Val Val Ser Gly Leu Met Val Ala Thr
                1685                1690                1695

Lys Tyr Glu Val Ser Val Tyr Ala Leu Lys Asp Thr Leu Thr Ser Arg
            1700                1705                1710

Pro Ala Gln Gly Val Val Thr Thr Leu Glu Asn Val Ser Pro Pro Arg
        1715                1720                1725

Arg Ala Arg Val Thr Asp Ala Thr Glu Thr Thr Ile Thr Ile Ser Trp
    1730                1735                1740

Arg Thr Lys Thr Glu Thr Ile Thr Gly Phe Gln Val Asp Ala Val Pro
1745                1750                1755                1760

Ala Asn Gly Gln Thr Pro Ile Gln Arg Thr Ile Lys Pro Asp Val Arg
```

```
                    1765           1770           1775
Ser Tyr Thr Ile Thr Gly Leu Gln Pro Gly Thr Asp Tyr Lys Ile Tyr
            1780             1785            1790

Leu Tyr Thr Leu Asn Asp Asn Ala Arg Ser Ser Pro Val Val Ile Asp
        1795            1800             1805

Ala Ser Thr Ala Ile Asp Ala Pro Ser Asn Leu Arg Phe Leu Ala Thr
    1810             1815            1820

Thr Pro Asn Ser Leu Leu Val Ser Trp Gln Pro Arg Ala Arg Ile
1825            1830            1835            1840

Thr Gly Tyr Ile Ile Lys Tyr Glu Lys Pro Gly Ser Pro Arg Glu
            1845            1850            1855

Val Val Pro Arg Pro Arg Pro Gly Val Thr Glu Ala Thr Ile Thr Gly
            1860            1865            1870

Leu Glu Pro Gly Thr Glu Tyr Thr Ile Tyr Val Ile Ala Leu Lys Asn
            1875            1880            1885

Asn Gln Lys Ser Glu Pro Leu Ile Gly Arg Lys Lys Thr Gly Gln Glu
        1890            1895            1900

Ala Leu Ser Gln Thr Thr Ile Ser Trp Ala Pro Phe Gln Asp Thr Ser
1905            1910            1915            1920

Glu Tyr Ile Ile Ser Cys His Pro Val Gly Thr Asp Glu Glu Pro Leu
            1925            1930            1935

Gln Phe Arg Val Pro Gly Thr Ser Thr Ser Ala Thr Leu Thr Gly Leu
            1940            1945            1950

Thr Arg Gly Ala Thr Tyr Asn Ile Ile Val Glu Ala Leu Lys Asp Gln
            1955            1960            1965

Gln Arg His Lys Val Arg Glu Glu Val Val Thr Val Gly Asn Ser Val
        1970            1975            1980

Asn Glu Gly Leu Asn Gln Pro Thr Asp Asp Ser Cys Phe Asp Pro Tyr
1985            1990            1995            2000

Thr Val Ser His Tyr Ala Val Gly Asp Glu Trp Glu Arg Met Ser Glu
            2005            2010            2015

Ser Gly Phe Lys Leu Leu Cys Gln Cys Leu Gly Phe Gly Ser Gly His
            2020            2025            2030

Phe Arg Cys Asp Ser Ser Arg Trp Cys His Asp Asn Gly Val Asn Tyr
        2035            2040            2045

Lys Ile Gly Glu Lys Trp Asp Arg Gln Gly Glu Asn Gly Gln Met Met
        2050            2055            2060

Ser Cys Thr Cys Leu Gly Asn Gly Lys Gly Glu Phe Lys Cys Asp Pro
2065            2070            2075            2080

His Glu Ala Thr Cys Tyr Asp Asp Gly Lys Thr Tyr His Val Gly Glu
            2085            2090            2095

Gln Trp Gln Lys Glu Tyr Leu Gly Ala Ile Cys Ser Cys Thr Cys Phe
            2100            2105            2110

Gly Gly Gln Arg Gly Trp Arg Cys Asp Asn Cys Arg Arg Pro Gly Gly
            2115            2120            2125

Glu Pro Ser Pro Glu Gly Thr Thr Gly Gln Ser Tyr Asn Gln Tyr Ser
    2130            2135            2140

Gln Arg Tyr His Gln Arg Thr Asn Thr Asn Val Asn Cys Pro Ile Glu
2145            2150            2155            2160

Cys Phe Met Pro Leu Asp Val Gln Ala Asp Arg Glu Asp Ser Arg Glu
            2165            2170            2175

<210> SEQ ID NO 9
```

<211> LENGTH: 8647
<212> TYPE: DNA
<213> ORGANISM: Homo sapiens

<400> SEQUENCE: 9

```
gcccgcgccg gctgtgctgc acaggggag gagagggaac cccaggcgcg agcgggaaga      60
ggggacctgc agccacaact tctctggtcc tctgcatccc ttctgtccct ccacccgtcc     120
ccttccccac cctctggccc ccaccttctt ggaggcgaca accccggga ggcattagaa      180
gggattttttc ccgcaggttg cgaagggaag caaacttggt ggcaacttgc ctcccggtgc    240
gggcgtctct cccccaccgt ctcaacatgc ttaggggtcc ggggcccggg ctgctgctgc     300
tggccgtcca gtgcctgggg acagcggtgc cctccacggg agcctcgaag agcaagaggc     360
aggctcagca aatggttcag ccccagtccc cggtggctgt cagtcaaagc aagcccggtt     420
gttatgacaa tggaaaacac tatcagataa atcaacagtg ggagcggacc tacctaggca     480
atgcgttggt ttgtacttgt tatggaggaa gccgaggttt aactgcgag agtaaacctg      540
aagctgaaga gacttgcttt gacaagtaca ctgggaacac ttaccgagtg ggtgacactt     600
atgagcgtcc taaagactcc atgatctggg actgtacctg catcgggct gggcgaggga     660
gaataagctg taccatcgca aaccgctgcc atgaaggggg tcagtcctac aagattggtg     720
acacctggag gagaccacat gagactggtg gttacatgtt agagtgtgtg tgtcttggta    780
atggaaaagg agaatggacc tgcaagccca tagctgagaa gtgttttgat catgctgctg     840
ggacttccta tgtggtcgga gaaacgtggg agaagcccta ccaaggctgg atgatggtag     900
attgtacttg cctgggagaa ggcagcggac gcatcacttg cacttctaga aatagatgca    960
acgatcagga cacaaggaca tcctatagaa ttggagacac ctggagcaag aaggataatc    1020
gaggaaacct gctccagtgc atctgcacag gcaacggccg aggagagtgg aagtgtgaga    1080
ggcacacctc tgtgcagacc acatcgagcg gatctggccc cttcaccgat gttcgtgcag    1140
ctgtttacca accgcagcct cacccccagc ctcctcccta tggccactgt gtcacagaca    1200
gtggtgtggt ctactctgtg gggatgcagt ggctgaagac acaaggaaat aagcaaatgc    1260
tttgcacgtg cctgggcaac ggagtcagct gccaagagac agctgtaacc cagacttacg    1320
gtggcaactc aaatggagag ccatgtgtct taccattcac ctacaatggc aggacgttct    1380
actcctgcac cacagaaggg cgacaggacg gacatctttg gtgcagcaca acttcgaatt    1440
atgagcagga ccagaaatac tcttttctgca cagaccacac tgttttggtt cagactcgag    1500
gaggaaattc caatggtgcc ttgtgccact tccccttcct atacaacaac cacaattaca    1560
ctgattgcac ttctgagggc agaagagaca acatgaagtg gtgtgggacc acacagaact    1620
atgatgccga ccagaagttt ggttctgcc ccatggctgc ccacgaggaa atctgcacaa    1680
ccaatgaagg ggtcatgtac cgcattggag atcagtggga taagcagcat gacatgggtc    1740
acatgatgag gtgcacgtgt gttgggaatg tcgtgggga atggacatgc attgcctact    1800
cgcagcttcg agatcagtgc attgttgatg acatcactta caatgtgaac gacacattcc    1860
acaagcgtca tgaagagggg cacatgctga actgtacatg cttcggtcag ggtcggggca    1920
ggtggaagtg tgatcccgtc gaccaatgcc aggattcaga gactgggacg ttttatcaaa    1980
ttggagattc atgggagaag tatgtgcatg gtgtcagata ccagtgctac tgctatggcc    2040
gtggcattgg ggagtggcat tgccaaccct tacagaccta tccaagctca agtggtcctg    2100
tcgaagtatt tatcactgag actccgagtc agcccaactc ccaccccatc agtggaatg    2160
caccacagcc atctctcacatt tccaagtaca ttctcaggtg gagacctaaa aattctgtag    2220
```

```
gccgttggaa ggaagctacc ataccaggcc acttaaactc ctacaccatc aaaggcctga    2280
agcctggtgt ggtatacgag ggccagctca tcagcatcca gcagtacggc caccaagaag    2340
tgactcgctt tgacttcacc accaccagca ccagcacacc tgtgaccagc aacaccgtga    2400
caggagagac gactcccttt tctcctcttg tggccacttc tgaatctgtg accgaaatca    2460
cagccagtag ctttgtggtc tcctgggtct cagcttccga caccgtgtcg ggattccggg    2520
tggaatatga gctgagtgag gagggagatg agccacagta cctggatctt ccaagcacag    2580
ccacttctgt gaacatccct gacctgcttc ctggccgaaa atacattgta aatgtctatc    2640
agatatctga ggatggggag cagagtttga tcctgtctac ttcacaaaca acagcgcctg    2700
atgcccctcc tgacccgact gtggaccaag ttgatgacac ctcaattgtt gttcgctgga    2760
gcagacccca ggctcccatc acagggtaca gaatagtcta ttcgccatca gtagaaggta    2820
gcagcacaga actcaacctt cctgaaactg caaactccgt caccctcagt gacttgcaac    2880
ctggtgttca gtataacatc actatctatg ctgtggaaga aaatcaagaa agtacacctg    2940
ttgtcattca acaagaaacc actggcaccc cacgctcaga tacagtgccc tctcccaggg    3000
acctgcagtt tgtggaagtg acagacgtga aggtcaccat catgtggaca ccgcctgaga    3060
gtgcagtgac cggctaccgt gtggatgtga tccccgtcaa cctgcctggc gagcacgggc    3120
agaggctgcc catcagcagg aacacctttg cagaagtcac cggcctgtcc cctgggtca    3180 cctattactt caaagtcttt gcagtgagcc atggagggga gagcaagcct ctgactgctc    3240
aacagacaac caaactggat gctcccacta acctccagtt tgtcaatgaa actgattcta    3300
ctgtcctggt gagatggact ccacctcggg cccagataac aggataccga ctgaccgtgg    3360
gccttacccg aagaggacag cccaggcagt acaatgtggg tccctctgtc tccaagtacc    3420
cactgaggaa tctgcagcct gcatctgagt acaccgtatc cctcgtggcc ataaagggca    3480
accaagagag ccccaaagcc actggagtct ttaccacact gcagcctggg agctctattc    3540
caccttacaa caccgaggtg actgagacca ccattgtgat cacatggacg cctgctccaa    3600
gaattggttt taagctgggt gtacgaccaa gccaggagg agaggcacca cgagaagtga    3660
cttcagactc aggaagcatc gttgtgtccg gcttgactcc aggagtagaa tacgtctaca    3720
ccatccaagt cctgagagat ggacaggaaa gagatgcgcc aattgtaaac aaagtggtga    3780
caccattgtc tccaccaaca aacttgcatc tggaggcaaa ccctgacact ggagtgctca    3840
cagtctcctg ggagaggagc accaccccag acattactgg ttatagaatt accacaaccc    3900
ctacaaacgg ccagcaggga aattctttgg aagaagtggt ccatgctgat cagagctcct    3960
gcacttttga taacctgagt cccggcctgg agtacaatgt cagtgtttac actgtcaagg    4020
atgacaagga aagtgtccct atctctgata ccatcatccc agaggtgccc caactcactg    4080
acctaagctt tgttgatata accgattcaa gcatcggcct gaggtggacc ccgctaaact    4140
cttccaccat tattgggtac cgcatcacag tagttgcggc aggagaaggt atccctattt    4200
ttgaagattt tgtggactcc tcagtaggat actacacagt cacagggctg agccgggca    4260 ttgactatga tatcagcgtt atcactctca ttaatggcgg cgagagtgcc cctactacac    4320
tgacacaaca aacggctgtt cctcctccca ctgacctgcg attcaccaac attggtccag    4380
acaccatgcg tgtcacctgg gctccacccc catccattga tttaaccaac ttcctggtgc    4440
gttactcacc tgtgaaaaat gaggaagatg ttgcagagtt gtcaatttct ccttcagaca    4500
atgcagtggt cttaacaaat ctcctgcctg gtacagaata tgtagtgagt gtctccagtg    4560
```

```
tctacgaaca acatgagagc acacctctta gaggaagaca gaaaacaggt cttgattccc    4620
caactggcat tgactttct gatattactg ccaactcttt tactgtgcac tggattgctc    4680
ctcgagccac catcactggc tacaggatcc gccatcatcc cgagcacttc agtgggagac    4740
ctcgagaaga tcgggtgccc cactctcgga attccatcac cctcaccaac ctcactccag    4800
gcacagagta tgtggtcagc atcgttgctc ttaatggcag agaggaaagt cccttattga    4860
ttggccaaca atcaacagtt tctgatgttc cgagggacct ggaagttgtt gctgcgaccc    4920
ccaccagcct actgatcagc tgggatgctc ctgctgtcac agtgagatat tacaggatca    4980
cttacgagga gacaggagga aatagccctg tccaggagtt cactgtgcct gggagcaagt    5040
ctacagctac catcagcggc cttaaacctg agttgatta taccatcact gtgtatgctg    5100
tcactggccg tggagacagc cccgcaagca gcaagccaat ttccattaat taccgaacag    5160
aaattgacaa accatcccag atgcaagtga ccgatgttca ggacaacagc attagtgtca    5220
agtggctgcc ttcaagttcc cctgttactg gttacagagt aaccaccact cccaaaaatg    5280
gaccaggacc aacaaaaact aaaactgcag gtccagatca aacagaaatg actattgaag    5340
gcttgcagcc cacagtggag tatgtggtta gtgtctatgc tcagaatcca agcggagaga    5400
gtcagcctct ggttcagact gcagtaacca acattgatcg ccctaaagga ctggcattca    5460
ctgatgtgga tgtcgattcc atcaaaattg cttgggaaag cccacagggg caagtttcca    5520
ggtacagggt gacctactcg agccctgagg atggaatcca tgagctattc cctgcacctg    5580
atggtgaaga agacactgca gagctgcaag gcctcagacc gggttctgag tacacagtca    5640
gtgtggttgc cttgcacgat gatatggaga ccagcccct gattggaacc cagtccacag    5700
ctattcctgc accaactgac ctgaagttca tcaggtcac acccacaagc ctgagcgccc    5760
agtggacacc acccaatgtt cagctcactg gatatcgagt gcgggtgacc cccaaggaga    5820
agaccggacc aatgaaagaa atcaaccttg ctcctgacag ctcatccgtg gttgtatcag    5880
gacttatggt ggccaccaaa tatgaagtga gtgtctatgc tcttaaggac actttgacaa    5940
gcagaccagc tcagggagtt gtcaccactc tggagaatgt cagcccacca agaagggctc    6000
gtgtgacaga tgctactgag accaccatca ccattagctg gagaaccaag actgagacga    6060
tcactggctt ccaagttgat gccgttccag ccaatggcca gactccaatc cagagaacca    6120
tcaagccaga tgtcagaagc tacaccatca caggtttaca accaggcact gactacaaga    6180
tctacctgta caccttgaat gacaatgctc ggagctcccc tgtggtcatc gacgcctcca    6240
ctgccattga tgcaccatcc aacctgcgtt tcctggccac cacacccaat tccttgctgg    6300
tatcatggca gccgccacgt gccaggatta ccggctacat catcaagtat gagaagcctg    6360
ggtctcctcc cagagaagtg gtccctcggc ccgccctgg tgtcacagag ctactatta    6420 ctggcctgga accgggaacc gaatatacaa tttatgtcat tgccctgaag aataatcaga    6480
agagcgagcc cctgattgga aggaaaaaga cagttcaaaa gacccctttc gtcacccacc    6540
ctgggtatga cactggaaat ggtattcagc ttcctggcac ttctggtcag caacccagtg    6600
ttgggcaaca aatgatcttt gaggaacatg ttttaggcg gaccacaccg cccacaacgg    6660 ccaccccat aaggcatagg ccaagaccat acccgccgaa tgtaggacaa gaagctctct    6720
ctcagacaac catctcatgg gccccattcc aggacacttc tgagtacatc atttcatgtc    6780
atcctgttgg cactgatgaa gaaccccttac agttcagggt tcctggaact tctaccagtg    6840
ccactctgac aggcctcacc agaggtgcca cctacaacat catagtggag gcactgaaag    6900
accagcagag gcataaggtt cgggaagagg ttgttaccgt gggcaactct gtcaacgaag    6960
```

```
gcttgaacca acctacggat gactcgtgct ttgaccccta cacagtttcc cattatgccg   7020
ttggagatga gtgggaacga atgtctgaat caggctttaa actgttgtgc cagtgcttag   7080
gctttggaag tggtcatttc agatgtgatt catctagatg gtgccatgac aatggtgtga   7140
actacaagat tggagagaag tgggaccgtc agggagaaaa tggccagatg atgagctgca   7200
catgtcttgg gaacggaaaa ggagaattca agtgtgaccc tcatgaggca acgtgttatg   7260
atgatgggaa gacataccac gtaggagaac agtggcagaa ggaatatctc ggtgccattt   7320
gctcctgcac atgctttgga ggccagcggg gctggcgctg tgacaactgc cgcagacctg   7380
ggggtgaacc cagtcccgaa ggcactactg gccagtccta caaccagtat tctcagagat   7440
accatcagag aacaaacact aatgttaatt gcccaattga gtgcttcatg cctttagatg   7500
tacaggctga cagagaagat tcccgagagt aaatcatctt tccaatccag aggaacaagc   7560
atgtctctct gccaagatcc atctaaactg gagtgatgtt agcagaccca gcttagagtt   7620
cttctttctt tcttaagccc tttgctctgg aggaagttct ccagcttcag ctcaactcac   7680
agcttctcca agcatcaccc tgggagtttc ctgagggttt tctcataaat gagggctgca   7740
cattgcctgt tctgcttcga agtattcaat accgctcagt atttttaaatg aagtgattct   7800 aagatttggt ttgggatcaa taggaaagca tatgcagcca accaagatgc aaatgttttg   7860
aaatgatatg accaaaattt taagtaggaa agtcacccaa acacttctgc tttcacttaa   7920
gtgtctggcc cgcaatactg taggaacaag catgatcttg ttactgtgat attttaaata   7980
tccacagtac tcacttttttc caaatgatcc tagtaattgc ctagaaatat ctttctctta   8040
cctgttattt atcaattttt cccagtatttt ttatacggaa aaaattgtat tgaaaacact   8100
tagtatgcag ttgataagag gaatttggta taatttatggt gggtgattat ttttttatact   8160 gtatgtgcca aagctttact actgtggaaa gacaactgtt ttaataaaag atttacattc   8220
cacaacttga agttcatcta tttgatataa gacaccttcg ggggaaataa ttcctgtgaa   8280
tattcttttt caattcagca aacatttgaa aatctatgat gtgcaagtct aattgttgat   8340
ttcagtacaa gattttctaa atcagttgct acaaaaactg attggttttt gtcacttcat   8400
ctcttcacta atggagatag ctttacactt tctgctttaa tagatttaag tggacccaa   8460 tatttattaa aattgctagt ttaccgttca gaagtataat agaaataatc tttagttgct   8520
cttttctaac cattgtaatt cttccttctt tccctccacc tttccttcat tgaataaacc   8580
tctgttcaaa gagattgcct gcaagggaaa taaaaatgac taagatatta aaaaaaaaa   8640 aaaaaaa                                                             8647
```

<210> SEQ ID NO 10
<211> LENGTH: 2421
<212> TYPE: PRT
<213> ORGANISM: Homo sapiens

<400> SEQUENCE: 10

Met Leu Arg Gly Pro Gly Pro Gly Leu Leu Leu Leu Ala Val Gln Cys
 1               5                  10                  15

Leu Gly Thr Ala Val Pro Ser Thr Gly Ala Ser Lys Ser Lys Arg Gln
            20                  25                  30

Ala Gln Gln Met Val Gln Pro Gln Ser Pro Val Ala Val Ser Gln Ser
        35                  40                  45

Lys Pro Gly Cys Tyr Asp Asn Gly Lys His Tyr Gln Ile Asn Gln Gln
    50                  55                  60

```
Trp Glu Arg Thr Tyr Leu Gly Asn Ala Leu Val Cys Thr Cys Tyr Gly
 65                  70                  75                  80

Gly Ser Arg Gly Phe Asn Cys Glu Ser Lys Pro Glu Ala Glu Glu Thr
             85                  90                  95

Cys Phe Asp Lys Tyr Thr Gly Asn Thr Tyr Arg Val Gly Asp Thr Tyr
            100                 105                 110

Glu Arg Pro Lys Asp Ser Met Ile Trp Asp Cys Thr Cys Ile Gly Ala
        115                 120                 125

Gly Arg Gly Arg Ile Ser Cys Thr Ile Ala Asn Arg Cys His Glu Gly
    130                 135                 140

Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
                165                 170                 175

Trp Thr Cys Lys Pro Ile Ala Glu Lys Cys Phe Asp His Ala Ala Gly
            180                 185                 190

Thr Ser Tyr Val Val Gly Glu Thr Trp Glu Lys Pro Tyr Gln Gly Trp
        195                 200                 205

Met Met Val Asp Cys Thr Cys Leu Gly Glu Gly Ser Gly Arg Ile Thr
    210                 215                 220

Cys Thr Ser Arg Asn Arg Cys Asn Asp Gln Asp Thr Arg Thr Ser Tyr
225                 230                 235                 240

Arg Ile Gly Asp Thr Trp Ser Lys Lys Asp Asn Arg Gly Asn Leu Leu
                245                 250                 255

Gln Cys Ile Cys Thr Gly Asn Gly Arg Gly Glu Trp Lys Cys Glu Arg
            260                 265                 270

His Thr Ser Val Gln Thr Thr Ser Ser Gly Ser Gly Pro Phe Thr Asp
        275                 280                 285

Val Arg Ala Ala Val Tyr Gln Pro Gln Pro His Pro Gln Pro Pro Pro
    290                 295                 300

Tyr Gly His Cys Val Thr Asp Ser Gly Val Val Tyr Ser Val Gly Met
305                 310                 315                 320

Gln Trp Leu Lys Thr Gln Gly Asn Lys Gln Met Leu Cys Thr Cys Leu
                325                 330                 335

Gly Asn Gly Val Ser Cys Gln Glu Thr Ala Val Thr Gln Thr Tyr Gly
            340                 345                 350

Gly Asn Ser Asn Gly Glu Pro Cys Val Leu Pro Phe Thr Tyr Asn Gly
        355                 360                 365

Arg Thr Phe Tyr Ser Cys Thr Thr Glu Gly Arg Gln Asp Gly His Leu
    370                 375                 380

Trp Cys Ser Thr Thr Ser Asn Tyr Glu Gln Asp Gln Lys Tyr Ser Phe
385                 390                 395                 400

Cys Thr Asp His Thr Val Leu Val Gln Thr Arg Gly Gly Asn Ser Asn
                405                 410                 415

Gly Ala Leu Cys His Phe Pro Phe Leu Tyr Asn Asn His Asn Tyr Thr
            420                 425                 430

Asp Cys Thr Ser Glu Gly Arg Arg Asp Asn Met Lys Trp Cys Gly Thr
        435                 440                 445

Thr Gln Asn Tyr Asp Ala Asp Gln Lys Phe Gly Phe Cys Pro Met Ala
    450                 455                 460

Ala His Glu Glu Ile Cys Thr Thr Asn Glu Gly Val Met Tyr Arg Ile
465                 470                 475                 480

Gly Asp Gln Trp Asp Lys Gln His Asp Met Gly His Met Met Arg Cys
```

-continued

```
                485                 490                 495
Thr Cys Val Gly Asn Gly Arg Gly Glu Trp Thr Cys Ile Ala Tyr Ser
                500                 505                 510
Gln Leu Arg Asp Gln Cys Ile Val Asp Asp Ile Thr Tyr Asn Val Asn
                515                 520                 525
Asp Thr Phe His Lys Arg His Glu Glu Gly His Met Leu Asn Cys Thr
            530                 535                 540
Cys Phe Gly Gln Gly Arg Gly Arg Trp Lys Cys Asp Pro Val Asp Gln
545                 550                 555                 560
Cys Gln Asp Ser Glu Thr Gly Thr Phe Tyr Gln Ile Gly Asp Ser Trp
                565                 570                 575
Glu Lys Tyr Val His Gly Val Arg Tyr Gln Cys Tyr Cys Tyr Gly Arg
                580                 585                 590
Gly Ile Gly Glu Trp His Cys Gln Pro Leu Gln Thr Tyr Pro Ser Ser
                595                 600                 605
Ser Gly Pro Val Glu Val Phe Ile Thr Glu Thr Pro Ser Gln Pro Asn
            610                 615                 620
Ser His Pro Ile Gln Trp Asn Ala Pro Gln Pro Ser His Ile Ser Lys
625                 630                 635                 640
Tyr Ile Leu Arg Trp Arg Pro Lys Asn Ser Val Gly Arg Trp Lys Glu
                645                 650                 655
Ala Thr Ile Pro Gly His Leu Asn Ser Tyr Thr Ile Lys Gly Leu Lys
                660                 665                 670
Pro Gly Val Val Tyr Glu Gly Gln Leu Ile Ser Ile Gln Gln Tyr Gly
                675                 680                 685
His Gln Glu Val Thr Arg Phe Asp Phe Thr Thr Thr Ser Thr Ser Thr
            690                 695                 700
Pro Val Thr Ser Asn Thr Val Thr Gly Glu Thr Thr Pro Phe Ser Pro
705                 710                 715                 720
Leu Val Ala Thr Ser Glu Ser Val Thr Glu Ile Thr Ala Ser Ser Phe
                725                 730                 735
Val Val Ser Trp Val Ser Ala Ser Asp Thr Val Ser Gly Phe Arg Val
                740                 745                 750
Glu Tyr Glu Leu Ser Glu Glu Gly Asp Glu Pro Gln Tyr Leu Asp Leu
                755                 760                 765
Pro Ser Thr Ala Thr Ser Val Asn Ile Pro Asp Leu Leu Pro Gly Arg
            770                 775                 780
Lys Tyr Ile Val Asn Val Tyr Gln Ile Ser Glu Asp Gly Glu Gln Ser
785                 790                 795                 800
Leu Ile Leu Ser Thr Ser Gln Thr Thr Ala Pro Asp Ala Pro Pro Asp
                805                 810                 815
Pro Thr Val Asp Gln Val Asp Asp Thr Ser Ile Val Val Arg Trp Ser
                820                 825                 830
Arg Pro Gln Ala Pro Ile Thr Gly Tyr Arg Ile Val Tyr Ser Pro Ser
                835                 840                 845
Val Glu Gly Ser Ser Thr Glu Leu Asn Leu Pro Glu Thr Ala Asn Ser
                850                 855                 860
Val Thr Leu Ser Asp Leu Gln Pro Gly Val Gln Tyr Asn Ile Thr Ile
865                 870                 875                 880
Tyr Ala Val Glu Glu Asn Gln Glu Ser Thr Pro Val Val Ile Gln Gln
                885                 890                 895
Glu Thr Thr Gly Thr Pro Arg Ser Asp Thr Val Pro Ser Pro Arg Asp
                900                 905                 910
```

-continued

```
Leu Gln Phe Val Glu Val Thr Asp Val Lys Val Thr Ile Met Trp Thr
            915                 920                 925
Pro Pro Glu Ser Ala Val Thr Gly Tyr Arg Val Asp Val Ile Pro Val
        930                 935                 940
Asn Leu Pro Gly Glu His Gly Gln Arg Leu Pro Ile Ser Arg Asn Thr
945                 950                 955                 960
Phe Ala Glu Val Thr Gly Leu Ser Pro Gly Val Thr Tyr Tyr Phe Lys
                965                 970                 975
Val Phe Ala Val Ser His Gly Arg Glu Ser Lys Pro Leu Thr Ala Gln
            980                 985                 990
Gln Thr Thr Lys Leu Asp Ala Pro Thr Asn Leu Gln Phe Val Asn Glu
        995                 1000                1005
Thr Asp Ser Thr Val Leu Val Arg Trp Thr Pro Pro Arg Ala Gln Ile
    1010                1015                1020
Thr Gly Tyr Arg Leu Thr Val Gly Leu Thr Arg Arg Gly Gln Pro Arg
1025                1030                1035                1040
Gln Tyr Asn Val Gly Pro Ser Val Ser Lys Tyr Pro Leu Arg Asn Leu
                1045                1050                1055
Gln Pro Ala Ser Glu Tyr Thr Val Ser Leu Val Ala Ile Lys Gly Asn
            1060                1065                1070
Gln Glu Ser Pro Lys Ala Thr Gly Val Phe Thr Thr Leu Gln Pro Gly
        1075                1080                1085
Ser Ser Ile Pro Pro Tyr Asn Thr Glu Val Thr Glu Thr Thr Ile Val
    1090                1095                1100
Ile Thr Trp Thr Pro Ala Pro Arg Ile Gly Phe Lys Leu Gly Val Arg
1105                1110                1115                1120
Pro Ser Gln Gly Gly Glu Ala Pro Arg Glu Val Thr Ser Asp Ser Gly
                1125                1130                1135
Ser Ile Val Val Ser Gly Leu Thr Pro Gly Val Glu Tyr Val Tyr Thr
            1140                1145                1150
Ile Gln Val Leu Arg Asp Gly Gln Glu Arg Asp Ala Pro Ile Val Asn
        1155                1160                1165
Lys Val Val Thr Pro Leu Ser Pro Pro Thr Asn Leu His Leu Glu Ala
    1170                1175                1180
Asn Pro Asp Thr Gly Val Leu Thr Val Ser Trp Glu Arg Ser Thr Thr
1185                1190                1195                1200
Pro Asp Ile Thr Gly Tyr Arg Ile Thr Thr Thr Pro Thr Asn Gly Gln
                1205                1210                1215
Gln Gly Asn Ser Leu Glu Glu Val Val His Ala Asp Gln Ser Ser Cys
            1220                1225                1230
Thr Phe Asp Asn Leu Ser Pro Gly Leu Glu Tyr Asn Val Ser Val Tyr
        1235                1240                1245
Thr Val Lys Asp Asp Lys Glu Ser Val Pro Ile Ser Asp Thr Ile Ile
    1250                1255                1260
Pro Glu Val Pro Gln Leu Thr Asp Leu Ser Phe Val Asp Ile Thr Asp
1265                1270                1275                1280
Ser Ser Ile Gly Leu Arg Trp Thr Pro Leu Asn Ser Ser Thr Ile Ile
                1285                1290                1295
Gly Tyr Arg Ile Thr Val Val Ala Ala Gly Glu Gly Ile Pro Ile Phe
            1300                1305                1310
Glu Asp Phe Val Asp Ser Ser Val Gly Tyr Tyr Thr Val Thr Gly Leu
        1315                1320                1325
```

-continued

Glu Pro Gly Ile Asp Tyr Asp Ile Ser Val Ile Thr Leu Ile Asn Gly
1330                1335                1340

Gly Glu Ser Ala Pro Thr Thr Leu Thr Gln Gln Thr Ala Val Pro Pro
1345                1350                1355                1360

Pro Thr Asp Leu Arg Phe Thr Asn Ile Gly Pro Asp Thr Met Arg Val
                1365                1370                1375

Thr Trp Ala Pro Pro Ser Ile Asp Leu Thr Asn Phe Leu Val Arg
        1380                1385                1390

Tyr Ser Pro Val Lys Asn Glu Glu Asp Val Ala Glu Leu Ser Ile Ser
            1395                1400                1405

Pro Ser Asp Asn Ala Val Val Leu Thr Asn Leu Leu Pro Gly Thr Glu
        1410                1415                1420

Tyr Val Val Ser Val Ser Ser Val Tyr Glu Gln His Glu Ser Thr Pro
1425                1430                1435                1440

Leu Arg Gly Arg Gln Lys Thr Gly Leu Asp Ser Pro Thr Gly Ile Asp
                1445                1450                1455

Phe Ser Asp Ile Thr Ala Asn Ser Phe Thr Val His Trp Ile Ala Pro
        1460                1465                1470

Arg Ala Thr Ile Thr Gly Tyr Arg Ile Arg His His Pro Glu His Phe
        1475                1480                1485

Ser Gly Arg Pro Arg Glu Asp Arg Val Pro His Ser Arg Asn Ser Ile
    1490                1495                1500

Thr Leu Thr Asn Leu Thr Pro Gly Thr Glu Tyr Val Val Ser Ile Val
1505                1510                1515                1520

Ala Leu Asn Gly Arg Glu Glu Ser Pro Leu Leu Ile Gly Gln Gln Ser
        1525                1530                1535

Thr Val Ser Asp Val Pro Arg Asp Leu Glu Val Val Ala Ala Thr Pro
        1540                1545                1550

Thr Ser Leu Leu Ile Ser Trp Asp Ala Pro Ala Val Thr Val Arg Tyr
        1555                1560                1565

Tyr Arg Ile Thr Tyr Gly Glu Thr Gly Gly Asn Ser Pro Val Gln Glu
    1570                1575                1580

Phe Thr Val Pro Gly Ser Lys Ser Thr Ala Thr Ile Ser Gly Leu Lys
1585                1590                1595                1600

Pro Gly Val Asp Tyr Thr Ile Thr Val Tyr Ala Val Thr Gly Arg Gly
            1605                1610                1615

Asp Ser Pro Ala Ser Ser Lys Pro Ile Ser Ile Asn Tyr Arg Thr Glu
        1620                1625                1630

Ile Asp Lys Pro Ser Gln Met Gln Val Thr Asp Val Gln Asp Asn Ser
        1635                1640                1645

Ile Ser Val Lys Trp Leu Pro Ser Ser Ser Pro Val Thr Gly Tyr Arg
    1650                1655                1660

Val Thr Thr Thr Pro Lys Asn Gly Pro Gly Pro Thr Lys Thr Lys Thr
1665                1670                1675                1680

Ala Gly Pro Asp Gln Thr Glu Met Thr Ile Glu Gly Leu Gln Pro Thr
            1685                1690                1695

Val Glu Tyr Val Val Ser Val Tyr Ala Gln Asn Pro Ser Gly Glu Ser
            1700                1705                1710

Gln Pro Leu Val Gln Thr Ala Val Thr Asn Ile Asp Arg Pro Lys Gly
        1715                1720                1725

Leu Ala Phe Thr Asp Val Asp Val Asp Ser Ile Lys Ile Ala Trp Glu
    1730                1735                1740

Ser Pro Gln Gly Gln Val Ser Arg Tyr Arg Val Thr Tyr Ser Ser Pro

```
                1745                1750                1755                1760
        Glu Asp Gly Ile His Glu Leu Phe Pro Ala Pro Asp Gly Glu Asp
                    1765                1770                1775

Thr Ala Glu Leu Gln Gly Leu Arg Pro Gly Ser Glu Tyr Thr Val Ser
                    1780                1785                1790

Val Val Ala Leu His Asp Asp Met Glu Ser Gln Pro Leu Ile Gly Thr
                    1795                1800                1805

Gln Ser Thr Ala Ile Pro Ala Pro Thr Asp Leu Lys Phe Thr Gln Val
                    1810                1815                1820

Thr Pro Thr Ser Leu Ser Ala Gln Trp Thr Pro Pro Asn Val Gln Leu
        1825                1830                1835                1840

Thr Gly Tyr Arg Val Arg Val Thr Pro Lys Glu Lys Thr Gly Pro Met
                    1845                1850                1855

Lys Glu Ile Asn Leu Ala Pro Asp Ser Ser Val Val Val Ser Gly
                    1860                1865                1870

Leu Met Val Ala Thr Lys Tyr Glu Val Ser Val Tyr Ala Leu Lys Asp
                    1875                1880                1885

Thr Leu Thr Ser Arg Pro Ala Gln Gly Val Val Thr Leu Glu Asn
                    1890                1895                1900

Val Ser Pro Pro Arg Arg Ala Arg Val Thr Asp Ala Thr Glu Thr Thr
        1905                1910                1915                1920

Ile Thr Ile Ser Trp Arg Thr Lys Thr Glu Thr Ile Thr Gly Phe Gln
                    1925                1930                1935

Val Asp Ala Val Pro Ala Asn Gly Gln Thr Pro Ile Gln Arg Thr Ile
                    1940                1945                1950

Lys Pro Asp Val Arg Ser Tyr Thr Ile Thr Gly Leu Gln Pro Gly Thr
                    1955                1960                1965

Asp Tyr Lys Ile Tyr Leu Tyr Thr Leu Asn Asp Asn Ala Arg Ser Ser
                    1970                1975                1980

Pro Val Val Ile Asp Ala Ser Thr Ala Ile Asp Ala Pro Ser Asn Leu
        1985                1990                1995                2000

Arg Phe Leu Ala Thr Thr Pro Asn Ser Leu Leu Val Ser Trp Gln Pro
                    2005                2010                2015

Pro Arg Ala Arg Ile Thr Gly Tyr Ile Ile Lys Tyr Glu Lys Pro Gly
                    2020                2025                2030

Ser Pro Pro Arg Glu Val Val Pro Arg Pro Arg Pro Gly Val Thr Glu
                    2035                2040                2045

Ala Thr Ile Thr Gly Leu Glu Pro Gly Thr Glu Tyr Thr Ile Tyr Val
                    2050                2055                2060

Ile Ala Leu Lys Asn Asn Gln Lys Ser Glu Pro Leu Ile Gly Arg Lys
        2065                2070                2075                2080

Lys Thr Val Gln Lys Thr Pro Phe Val Thr His Pro Gly Tyr Asp Thr
                    2085                2090                2095

Gly Asn Gly Ile Gln Leu Pro Gly Thr Ser Gly Gln Gln Pro Ser Val
                    2100                2105                2110

Gly Gln Gln Met Ile Phe Glu Glu His Gly Phe Arg Arg Thr Thr Pro
                    2115                2120                2125

Pro Thr Thr Ala Thr Pro Ile Arg His Arg Pro Arg Pro Tyr Pro Pro
                    2130                2135                2140

Asn Val Gly Gln Glu Ala Leu Ser Gln Thr Thr Ile Ser Trp Ala Pro
        2145                2150                2155                2160

Phe Gln Asp Thr Ser Glu Tyr Ile Ile Ser Cys His Pro Val Gly Thr
                    2165                2170                2175
```

Asp Glu Glu Pro Leu Gln Phe Arg Val Pro Gly Thr Thr Ser Ala
            2180                2185                2190

Thr Leu Thr Gly Leu Thr Arg Gly Ala Thr Tyr Asn Ile Ile Val Glu
        2195                2200                2205

Ala Leu Lys Asp Gln Gln Arg His Lys Val Arg Glu Glu Val Val Thr
    2210                2215                2220

Val Gly Asn Ser Val Asn Glu Gly Leu Asn Gln Pro Thr Asp Asp Ser
2225                2230                2235                2240

Cys Phe Asp Pro Tyr Thr Val Ser His Tyr Ala Val Gly Asp Glu Trp
            2245                2250                2255

Glu Arg Met Ser Glu Ser Gly Phe Lys Leu Leu Cys Gln Cys Leu Gly
        2260                2265                2270

Phe Gly Ser Gly His Phe Arg Cys Asp Ser Ser Arg Trp Cys His Asp
        2275                2280                2285

Asn Gly Val Asn Tyr Lys Ile Gly Glu Lys Trp Asp Arg Gln Gly Glu
        2290                2295                2300

Asn Gly Gln Met Met Ser Cys Thr Cys Leu Gly Asn Gly Lys Gly Glu
2305                2310                2315                2320

Phe Lys Cys Asp Pro His Glu Ala Thr Cys Tyr Asp Asp Gly Lys Thr
            2325                2330                2335

Tyr His Val Gly Glu Gln Trp Gln Lys Glu Tyr Leu Gly Ala Ile Cys
        2340                2345                2350

Ser Cys Thr Cys Phe Gly Gly Gln Arg Gly Trp Arg Cys Asp Asn Cys
        2355                2360                2365

Arg Arg Pro Gly Gly Glu Pro Ser Pro Glu Gly Thr Thr Gly Gln Ser
    2370                2375                2380

Tyr Asn Gln Tyr Ser Gln Arg Tyr His Gln Arg Thr Asn Thr Asn Val
2385                2390                2395                2400

Asn Cys Pro Ile Glu Cys Phe Met Pro Leu Asp Val Gln Ala Asp Arg
            2405                2410                2415

Glu Asp Ser Arg Glu
            2420

<210> SEQ ID NO 11
<211> LENGTH: 8272
<212> TYPE: DNA
<213> ORGANISM: Homo sapiens

<400> SEQUENCE: 11
gcccgcgccg gctgtgctgc acaggggag gagagggaac cccaggcgcg agcgggaaga        60
ggggacctgc agccacaact tctctggtcc tctgcatccc ttctgtccct ccacccgtcc      120
ccttccccac cctctggccc ccaccttctt ggaggcgaca accccggga ggcattagaa       180 gggattttc ccgcaggttg cgaagggaag caaacttggt ggcaacttgc ctcccggtgc      240
gggcgtctct cccccaccgt ctcaacatgc ttagggtcc ggggcccggg ctgctgctgc      300
tggccgtcca gtgcctgggg acagcggtgc cctccacggg agcctcgaag agcaagaggc      360
aggctcagca aatggttcag ccccagtccc cggtggctgt cagtcaaagc aagcccggtt      420
gttatgacaa tggaaaacac tatcagataa atcaacagtg ggagcggacc tacctaggca      480
atgcgttggt ttgtacttgt tatggaggaa gccgaggttt taactgcgag agtaaacctg      540
aagctgaaga gacttgcttt gacaagtaca ctgggaacac ttaccgagtg ggtgacactt      600
atgagcgtcc taaagactcc atgatctggg actgtacctg catcggggct gggcgaggga      660

```
gaataagctg taccatcgca aaccgctgcc atgaaggggg tcagtcctac aagattggtg    720
acacctggag gagaccacat gagactggtg gttacatgtt agagtgtgtg tgtcttggta    780
atggaaaagg agaatggacc tgcaagccca tagctgagaa gtgttttgat catgctgctg    840
ggacttccta tgtggtcgga gaaacgtggg agaagcccta ccaaggctgg atgatggtag    900
attgtacttg cctgggagaa ggcagcggac gcatcacttg cacttctaga aatagatgca    960
acgatcagga cacaaggaca tcctatagaa ttggagacac ctggagcaag aaggataatc   1020
gaggaaacct gctccagtgc atctgcacag gcaacggccg aggagagtgg aagtgtgaga   1080
ggcacacctc tgtgcagacc acatcgagcg gatctggccc cttcaccgat gttcgtgcag   1140
ctgtttacca accgcagcct cacccccagc ctcctcccta tggccactgt gtcacagaca   1200
gtggtgtggt ctactctgtg gggatgcagt ggctgaagac acaaggaaat aagcaaatgc   1260
tttgcacgtg cctgggcaac ggagtcagct gccaagagac agctgtaacc cagacttacg   1320
gtggcaactc aaatggagag ccatgtgtct taccattcac ctacaatggc aggacgttct   1380
actcctgcac cacagaaggg cgacaggacg gacatctttg gtgcagcaca acttcgaatt   1440
atgagcagga ccagaaatac tcttttctgca cagaccacac tgttttggtt cagactcgag   1500
gaggaaattc caatggtgcc ttgtgccact tccccttcct atacaacaac cacaattaca   1560
ctgattgcac ttctgagggc agaagagaca acatgaagtg gtgtgggacc acacagaact   1620
atgatgccga ccagaagttt gggttctgcc ccatggctgc ccacgaggaa atctgcacaa   1680
ccaatgaagg ggtcatgtac cgcattgagg atcagtggga taagcagcat gacatgggtc   1740
acatgatgag gtgcacgtgt gttgggaatg gtcgtgggga atggacatgc attgcctact   1800
cgcagcttcg agatcagtgc attgttgatg acatcactta caatgtgaac gacacattcc   1860
acaagcgtca tgaagagggg cacatgctga actgtacatg cttcggtcag ggtcggggca   1920
ggtggaagtg tgatcccgtc gaccaatgcc aggattcaga gactgggacg ttttatcaaa   1980
ttggagattc atgggagaag tatgtgcatg gtgtcagata ccagtgctac tgctatggcc   2040
gtggcattgg ggagtggcat tgccaacctt tacagaccta tccaagctca gtggtcctg    2100 tcgaagtatt tatcactgag actccgagtc agcccaactc ccacccccatc cagtggaatg   2160 caccacagcc atctcacatt tccaagtaca ttctcaggtg gagacctaaa aattctgtag   2220
gccgttggaa ggaagctacc ataccaggcc acttaaactc ctacaccatc aaaggcctga   2280
agcctggtgt ggtatacgag ggccagctca tcagcatcca gcagtacggc caccaagaag   2340
tgactcgctt tgacttcacc accaccagca ccagcacacc tgtgaccagc aacaccgtga   2400
caggagagac gactcccttt tctcctcttg tggccacttc tgaatctgtg accgaaatca   2460
cagccagtag ctttgtggtc cctgggtct cagcttccga caccgtgtcg ggattccggg    2520
tggaatatga gctgagtgag gagggagatg agccacagta cctggatctt ccaagcacag   2580
ccacttctgt gaacatccct gacctgcttc ctggccgaaa atacattgta aatgtctatc   2640
agatatctga ggatgggag cagagtttga tcctgtctac ttcacaaaca acagcgcctg    2700
atgcccctcc tgacccgact gtggaccaag ttgatgacac ctcaattgtt gttcgctgga   2760
gcagacccca ggctcccatc acagggtaca gaatagtcta ttcgccatca gtagaaggta   2820
gcagcacaga actcaacctt cctgaaactg caaactccgt caccctcagt gacttgcaac   2880
ctggtgttca gtataacatc actatctatg ctgtggaaga aaatcaagaa agtacacctg   2940
ttgtcattca acaagaaacc actggcaccc cacgctcaga tacagtgccc tctcccaggg   3000
acctgcagtt tgtggaagtg acagacgtga aggtcaccat catgtggaca ccgcctgaga   3060
```

```
gtgcagtgac cggctaccgt gtggatgtga tccccgtcaa cctgcctggc gagcacgggc    3120
agaggctgcc catcagcagg aacacctttg cagaagtcac cgggctgtcc cctggggtca    3180
cctattactt caaagtcttt gcagtgagcc atgggaggga gagcaagcct ctgactgctc    3240
aacagacaac caaactggat gctcccacta acctccagtt tgtcaatgaa actgattcta    3300
ctgtcctggt gagatggact ccacctcggg cccagataac aggataccga ctgaccgtgg    3360
gccttacccg aagaggacag cccaggcagt acaatgtggg tccctctgtc tccaagtacc    3420
cactgaggaa tctgcagcct gcatctgagt acaccgtatc cctcgtggcc ataaagggca    3480
accaagagag ccccaaagcc actggagtct ttaccacact gcagcctggg agctctattc    3540
caccttacaa caccgaggtg actgagacca ccattgtgat cacatggacg cctgctccaa    3600
gaattggttt taagctgggt gtacgaccaa gccaggagg agaggcacca cgagaagtga    3660
cttcagactc aggaagcatc gttgtgtccg gcttgactcc aggagtagaa tacgtctaca    3720
ccatccaagt cctgagagat ggacaggaaa gagatgcgcc aattgtaaac aaagtggtga    3780
caccattgtc tccaccaaca aacttgcatc tggaggcaaa ccctgacact ggagtgctca    3840
cagtctcctg ggagaggagc accaccccag acattactgg ttatagaatt accacaaccc    3900
ctacaaacgg ccagcaggga aattctttgg aagaagtggt ccatgctgat cagagctcct    3960
gcacttttga taacctgagt cccggcctgg agtacaatgt cagtgtttac actgtcaagg    4020
atgacaagga aagtgtccct atctctgata ccatcatccc agctgttcct cctcccactg    4080
acctgcgatt caccaacatt ggtccagaca ccatgcgtgt cacctgggct ccaccccat    4140 ccattgattt aaccaacttc ctggtgcgtt actcacctgt gaaaaatgag gaagatgttg    4200
cagagttgtc aatttctcct tcagacaatg cagtggtctt aacaaatctc ctgcctggta    4260
cagaatatgt agtgagtgtc tccagtgtct acgaacaaca tgagagcaca cctcttagag    4320
gaagacagaa aacaggtctt gattccccaa ctggcattga cttttctgat attactgcca    4380
actcttttac tgtgcactgg attgctcctc gagccaccat cactggctac aggatccgcc    4440
atcatcccga gcacttcagt gggagacctc gagaagatcg ggtgccccac tctcggaatt    4500
ccatcaccct caccaacctc actccaggca cagagtatgt ggtcagcatc gttgctctta    4560
atggcagaga ggaaagtccc ttattgattg gccaacaatc aacagtttct gatgttccga    4620
gggacctgga agttgttgct gcgaccccca ccagcctact gatcagctgg gatgctcctg    4680
ctgtcacagt gagatattac aggatcactt acggagagac aggaggaaat agccctgtcc    4740
aggagttcac tgtgcctggg agcaagtcta cagctaccat cagcggcctt aaacctggag    4800
ttgattatac catcactgtg tatgctgtca ctggccgtgg agacagcccc gcaagcagca    4860
agccaatttc cattaattac cgaacagaaa ttgacaaacc atcccagatg caagtgaccg    4920
atgttcagga caacagcatt agtgtcaagt ggctgccttc aagttcccct gttactggtt    4980
acagagtaac caccactccc aaaaatggac caggaccaac aaaaactaaa actgcaggtc    5040
cagatcaaac agaaatgact attgaaggct gcagcccac agtggagtat gtggttagtg    5100
tctatgctca gaatccaagc ggagagagtc agcctctggt tcagactgca gtaaccacta    5160
ttcctgcacc aactgacctg aagttcactc aggtcacacc cacaagcctg agcgcccagt    5220
ggacaccacc caatgttcag ctcactggat atcgagtgcg ggtgacccc aaggagaaga    5280 ccggaccaat gaaagaaatc aaccttgctc ctgacagctc atccgtggtt gtatcaggac    5340
ttatggtggc caccaaatat gaagtgagtg tctatgctct taaggacact ttgacaagca    5400
```

```
gaccagctca gggagttgtc accactctgg agaatgtcag cccaccaaga agggctcgtg    5460
tgacagatgc tactgagacc accatcacca ttagctggag aaccaagact gagacgatca    5520
ctggcttcca agttgatgcc gttccagcca atggccagac tccaatccag agaaccatca    5580
agccagatgt cagaagctac accatcacag gtttacaacc aggcactgac tacaagatct    5640
acctgtacac cttgaatgac aatgctcgga gctcccctgt ggtcatcgac gcctccactg    5700
ccattgatgc accatccaac ctgcgtttcc tggccaccac acccaattcc ttgctggtat    5760
catggcagcc gccacgtgcc aggattaccg gctacatcat caagtatgag aagcctgggt    5820
ctcctcccag agaagtggtc cctcggcccc gccctggtgt cacagaggct actattactg    5880
gcctggaacc gggaaccgaa tatacaattt atgtcattgc cctgaagaat aatcagaaga    5940
gcgagcccct gattggaagg aaaaagacag acgagcttcc ccaactggta acccttccac    6000
accccaatct tcatggacca gagatcttgg atgttccttc cacagttcaa aagacccctt    6060
tcgtcaccca ccctgggtat gacactggaa atggtattca gcttcctggc acttctggtc    6120
agcaacccag tgttgggcaa caaatgatct ttgaggaaca tggttttagg cggaccacac    6180
cgcccacaac ggccaccccc ataaggcata ggccaagacc atacccgccg aatgtaggtg    6240
aggaaatcca aattggtcac atccccaggg aagatgtaga ctatcacctg tacccacacg    6300
gtccgggact caatccaaat gcctctacag acaagaagc tctctctcag acaaccatct    6360
catgggcccc attccaggac acttctgagt acatcatttc atgtcatcct gttggcactg    6420
atgaagaacc cttacagttc agggttcctg aacttctac cagtgccact ctgacaggcc    6480
tcaccagagg tgccacctac aacatcatag tggaggcact gaaagaccag cagaggcata    6540
aggttcggga agaggttgtt accgtgggca actctgtcaa cgaaggcttg aaccaaccta    6600
cggatgactc gtgctttgac ccctacacag tttcccatta tgccgttgga gatgagtggg    6660
aacgaatgtc tgaatcaggc tttaaactgt tgtgccagtg cttaggcttt ggaagtggtc    6720
atttcagatg tgattcatct agatggtgcc atgacaatgg tgtgaactac aagattggag    6780
agaagtggga ccgtcaggga gaaaatggcc agatgatgag ctgcacatgt cttgggaacg    6840
gaaaaggaga attcaagtgt gaccctcatg aggcaacgtg ttatgatgat gggaagacat    6900
accacgtagg agaacagtgg cagaaggaat atctcggtgc catttgctcc tgcacatgct    6960
ttggaggcca gcggggctgg cgctgtgaca actgccgcag acctgggggt gaacccagtc    7020
ccgaaggcac tactggccag tcctacaacc agtattctca gagataccat cagagaacaa    7080
acactaatgt taattgccca attgagtgct tcatgccttt agatgtacag gctgacagag    7140
aagattcccg agagtaaatc atctttccaa tccagaggaa caagcatgtc tctctgccaa    7200
gatccatcta aactggagtg atgttagcag acccagctta gagttcttct ttctttctta    7260 agcccttgc tctggaggaa gttctccagc ttcagctcaa ctcacagctt ctccaagcat    7320
caccctggga gtttcctgag ggttttctca taaatgaggg ctgcacattg cctgttctgc    7380
ttcgaagtat tcaataccgc tcagtatttt aaatgaagtg attctaagat ttggtttggg    7440
atcaatagga aagcatatgc agccaaccaa gatgcaaatg ttttgaaatg atatgaccaa    7500
aattttaagt aggaaagtca cccaaacact tctgctttca cttaagtgtc tggcccgcaa    7560
tactgtagga acaagcatga tcttgttact gtgatatttt aaatatccac agtactcact    7620
ttttccaaat gatcctagta attgcctaga aatatctttc tcttacctgt tatttatcaa    7680
tttttcccag tatttttata cggaaaaaat tgtattgaaa acacttagta tgcagttgat    7740
aagaggaatt tggtataatt atggtgggtg attattttt atactgtatg tgccaaagct    7800
```

-continued

```
ttactactgt ggaaagacaa ctgttttaat aaaagattta cattccacaa cttgaagttc    7860
atctatttga tataagacac cttcggggga ataattcct gtgaatattc tttttcaatt    7920
cagcaaacat ttgaaaatct atgatgtgca agtctaattg ttgatttcag tacaagattt    7980
tctaaatcag ttgctacaaa aactgattgg tttttgtcac ttcatctctt cactaatgga    8040
gatagcttta cactttctgc tttaatagat ttaagtggac cccaatattt attaaaattg    8100
ctagtttacc gttcagaagt ataatagaaa taatctttag ttgctctttt ctaaccattg    8160
taattcttcc cttcttccct ccacctttcc ttcattgaat aaacctctgt tcaaagagat    8220
tgcctgcaag ggaaataaaa atgactaaga tattaaaaaa aaaaaaaaaa aa            8272
```

<210> SEQ ID NO 12
<211> LENGTH: 2296
<212> TYPE: PRT
<213> ORGANISM: Homo sapiens

<400> SEQUENCE: 12

```
Met Leu Arg Gly Pro Gly Pro Gly Leu Leu Leu Leu Ala Val Gln Cys
  1               5                  10                  15

Leu Gly Thr Ala Val Pro Ser Thr Gly Ala Ser Lys Ser Lys Arg Gln
             20                  25                  30

Ala Gln Gln Met Val Gln Pro Gln Ser Pro Val Ala Val Ser Gln Ser
         35                  40                  45

Lys Pro Gly Cys Tyr Asp Asn Gly Lys His Tyr Gln Ile Asn Gln Gln
     50                  55                  60

Trp Glu Arg Thr Tyr Leu Gly Asn Ala Leu Val Cys Thr Cys Tyr Gly
 65                  70                  75                  80

Gly Ser Arg Gly Phe Asn Cys Glu Ser Lys Pro Glu Ala Glu Glu Thr
                 85                  90                  95

Cys Phe Asp Lys Tyr Thr Gly Asn Thr Tyr Arg Val Gly Asp Thr Tyr
            100                 105                 110

Glu Arg Pro Lys Asp Ser Met Ile Trp Asp Cys Thr Cys Ile Gly Ala
        115                 120                 125

Gly Arg Gly Arg Ile Ser Cys Thr Ile Ala Asn Arg Cys His Glu Gly
    130                 135                 140

Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
                165                 170                 175

Trp Thr Cys Lys Pro Ile Ala Glu Lys Cys Phe Asp His Ala Ala Gly
            180                 185                 190

Thr Ser Tyr Val Val Gly Glu Thr Trp Glu Lys Pro Tyr Gln Gly Trp
        195                 200                 205

Met Met Val Asp Cys Thr Cys Leu Gly Glu Gly Ser Gly Arg Ile Thr
    210                 215                 220

Cys Thr Ser Arg Asn Arg Cys Asn Asp Gln Asp Thr Arg Thr Ser Tyr
225                 230                 235                 240

Arg Ile Gly Asp Thr Trp Ser Lys Lys Asp Asn Arg Gly Asn Leu Leu
                245                 250                 255

Gln Cys Ile Cys Thr Gly Asn Gly Arg Gly Glu Trp Lys Cys Glu Arg
            260                 265                 270

His Thr Ser Val Gln Thr Thr Ser Ser Gly Ser Gly Pro Phe Thr Asp
        275                 280                 285
```

```
Val Arg Ala Ala Val Tyr Gln Pro Gln Pro His Pro Gln Pro Pro Pro
    290                 295                 300

Tyr Gly His Cys Val Thr Asp Ser Gly Val Val Tyr Ser Val Gly Met
305                 310                 315                 320

Gln Trp Leu Lys Thr Gln Gly Asn Lys Gln Met Leu Cys Thr Cys Leu
                325                 330                 335

Gly Asn Gly Val Ser Cys Gln Glu Thr Ala Val Thr Gln Thr Tyr Gly
            340                 345                 350

Gly Asn Ser Asn Gly Glu Pro Cys Val Leu Pro Phe Thr Tyr Asn Gly
        355                 360                 365

Arg Thr Phe Tyr Ser Cys Thr Thr Glu Gly Arg Gln Asp Gly His Leu
370                 375                 380

Trp Cys Ser Thr Thr Ser Asn Tyr Glu Gln Asp Gln Lys Tyr Ser Phe
385                 390                 395                 400

Cys Thr Asp His Thr Val Leu Val Gln Thr Arg Gly Gly Asn Ser Asn
                405                 410                 415

Gly Ala Leu Cys His Phe Pro Phe Leu Tyr Asn Asn His Asn Tyr Thr
            420                 425                 430

Asp Cys Thr Ser Glu Gly Arg Arg Asp Asn Met Lys Trp Cys Gly Thr
        435                 440                 445

Thr Gln Asn Tyr Asp Ala Asp Gln Lys Phe Gly Phe Cys Pro Met Ala
    450                 455                 460

Ala His Glu Glu Ile Cys Thr Thr Asn Glu Gly Val Met Tyr Arg Ile
465                 470                 475                 480

Gly Asp Gln Trp Asp Lys Gln His Asp Met Gly His Met Met Arg Cys
                485                 490                 495

Thr Cys Val Gly Asn Gly Arg Gly Glu Trp Thr Cys Ile Ala Tyr Ser
            500                 505                 510

Gln Leu Arg Asp Gln Cys Ile Val Asp Asp Ile Thr Tyr Asn Val Asn
        515                 520                 525

Asp Thr Phe His Lys Arg His Glu Glu Gly His Met Leu Asn Cys Thr
    530                 535                 540

Cys Phe Gly Gln Gly Arg Gly Arg Trp Lys Cys Asp Pro Val Asp Gln
545                 550                 555                 560

Cys Gln Asp Ser Glu Thr Gly Thr Phe Tyr Gln Ile Gly Asp Ser Trp
                565                 570                 575

Glu Lys Tyr Val His Gly Val Arg Tyr Gln Cys Tyr Cys Tyr Gly Arg
            580                 585                 590

Gly Ile Gly Glu Trp His Cys Gln Pro Leu Gln Thr Tyr Pro Ser Ser
        595                 600                 605

Ser Gly Pro Val Glu Val Phe Ile Thr Glu Thr Pro Ser Gln Pro Asn
    610                 615                 620

Ser His Pro Ile Gln Trp Asn Ala Pro Gln Pro Ser His Ile Ser Lys
625                 630                 635                 640

Tyr Ile Leu Arg Trp Arg Pro Lys Asn Ser Val Gly Arg Trp Lys Glu
                645                 650                 655

Ala Thr Ile Pro Gly His Leu Asn Ser Tyr Thr Ile Lys Gly Leu Lys
            660                 665                 670

Pro Gly Val Val Tyr Glu Gly Gln Leu Ile Ser Ile Gln Gln Tyr Gly
        675                 680                 685

His Gln Glu Val Thr Arg Phe Asp Phe Thr Thr Ser Thr Ser Thr
    690                 695                 700

Pro Val Thr Ser Asn Thr Val Thr Gly Glu Thr Thr Pro Phe Ser Pro
```

```
            705                 710                 715                 720
Leu Val Ala Thr Ser Glu Ser Val Thr Glu Ile Thr Ala Ser Ser Phe
                725                 730                 735

Val Val Ser Trp Val Ser Ala Ser Asp Thr Val Ser Gly Phe Arg Val
                740                 745                 750

Glu Tyr Glu Leu Ser Glu Glu Gly Asp Glu Pro Gln Tyr Leu Asp Leu
                755                 760                 765

Pro Ser Thr Ala Thr Ser Val Asn Ile Pro Asp Leu Leu Pro Gly Arg
                770                 775                 780

Lys Tyr Ile Val Asn Val Tyr Gln Ile Ser Glu Asp Gly Glu Gln Ser
785                 790                 795                 800

Leu Ile Leu Ser Thr Ser Gln Thr Thr Ala Pro Asp Ala Pro Pro Asp
                805                 810                 815

Pro Thr Val Asp Gln Val Asp Asp Thr Ser Ile Val Val Arg Trp Ser
                820                 825                 830

Arg Pro Gln Ala Pro Ile Thr Gly Tyr Arg Ile Val Tyr Ser Pro Ser
                835                 840                 845

Val Glu Gly Ser Ser Thr Glu Leu Asn Leu Pro Glu Thr Ala Asn Ser
                850                 855                 860

Val Thr Leu Ser Asp Leu Gln Pro Gly Val Gln Tyr Asn Ile Thr Ile
865                 870                 875                 880

Tyr Ala Val Glu Glu Asn Gln Glu Ser Thr Pro Val Val Ile Gln Gln
                885                 890                 895

Glu Thr Thr Gly Thr Pro Arg Ser Asp Thr Val Pro Ser Pro Arg Asp
                900                 905                 910

Leu Gln Phe Val Glu Val Thr Asp Val Lys Val Thr Ile Met Trp Thr
                915                 920                 925

Pro Pro Glu Ser Ala Val Thr Gly Tyr Arg Val Asp Val Ile Pro Val
                930                 935                 940

Asn Leu Pro Gly Glu His Gly Gln Arg Leu Pro Ile Ser Arg Asn Thr
945                 950                 955                 960

Phe Ala Glu Val Thr Gly Leu Ser Pro Gly Val Thr Tyr Tyr Phe Lys
                965                 970                 975

Val Phe Ala Val Ser His Gly Arg Glu Ser Lys Pro Leu Thr Ala Gln
                980                 985                 990

Gln Thr Thr Lys Leu Asp Ala Pro Thr Asn Leu Gln Phe Val Asn Glu
                995                 1000                1005

Thr Asp Ser Thr Val Leu Val Arg Trp Thr Pro Pro Arg Ala Gln Ile
                1010                1015                1020

Thr Gly Tyr Arg Leu Thr Val Gly Leu Thr Arg Arg Gly Gln Pro Arg
1025                1030                1035                1040

Gln Tyr Asn Val Gly Pro Ser Val Ser Lys Tyr Pro Leu Arg Asn Leu
                1045                1050                1055

Gln Pro Ala Ser Glu Tyr Thr Val Ser Leu Val Ala Ile Lys Gly Asn
                1060                1065                1070

Gln Glu Ser Pro Lys Ala Thr Gly Val Phe Thr Thr Leu Gln Pro Gly
                1075                1080                1085

Ser Ser Ile Pro Pro Tyr Asn Thr Glu Val Thr Glu Thr Thr Ile Val
                1090                1095                1100

Ile Thr Trp Thr Pro Ala Pro Arg Ile Gly Phe Lys Leu Gly Val Arg
1105                1110                1115                1120

Pro Ser Gln Gly Gly Glu Ala Pro Arg Glu Val Thr Ser Asp Ser Gly
                1125                1130                1135
```

```
Ser Ile Val Val Ser Gly Leu Thr Pro Gly Val Glu Tyr Val Tyr Thr
            1140                1145                1150

Ile Gln Val Leu Arg Asp Gly Gln Glu Arg Asp Ala Pro Ile Val Asn
            1155                1160                1165

Lys Val Val Thr Pro Leu Ser Pro Pro Thr Asn Leu His Leu Glu Ala
            1170                1175                1180

Asn Pro Asp Thr Gly Val Leu Thr Val Ser Trp Glu Arg Ser Thr Thr
1185                1190                1195                1200

Pro Asp Ile Thr Gly Tyr Arg Ile Thr Thr Thr Pro Thr Asn Gly Gln
            1205                1210                1215

Gln Gly Asn Ser Leu Glu Glu Val Val His Ala Asp Gln Ser Ser Cys
            1220                1225                1230

Thr Phe Asp Asn Leu Ser Pro Gly Leu Glu Tyr Asn Val Ser Val Tyr
            1235                1240                1245

Thr Val Lys Asp Asp Lys Glu Ser Val Pro Ile Ser Asp Thr Ile Ile
            1250                1255                1260

Pro Ala Val Pro Pro Thr Asp Leu Arg Phe Thr Asn Ile Gly Pro
1265                1270                1275                1280

Asp Thr Met Arg Val Thr Trp Ala Pro Pro Ser Ile Asp Leu Thr
            1285                1290                1295

Asn Phe Leu Val Arg Tyr Ser Pro Val Lys Asn Glu Glu Asp Val Ala
            1300                1305                1310

Glu Leu Ser Ile Ser Pro Ser Asp Asn Ala Val Val Leu Thr Asn Leu
            1315                1320                1325

Leu Pro Gly Thr Glu Tyr Val Val Ser Val Ser Ser Val Tyr Glu Gln
            1330                1335                1340

His Glu Ser Thr Pro Leu Arg Gly Arg Gln Lys Thr Gly Leu Asp Ser
1345                1350                1355                1360

Pro Thr Gly Ile Asp Phe Ser Asp Ile Thr Ala Asn Ser Phe Thr Val
            1365                1370                1375

His Trp Ile Ala Pro Arg Ala Thr Ile Thr Gly Tyr Arg Ile Arg His
            1380                1385                1390

His Pro Glu His Phe Ser Gly Arg Pro Arg Glu Asp Arg Val Pro His
            1395                1400                1405

Ser Arg Asn Ser Ile Thr Leu Thr Asn Leu Thr Pro Gly Thr Glu Tyr
            1410                1415                1420

Val Val Ser Ile Val Ala Leu Asn Gly Arg Glu Glu Ser Pro Leu Leu
1425                1430                1435                1440

Ile Gly Gln Gln Ser Thr Val Ser Asp Val Pro Arg Asp Leu Glu Val
            1445                1450                1455

Val Ala Ala Thr Pro Thr Ser Leu Leu Ile Ser Trp Asp Ala Pro Ala
            1460                1465                1470

Val Thr Val Arg Tyr Tyr Arg Ile Thr Tyr Gly Glu Thr Gly Gly Asn
            1475                1480                1485

Ser Pro Val Gln Glu Phe Thr Val Pro Gly Ser Lys Ser Thr Ala Thr
            1490                1495                1500

Ile Ser Gly Leu Lys Pro Gly Val Asp Tyr Thr Ile Thr Val Tyr Ala
1505                1510                1515                1520

Val Thr Gly Arg Gly Asp Ser Pro Ala Ser Ser Lys Pro Ile Ser Ile
            1525                1530                1535

Asn Tyr Arg Thr Glu Ile Asp Lys Pro Ser Gln Met Gln Val Thr Asp
            1540                1545                1550
```

Val Gln Asp Asn Ser Ile Ser Val Lys Trp Leu Pro Ser Ser Pro
1555                1560                1565

Val Thr Gly Tyr Arg Val Thr Thr Pro Lys Asn Gly Pro Gly Pro
1570                1575                1580

Thr Lys Thr Lys Thr Ala Gly Pro Asp Gln Thr Glu Met Thr Ile Glu
1585                1590                1595                1600

Gly Leu Gln Pro Thr Val Glu Tyr Val Val Ser Val Tyr Ala Gln Asn
                1605                1610                1615

Pro Ser Gly Glu Ser Gln Pro Leu Val Gln Thr Ala Val Thr Thr Ile
                1620                1625                1630

Pro Ala Pro Thr Asp Leu Lys Phe Thr Gln Val Thr Pro Thr Ser Leu
                1635                1640                1645

Ser Ala Gln Trp Thr Pro Pro Asn Val Gln Leu Thr Gly Tyr Arg Val
                1650                1655                1660

Arg Val Thr Pro Lys Glu Lys Thr Gly Pro Met Lys Glu Ile Asn Leu
1665                1670                1675                1680

Ala Pro Asp Ser Ser Ser Val Val Val Ser Gly Leu Met Val Ala Thr
                1685                1690                1695

Lys Tyr Glu Val Ser Val Tyr Ala Leu Lys Asp Thr Leu Thr Ser Arg
                1700                1705                1710

Pro Ala Gln Gly Val Val Thr Thr Leu Glu Asn Val Ser Pro Pro Arg
                1715                1720                1725

Arg Ala Arg Val Thr Asp Ala Thr Glu Thr Thr Ile Thr Ile Ser Trp
                1730                1735                1740

Arg Thr Lys Thr Glu Thr Ile Thr Gly Phe Gln Val Asp Ala Val Pro
1745                1750                1755                1760

Ala Asn Gly Gln Thr Pro Ile Gln Arg Thr Ile Lys Pro Asp Val Arg
                1765                1770                1775

Ser Tyr Thr Ile Thr Gly Leu Gln Pro Gly Thr Asp Tyr Lys Ile Tyr
                1780                1785                1790

Leu Tyr Thr Leu Asn Asp Asn Ala Arg Ser Ser Pro Val Val Ile Asp
                1795                1800                1805

Ala Ser Thr Ala Ile Asp Ala Pro Ser Asn Leu Arg Phe Leu Ala Thr
                1810                1815                1820

Thr Pro Asn Ser Leu Leu Val Ser Trp Gln Pro Pro Arg Ala Arg Ile
1825                1830                1835                1840

Thr Gly Tyr Ile Ile Lys Tyr Glu Lys Pro Gly Ser Pro Pro Arg Glu
                1845                1850                1855

Val Val Pro Arg Pro Arg Pro Gly Val Thr Glu Ala Thr Ile Thr Gly
                1860                1865                1870

Leu Glu Pro Gly Thr Glu Tyr Thr Ile Tyr Val Ile Ala Leu Lys Asn
                1875                1880                1885

Asn Gln Lys Ser Glu Pro Leu Ile Gly Arg Lys Lys Thr Asp Glu Leu
                1890                1895                1900

Pro Gln Leu Val Thr Leu Pro His Pro Asn Leu His Gly Pro Glu Ile
1905                1910                1915                1920

Leu Asp Val Pro Ser Thr Val Gln Lys Thr Pro Phe Val Thr His Pro
                1925                1930                1935

Gly Tyr Asp Thr Gly Asn Gly Ile Gln Leu Pro Gly Thr Ser Gly Gln
                1940                1945                1950

Gln Pro Ser Val Gly Gln Gln Met Ile Phe Glu Glu His Gly Phe Arg
                1955                1960                1965

Arg Thr Thr Pro Pro Thr Thr Ala Thr Pro Ile Arg His Arg Pro Arg

```
                1970            1975            1980
Pro Tyr Pro Pro Asn Val Gly Glu Glu Ile Gln Ile Gly His Ile Pro
1985            1990            1995            2000

Arg Glu Asp Val Asp Tyr His Leu Tyr Pro His Gly Pro Gly Leu Asn
        2005            2010            2015

Pro Asn Ala Ser Thr Gly Gln Glu Ala Leu Ser Gln Thr Thr Ile Ser
            2020            2025            2030

Trp Ala Pro Phe Gln Asp Thr Ser Glu Tyr Ile Ile Ser Cys His Pro
        2035            2040            2045

Val Gly Thr Asp Glu Glu Pro Leu Gln Phe Arg Val Pro Gly Thr Ser
        2050            2055            2060

Thr Ser Ala Thr Leu Thr Gly Leu Thr Arg Gly Ala Thr Tyr Asn Ile
2065            2070            2075            2080

Ile Val Glu Ala Leu Lys Asp Gln Gln Arg His Lys Val Arg Glu Glu
            2085            2090            2095

Val Val Thr Val Gly Asn Ser Val Asn Glu Gly Leu Asn Gln Pro Thr
            2100            2105            2110

Asp Asp Ser Cys Phe Asp Pro Tyr Thr Val Ser His Tyr Ala Val Gly
            2115            2120            2125

Asp Glu Trp Glu Arg Met Ser Glu Ser Gly Phe Lys Leu Leu Cys Gln
        2130            2135            2140

Cys Leu Gly Phe Gly Ser Gly His Phe Arg Cys Asp Ser Ser Arg Trp
2145            2150            2155            2160

Cys His Asp Asn Gly Val Asn Tyr Lys Ile Gly Glu Lys Trp Asp Arg
        2165            2170            2175

Gln Gly Glu Asn Gly Gln Met Met Ser Cys Thr Cys Leu Gly Asn Gly
            2180            2185            2190

Lys Gly Glu Phe Lys Cys Asp Pro His Glu Ala Thr Cys Tyr Asp Asp
        2195            2200            2205

Gly Lys Thr Tyr His Val Gly Glu Gln Trp Gln Lys Glu Tyr Leu Gly
        2210            2215            2220

Ala Ile Cys Ser Cys Thr Cys Phe Gly Gly Gln Arg Gly Trp Arg Cys
2225            2230            2235            2240

Asp Asn Cys Arg Arg Pro Gly Gly Glu Pro Ser Pro Glu Gly Thr Thr
            2245            2250            2255

Gly Gln Ser Tyr Asn Gln Tyr Ser Gln Arg Tyr His Gln Arg Thr Asn
            2260            2265            2270

Thr Asn Val Asn Cys Pro Ile Glu Cys Phe Met Pro Leu Asp Val Gln
            2275            2280            2285

Ala Asp Arg Glu Asp Ser Arg Glu
        2290            2295

<210> SEQ ID NO 13
<211> LENGTH: 8374
<212> TYPE: DNA
<213> ORGANISM: Homo sapiens

<400> SEQUENCE: 13
gcccgcgccg gctgtgctgc acaggggag gagagggaac cccaggcgcg agcgggaaga      60
ggggacctgc agccacaact tctctggtcc tctgcatccc ttctgtccct ccacccgtcc    120
ccttccccac cctctggccc ccaccttctt ggaggcgaca accccgggga ggcattagaa    180 gggattttc ccgcaggttg cgaagggaag caaacttggt ggcaacttgc ctcccggtgc    240
gggcgtctct cccccaccgt ctcaacatgc ttaggggtcc ggggcccggg ctgctgctgc    300
```

```
tggccgtcca gtgcctgggg acagcggtgc cctccacggg agcctcgaag agcaagaggc    360
aggctcagca aatggttcag ccccagtccc cggtggctgt cagtcaaagc aagcccggtt    420
gttatgacaa tggaaaacac tatcagataa atcaacagtg ggagcggacc tacctaggca    480
atgcgttggt ttgtacttgt tatggaggaa gccgaggttt taactgcgag agtaaacctg    540
aagctgaaga gacttgcttt gacaagtaca ctgggaacac ttaccgagtg ggtgacactt    600
atgagcgtcc taaagactcc atgatctggg actgtacctg catcggggct gggcgaggga    660
gaataagctg taccatcgca aaccgctgcc atgaaggggg tcagtcctac aagattggtg    720
acacctggag gagaccacat gagactggtg gttacatgtt agagtgtgtg tgtcttggta    780
atggaaaagg agaatggacc tgcaagccca tagctgagaa gtgttttgat catgctgctg    840
ggacttccta tgtggtcgga gaaacgtggg agaagcccta ccaaggctgg atgatggtag    900
attgtacttg cctgggagaa ggcagcggac gcatcacttg cacttctaga aatagatgca    960
acgatcagga cacaaggaca tcctatagaa ttggagacac ctggagcaag aaggataatc   1020
gaggaaacct gctccagtgc atctgcacag gcaacggccg aggagagtgg aagtgtgaga   1080
ggcacacctc tgtgcagacc acatcgagcg gatctggccc cttcaccgat gttcgtgcag   1140
ctgtttacca accgcagcct caccccagc ctcctcccta tggccactgt gtcacagaca   1200
gtggtgtggt ctactctgtg gggatgcagt ggctgaagac acaaggaaat aagcaaatgc   1260
tttgcacgtg cctgggcaac ggagtcagct gccaagagac agctgtaacc cagacttacg   1320
gtggcaactc aaatggagag ccatgtgtct taccattcac ctacaatggc aggacgttct   1380
actcctgcac cacagaaggg cgacaggacg acatctttg gtgcagcaca acttcgaatt   1440
atgagcagga ccagaaatac tctttctgca cagaccacac tgttttggtt cagactcgag   1500
gaggaaattc caatggtgcc ttgtgccact tccccttcct atacaacaac cacaattaca   1560
ctgattgcac ttctgagggc agaagagaca acatgaagtg gtgtgggacc acacagaact   1620
atgatgccga ccagaagttt gggttctgcc ccatggctgc ccacgaggaa atctgcacaa   1680
ccaatgaagg ggtcatgtac cgcattgag atcagtggga taagcagcat gacatgggtc   1740
acatgatgag gtgcacgtgt gttgggaatg gtcgtgggga atggacatgc attgcctact   1800
cgcagcttcg agatcagtgc attgttgatg acatcactta caatgtgaac gacacattcc   1860
acaagcgtca tgaagagggg cacatgctga actgtacatg cttcggtcag ggtcggggca   1920
ggtggaagtg tgatcccgtc gaccaatgcc aggattcaga gactgggacg ttttatcaaa   1980
ttggagattc atgggagaag tatgtgcatg gtgtcagata ccagtgctac tgctatggcc   2040
gtggcattgg ggagtggcat tgccaaacctt tacagaccta tccaagctca agtggtcctg   2100
tcgaagtatt tatcactgag actccgagtc agcccaactc ccaccccatc cagtggaatg   2160
caccacagcc atctcacatt tccaagtaca ttctcaggtg agacctaaa aattctgtag    2220
gccgttggaa ggaagctacc ataccaggcc acttaaactc ctacaccatc aaaggcctga   2280
agcctggtgt ggtatacgag ggccagctca tcagcatcca gcagtacggc caccaagaag   2340
tgactcgctt tgacttcacc accaccagca ccagcacacc tgtgaccagc aacaccgtga   2400
caggagagac gactcccttt tctcctcttg tggccacttc tgaatctgtg accgaaatca   2460
cagccagtag cttgtggtc tcctgggtct cagcttccga caccgtgtcg ggattccggg   2520
tggaatatga gctgagtgag gagggagatg agccacagta cctggatctt ccaagcacag   2580
ccacttctgt gaacatccct gacctgcttc ctggccgaaa atacattgta aatgtctatc   2640
```

```
agatatctga ggatggggag cagagtttga tcctgtctac ttcacaaaca acagcgcctg    2700
atgcccctcc tgacccgact gtggaccaag ttgatgacac ctcaattgtt gttcgctgga    2760
gcagacccca ggctcccatc acagggtaca gaatagtcta ttcgccatca gtagaaggta    2820
gcagcacaga actcaacctt cctgaaactg caaactccgt caccctcagt gacttgcaac    2880
ctggtgttca gtataacatc actatctatg ctgtggaaga aaatcaagaa agtacacctg    2940
ttgtcattca acaagaaacc actggcaccc cacgctcaga tacagtgccc tctcccaggg    3000
acctgcagtt tgtggaagtg acagacgtga aggtcaccat catgtggaca ccgcctgaga    3060
gtgcagtgac cggctaccgt gtggatgtga tccccgtcaa cctgcctggc gagcacgggc    3120
agaggctgcc catcagcagg aacacctttg cagaagtcac cgggctgtcc cctggggtca    3180
cctattactt caaagtcttt gcagtgagcc atgggaggga gagcaagcct ctgactgctc    3240
aacagacaac caaactggat gctcccacta acctccagtt tgtcaatgaa actgattcta    3300
ctgtcctggt gagatggact ccacctcggg cccagataac aggataccga ctgaccgtgg    3360
gccttacccg aagaggacag cccaggcagt acaatgtggg tccctctgtc tccaagtacc    3420
cactgaggaa tctgcagcct gcatctgagt acaccgtatc cctcgtggcc ataaagggca    3480
accaagagag ccccaaagcc actggagtct ttaccacact gcagcctggg agctctattc    3540
caccttacaa caccgaggtg actgagacca ccattgtgat cacatggacg cctgctccaa    3600
gaattggttt taagctgggt gtacgaccaa gccaggagg agaggcacca cgagaagtga    3660
cttcagactc aggaagcatc gttgtgtccg gcttgactcc aggagtagaa tacgtctaca    3720
ccatccaagt cctgagagat ggacaggaaa gagatgcgcc aattgtaaac aaagtggtga    3780
caccattgtc tccaccaaca aacttgcatc tggaggcaaa ccctgacact ggagtgctca    3840
cagtctcctg ggagaggagc accaccccag acattactgg ttatagaatt accacaaccc    3900
ctacaaacgg ccagcaggga aattctttgg aagaagtggt ccatgctgat cagagctcct    3960 gcactttga taacctgagt cccggcctgg agtacaatgt cagtgtttac actgtcaagg    4020
atgacaagga aagtgtccct atctctgata ccatcatccc agctgttcct cctcccactg    4080
acctgcgatt caccaacatt ggtccagaca ccatgcgtgt cacctgggct ccaccccat    4140 ccattgattt aaccaacttc ctggtgcgtt actcacctgt gaaaaatgag gaagatgttg    4200
cagagttgtc aatttctcct tcagacaatg cagtggtctt aacaaatctc ctgcctggta    4260
cagaatatgt agtgagtgtc tccagtgtct acgaacaaca tgagagcaca cctcttagag    4320
gaagacagaa aacaggtctt gattccccaa ctggcattga cttttctgat attactgcca    4380
actcttttac tgtgcactgg attgctcctc gagccaccat cactggctac aggatccgcc    4440
atcatcccga gcacttcagt gggagacctc gagaagatcg ggtgcccac tctcggaatt    4500 ccatcaccct caccaacctc actccaggca cagagtatgt ggtcagcatc gttgctctta    4560
atggcagaga ggaaagtccc ttattgattg ccaacaatc aacagtttct gatgttccga    4620
gggacctgga agttgttgct gcgacccca ccagcctact gatcagctgg gatgctcctg    4680
ctgtcacagt gagatattac aggatcactt acggagagac aggaggaaat agccctgtcc    4740
aggagttcac tgtgcctggg agcaagtcta cagctaccat cagcggcctt aaacctggag    4800
ttgattatac catcactgtg tatgctgtca ctggccgtgg agacagcccc gcaagcagca    4860
agccaatttc cattaattac cgaacagaaa ttgacaaacc atcccagatg caagtgaccg    4920
atgttcagga caacagcatt agtgtcaagt ggctgccttc aagttcccct gttactggtt    4980
acagagtaac caccactccc aaaaatggac caggaccaac aaaaactaaa actgcaggtc    5040
```

```
cagatcaaac agaaatgact attgaaggct tgcagcccac agtggagtat gtggttagtg    5100
tctatgctca gaatccaagc ggagagagtc agcctctggt tcagactgca gtaaccaaca    5160
ttgatcgccc taaaggactg gcattcactg atgtggatgt cgattccatc aaaattgctt    5220
gggaaagccc acaggggcaa gtttccaggt acagggtgac ctactcgagc cctgaggatg    5280
gaatccatga gctattccct gcacctgatg gtgaagaaga cactgcagag ctgcaaggcc    5340
tcagaccggg ttctgagtac acagtcagtg tggttgcctt gcacgatgat atggagagcc    5400 agccccctgat tggaacccag tccacagcta ttcctgcacc aactgacctg aagttcactc    5460
aggtcacacc cacaagcctg agcgcccagt ggacaccacc caatgttcag ctcactggat    5520
atcgagtgcg ggtgaccccc aaggagaaga ccggaccaat gaaagaaatc aaccttgctc    5580
ctgacagctc atccgtggtt gtatcaggac ttatggtggc caccaaatat gaagtgagtg    5640
tctatgctct taaggacact ttgacaagca gaccagctca gggagttgtc accactctgg    5700
agaatgtcag cccaccaaga agggctcgtg tgacagatgc tactgagacc accatcacca    5760
ttagctggag aaccaagact gagacgatca ctggcttcca agttgatgcc gttccagcca    5820
atggccagac tccaatccag agaaccatca agccagatgt cagaagctac accatcacag    5880
gtttacaacc aggcactgac tacaagatct acctgtacac cttgaatgac aatgctcgga    5940
gctcccctgt ggtcatcgac gcctccactg ccattgatgc accatccaac ctgcgtttcc    6000
tggccaccac acccaattcc ttgctggtat catggcagcc gccacgtgcc aggattaccg    6060
gctacatcat caagtatgag aagcctgggt ctcctcccag agaagtggtc cctcggcccc    6120
gccctggtgt cacagaggct actattactg gcctggaacc gggaaccgaa tatacaattt    6180
atgtcattgc cctgaagaat aatcagaaga gcgagcccct gattggaagg aaaaagacag    6240
ttcaaaagac cccctttcgtc acccaccctg ggtatgacac tggaaatggt attcagcttc    6300
ctggcacttc tggtcagcaa cccagtgttg ggcaacaaat gatctttgag gaacatggtt    6360
ttaggcggac cacaccgccc acaacggcca ccccccataag gcataggcca agaccatacc    6420
cgccgaatgt aggacaagaa gctctctctc agacaaccat ctcatgggcc ccattccagg    6480
acacttctga gtacatcatt tcatgtcatc ctgttggcac tgatgaagaa cccttacagt    6540
tcagggttcc tggaacttct accagtgcca ctctgacagg cctcaccaga ggtgccacct    6600
acaacatcat agtggaggca ctgaaagacc agcagaggca taaggttcgg gaagaggttg    6660
ttaccgtggg caactctgtc aacgaaggct tgaaccaacc tacggatgac tcgtgctttg    6720 accctacac agtttcccat tatgccgttg gagatgagtg ggaacgaatg tctgaatcag    6780
gcttaaaact gttgtgccag tgcttaggct ttggaagtgg tcatttcaga tgtgattcat    6840
ctagatggtg ccatgacaat ggtgtgaact acaagattgg agagaagtgg gaccgtcagg    6900
gagaaaatgg ccagatgatg agctgcacat gtcttgggaa cggaaaagga gaattcaagt    6960
gtgaccctca tgaggcaacg tgttatgatg atgggaagac ataccacgta ggagaacagt    7020
ggcagaagga atatctcggt gccatttgct cctgcacatg ctttggaggc cagcggggct    7080
ggcgctgtga caactgccgc agacctgggg gtgaacccag tcccgaaggc actactggcc    7140
agtcctacaa ccagtattct cagagatacc atcagagaac aaacactaat gttaattgcc    7200
caattgagtg cttcatgcct ttagatgtac aggctgacag agaagattcc cgagagtaaa    7260
tcatctttcc aatccagagg aacaagcatg tctctctgcc aagatccatc taaactggag    7320
tgatgttagc agacccagct tagagttctt cttttctttct taagccctttt gctctggagg    7380
```

```
aagttctcca gcttcagctc aactcacagc ttctccaagc atcaccctgg gagtttcctg    7440
agggttttct cataaatgag ggctgcacat tgcctgttct gcttcgaagt attcaatacc    7500
gctcagtatt ttaaatgaag tgattctaag atttggtttg ggatcaatag gaaagcatat    7560
gcagccaacc aagatgcaaa tgttttgaaa tgatatgacc aaaattttaa gtaggaaagt    7620
cacccaaaca cttctgcttt cacttaagtg tctggcccgc aatactgtag gaacaagcat    7680
gatcttgtta ctgtgatatt ttaaatatcc acagtactca cttttccaa atgatcctag     7740 taattgccta gaaatatctt tctcttacct gttatttatc aattttccc agtattttta     7800 tacggaaaaa attgtattga aaacacttag tatgcagttg ataagaggaa tttggtataa    7860
ttatggtggg tgattatttt ttatactgta tgtgccaaag ctttactact gtggaaagac    7920
aactgtttta ataaaagatt tacattccac aacttgaagt tcatctattt gatataagac    7980
accttcgggg gaaataattc ctgtgaatat tcttttcaa ttcagcaaac atttgaaat     8040 ctatgatgtg caagtctaat tgttgatttc agtacaagat tttctaaatc agttgctaca    8100
aaaactgatt ggttttgtc acttcatctc ttcactaatg gagatagctt tacactttct    8160
gctttaatag atttaagtgg accccaatat ttattaaaat tgctagttta ccgttcagaa    8220
gtataataga aataatcttt agttgctctt ttctaaccat tgtaattctt cccttcttcc    8280
ctccaccttt ccttcattga ataaacctct gttcaaagag attgcctgca agggaaataa    8340
aaatgactaa gatattaaaa aaaaaaaaa aaaa                                 8374
```

<210> SEQ ID NO 14
<211> LENGTH: 2330
<212> TYPE: PRT
<213> ORGANISM: Homo sapiens

<400> SEQUENCE: 14

```
Met Leu Arg Gly Pro Gly Pro Gly Leu Leu Leu Leu Ala Val Gln Cys
1               5                   10                  15

Leu Gly Thr Ala Val Pro Ser Thr Gly Ala Ser Lys Ser Lys Arg Gln
            20                  25                  30

Ala Gln Gln Met Val Gln Pro Gln Ser Pro Val Ala Val Ser Gln Ser
        35                  40                  45

Lys Pro Gly Cys Tyr Asp Asn Gly Lys His Tyr Gln Ile Asn Gln Gln
    50                  55                  60

Trp Glu Arg Thr Tyr Leu Gly Asn Ala Leu Val Cys Thr Cys Tyr Gly
65                  70                  75                  80

Gly Ser Arg Gly Phe Asn Cys Glu Ser Lys Pro Glu Ala Glu Glu Thr
                85                  90                  95

Cys Phe Asp Lys Tyr Thr Gly Asn Thr Tyr Arg Val Gly Asp Thr Tyr
            100                 105                 110

Glu Arg Pro Lys Asp Ser Met Ile Trp Asp Cys Thr Cys Ile Gly Ala
        115                 120                 125

Gly Arg Gly Arg Ile Ser Cys Thr Ile Ala Asn Arg Cys His Glu Gly
    130                 135                 140

Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
                165                 170                 175

Trp Thr Cys Lys Pro Ile Ala Glu Lys Cys Phe Asp His Ala Ala Gly
            180                 185                 190

Thr Ser Tyr Val Val Gly Glu Thr Trp Glu Lys Pro Tyr Gln Gly Trp
```

```
            195                 200                 205
Met Met Val Asp Cys Thr Cys Leu Gly Glu Gly Ser Gly Arg Ile Thr
210                 215                 220

Cys Thr Ser Arg Asn Arg Cys Asn Asp Gln Asp Thr Arg Thr Ser Tyr
225                 230                 235                 240

Arg Ile Gly Asp Thr Trp Ser Lys Lys Asp Asn Arg Gly Asn Leu Leu
                245                 250                 255

Gln Cys Ile Cys Thr Gly Asn Gly Arg Gly Glu Trp Lys Cys Glu Arg
                260                 265                 270

His Thr Ser Val Gln Thr Thr Ser Ser Gly Ser Gly Pro Phe Thr Asp
            275                 280                 285

Val Arg Ala Ala Val Tyr Gln Pro Gln Pro His Pro Gln Pro Pro Pro
290                 295                 300

Tyr Gly His Cys Val Thr Asp Ser Gly Val Val Tyr Ser Val Gly Met
305                 310                 315                 320

Gln Trp Leu Lys Thr Gln Gly Asn Lys Gln Met Leu Cys Thr Cys Leu
                325                 330                 335

Gly Asn Gly Val Ser Cys Gln Glu Thr Ala Val Thr Gln Thr Tyr Gly
                340                 345                 350

Gly Asn Ser Asn Gly Glu Pro Cys Val Leu Pro Phe Thr Tyr Asn Gly
            355                 360                 365

Arg Thr Phe Tyr Ser Cys Thr Thr Glu Gly Arg Gln Asp Gly His Leu
370                 375                 380

Trp Cys Ser Thr Thr Ser Asn Tyr Glu Gln Asp Gln Lys Tyr Ser Phe
385                 390                 395                 400

Cys Thr Asp His Thr Val Leu Val Gln Thr Arg Gly Gly Asn Ser Asn
                405                 410                 415

Gly Ala Leu Cys His Phe Pro Phe Leu Tyr Asn Asn His Asn Tyr Thr
                420                 425                 430

Asp Cys Thr Ser Glu Gly Arg Arg Asp Asn Met Lys Trp Cys Gly Thr
            435                 440                 445

Thr Gln Asn Tyr Asp Ala Asp Gln Lys Phe Gly Phe Cys Pro Met Ala
450                 455                 460

Ala His Glu Glu Ile Cys Thr Thr Asn Glu Gly Val Met Tyr Arg Ile
465                 470                 475                 480

Gly Asp Gln Trp Asp Lys Gln His Asp Met Gly His Met Met Arg Cys
                485                 490                 495

Thr Cys Val Gly Asn Gly Arg Gly Glu Trp Thr Cys Ile Ala Tyr Ser
                500                 505                 510

Gln Leu Arg Asp Gln Cys Ile Val Asp Asp Ile Thr Tyr Asn Val Asn
            515                 520                 525

Asp Thr Phe His Lys Arg His Glu Glu Gly His Met Leu Asn Cys Thr
530                 535                 540

Cys Phe Gly Gln Gly Arg Gly Arg Trp Lys Cys Asp Pro Val Asp Gln
545                 550                 555                 560

Cys Gln Asp Ser Glu Thr Gly Thr Phe Tyr Gln Ile Gly Asp Ser Trp
                565                 570                 575

Glu Lys Tyr Val His Gly Val Arg Tyr Gln Cys Tyr Cys Tyr Gly Arg
                580                 585                 590

Gly Ile Gly Glu Trp His Cys Gln Pro Leu Gln Thr Tyr Pro Ser Ser
            595                 600                 605

Ser Gly Pro Val Glu Val Phe Ile Thr Glu Thr Pro Ser Gln Pro Asn
610                 615                 620
```

```
Ser His Pro Ile Gln Trp Asn Ala Pro Gln Pro Ser His Ile Ser Lys
625                 630                 635                 640

Tyr Ile Leu Arg Trp Arg Pro Lys Asn Ser Val Gly Arg Trp Lys Glu
            645                 650                 655

Ala Thr Ile Pro Gly His Leu Asn Ser Tyr Thr Ile Lys Gly Leu Lys
        660                 665                 670

Pro Gly Val Val Tyr Glu Gly Gln Leu Ile Ser Ile Gln Gln Tyr Gly
            675                 680                 685

His Gln Glu Val Thr Arg Phe Asp Phe Thr Thr Ser Thr Ser Thr
690                 695                 700

Pro Val Thr Ser Asn Thr Val Thr Gly Glu Thr Thr Pro Phe Ser Pro
705                 710                 715                 720

Leu Val Ala Thr Ser Glu Ser Val Thr Glu Ile Thr Ala Ser Ser Phe
                725                 730                 735

Val Val Ser Trp Val Ser Ala Ser Asp Thr Val Ser Gly Phe Arg Val
            740                 745                 750

Glu Tyr Glu Leu Ser Glu Glu Gly Asp Glu Pro Gln Tyr Leu Asp Leu
                755                 760                 765

Pro Ser Thr Ala Thr Ser Val Asn Ile Pro Asp Leu Leu Pro Gly Arg
770                 775                 780

Lys Tyr Ile Val Asn Val Tyr Gln Ile Ser Glu Asp Gly Glu Gln Ser
785                 790                 795                 800

Leu Ile Leu Ser Thr Ser Gln Thr Thr Ala Pro Asp Ala Pro Pro Asp
                805                 810                 815

Pro Thr Val Asp Gln Val Asp Asp Thr Ser Ile Val Val Arg Trp Ser
            820                 825                 830

Arg Pro Gln Ala Pro Ile Thr Gly Tyr Arg Ile Val Tyr Ser Pro Ser
            835                 840                 845

Val Glu Gly Ser Ser Thr Glu Leu Asn Leu Pro Glu Thr Ala Asn Ser
850                 855                 860

Val Thr Leu Ser Asp Leu Gln Pro Gly Val Gln Tyr Asn Ile Thr Ile
865                 870                 875                 880

Tyr Ala Val Glu Glu Asn Gln Glu Ser Thr Pro Val Val Ile Gln Gln
                885                 890                 895

Glu Thr Thr Gly Thr Pro Arg Ser Asp Thr Val Pro Ser Pro Arg Asp
                900                 905                 910

Leu Gln Phe Val Glu Val Thr Asp Val Lys Val Thr Ile Met Trp Thr
        915                 920                 925

Pro Pro Glu Ser Ala Val Thr Gly Tyr Arg Val Asp Val Ile Pro Val
        930                 935                 940

Asn Leu Pro Gly Glu His Gly Gln Arg Leu Pro Ile Ser Arg Asn Thr
945                 950                 955                 960

Phe Ala Glu Val Thr Gly Leu Ser Pro Gly Val Thr Tyr Tyr Phe Lys
                965                 970                 975

Val Phe Ala Val Ser His Gly Arg Glu Ser Lys Pro Leu Thr Ala Gln
                980                 985                 990

Gln Thr Thr Lys Leu Asp Ala Pro Thr Asn Leu Gln Phe Val Asn Glu
        995                 1000                1005

Thr Asp Ser Thr Val Leu Val Arg Trp Thr Pro Pro Arg Ala Gln Ile
        1010                1015                1020

Thr Gly Tyr Arg Leu Thr Val Gly Leu Thr Arg Arg Gly Gln Pro Arg
1025                1030                1035                1040
```

```
Gln Tyr Asn Val Gly Pro Ser Val Ser Lys Tyr Pro Leu Arg Asn Leu
            1045                1050                1055

Gln Pro Ala Ser Glu Tyr Thr Val Ser Leu Val Ala Ile Lys Gly Asn
        1060                1065                1070

Gln Glu Ser Pro Lys Ala Thr Gly Val Phe Thr Thr Leu Gln Pro Gly
        1075                1080                1085

Ser Ser Ile Pro Pro Tyr Asn Thr Glu Val Thr Glu Thr Thr Ile Val
        1090                1095                1100

Ile Thr Trp Thr Pro Ala Pro Arg Ile Gly Phe Lys Leu Gly Val Arg
1105                1110                1115                1120

Pro Ser Gln Gly Gly Glu Ala Pro Arg Glu Val Thr Ser Asp Ser Gly
        1125                1130                1135

Ser Ile Val Val Ser Gly Leu Thr Pro Gly Val Glu Tyr Val Tyr Thr
        1140                1145                1150

Ile Gln Val Leu Arg Asp Gly Gln Glu Arg Asp Ala Pro Ile Val Asn
        1155                1160                1165

Lys Val Val Thr Pro Leu Ser Pro Pro Thr Asn Leu His Leu Glu Ala
        1170                1175                1180

Asn Pro Asp Thr Gly Val Leu Thr Val Ser Trp Glu Arg Ser Thr Thr
1185                1190                1195                1200

Pro Asp Ile Thr Gly Tyr Arg Ile Thr Thr Thr Pro Thr Asn Gly Gln
        1205                1210                1215

Gln Gly Asn Ser Leu Glu Glu Val Val His Ala Asp Gln Ser Ser Cys
        1220                1225                1230

Thr Phe Asp Asn Leu Ser Pro Gly Leu Glu Tyr Asn Val Ser Val Tyr
        1235                1240                1245

Thr Val Lys Asp Asp Lys Glu Ser Val Pro Ile Ser Asp Thr Ile Ile
        1250                1255                1260

Pro Ala Val Pro Pro Thr Asp Leu Arg Phe Thr Asn Ile Gly Pro
1265                1270                1275                1280

Asp Thr Met Arg Val Thr Trp Ala Pro Pro Ser Ile Asp Leu Thr
        1285                1290                1295

Asn Phe Leu Val Arg Tyr Ser Pro Val Lys Asn Glu Glu Asp Val Ala
        1300                1305                1310

Glu Leu Ser Ile Ser Pro Ser Asp Asn Ala Val Val Leu Thr Asn Leu
        1315                1320                1325

Leu Pro Gly Thr Glu Tyr Val Val Ser Val Ser Ser Val Tyr Glu Gln
        1330                1335                1340

His Glu Ser Thr Pro Leu Arg Gly Arg Gln Lys Thr Gly Leu Asp Ser
1345                1350                1355                1360

Pro Thr Gly Ile Asp Phe Ser Asp Ile Thr Ala Asn Ser Phe Thr Val
        1365                1370                1375

His Trp Ile Ala Pro Arg Ala Thr Ile Thr Gly Tyr Arg Ile Arg His
        1380                1385                1390

His Pro Glu His Phe Ser Gly Arg Pro Arg Glu Asp Arg Val Pro His
        1395                1400                1405

Ser Arg Asn Ser Ile Thr Leu Thr Asn Leu Thr Pro Gly Thr Glu Tyr
        1410                1415                1420

Val Val Ser Ile Val Ala Leu Asn Gly Arg Glu Glu Ser Pro Leu Leu
1425                1430                1435                1440

Ile Gly Gln Gln Ser Thr Val Ser Asp Val Pro Arg Asp Leu Glu Val
        1445                1450                1455

Val Ala Ala Thr Pro Thr Ser Leu Leu Ile Ser Trp Asp Ala Pro Ala
```

-continued

```
                1460                1465                1470
Val Thr Val Arg Tyr Tyr Arg Ile Thr Tyr Gly Glu Thr Gly Gly Asn
            1475                1480                1485

Ser Pro Val Gln Glu Phe Thr Val Pro Gly Ser Lys Ser Thr Ala Thr
        1490                1495                1500

Ile Ser Gly Leu Lys Pro Gly Val Asp Tyr Thr Ile Thr Val Tyr Ala
1505                1510                1515                1520

Val Thr Gly Arg Gly Asp Ser Pro Ala Ser Ser Lys Pro Ile Ser Ile
            1525                1530                1535

Asn Tyr Arg Thr Glu Ile Asp Lys Pro Ser Gln Met Gln Val Thr Asp
        1540                1545                1550

Val Gln Asp Asn Ser Ile Ser Val Lys Trp Leu Pro Ser Ser Ser Pro
    1555                1560                1565

Val Thr Gly Tyr Arg Val Thr Thr Thr Pro Lys Asn Gly Pro Gly Pro
    1570                1575                1580

Thr Lys Thr Lys Thr Ala Gly Pro Asp Gln Thr Glu Met Thr Ile Glu
1585                1590                1595                1600

Gly Leu Gln Pro Thr Val Glu Tyr Val Val Ser Val Tyr Ala Gln Asn
            1605                1610                1615

Pro Ser Gly Glu Ser Gln Pro Leu Val Gln Thr Ala Val Thr Asn Ile
        1620                1625                1630

Asp Arg Pro Lys Gly Leu Ala Phe Thr Asp Val Asp Val Asp Ser Ile
        1635                1640                1645

Lys Ile Ala Trp Glu Ser Pro Gln Gly Gln Val Ser Arg Tyr Arg Val
        1650                1655                1660

Thr Tyr Ser Ser Pro Glu Asp Gly Ile His Glu Leu Phe Pro Ala Pro
1665                1670                1675                1680

Asp Gly Glu Glu Asp Thr Ala Glu Leu Gln Gly Leu Arg Pro Gly Ser
            1685                1690                1695

Glu Tyr Thr Val Ser Val Val Ala Leu His Asp Asp Met Glu Ser Gln
            1700                1705                1710

Pro Leu Ile Gly Thr Gln Ser Thr Ala Ile Pro Ala Pro Thr Asp Leu
        1715                1720                1725

Lys Phe Thr Gln Val Thr Pro Thr Ser Leu Ser Ala Gln Trp Thr Pro
        1730                1735                1740

Pro Asn Val Gln Leu Thr Gly Tyr Arg Val Arg Val Thr Pro Lys Glu
1745                1750                1755                1760

Lys Thr Gly Pro Met Lys Glu Ile Asn Leu Ala Pro Asp Ser Ser Ser
            1765                1770                1775

Val Val Val Ser Gly Leu Met Val Ala Thr Lys Tyr Glu Val Ser Val
        1780                1785                1790

Tyr Ala Leu Lys Asp Thr Leu Thr Ser Arg Pro Ala Gln Gly Val Val
        1795                1800                1805

Thr Thr Leu Glu Asn Val Ser Pro Pro Arg Arg Ala Arg Val Thr Asp
        1810                1815                1820

Ala Thr Glu Thr Thr Ile Thr Ile Ser Trp Arg Thr Lys Thr Glu Thr
1825                1830                1835                1840

Ile Thr Gly Phe Gln Val Asp Ala Val Pro Ala Asn Gly Gln Thr Pro
            1845                1850                1855

Ile Gln Arg Thr Ile Lys Pro Asp Val Arg Ser Tyr Thr Ile Thr Gly
            1860                1865                1870

Leu Gln Pro Gly Thr Asp Tyr Lys Ile Tyr Leu Tyr Thr Leu Asn Asp
            1875                1880                1885
```

```
Asn Ala Arg Ser Ser Pro Val Val Ile Asp Ala Ser Thr Ala Ile Asp
        1890                1895                1900

Ala Pro Ser Asn Leu Arg Phe Leu Ala Thr Thr Pro Asn Ser Leu Leu
1905                1910                1915                1920

Val Ser Trp Gln Pro Pro Arg Ala Arg Ile Thr Gly Tyr Ile Ile Lys
                1925                1930                1935

Tyr Glu Lys Pro Gly Ser Pro Arg Glu Val Val Pro Arg Pro Arg
            1940                1945                1950

Pro Gly Val Thr Glu Ala Thr Ile Thr Gly Leu Glu Pro Gly Thr Glu
            1955                1960                1965

Tyr Thr Ile Tyr Val Ile Ala Leu Lys Asn Asn Gln Lys Ser Glu Pro
        1970                1975                1980

Leu Ile Gly Arg Lys Lys Thr Val Gln Lys Thr Pro Phe Val Thr His
1985                1990                1995                2000

Pro Gly Tyr Asp Thr Gly Asn Gly Ile Gln Leu Pro Gly Thr Ser Gly
            2005                2010                2015

Gln Gln Pro Ser Val Gly Gln Gln Met Ile Phe Glu Glu His Gly Phe
            2020                2025                2030

Arg Arg Thr Thr Pro Pro Thr Thr Ala Thr Pro Ile Arg His Arg Pro
        2035                2040                2045

Arg Pro Tyr Pro Pro Asn Val Gly Gln Glu Ala Leu Ser Gln Thr Thr
        2050                2055                2060

Ile Ser Trp Ala Pro Phe Gln Asp Thr Ser Glu Tyr Ile Ile Ser Cys
2065                2070                2075                2080

His Pro Val Gly Thr Asp Glu Glu Pro Leu Gln Phe Arg Val Pro Gly
            2085                2090                2095

Thr Ser Thr Ser Ala Thr Leu Thr Gly Leu Thr Arg Gly Ala Thr Tyr
            2100                2105                2110

Asn Ile Ile Val Glu Ala Leu Lys Asp Gln Gln Arg His Lys Val Arg
        2115                2120                2125

Glu Glu Val Val Thr Val Gly Asn Ser Val Asn Glu Gly Leu Asn Gln
        2130                2135                2140

Pro Thr Asp Asp Ser Cys Phe Asp Pro Tyr Thr Val Ser His Tyr Ala
2145                2150                2155                2160

Val Gly Asp Glu Trp Glu Arg Met Ser Glu Ser Gly Phe Lys Leu Leu
            2165                2170                2175

Cys Gln Cys Leu Gly Phe Gly Ser Gly His Phe Arg Cys Asp Ser Ser
            2180                2185                2190

Arg Trp Cys His Asp Asn Gly Val Asn Tyr Lys Ile Gly Glu Lys Trp
        2195                2200                2205

Asp Arg Gln Gly Glu Asn Gly Gln Met Met Ser Cys Thr Cys Leu Gly
        2210                2215                2220

Asn Gly Lys Gly Glu Phe Lys Cys Asp Pro His Glu Ala Thr Cys Tyr
2225                2230                2235                2240

Asp Asp Gly Lys Thr Tyr His Val Gly Glu Gln Trp Gln Lys Glu Tyr
            2245                2250                2255

Leu Gly Ala Ile Cys Ser Cys Thr Cys Phe Gly Gly Gln Arg Gly Trp
            2260                2265                2270

Arg Cys Asp Asn Cys Arg Arg Pro Gly Gly Glu Pro Ser Pro Glu Gly
            2275                2280                2285

Thr Thr Gly Gln Ser Tyr Asn Gln Tyr Ser Gln Arg Tyr His Gln Arg
            2290                2295                2300
```

```
Thr Asn Thr Asn Val Asn Cys Pro Ile Glu Cys Phe Met Pro Leu Asp
2305                2310                2315                2320

Val Gln Ala Asp Arg Glu Asp Ser Arg Glu
            2325                2330

<210> SEQ ID NO 15
<211> LENGTH: 8815
<212> TYPE: DNA
<213> ORGANISM: Homo sapiens

<400> SEQUENCE: 15
gcccgcgccg gctgtgctgc acaggggggag gagagggaac cccaggcgcg agcgggaaga       60
ggggacctgc agccacaact tctctggtcc tctgcatccc ttctgtccct ccacccgtcc      120
ccttccccac cctctggccc ccaccttctt ggaggcgaca accccgggga ggcattagaa      180 gggattttc ccgcaggttg cgaagggaag caaacttggt ggcaacttgc ctcccggtgc       240
gggcgtctct cccccaccgt ctcaacatgc ttaggggtcc gggcccggg ctgctgctgc       300 tggccgtcca gtgcctgggg acagcggtgc cctccacggg agcctcgaag agcaagaggc      360
aggctcagca aatggttcag ccccagtccc cggtggctgt cagtcaaagc aagcccggtt      420
gttatgacaa tggaaaacac tatcagataa atcaacagtg ggagcggacc tacctaggca      480
atgcgttggt ttgtacttgt tatggaggaa gccgaggttt taactgcgag agtaaacctg      540
aagctgaaga gacttgcttt gacaagtaca ctggaacac ttaccgagtg ggtgacactt       600
atgagcgtcc taaagactcc atgatctggg actgtacctg catcggggct gggcgaggga      660
gaataagctg taccatcgca aaccgctgcc atgaaggggg tcagtcctac aagattggtg      720
acacctggag gagaccacat gagactggtg ttacatgtt agagtgtgtg tgtcttggta       780
atggaaaagg agaatggacc tgcaagccca tagctgagaa gtgttttgat catgctgctg      840 gacttcta tgtggtcgga gaaacgtggg agaagcccta ccaaggctgg atgatggtag        900
attgtacttg cctgggagaa ggcagcggac gcatcacttg cacttctaga aatagatgca      960
acgatcagga cacaaggaca tcctataga ttggagacac ctggagcaag aaggataatc      1020
gaggaaacct gctccagtgc atctgcacag gcaacgcccg aggagagtgg aagtgtgaga     1080
ggcacacctc tgtgcagacc acatcgagcg gatctggccc cttcaccgat gttcgtgcag     1140
ctgtttacca accgcagcct caccccccagc ctcctcccta tggccactgt gtcacagaca     1200
gtggtgtggt ctactctgtg gggatgcagt ggctgaagac acaaggaaat aagcaaatgc     1260
tttgcacgtg cctgggcaac ggagtcagct gccaagagac agctgtaacc cagacttacg     1320
gtggcaactc aaatggagag ccatgtgtct taccattcac ctacaatggc aggacgttct     1380
actcctgcac cacagaaggg cgacaggacg gacatctttg gtgcagcaca acttcgaatt     1440
atgagcagga ccagaaatac tctttctgca cagaccacac tgttttggtt cagactcgag     1500
gaggaaattc caatggtgcc ttgtgccact ccccttcct atacaacaac cacaattaca     1560
ctgattgcac ttctgagggc agaagagaca acatgaagtg gtgtgggacc acacagaact     1620
atgatgccga ccagaagttt gggttctgcc ccatggctgc ccacgaggaa atctgcacaa     1680
ccaatgaagg ggtcatgtac cgcattgag atcagtggga taagcagcat gacatgggtc     1740
acatgatgag gtgcacgtgt gttgggaatg tcgtgggga atggacatgc attgcctact     1800
cgcagcttcg agatcagtgc attgttgatg acatcactta caatgtgaac gacacattcc     1860
acaagcgtca tgaagagggg cacatgctga actgtacatg cttcggtcag gtcggggca     1920 ggtggaagtg tgatcccgtc gaccaatgcc aggattcaga gactgggacg ttttatcaaa     1980
```

```
ttggagattc atgggagaag tatgtgcatg gtgtcagata ccagtgctac tgctatggcc    2040
gtggcattgg ggagtggcat tgccaacctt tacagaccta tccaagctca agtggtcctg    2100
tcgaagtatt tatcactgag actccgagtc agcccaactc ccaccccatc cagtggaatg    2160
caccacagcc atctcacatt tccaagtaca ttctcaggtg gagacctaaa aattctgtag    2220
gccgttggaa ggaagctacc ataccaggcc acttaaactc ctacaccatc aaaggcctga    2280
agcctggtgt ggtatacgag ggccagctca tcagcatcca gcagtacggc caccaagaag    2340
tgactcgctt tgacttcacc accaccagca ccagcacacc tgtgaccagc aacaccgtga    2400
caggagagac gactcccttt tctcctcttg tggccacttc tgaatctgtg accgaaatca    2460
cagccagtag ctttgtggtc tcctgggtct cagcttccga caccgtgtcg ggattccggg    2520
tggaatatga gctgagtgag gagggagatg agccacagta cctggatctt ccaagcacag    2580
ccacttctgt gaacatccct gacctgcttc ctggccgaaa atacattgta aatgtctatc    2640
agatatctga ggatggggag cagagtttga tcctgtctac ttcacaaaca acagcgcctg    2700
atgcccctcc tgacccgact gtggaccaag ttgatgacac ctcaattgtt gttcgctgga    2760
gcagacccca ggctcccatc acagggtaca gaatagtcta ttcgccatca gtagaaggta    2820
gcagcacaga actcaacctt cctgaaactg caaactccgt caccctcagt gacttgcaac    2880
ctggtgttca gtataacatc actatctatg ctgtggaaga aaatcaagaa agtacacctg    2940
ttgtcattca acaagaaacc actggcaccc cacgctcaga tacagtgccc tctcccaggg    3000
acctgcagtt tgtggaagtg acagacgtga aggtcaccat catgtggaca ccgcctgaga    3060
gtgcagtgac cggctaccgt gtggatgtga tccccgtcaa cctgcctggc gagcacgggc    3120
agaggctgcc catcagcagg aacacctttg cagaagtcac cggctgtcc cctgggtca    3180 cctattactt caaagtcttt gcagtgagcc atggaggga gagcaagcct ctgactgctc    3240
aacagacaac caaactggat gctcccacta acctccagtt tgtcaatgaa actgattcta    3300
ctgtcctggt gagatggact ccacctcggg cccagataac aggataccga ctgaccgtgg    3360
gccttacccg aagaggacag cccaggcagt acaatgtggg tcctctgtc tccaagtacc    3420 cactgaggaa tctgcagcct gcatctgagt acaccgtatc cctcgtggcc ataaagggca    3480
accaagagag ccccaaagcc actggagtct ttaccacact gcagcctggg agctctattc    3540
caccttacaa caccgaggtg actgagacca ccattgtgat cacatggacg cctgctccaa    3600
gaattggttt taagctgggt gtacgaccaa gccagggagg agaggcacca cgagaagtga    3660
cttcagactc aggaagcatc gttgtgtccg gcttgactcc aggagtagaa tacgtctaca    3720
ccatccaagt cctgagagat ggacaggaaa gagatgcgcc aattgtaaac aaagtggtga    3780
caccattgtc tccaccaaca aacttgcatc tggaggcaaa ccctgacact ggagtgctca    3840
cagtctcctg ggagaggagc accaccccag acattactgg ttatagaatt accacaaccc    3900
ctacaaacgg ccagcaggga aattctttgg aagaagtggt ccatgctgat cagagctcct    3960 gcactttga taacctgagt cccggcctgg agtacaatgt cagtgtttac actgtcaagg    4020
atgacaagga aagtgtccct atctctgata ccatcatccc agaggtgccc caactcactg    4080
acctaagctt tgttgatata accgattcaa gcatcggcct gaggtggacc ccgctaaact    4140
cttccaccat tattgggtac cgcatcacag tagttgcggc aggagaaggt atccctattt    4200
ttgaagattt tgtggactcc tcagtaggat actacacagt cacagggctg agccgggca    4260 ttgactatga tatcagcgtt atcactctca ttaatggcgg cgagagtgcc cctactacac    4320
```

```
tgacacaaca aacggctgtt cctcctccca ctgacctgcg attcaccaac attggtccag    4380
acaccatgcg tgtcacctgg gctccacccc catccattga tttaaccaac ttcctggtgc    4440
gttactcacc tgtgaaaaat gaggaagatg ttgcagagtt gtcaatttct ccttcagaca    4500
atgcagtggt cttaacaaat ctcctgcctg gtacagaata tgtagtgagt gtctccagtg    4560
tctacgaaca acatgagagc acacctctta gaggaagaca gaaaacaggt cttgattccc    4620
caactggcat tgactttct gatattactg ccaactcttt tactgtgcac tggattgctc    4680
ctcgagccac catcactggc tacaggatcc gccatcatcc cgagcacttc agtgggagac    4740
ctcgagaaga tcgggtgccc cactctcgga attccatcac cctcaccaac ctcactccag    4800
gcacagagta tgtggtcagc atcgttgctc ttaatggcag agaggaaagt cccttattga    4860
ttggccaaca atcaacagtt tctgatgttc cgagggacct ggaagttgtt gctgcgaccc    4920
ccaccagcct actgatcagc tgggatgctc ctgctgtcac agtgagatat tacaggatca    4980
cttacgaaga gacaggagga aatagccctg tccaggagtt cactgtgcct gggagcaagt    5040
ctacagctac catcagcggc cttaaacctg gagttgatta ccatcact gtgtatgctg    5100 tcactggccg tggagacagc cccgcaagca gcaagccaat ttccattaat taccgaacag    5160
aaattgacaa accatcccag atgcaagtga ccgatgttca ggcaacagc attagtgtca    5220 agtggctgcc ttcaagttcc cctgttactg gttacagagt aaccaccact cccaaaaatg    5280
gaccaggacc aacaaaaact aaaactgcag gtccagatca aacagaaatg actattgaag    5340
gcttgcagcc cacagtggag tatgtggtta gtgtctatgc tcagaatcca gcggagaga    5400 gtcagcctct ggttcagact gcagtaacca acattgatcg ccctaaagga ctggcattca    5460
ctgatgtgga tgtcgattcc atcaaaattg cttgggaaag cccacagggg caagtttcca    5520
ggtacagggt gacctactcg agccctgagg atggaatcca tgagctattc cctgcacctg    5580
atggtgaaga agacactgca gagctgcaag gcctcagacc gggttctgag tacacagtca    5640
gtgtggttgc cttgcacgat gatatggaga ccagcccct gattgaacc cagtccacag    5700 ctattcctgc accaactgac ctgaagttca ctcaggtcac acccacaagc ctgagcgccc    5760
agtggacacc acccaatgtt cagctcactg gatatcgagt gcgggtgacc cccaaggaga    5820
agaccggacc aatgaaagaa atcaaccttg ctcctgacag ctcatccgtg gttgtatcag    5880
gacttatggt ggccaccaaa tatgaagtga gtgtctatgc tcttaaggac actttgacaa    5940
gcagaccagc tcagggagtt gtcaccactc tggagaatgt cagcccacca agaagggctc    6000
gtgtgacaga tgctactgag accaccatca ccattagctg gagaaccaag actgagcga    6060 tcactggctt ccaagttgat gccgttccag ccaatggcca gactccaatc cagagaacca    6120
tcaagccaga tgtcagaagc tacaccatca caggttaca accaggcact gactacaaga    6180
tctacctgta caccttgaat gacaatgctc ggagctcccc tgtggtcatc gacgcctcca    6240
ctgccattga tgcaccatcc aacctgcgtt tcctggccac cacacccaat tccttgctgg    6300
tatcatggca gccgccacgt gccaggatta ccggctacat catcaagtat gagaagcctg    6360
ggtctcctcc cagagaagtg gtccctcggc cccgccctgg tgtcacagag gctactatta    6420
ctgggcctga accgggaacc gaatatacaa tttatgtcat tgccctgaag aataatcaga    6480
agagcgagcc cctgattgga aggaaaaaga cagacgagct tccccaactg gtaaccttc    6540 cacaccccaa tcttcatgga ccagagatct tggatgttcc ttccacagtt caaagaccc    6600 ctttcgtcac ccaccctggg tatgacactg gaaatggtat tcagcttcct ggcacttctg    6660
gtcagcaacc cagtgttggg caacaaatga tctttgagga acatggtttt aggcggacca    6720
```

```
caccgcccac aacggccacc cccataaggc ataggccaag accatacccg ccgaatgtag    6780
gtgaggaaat ccaaattggt cacatcccca gggaagatgt agactatcac ctgtacccac    6840
acggtccggg actcaatcca aatgcctcta caggacaaga agctctctct cagacaacca    6900
tctcatgggc cccattccag gacacttctg agtacatcat ttcatgtcat cctgttggca    6960
ctgatgaaga acccttacag ttcagggttc ctggaacttc taccagtgcc actctgacag    7020
gcctcaccag aggtgccacc tacaacatca tagtggaggc actgaaagac cagcagaggc    7080
ataaggttcg ggaagaggtt gttaccgtgg gcaactctgt caacgaaggc ttgaaccaac    7140
ctacggatga ctcgtgcttt gacccctaca cagtttccca ttatgccgtt ggagatgagt    7200
gggaacgaat gtctgaatca ggctttaaac tgttgtgcca gtgcttaggc tttggaagtg    7260
gtcatttcag atgtgattca tctagatggt gccatgacaa tggtgtgaac tacaagattg    7320
gagagaagtg ggaccgtcag ggagaaaatg gccagatgat gagctgcaca tgtcttggga    7380
acggaaaagg agaattcaag tgtgaccctc atgaggcaac gtgttatgat gatgggaaga    7440
cataccacgt aggagaacag tggcagaagg aatatctcgg tgccatttgc tcctgcacat    7500
gctttggagg ccagcggggc tggcgctgtg acaactgccg cagacctggg ggtgaaccca    7560
gtcccgaagg cactactggc cagtcctaca accagtattc tcagagatac catcagagaa    7620
caaacactaa tgttaattgc ccaattgagt gcttcatgcc tttagatgta caggctgaca    7680
gagaagattc ccgagagtaa atcatctttc caatccagag aacaagcat gtctctctgc     7740 caagatccat ctaaactgga gtgatgttag cagacccagc ttagagttct tctttcttc     7800 ttaagccctt tgctctggag aagttctcc agcttcagct caactcacag cttctccaag     7860
catcaccctg ggagtttcct gagggttttc tcataaatga gggctgcaca ttgcctgttc    7920
tgcttcgaag tattcaatac cgctcagtat tttaaatgaa gtgattctaa gatttggttt    7980
gggatcaata ggaaagcata tgcagccaac caagatgcaa atgttttgaa atgatatgac    8040
caaaatttta agtaggaaag tcacccaaac acttctgctt tcacttaagt gtctggcccg    8100
caatactgta ggaacaagca tgatcttgtt actgtgatat tttaaatatc cacagtactc    8160 acttttcca aatgatccta gtaattgcct agaaatatct ttctcttacc tgttatttat    8220 caattttcc cagtatttt atacggaaaa aattgtattg aaaacactta gtatgcagtt     8280
gataagagga atttggtata attatggtgg gtgattattt tttatactgt atgtgccaaa    8340
gctttactac tgtggaaaga caactgtttt aataaaagat ttacattcca caacttgaag    8400
ttcatctatt tgatataaga caccttcggg ggaaataatt cctgtgaata ttcttttca     8460 attcagcaaa catttgaaaa tctatgatgt gcaagtctaa ttgttgattt cagtacaaga    8520
ttttctaaat cagttgctac aaaaactgat tggttttgt cacttcatct cttcactaat     8580
ggagatagct ttacactttc tgctttaata gatttaagtg gaccccaata tttattaaaa    8640
ttgctagttt accgttcaga agtataatag aaataatctt tagttgctct tttctaacca    8700
ttgtaattct tcccttcttc cctccacctt tccttcattg aataaacctc tgttcaaaga    8760
gattgcctgc aagggaaata aaatgacta agatattaaa aaaaaaaaa aaaaa            8815
```

<210> SEQ ID NO 16
<211> LENGTH: 2477
<212> TYPE: PRT
<213> ORGANISM: Homo sapiens

<400> SEQUENCE: 16

-continued

```
Met Leu Arg Gly Pro Gly Pro Gly Leu Leu Leu Ala Val Gln Cys
 1               5                  10                  15

Leu Gly Thr Ala Val Pro Ser Thr Gly Ala Ser Lys Ser Lys Arg Gln
             20                  25                  30

Ala Gln Gln Met Val Gln Pro Gln Ser Pro Val Ala Val Ser Gln Ser
         35                  40                  45

Lys Pro Gly Cys Tyr Asp Asn Gly Lys His Tyr Gln Ile Asn Gln Gln
     50                  55                  60

Trp Glu Arg Thr Tyr Leu Gly Asn Ala Leu Val Cys Thr Cys Tyr Gly
 65                  70                  75                  80

Gly Ser Arg Gly Phe Asn Cys Glu Ser Lys Pro Glu Ala Glu Glu Thr
                 85                  90                  95

Cys Phe Asp Lys Tyr Thr Gly Asn Thr Tyr Arg Val Gly Asp Thr Tyr
            100                 105                 110

Glu Arg Pro Lys Asp Ser Met Ile Trp Asp Cys Thr Cys Ile Gly Ala
            115                 120                 125

Gly Arg Gly Arg Ile Ser Cys Thr Ile Ala Asn Arg Cys His Glu Gly
        130                 135                 140

Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
                165                 170                 175

Trp Thr Cys Lys Pro Ile Ala Glu Lys Cys Phe Asp His Ala Ala Gly
            180                 185                 190

Thr Ser Tyr Val Val Gly Glu Thr Trp Glu Lys Pro Tyr Gln Gly Trp
        195                 200                 205

Met Met Val Asp Cys Thr Cys Leu Gly Glu Gly Ser Gly Arg Ile Thr
    210                 215                 220

Cys Thr Ser Arg Asn Arg Cys Asn Asp Gln Asp Thr Arg Thr Ser Tyr
225                 230                 235                 240

Arg Ile Gly Asp Thr Trp Ser Lys Lys Asp Asn Arg Gly Asn Leu Leu
                245                 250                 255

Gln Cys Ile Cys Thr Gly Asn Gly Arg Gly Glu Trp Lys Cys Glu Arg
            260                 265                 270

His Thr Ser Val Gln Thr Thr Ser Ser Gly Ser Gly Pro Phe Thr Asp
        275                 280                 285

Val Arg Ala Ala Val Tyr Gln Pro Gln Pro His Pro Gln Pro Pro Pro
    290                 295                 300

Tyr Gly His Cys Val Thr Asp Ser Gly Val Val Tyr Ser Val Gly Met
305                 310                 315                 320

Gln Trp Leu Lys Thr Gln Gly Asn Lys Gln Met Leu Cys Thr Cys Leu
                325                 330                 335

Gly Asn Gly Val Ser Cys Gln Glu Thr Ala Val Thr Gln Thr Tyr Gly
            340                 345                 350

Gly Asn Ser Asn Gly Glu Pro Cys Val Leu Pro Phe Thr Tyr Asn Gly
        355                 360                 365

Arg Thr Phe Tyr Ser Cys Thr Thr Glu Gly Arg Gln Asp Gly His Leu
    370                 375                 380

Trp Cys Ser Thr Thr Ser Asn Tyr Glu Gln Asp Gln Lys Tyr Ser Phe
385                 390                 395                 400

Cys Thr Asp His Thr Val Leu Val Gln Thr Arg Gly Gly Asn Ser Asn
                405                 410                 415

Gly Ala Leu Cys His Phe Pro Phe Leu Tyr Asn Asn His Asn Tyr Thr
```

-continued

```
              420                 425                 430
Asp Cys Thr Ser Glu Gly Arg Arg Asp Asn Met Lys Trp Cys Gly Thr
                435                 440                 445

Thr Gln Asn Tyr Asp Ala Asp Gln Lys Phe Gly Phe Cys Pro Met Ala
        450                 455                 460

Ala His Glu Glu Ile Cys Thr Thr Asn Glu Gly Val Met Tyr Arg Ile
465                 470                 475                 480

Gly Asp Gln Trp Asp Lys Gln His Asp Met Gly His Met Met Arg Cys
                485                 490                 495

Thr Cys Val Gly Asn Gly Arg Gly Glu Trp Thr Cys Ile Ala Tyr Ser
        500                 505                 510

Gln Leu Arg Asp Gln Cys Ile Val Asp Asp Ile Thr Tyr Asn Val Asn
        515                 520                 525

Asp Thr Phe His Lys Arg His Glu Glu Gly His Met Leu Asn Cys Thr
        530                 535                 540

Cys Phe Gly Gln Gly Arg Gly Arg Trp Lys Cys Asp Pro Val Asp Gln
545                 550                 555                 560

Cys Gln Asp Ser Glu Thr Gly Thr Phe Tyr Gln Ile Gly Asp Ser Trp
                565                 570                 575

Glu Lys Tyr Val His Gly Val Arg Tyr Gln Cys Tyr Cys Tyr Gly Arg
                580                 585                 590

Gly Ile Gly Glu Trp His Cys Gln Pro Leu Gln Thr Tyr Pro Ser Ser
                595                 600                 605

Ser Gly Pro Val Glu Val Phe Ile Thr Glu Thr Pro Ser Gln Pro Asn
        610                 615                 620

Ser His Pro Ile Gln Trp Asn Ala Pro Gln Pro Ser His Ile Ser Lys
625                 630                 635                 640

Tyr Ile Leu Arg Trp Arg Pro Lys Asn Ser Val Gly Arg Trp Lys Glu
                645                 650                 655

Ala Thr Ile Pro Gly His Leu Asn Ser Tyr Thr Ile Lys Gly Leu Lys
                660                 665                 670

Pro Gly Val Val Tyr Glu Gly Gln Leu Ile Ser Ile Gln Gln Tyr Gly
        675                 680                 685

His Gln Glu Val Thr Arg Phe Asp Phe Thr Thr Thr Ser Thr Ser Thr
        690                 695                 700

Pro Val Thr Ser Asn Thr Val Thr Gly Glu Thr Thr Pro Phe Ser Pro
705                 710                 715                 720

Leu Val Ala Thr Ser Glu Ser Val Thr Glu Ile Thr Ala Ser Ser Phe
                725                 730                 735

Val Val Ser Trp Val Ser Ala Ser Asp Thr Val Ser Gly Phe Arg Val
                740                 745                 750

Glu Tyr Glu Leu Ser Glu Glu Gly Asp Glu Pro Gln Tyr Leu Asp Leu
                755                 760                 765

Pro Ser Thr Ala Thr Ser Val Asn Ile Pro Asp Leu Leu Pro Gly Arg
        770                 775                 780

Lys Tyr Ile Val Asn Val Tyr Gln Ile Ser Glu Asp Gly Glu Gln Ser
785                 790                 795                 800

Leu Ile Leu Ser Thr Ser Gln Thr Thr Ala Pro Asp Ala Pro Pro Asp
                805                 810                 815

Pro Thr Val Asp Gln Val Asp Asp Thr Ser Ile Val Val Arg Trp Ser
        820                 825                 830

Arg Pro Gln Ala Pro Ile Thr Gly Tyr Arg Ile Val Tyr Ser Pro Ser
        835                 840                 845
```

```
Val Glu Gly Ser Ser Thr Glu Leu Asn Leu Pro Glu Thr Ala Asn Ser
    850                 855                 860

Val Thr Leu Ser Asp Leu Gln Pro Gly Val Gln Tyr Asn Ile Thr Ile
865                 870                 875                 880

Tyr Ala Val Glu Glu Asn Gln Glu Ser Thr Pro Val Val Ile Gln Gln
                885                 890                 895

Glu Thr Thr Gly Thr Pro Arg Ser Asp Thr Val Pro Ser Pro Arg Asp
            900                 905                 910

Leu Gln Phe Val Glu Val Thr Asp Val Lys Val Thr Ile Met Trp Thr
        915                 920                 925

Pro Pro Glu Ser Ala Val Thr Gly Tyr Arg Val Asp Val Ile Pro Val
    930                 935                 940

Asn Leu Pro Gly Glu His Gly Gln Arg Leu Pro Ile Ser Arg Asn Thr
945                 950                 955                 960

Phe Ala Glu Val Thr Gly Leu Ser Pro Gly Val Thr Tyr Tyr Phe Lys
                965                 970                 975

Val Phe Ala Val Ser His Gly Arg Glu Ser Lys Pro Leu Thr Ala Gln
            980                 985                 990

Gln Thr Thr Lys Leu Asp Ala Pro Thr Asn Leu Gln Phe Val Asn Glu
        995                 1000                1005

Thr Asp Ser Thr Val Leu Val Arg Trp Thr Pro Pro Arg Ala Gln Ile
    1010                1015                1020

Thr Gly Tyr Arg Leu Thr Val Gly Leu Thr Arg Arg Gly Gln Pro Arg
1025                1030                1035                1040

Gln Tyr Asn Val Gly Pro Ser Val Ser Lys Tyr Pro Leu Arg Asn Leu
                1045                1050                1055

Gln Pro Ala Ser Glu Tyr Thr Val Ser Leu Val Ala Ile Lys Gly Asn
            1060                1065                1070

Gln Glu Ser Pro Lys Ala Thr Gly Val Phe Thr Thr Leu Gln Pro Gly
        1075                1080                1085

Ser Ser Ile Pro Pro Tyr Asn Thr Glu Val Thr Glu Thr Thr Ile Val
    1090                1095                1100

Ile Thr Trp Thr Pro Ala Pro Arg Ile Gly Phe Lys Leu Gly Val Arg
1105                1110                1115                1120

Pro Ser Gln Gly Gly Glu Ala Pro Arg Glu Val Thr Ser Asp Ser Gly
                1125                1130                1135

Ser Ile Val Val Ser Gly Leu Thr Pro Gly Val Glu Tyr Val Tyr Thr
            1140                1145                1150

Ile Gln Val Leu Arg Asp Gly Gln Glu Arg Asp Ala Pro Ile Val Asn
        1155                1160                1165

Lys Val Val Thr Pro Leu Ser Pro Pro Thr Asn Leu His Leu Glu Ala
    1170                1175                1180

Asn Pro Asp Thr Gly Val Leu Thr Val Ser Trp Glu Arg Ser Thr Thr
1185                1190                1195                1200

Pro Asp Ile Thr Gly Tyr Arg Ile Thr Thr Thr Pro Thr Asn Gly Gln
                1205                1210                1215

Gln Gly Asn Ser Leu Glu Glu Val Val His Ala Asp Gln Ser Ser Cys
            1220                1225                1230

Thr Phe Asp Asn Leu Ser Pro Gly Leu Glu Tyr Asn Val Ser Val Tyr
        1235                1240                1245

Thr Val Lys Asp Asp Lys Glu Ser Val Pro Ile Ser Asp Thr Ile Ile
    1250                1255                1260
```

```
Pro Glu Val Pro Gln Leu Thr Asp Leu Ser Phe Val Asp Ile Thr Asp
1265                1270                1275                1280

Ser Ser Ile Gly Leu Arg Trp Thr Pro Leu Asn Ser Thr Ile Ile
            1285                1290                1295

Gly Tyr Arg Ile Thr Val Val Ala Ala Gly Glu Gly Ile Pro Ile Phe
                1300                1305                1310

Glu Asp Phe Val Asp Ser Ser Val Gly Tyr Tyr Thr Val Thr Gly Leu
            1315                1320                1325

Glu Pro Gly Ile Asp Tyr Asp Ile Ser Val Ile Thr Leu Ile Asn Gly
        1330                1335                1340

Gly Glu Ser Ala Pro Thr Thr Leu Thr Gln Gln Thr Ala Val Pro Pro
1345                1350                1355                1360

Pro Thr Asp Leu Arg Phe Thr Asn Ile Gly Pro Asp Thr Met Arg Val
                1365                1370                1375

Thr Trp Ala Pro Pro Ser Ile Asp Leu Thr Asn Phe Leu Val Arg
            1380                1385                1390

Tyr Ser Pro Val Lys Asn Glu Glu Asp Val Ala Glu Leu Ser Ile Ser
            1395                1400                1405

Pro Ser Asp Asn Ala Val Val Leu Thr Asn Leu Leu Pro Gly Thr Glu
        1410                1415                1420

Tyr Val Val Ser Val Ser Ser Val Tyr Glu Gln His Glu Ser Thr Pro
1425                1430                1435                1440

Leu Arg Gly Arg Gln Lys Thr Gly Leu Asp Ser Pro Thr Gly Ile Asp
                1445                1450                1455

Phe Ser Asp Ile Thr Ala Asn Ser Phe Thr Val His Trp Ile Ala Pro
            1460                1465                1470

Arg Ala Thr Ile Thr Gly Tyr Arg Ile Arg His His Pro Glu His Phe
            1475                1480                1485

Ser Gly Arg Pro Arg Glu Asp Arg Val Pro His Ser Arg Asn Ser Ile
            1490                1495                1500

Thr Leu Thr Asn Leu Thr Pro Gly Thr Glu Tyr Val Val Ser Ile Val
1505                1510                1515                1520

Ala Leu Asn Gly Arg Glu Glu Ser Pro Leu Leu Ile Gly Gln Gln Ser
                1525                1530                1535

Thr Val Ser Asp Val Pro Arg Asp Leu Glu Val Val Ala Ala Thr Pro
            1540                1545                1550

Thr Ser Leu Leu Ile Ser Trp Asp Ala Pro Ala Val Thr Val Arg Tyr
            1555                1560                1565

Tyr Arg Ile Thr Tyr Gly Glu Thr Gly Gly Asn Ser Pro Val Gln Glu
        1570                1575                1580

Phe Thr Val Pro Gly Ser Lys Ser Thr Ala Thr Ile Ser Gly Leu Lys
1585                1590                1595                1600

Pro Gly Val Asp Tyr Thr Ile Thr Val Tyr Ala Val Thr Gly Arg Gly
                1605                1610                1615

Asp Ser Pro Ala Ser Ser Lys Pro Ile Ser Ile Asn Tyr Arg Thr Glu
            1620                1625                1630

Ile Asp Lys Pro Ser Gln Met Gln Val Thr Asp Val Gln Asp Asn Ser
            1635                1640                1645

Ile Ser Val Lys Trp Leu Pro Ser Ser Ser Pro Val Thr Gly Tyr Arg
            1650                1655                1660

Val Thr Thr Thr Pro Lys Asn Gly Pro Gly Pro Thr Lys Thr Lys Thr
1665                1670                1675                1680

Ala Gly Pro Asp Gln Thr Glu Met Thr Ile Glu Gly Leu Gln Pro Thr
```

```
                    1685                1690                1695
Val Glu Tyr Val Val Ser Val Tyr Ala Gln Asn Pro Ser Gly Glu Ser
            1700                1705                1710

Gln Pro Leu Val Gln Thr Ala Val Thr Asn Ile Asp Arg Pro Lys Gly
            1715                1720                1725

Leu Ala Phe Thr Asp Val Asp Val Asp Ser Ile Lys Ile Ala Trp Glu
            1730                1735                1740

Ser Pro Gln Gly Gln Val Ser Arg Tyr Arg Val Thr Tyr Ser Ser Pro
1745                1750                1755                1760

Glu Asp Gly Ile His Glu Leu Phe Pro Ala Pro Asp Gly Glu Glu Asp
            1765                1770                1775

Thr Ala Glu Leu Gln Gly Leu Arg Pro Gly Ser Glu Tyr Thr Val Ser
            1780                1785                1790

Val Val Ala Leu His Asp Asp Met Glu Ser Gln Pro Leu Ile Gly Thr
            1795                1800                1805

Gln Ser Thr Ala Ile Pro Ala Pro Thr Asp Leu Lys Phe Thr Gln Val
            1810                1815                1820

Thr Pro Thr Ser Leu Ser Ala Gln Trp Thr Pro Pro Asn Val Gln Leu
1825                1830                1835                1840

Thr Gly Tyr Arg Val Arg Val Thr Pro Lys Glu Lys Thr Gly Pro Met
            1845                1850                1855

Lys Glu Ile Asn Leu Ala Pro Asp Ser Ser Ser Val Val Val Ser Gly
            1860                1865                1870

Leu Met Val Ala Thr Lys Tyr Glu Val Ser Val Tyr Ala Leu Lys Asp
            1875                1880                1885

Thr Leu Thr Ser Arg Pro Ala Gln Gly Val Val Thr Thr Leu Glu Asn
            1890                1895                1900

Val Ser Pro Pro Arg Arg Ala Arg Val Thr Asp Ala Thr Glu Thr Thr
1905                1910                1915                1920

Ile Thr Ile Ser Trp Arg Thr Lys Thr Glu Thr Ile Thr Gly Phe Gln
            1925                1930                1935

Val Asp Ala Val Pro Ala Asn Gly Gln Thr Pro Ile Gln Arg Thr Ile
            1940                1945                1950

Lys Pro Asp Val Arg Ser Tyr Thr Ile Thr Gly Leu Gln Pro Gly Thr
            1955                1960                1965

Asp Tyr Lys Ile Tyr Leu Tyr Thr Leu Asn Asp Asn Ala Arg Ser Ser
            1970                1975                1980

Pro Val Val Ile Asp Ala Ser Thr Ala Ile Asp Ala Pro Ser Asn Leu
1985                1990                1995                2000

Arg Phe Leu Ala Thr Thr Pro Asn Ser Leu Leu Val Ser Trp Gln Pro
            2005                2010                2015

Pro Arg Ala Arg Ile Thr Gly Tyr Ile Ile Lys Tyr Glu Lys Pro Gly
            2020                2025                2030

Ser Pro Pro Arg Glu Val Val Pro Arg Pro Arg Pro Gly Val Thr Glu
            2035                2040                2045

Ala Thr Ile Thr Gly Leu Glu Pro Gly Thr Glu Tyr Thr Ile Tyr Val
            2050                2055                2060

Ile Ala Leu Lys Asn Asn Gln Lys Ser Glu Pro Leu Ile Gly Arg Lys
2065                2070                2075                2080

Lys Thr Asp Glu Leu Pro Gln Leu Val Thr Leu Pro His Pro Asn Leu
            2085                2090                2095

His Gly Pro Glu Ile Leu Asp Val Pro Ser Thr Val Gln Lys Thr Pro
            2100                2105                2110
```

Phe Val Thr His Pro Gly Tyr Asp Thr Gly Asn Gly Ile Gln Leu Pro
    2115                2120                2125
Gly Thr Ser Gly Gln Gln Pro Ser Val Gly Gln Gln Met Ile Phe Glu
    2130                2135                2140
Glu His Gly Phe Arg Arg Thr Thr Pro Pro Thr Thr Ala Thr Pro Ile
2145                2150                2155                2160
Arg His Arg Pro Arg Pro Tyr Pro Pro Asn Val Gly Glu Glu Ile Gln
            2165                2170                2175
Ile Gly His Ile Pro Arg Glu Asp Val Asp Tyr His Leu Tyr Pro His
            2180                2185                2190
Gly Pro Gly Leu Asn Pro Asn Ala Ser Thr Gly Gln Glu Ala Leu Ser
    2195                2200                2205
Gln Thr Thr Ile Ser Trp Ala Pro Phe Gln Asp Thr Ser Glu Tyr Ile
    2210                2215                2220
Ile Ser Cys His Pro Val Gly Thr Asp Glu Glu Pro Leu Gln Phe Arg
2225                2230                2235                2240
Val Pro Gly Thr Ser Thr Ser Ala Thr Leu Thr Gly Leu Thr Arg Gly
            2245                2250                2255
Ala Thr Tyr Asn Ile Ile Val Glu Ala Leu Lys Asp Gln Gln Arg His
            2260                2265                2270
Lys Val Arg Glu Glu Val Val Thr Val Gly Asn Ser Val Asn Glu Gly
    2275                2280                2285
Leu Asn Gln Pro Thr Asp Asp Ser Cys Phe Asp Pro Tyr Thr Val Ser
    2290                2295                2300
His Tyr Ala Val Gly Asp Glu Trp Glu Arg Met Ser Glu Ser Gly Phe
2305                2310                2315                2320
Lys Leu Leu Cys Gln Cys Leu Gly Phe Gly Ser Gly His Phe Arg Cys
            2325                2330                2335
Asp Ser Ser Arg Trp Cys His Asp Asn Gly Val Asn Tyr Lys Ile Gly
            2340                2345                2350
Glu Lys Trp Asp Arg Gln Gly Glu Asn Gly Gln Met Met Ser Cys Thr
    2355                2360                2365
Cys Leu Gly Asn Gly Lys Gly Glu Phe Lys Cys Asp Pro His Glu Ala
    2370                2375                2380
Thr Cys Tyr Asp Asp Gly Lys Thr Tyr His Val Gly Glu Gln Trp Gln
2385                2390                2395                2400
Lys Glu Tyr Leu Gly Ala Ile Cys Ser Cys Thr Cys Phe Gly Gly Gln
            2405                2410                2415
Arg Gly Trp Arg Cys Asp Asn Cys Arg Arg Pro Gly Gly Glu Pro Ser
            2420                2425                2430
Pro Glu Gly Thr Thr Gly Gln Ser Tyr Asn Gln Tyr Ser Gln Arg Tyr
    2435                2440                2445
His Gln Arg Thr Asn Thr Asn Val Asn Cys Pro Ile Glu Cys Phe Met
    2450                2455                2460
Pro Leu Asp Val Gln Ala Asp Arg Glu Asp Ser Arg Glu
2465                2470                2475

<210> SEQ ID NO 17
<211> LENGTH: 4678
<212> TYPE: DNA
<213> ORGANISM: Homo sapiens

<400> SEQUENCE: 17
gcacacagag cagcataaag cccagttgct ttgggaagtg tttgggacca gatggattgt    60

-continued

```
agggagtagg gtacaataca gtctgttctc ctccagctcc ttctttctgc aacatgggga    120
agaacaaact ccttcatcca agtctggttc ttctcctctt ggtcctcctg cccacagacg    180
cctcagtctc tggaaaaccg cagtatatgg ttctggtccc ctccctgctc cacactgaga    240
ccactgagaa gggctgtgtc cttctgagct acctgaatga gacagtgact gtaagtgctt    300
ccttggagtc tgtcagggga aacaggagcc tcttcactga cctggaggcg gagaatgacg    360
tactccactg tgtcgccttc gctgtcccaa agtcttcatc caatgaggag gtaatgttcc    420
tcactgtcca agtgaaagga ccaacccaag aatttaagaa gcggaccaca gtgatggtta    480
agaacgagga cagtctggtc tttgtccaga cagacaaatc aatctacaaa ccagggcaga    540
cagtgaaatt tcgtgttgtc tccatggatg aaaactttca ccccctgaat gagttgattc    600
cactagtata cattcaggat cccaaaggaa atcgcatcgc acaatggcag agtttccagt    660
tagagggtgg cctcaagcaa ttttcttttc ccctctcatc agagcccttc cagggctcct    720
acaaggtggg ggtacagaag aaatcaggtg aaggacaga gcacccttc accgtggagg    780 aatttgttct tcccaagttt gaagtacaag taacagtgcc aaagataatc accatcttgg    840
aagaagagat gaatgtatca gtgtgtggcc tatacacata tgggaagcct gtccctggac    900
atgtgactgt gagcatttgc agaaagtata gtgacgcttc cgactgccac ggtgaagatt    960
cacaggcttt ctgtgagaaa ttcagtggac agctaaacag ccatggctgc ttctatcagc   1020
aagtaaaaac caaggtcttc cagctgaaga ggaaggagta tgaaatgaaa cttcacactg   1080
aggcccagat ccaagaagaa ggaacagtgg tggaattgac tggaaggcag tccagtgaaa   1140
tcacaagaac cataaccaaa ctctcatttg tgaaagtgga ctcacacttt cgacagggaa   1200
ttcccttctt tgggcaggtg cgcctagtag atgggaaagg cgtccctata ccaaataaag   1260
tcatattcat cagaggaaat gaagcaaact attactccaa tgctaccacg gatgagcatg   1320
gccttgtaca gttctctatc aacaccacca atgttatggg tacctctctt actgttaggg   1380
tcaattacaa ggatcgtagt ccctgttacg gctaccagtg ggtgtcagaa gaacacgaag   1440
aggcacatca cactgcttat cttgtgttct ccccaagcaa gagctttgtc cacctttgagc  1500 ccatgtctca tgaactaccc tgtggccata ctcagacagt ccaggcacat tatattctga   1560
atggaggcac cctgctgggg ctgaagaagc tctccttcta ttatctgata atggcaaagg   1620
gaggcattgt ccgaactggg actcatggac tgcttgtgaa gcaggaagac atgaagggcc   1680 attttccat ctcaatccct gtgaagtcag acattgctcc tgtcgctcgg ttgctcatct    1740
atgctgtttt acctaccggg gacgtgattg gggattctgc aaaatatgat gttgaaaatt   1800
gtctggccaa caaggtggat ttgagcttca gcccatcaca aagtctccca gcctcacacg   1860
cccacctgcg agtcacagcg gctcctcagt ccgtctgcgc cctccgtgct gtggaccaaa   1920
gcgtgctgct catgaagcct gatgctgagc tctcggcgtc ctcggtttac aacctgctac   1980
cagaaaagga cctcactggc ttccctgggc ctttgaatga ccaggacgat gaagactgca   2040
tcaatcgtca taatgtctat attaatggaa tcacatatac tccagtatca agtacaaatg   2100
aaaaggatat gtacagcttc ctagaggaca tgggcttaaa ggcattcacc aactcaaaga   2160
ttcgtaaacc caaatgtgt ccacagcttc aacagtatga aatgcatgga cctgaaggtc    2220
tacgtgtagg ttttatgag tcagatgtaa tgggaagagg ccatgcacgc ctggtgcatg     2280
ttgaagagcc tcacacggag accgtacgaa agtacttccc tgagacatgg atctgggatt   2340
tggtggtggt aaactcagca ggtgtggctg aggtaggagt aacagtccct gacaccatca   2400
```

```
ccgagtggaa ggcagggggcc ttctgcctgt ctgaagatgc tggacttggt atctcttcca    2460
ctgcctctct ccgagccttc cagcccttct tgtggagct  cacaatgcct tactctgtga    2520
ttcgtggaga ggccttcaca ctcaaggcca cggtcctaaa ctaccttccc aaatgcatcc    2580
gggtcagtgt gcagctggaa gcctctcccg ccttcctagc tgtcccagtg gagaaggaac    2640
aagcgcctca ctgcatctgt gcaaacgggc ggcaaactgt gtcctgggca gtaaccccaa    2700
agtcattagg aaatgtgaat ttcactgtga gcgcagaggc actagagtct caagagctgt    2760
gtgggactga ggtgccttca gttcctgaac acggaaggaa agacacagtc atcaagcctc    2820
tgttggttga acctgaagga ctagagaagg aaacaacatt caactcccta ctttgtccat    2880
caggtggtga ggtttctgaa gaattatccc tgaaactgcc accaaatgtg gtagaagaat    2940
ctgcccgagc ttctgtctca gttttgggag acatattagg ctctgccatg caaaacacac    3000
aaaatcttct ccagatgccc tatggctgtg gagagcagaa tatggtcctc tttgctccta    3060
acatctatgt actggattat ctaaatgaaa cacagcagct tactccagag atcaagtcca    3120
aggccattgg ctatctcaac actggttacc agagacagtt gaactacaaa cactatgatg    3180
gctcctacag caccttttgg gagcgatatg caggaacca gggcaacacc tggctcacag    3240
cctttgttct gaagactttt gcccaagctc gagcctacat cttcatcgat gaagcacaca    3300
ttacccaagc cctcatatgg ctctcccaga ggcagaagga caatggctgt tcaggagct    3360
ctgggtcact gctcaacaat gccataaagg gaggagtaga agatgaagtg accctctccg    3420
cctatatcac catcgccctt ctggagattc ctctcacagt cactcaccct gttgtccgca    3480
atgccctgtt ttgcctggag tcagcctgga agacagcaca agaagggac  catggcagcc    3540
atgtatatac caaagcactg ctggcctatg cttttgccct ggcaggtaac caggacaaga    3600
ggaaggaagt actcaagtca cttaatgagg aagctgtgaa gaaagacaac tctgtccatt    3660
gggagcgccc tcagaaaccc aaggcaccag tggggcattt ttacgaaccc caggctccct    3720
ctgctgaggt ggagatgaca tcctatgtgc tcctcgctta tctcacggcc cagccagccc    3780
caacctcgga ggacctgacc tctgcaacca acatcgtgaa gtggatcacg aagcagcaga    3840
atgcccaggg cggtttctcc tccacccagg acacagtggt ggctctccat gctctgtcca    3900
aatatggagc agccacattt accaggactg ggaaggctgc acaggtgact atccagtctt    3960
cagggacatt ttccagcaaa ttccaagtgg acaacaacaa ccgcctgtta ctgcagcagg    4020
tctcattgcc agagctgcct ggggaataca gcatgaaagt gacaggagaa ggatgtgtct    4080
acctccagac atccttgaaa tacaatattc tcccagaaaa ggaagagttc ccctttgctt    4140
taggagtgca gactctgcct caaacttgtg atgaacccaa agcccacacc agcttccaaa    4200
tctccctaag tgtcagttac acagggagcc gctctgcctc caacatggcg atcgttgatg    4260
tgaagatggt ctctggcttc attcccctga agccaacagt gaaaatgctt gaaagatcta    4320
accatgtgag ccggacagaa gtcagcagca accatgtctt gatttacctt gataaggtgt    4380
caaatcagac actgagcttg ttcttcacgg ttctgcaaga tgtcccagta agagatctga    4440
aaccagccat agtgaaagtc tatgattact acgagacgga tgagtttgca attgctgagt    4500
acaatgctcc ttgcagcaaa gatcttggaa atgcttgaag accacaaggc tgaaaagtgc    4560
tttgctggag tcctgttctc agagctccac agaagacacg tgtttttgta tctttaaaga    4620
cttgatgaat aaacactttt tctggtcaat gtcaaaaaaa aaaaaaaaaa aaaaaaa      4678
```

<210> SEQ ID NO 18
<211> LENGTH: 1474

<212> TYPE: PRT
<213> ORGANISM: Homo sapiens

<400> SEQUENCE: 18

```
Met Gly Lys Asn Lys Leu Leu His Pro Ser Leu Val Leu Leu Leu
 1               5                  10                  15

Val Leu Leu Pro Thr Asp Ala Ser Val Ser Gly Lys Pro Gln Tyr Met
            20                  25                  30

Val Leu Val Pro Ser Leu Leu His Thr Glu Thr Thr Glu Lys Gly Cys
        35                  40                  45

Val Leu Leu Ser Tyr Leu Asn Glu Thr Val Thr Val Ser Ala Ser Leu
        50                  55                  60

Glu Ser Val Arg Gly Asn Arg Ser Leu Phe Thr Asp Leu Glu Ala Glu
65                  70                  75                  80

Asn Asp Val Leu His Cys Val Ala Phe Ala Val Pro Lys Ser Ser Ser
                85                  90                  95

Asn Glu Glu Val Met Phe Leu Thr Val Gln Val Lys Gly Pro Thr Gln
                100                 105                 110

Glu Phe Lys Lys Arg Thr Thr Val Met Val Lys Asn Glu Asp Ser Leu
            115                 120                 125

Val Phe Val Gln Thr Asp Lys Ser Ile Tyr Lys Pro Gly Gln Thr Val
        130                 135                 140

Lys Phe Arg Val Val Ser Met Asp Glu Asn Phe His Pro Leu Asn Glu
145                 150                 155                 160

Leu Ile Pro Leu Val Tyr Ile Gln Asp Pro Lys Gly Asn Arg Ile Ala
                165                 170                 175

Gln Trp Gln Ser Phe Gln Leu Glu Gly Gly Leu Lys Gln Phe Ser Phe
            180                 185                 190

Pro Leu Ser Ser Glu Pro Phe Gln Gly Ser Tyr Lys Val Val Val Gln
        195                 200                 205

Lys Lys Ser Gly Gly Arg Thr Glu His Pro Phe Thr Val Glu Glu Phe
210                 215                 220

Val Leu Pro Lys Phe Glu Val Gln Val Thr Val Pro Lys Ile Ile Thr
225                 230                 235                 240

Ile Leu Glu Glu Glu Met Asn Val Ser Val Cys Gly Leu Tyr Thr Tyr
                245                 250                 255

Gly Lys Pro Val Pro Gly His Val Thr Val Ser Ile Cys Arg Lys Tyr
            260                 265                 270

Ser Asp Ala Ser Asp Cys His Gly Glu Asp Ser Gln Ala Phe Cys Glu
        275                 280                 285

Lys Phe Ser Gly Gln Leu Asn Ser His Gly Cys Phe Tyr Gln Gln Val
        290                 295                 300

Lys Thr Lys Val Phe Gln Leu Lys Arg Lys Glu Tyr Glu Met Lys Leu
305                 310                 315                 320

His Thr Glu Ala Gln Ile Gln Glu Gly Thr Val Val Glu Leu Thr
                325                 330                 335

Gly Arg Gln Ser Ser Glu Ile Thr Arg Thr Ile Thr Lys Leu Ser Phe
            340                 345                 350

Val Lys Val Asp Ser His Phe Arg Gln Gly Ile Pro Phe Phe Gly Gln
        355                 360                 365

Val Arg Leu Val Asp Gly Lys Gly Val Pro Ile Pro Asn Lys Val Ile
        370                 375                 380

Phe Ile Arg Gly Asn Glu Ala Asn Tyr Tyr Ser Asn Ala Thr Thr Asp
385                 390                 395                 400
```

```
Glu His Gly Leu Val Gln Phe Ser Ile Asn Thr Thr Asn Val Met Gly
            405                 410                 415

Thr Ser Leu Thr Val Arg Val Asn Tyr Lys Asp Arg Ser Pro Cys Tyr
            420                 425                 430

Gly Tyr Gln Trp Val Ser Glu Glu His Glu Glu Ala His His Thr Ala
            435                 440                 445

Tyr Leu Val Phe Ser Pro Ser Lys Ser Phe Val His Leu Glu Pro Met
            450                 455                 460

Ser His Glu Leu Pro Cys Gly His Thr Gln Thr Val Gln Ala His Tyr
465                 470                 475                 480

Ile Leu Asn Gly Gly Thr Leu Leu Gly Leu Lys Lys Leu Ser Phe Tyr
                485                 490                 495

Tyr Leu Ile Met Ala Lys Gly Gly Ile Val Arg Thr Gly Thr His Gly
            500                 505                 510

Leu Leu Val Lys Gln Glu Asp Met Lys Gly His Phe Ser Ile Ser Ile
            515                 520                 525

Pro Val Lys Ser Asp Ile Ala Pro Val Ala Arg Leu Leu Ile Tyr Ala
            530                 535                 540

Val Leu Pro Thr Gly Asp Val Ile Gly Asp Ser Ala Lys Tyr Asp Val
545                 550                 555                 560

Glu Asn Cys Leu Ala Asn Lys Val Asp Leu Ser Phe Ser Pro Ser Gln
                565                 570                 575

Ser Leu Pro Ala Ser His Ala His Leu Arg Val Thr Ala Ala Pro Gln
            580                 585                 590

Ser Val Cys Ala Leu Arg Ala Val Asp Gln Ser Val Leu Leu Met Lys
            595                 600                 605

Pro Asp Ala Glu Leu Ser Ala Ser Ser Val Tyr Asn Leu Leu Pro Glu
            610                 615                 620

Lys Asp Leu Thr Gly Phe Pro Gly Pro Leu Asn Asp Gln Asp Asp Glu
625                 630                 635                 640

Asp Cys Ile Asn Arg His Asn Val Tyr Ile Asn Gly Ile Thr Tyr Thr
                645                 650                 655

Pro Val Ser Ser Thr Asn Glu Lys Asp Met Tyr Ser Phe Leu Glu Asp
            660                 665                 670

Met Gly Leu Lys Ala Phe Thr Asn Ser Lys Ile Arg Lys Pro Lys Met
            675                 680                 685

Cys Pro Gln Leu Gln Gln Tyr Glu Met His Gly Pro Glu Gly Leu Arg
            690                 695                 700

Val Gly Phe Tyr Glu Ser Asp Val Met Gly Arg Gly His Ala Arg Leu
705                 710                 715                 720

Val His Val Glu Glu Pro His Thr Glu Thr Val Arg Lys Tyr Phe Pro
                725                 730                 735

Glu Thr Trp Ile Trp Asp Leu Val Val Val Asn Ser Ala Gly Val Ala
            740                 745                 750

Glu Val Gly Val Thr Val Pro Asp Thr Ile Thr Glu Trp Lys Ala Gly
            755                 760                 765

Ala Phe Cys Leu Ser Glu Asp Ala Gly Leu Gly Ile Ser Ser Thr Ala
            770                 775                 780

Ser Leu Arg Ala Phe Gln Pro Phe Phe Val Glu Leu Thr Met Pro Tyr
785                 790                 795                 800

Ser Val Ile Arg Gly Glu Ala Phe Thr Leu Lys Ala Thr Val Leu Asn
                805                 810                 815
```

-continued

```
Tyr Leu Pro Lys Cys Ile Arg Val Ser Val Gln Leu Glu Ala Ser Pro
            820                 825                 830

Ala Phe Leu Ala Val Pro Val Glu Lys Glu Gln Ala Pro His Cys Ile
        835                 840                 845

Cys Ala Asn Gly Arg Gln Thr Val Ser Trp Ala Val Thr Pro Lys Ser
850                 855                 860

Leu Gly Asn Val Asn Phe Thr Val Ser Ala Glu Ala Leu Glu Ser Gln
865                 870                 875                 880

Glu Leu Cys Gly Thr Glu Val Pro Ser Val Pro Glu His Gly Arg Lys
                885                 890                 895

Asp Thr Val Ile Lys Pro Leu Leu Val Glu Pro Glu Gly Leu Glu Lys
            900                 905                 910

Glu Thr Thr Phe Asn Ser Leu Leu Cys Pro Ser Gly Gly Glu Val Ser
        915                 920                 925

Glu Glu Leu Ser Leu Lys Leu Pro Pro Asn Val Val Glu Glu Ser Ala
    930                 935                 940

Arg Ala Ser Val Ser Val Leu Gly Asp Ile Leu Gly Ser Ala Met Gln
945                 950                 955                 960

Asn Thr Gln Asn Leu Leu Gln Met Pro Tyr Gly Cys Gly Glu Gln Asn
                965                 970                 975

Met Val Leu Phe Ala Pro Asn Ile Tyr Val Leu Asp Tyr Leu Asn Glu
            980                 985                 990

Thr Gln Gln Leu Thr Pro Glu Ile Lys Ser Lys Ala Ile Gly Tyr Leu
        995                 1000                1005

Asn Thr Gly Tyr Gln Arg Gln Leu Asn Tyr Lys His Tyr Asp Gly Ser
    1010                1015                1020

Tyr Ser Thr Phe Gly Glu Arg Tyr Gly Arg Asn Gln Gly Asn Thr Trp
1025                1030                1035                1040

Leu Thr Ala Phe Val Leu Lys Thr Phe Ala Gln Ala Arg Ala Tyr Ile
                1045                1050                1055

Phe Ile Asp Glu Ala His Ile Thr Gln Ala Leu Ile Trp Leu Ser Gln
            1060                1065                1070

Arg Gln Lys Asp Asn Gly Cys Phe Arg Ser Ser Gly Ser Leu Leu Asn
        1075                1080                1085

Asn Ala Ile Lys Gly Gly Val Glu Asp Glu Val Thr Leu Ser Ala Tyr
    1090                1095                1100

Ile Thr Ile Ala Leu Leu Glu Ile Pro Leu Thr Val Thr His Pro Val
1105                1110                1115                1120

Val Arg Asn Ala Leu Phe Cys Leu Glu Ser Ala Trp Lys Thr Ala Gln
                1125                1130                1135

Glu Gly Asp His Gly Ser His Val Tyr Thr Lys Ala Leu Leu Ala Tyr
            1140                1145                1150

Ala Phe Ala Leu Ala Gly Asn Gln Asp Lys Arg Lys Glu Val Leu Lys
        1155                1160                1165

Ser Leu Asn Glu Glu Ala Val Lys Lys Asp Asn Ser Val His Trp Glu
    1170                1175                1180

Arg Pro Gln Lys Pro Lys Ala Pro Val Gly His Phe Tyr Glu Pro Gln
1185                1190                1195                1200

Ala Pro Ser Ala Glu Val Glu Met Thr Ser Tyr Val Leu Leu Ala Tyr
                1205                1210                1215

Leu Thr Ala Gln Pro Ala Pro Thr Ser Glu Asp Leu Thr Ser Ala Thr
            1220                1225                1230

Asn Ile Val Lys Trp Ile Thr Lys Gln Gln Asn Ala Gln Gly Gly Phe
```

-continued

```
              1235                1240                1245
Ser Ser Thr Gln Asp Thr Val Val Ala Leu His Ala Leu Ser Lys Tyr
         1250                1255                1260

Gly Ala Ala Thr Phe Thr Arg Thr Gly Lys Ala Ala Gln Val Thr Ile
1265                1270                1275                1280

Gln Ser Ser Gly Thr Phe Ser Ser Lys Phe Gln Val Asp Asn Asn Asn
                1285                1290                1295

Arg Leu Leu Leu Gln Gln Val Ser Leu Pro Glu Leu Pro Gly Glu Tyr
             1300                1305                1310

Ser Met Lys Val Thr Gly Glu Gly Cys Val Tyr Leu Gln Thr Ser Leu
             1315                1320                1325

Lys Tyr Asn Ile Leu Pro Glu Lys Glu Glu Phe Pro Phe Ala Leu Gly
         1330                1335                1340

Val Gln Thr Leu Pro Gln Thr Cys Asp Glu Pro Lys Ala His Thr Ser
1345                1350                1355                1360

Phe Gln Ile Ser Leu Ser Val Ser Tyr Thr Gly Ser Arg Ser Ala Ser
                1365                1370                1375

Asn Met Ala Ile Val Asp Val Lys Met Val Ser Gly Phe Ile Pro Leu
                1380                1385                1390

Lys Pro Thr Val Lys Met Leu Glu Arg Ser Asn His Val Ser Arg Thr
             1395                1400                1405

Glu Val Ser Ser Asn His Val Leu Ile Tyr Leu Asp Lys Val Ser Asn
         1410                1415                1420

Gln Thr Leu Ser Leu Phe Phe Thr Val Leu Gln Asp Val Pro Val Arg
1425                1430                1435                1440

Asp Leu Lys Pro Ala Ile Val Lys Val Tyr Asp Tyr Tyr Glu Thr Asp
                1445                1450                1455

Glu Phe Ala Ile Ala Glu Tyr Asn Ala Pro Cys Ser Lys Asp Leu Gly
                1460                1465                1470

Asn Ala
```

METHODS OF PREDICTING AND DECREASING THE RISK OF PREGNANCY LOSS

CROSS REFERENCE TO RELATED APPLICATION

This application is a continuation of U.S. application Ser. No. 13/583,981, filed on Sep. 11, 2012, which is a U.S. National Phase Application of International Patent Application No. PCT/US2011/028192, filed Mar. 11, 2011, entitled "METHODS OF PREDICTING AND DECREASING THE RISK OF PREGNANCY LOSS," which claims priority to U.S. Application No. 61/313,024, filed on Mar. 11, 2010, the entire contents of each of which are hereby incorporated by reference in their entirety.

TECHNICAL FIELD

This invention relates to biomarkers of recurrent pregnancy loss, and methods of use thereof.

BACKGROUND

Miscarriage occurs in an estimated 10% to 15% of all pregnancies of less than 20 weeks gestation (Stirrat, *Lancet* 336:673-675, 1990). Recurrent miscarriage is classically defined as the occurrence of three or more consecutive losses of clinically-recognized pregnancies prior to the 20th week of gestation, exclusive of molar and ectopic pregnancies. Prospective studies have assessed the risks of subsequent miscarriage after one miscarriage to be 15%, rising to 17% to 31% after two miscarriages, and 25% to 46% after three or more miscarriages. Although the loss of one pregnancy (or sometimes even two pregnancies) is considered by many clinicians to be within the range of normal (and likely due to gamete failure), loss of three or more pregnancies is generally considered to be associated with a pathological condition. Most providers will initiate an evaluation for recurrent pregnancy loss (RPL) after two or more consecutive miscarriages.

SUMMARY

The present invention is based, at least in part, on the discovery and characterization of differences in the humoral immune responses from women with a history of recurrent pregnancy loss (RPL) compared to multiparous women with an uncomplicated obstetrical history in terms of IgG subclasses and trophoblast cell antigens recognized. Thus, the present invention includes methods for diagnosing and predicting the risk of pregnancy loss based on the presence of an aberrant humoral response, specifically to three proteins, Apolipoprotein B-100 (ApoB-100), alpha2macroglobin ($\alpha$2M), and fibronectin. The presence, a detectable level, or an increase of maternal IgG antibodies to trophoblast-derived fibronectin and/or Apolipoprotein B-100, and/or the presence, a detectable level, or a increase of antibody recognition to $\alpha$2M is associated with a history of RPL and an increased risk of future pregnancy loss.

Provided are methods of predicting the risk of pregnancy loss in a subject (i.e., a female subject) including providing a sample containing serum from the subject; and detecting the presence, absence, or levels of antibodies to one or more (e.g., one, two, or three) of fibronectin (protein or nucleic acid), $\alpha$2M (protein or nucleic acid), and ApoB-100 (protein or nucleic acid) in the sample, wherein the presence or a detectable level of antibodies to fibronectin (protein or nucleic acid) and/or ApoB-100 (protein or nucleic acid), and/or the presence or a detectable level of antibodies to $\alpha$2M (protein or nucleic acid) in the sample indicates that the subject has an increased risk of pregnancy loss. Some embodiments of these methods include providing a sample containing serum from the subject, detecting the presence or absence of antibodies to fibronectin in the sample, wherein the presence of antibodies to fibronectin in the sample indicates that the subject has an increased risk of pregnancy loss. Some embodiments of these methods further include detecting the presence or absence of antibodies to ApoB-100 in the sample, wherein the presence of antibodies to fibronectin to ApoB-100 indicates that the subject has an increased risk of pregnancy loss. Some embodiments of these methods further include detecting the absence or presence of antibodies to $\alpha$2M in the sample, wherein the presence of antibodies to fibronectin or ApoB-100, or the presence of antibodies to $\alpha$2M indicates that the subject has an increased risk of pregnancy loss.

Also provided are methods of identifying a subject at risk of pregnancy loss including providing a sample containing serum from the subject, and detecting the presence, absence, or level of antibodies to one or more (e.g., one, two, or three) of fibronectin (protein or nucleic acid), $\alpha$2M (protein or nucleic acid), and ApoB-100 (protein or nucleic acid) in the sample, wherein a subject having antibodies to fibronectin (protein or nucleic acid) and/or ApoB-100 (protein or nucleic acid), and/or having or having a detectable level of antibodies to $\alpha$2M (protein or nucleic acid) in the sample is identified as being at risk of pregnancy loss. Some embodiments of these methods include providing a sample containing serum from the subject, and detecting the presence or absence of antibodies to fibronectin in the sample, wherein a subject having antibodies to fibronectin present in the sample is identified as being at risk of pregnancy loss. Some embodiments of these methods further include detecting the presence or absence of antibodies to ApoB-100 in the sample, wherein a subject having antibodies to fibronectin or ApoB-100 present in the sample is identified as being at risk of pregnancy loss. Some embodiments of these methods further include detecting the presence or absence of antibodies to $\alpha$2M in the sample, wherein a subject having antibodies to fibronectin or ApoB-100, or having antibodies to $\alpha$2M present in the sample is identified as being at risk of pregnancy loss.

Also provided are methods of selecting a subject for participation in a clinical study including providing a sample containing serum from the sample, and detecting the presence or absence of antibodies to one or more (e.g., one, two, or three) of fibronectin (protein or nucleic acid), $\alpha$2M (protein or nucleic acid), and apoliprotein B (protein or nucleic acid) in the sample, wherein a subject having antibodies to fibronectin (protein or nucleic acid) and/or ApoB-100 (protein or nucleic acid), and/or having or having a detectable level of antibodies to $\alpha$2M (protein or nucleic acid) in the sample is selected for participation in a clinical study. Some embodiments of these methods include providing a sample containing serum from the subject and detecting the presence or absence of antibodies to fibronectin in the sample, wherein a subject having antibodies to fibronectin present in the sample is selected for participation in a clinical study. Some embodiments of these methods further include detecting the presence or absence of antibodies to ApoB-100 in the sample, wherein a subject having antibodies to fibronectin or ApoB-100 present in the sample is selected for participation in a clinical study. Some embodiments of these methods further include detecting the presence of absence of antibodies to $\alpha$2M in the sample, wherein a subject having antibodies to fibronectin or ApoB- 100, or having antibodies to α2M present in the sample is selected for participation in a clinical study.

Also provided are methods of decreasing the risk of pregnancy loss in a subject including providing a sample containing serum from the subject, detecting the presence or absence of antibodies to one or more (e.g., one, two, or three) of fibronectin (protein or nucleic acid), α2M (protein or nucleic acid), and ApoB-100 (protein or nucleic acid) in the sample, and administering a therapeutic treatment to a subject having antibodies to fibronectin (protein or nucleic acid) and/or ApoB-100 (protein or nucleic acid), and/or having or having a detectable level of antibodies to α2M (protein or mRNA) in the sample. Some embodiments of these methods include providing a sample comprising serum from the subject, detecting the presence or absence of antibodies to fibronectin in the sample, and administering a therapeutic treatment to a subject having antibodies to fibronectin present in the sample. Some embodiments of these methods further include detecting the presence or absence of antibodies to ApoB-100 in the sample, and administering a therapeutic treatment to a subject having antibodies to fibronectin or ApoB-100 present in the sample. Some embodiments of these methods further include detecting the presence or absence of antibodies to α2M in the sample, and administering a therapeutic treatment to a subject having antibodies to fibronectin or ApoB-100, or having antibodies to α2M present in the sample. In some embodiments of these methods, the therapeutic treatment is selected from complement inhibitors, hormone treatment, steroid treatment, passive immunotherapy with intravenous immunoglobulins, aspirin, and tumor necrosis factor-α (TNF-α) antagonists.

In any of the methods described herein, the subject is pregnant. In any of the embodiments of all the methods described herein, the sample is obtained from the pregnant subject within the first 20 weeks (e.g., within the first 19 weeks, 18 weeks, 17 weeks, 16 weeks, 15 weeks, 14 weeks, 13 weeks, 12 weeks, 11 weeks, 10 weeks, 9 weeks, 8 weeks, 7 weeks, 6 weeks, 5 weeks, 4 weeks, 3 weeks, 2 weeks, or 1 week), within the first 13 weeks, or within the first 12 weeks of pregnancy.

In some embodiments of all of the methods described herein, the subject has had at least one (e.g., two, three, four, or five) previous pregnancy loss or is suspected of having had at least one (e.g., two, three, four, or five) previous pregnancy loss. In some embodiments of all of the methods described herein, the subject is not pregnant, but is planning or considering a future pregnancy.

In some embodiments of all of the methods described herein, the subject having had at least one previous pregnancy loss or suspected of having had at least one previous pregnancy loss may be pregnant or may not be pregnant. In some embodiments of all of the methods described herein, the sample is obtained within the first 20 weeks (e.g., within the first 19 weeks, 18 weeks, 17 weeks, 16 weeks, 15 weeks, 14 weeks, 13 weeks, 12 weeks, 11 weeks, 10 weeks, 9 weeks, 8 weeks, 7 weeks, 6 weeks, 5 weeks, 4 weeks, 3 weeks, 2 weeks, or 1 week), the first 13 weeks, or within the first 12 weeks of pregnancy from the pregnant subject that has had at least one previous pregnancy loss or is suspected of having had at least one previous pregnancy loss.

In some embodiments of all of the methods described herein, the detecting of the presence, absence, or levels of antibodies includes contacting the sample with one or more (e.g., one, two, and three) antigens selected from the group consisting of ApoB-100 (protein or nucleic acid), fibronectin (protein or nucleic acid), and α2M (protein or nucleic acid), or antigenic fragments thereof, and detecting the binding of antibodies in the sample to the antigens. In some embodiments, the antigens are immobilized on a surface, e.g., in an array or on beads. In some embodiments of all of the methods described herein, the ApoB-100 (protein or nucleic acid), fibronectin (protein or nucleic acid), and/or α2M (protein or nucleic acid) are trophoblast-derived. In some embodiments of all of the methods described herein, the subject is human.

Also provided are kits, containing essentially, one or more (e.g., one, two, or three) ApoB-100 (protein or nucleic acid), fibronectin (protein or nucleic acid), and α2M (protein or nucleic acid), or antigenic fragments thereof.

As used herein, a "subject" is a vertebrate, including any member of the class mammalia, including humans, domestic and farm animals, and zoo, sports or pet animals, such as mouse, rabbit, pig, sheep, goat, cattle, and higher primates. In preferred embodiments, the subject is a human.

By the phrase "suspected of having had a previous pregnancy loss" is meant a subject who previously experienced one or more (e.g., one, two, three, or four) symptoms of a miscarriage (e.g., vaginal bleeding, pelvic cramps, abdominal pain, persistent lower back ache, and blood clots or grayish tissue passing from the vagina), but was not diagnosed as being pregnant (e.g., not diagnosed by a health care professional or through the use of a home diagnostic kit) at the time these symptoms occurred.

By the phrase "a subject having had a previous pregnancy loss" is meant a subject that has previously had at least one (e.g., two, three, four, or five) miscarriage. For example, a subject may have been diagnosed as being pregnant by a health care professional (e.g., a physician, nurse, physician's assistant, or a laboratory technician) or through the use of a home diagnostic kit, and thereafter experienced one or more (e.g., two, three, four, or five) symptoms of a miscarriage (e.g., vaginal bleeding, pelvic cramps, abdominal pain, persistent lower back ache, and blood clots or grayish tissue passing from the vagina) or failed to carry the fetus to term. The one or more previous miscarriages may also be confirmed by a health care professional (e.g., a physician, a nurse, a physician's assistant, or a laboratory technician).

By the term "antigen" or "antigenic fragment" is meant any portion of a molecule (e.g., peptide, nucleic acid (e.g., mRNA), carbohydrate, or lipid, or any combination thereof) that is specifically recognized by an antibody. For example, an antigen or antigenic fragment may be a peptide containing at least 5 (e.g., at least 6, 7, 8, 9, 10, 11, 12, 13, 14, 15, 16, 17, 18, 19, or 20 amino acids) contiguous amino acids. Exemplary peptide antigens or antigenic fragments contain at least 5 (e.g., at least 6, 7, 8, 9, 10, 11, 12, 13, 14, 15, 16, 17, 18, 19, or 20 amino acids) contiguous amino acids of the sequence within any one of SEQ ID NOS: 2, 4, 6, 8, 10, 12, 14, 16, and 18. The contiguous amino acid sequence may be present within any portion of the sequence of SEQ ID NOS: 2, 4, 6, 8, 10, 12, 14, 16, or 18, for example, a sequence starting at the N-terminus, a sequence ending at the C-terminus, or a sequence starting at any single amino acid within the sequence (with the exception of the last four amino acids at the C-terminus of the protein). Additional exemplary peptide antigens contain the sequence of SEQ ID NO: 2, 4, 6, 8, 10, 12, 14, 16, or 18.

Exemplary antigens or antigenic fragments that are nucleic acids contain at least 5 (e.g., at least 6, 7, 8, 9, 10, 11, 12, 13, 14, 15, 16, 17, 18, 19, or 20) contiguous nucleotides of the sequence within any one of SEQ ID NOS: 1, 3, 5, 7, 9, 11, 13, 15, and 17. The contiguous nucleotide sequence may be present within any portion of the sequence of SEQ ID NOS: 1, 3, 5, 7, 9, 11, 13, 15, or 17, for example, a sequence starting at the 5'-terminus, a sequence ending at the 3'-terminus, or a sequence starting at any single nucleotide within the sequence (with the exception of the last four nucleotides at the 3'-terminus of the nucleic acid). Additional exemplary nucleic acid antigens contain the sequence of SEQ ID NO: 1, 3, 5, 7, 9, 11, 13, 15, or 17.

By the term "at risk of pregnancy loss" is meant a subject that has an increased risk of having a miscarriage during pregnancy as compared to a control population (e.g., a group of subjects of the same age, a group of subjects not diagnosed as having recurrent pregnancy loss, a group of subjects that have never have had a miscarriage, or a group of subjects that have never experienced, at a single time, a combination of three or more symptoms of a miscarriage).

By the phrase "a subject planning or considering future pregnancy" is meant a subject who is not pregnant, but is planning a future pregnancy or considering becoming pregnant in the future.

By the phrase "therapeutic treatment" is meant a treatment that may decrease (e.g., a significant decrease (as used herein, the term "decrease" is meant a statistically significant decrease), such as by at least 5%, 10%, 15%, 20%, 25%, 30%, 35%, 40%, 45%, or 50%) the risk of having a miscarriage in a subject. Non-limiting examples of therapeutic treatment are known in the art and include, without limitation, complement inhibitors, hormone treatment, steroid treatment, passive immunotherapy with intravenous immunoglobulins, aspirin, and TNF-α antagonists. Examples of therapeutic treatments are described herein and additional examples of therapeutic treatments are known in the art.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1:
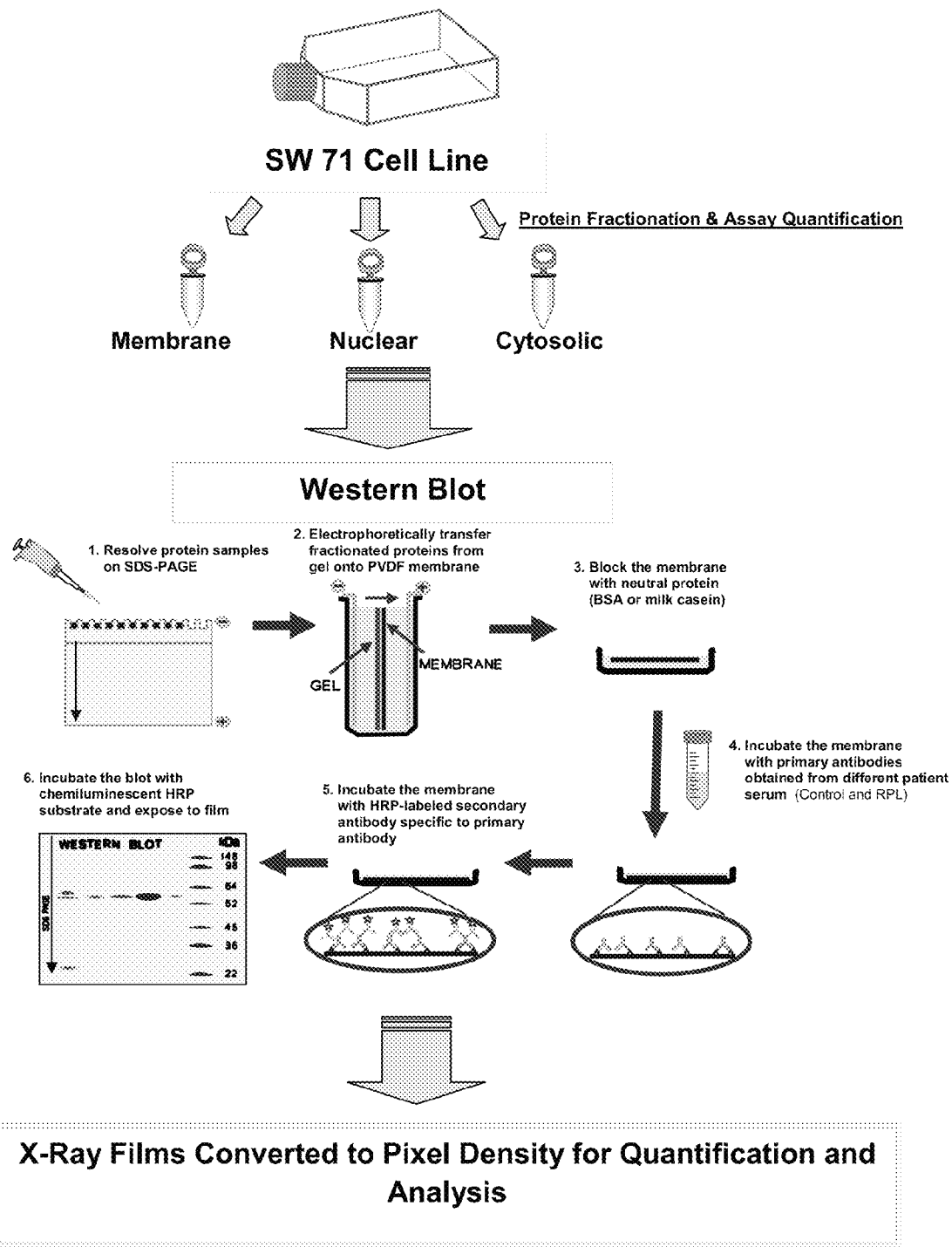
FIG. 1 is a schematic illustration of exemplary methods for obtaining trophoblast cellular proteins and performing Western blot analysis.
Figure 2:
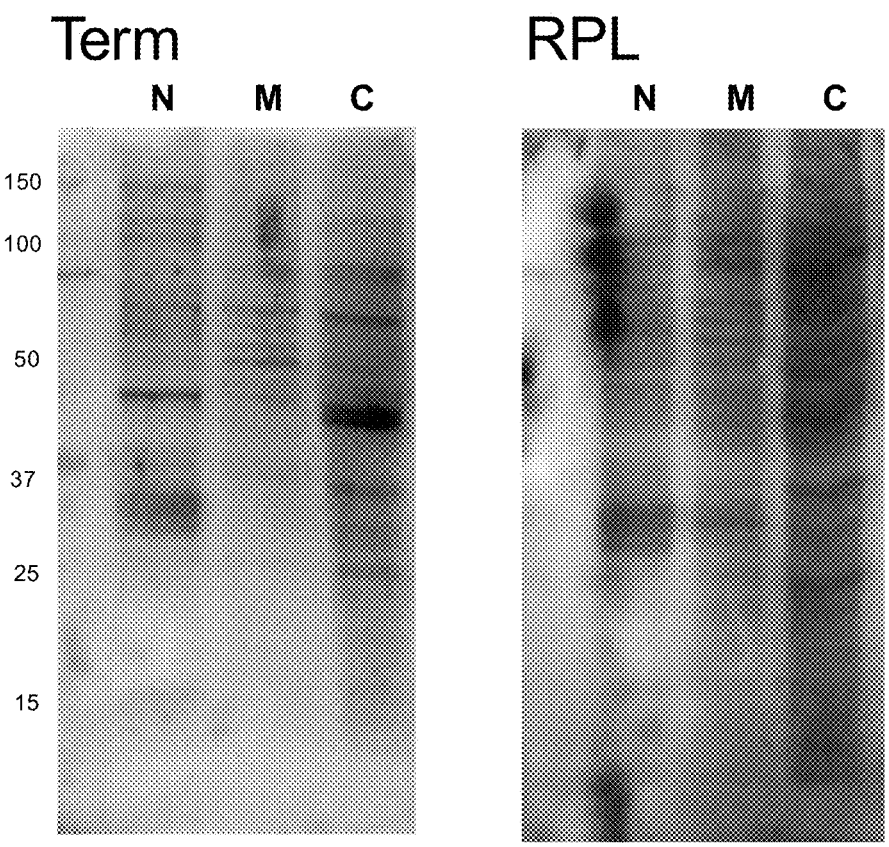
FIG. 2 is a representative Western immunoblot demonstrating the reactivity profile of total circulating antibody derived from control term-derived patients compared to RPL parients. First trimester SW-71 cell-line derived nuclear, cellular, and cytosolic proteins were applied to 10% SDS-PAGE gel, electrophoretically separated, and analyzed for subject autoantibody reactivity by Western immunoblotting utilizing sera derived from control and test (RPL) subjects. When comparing all RPL and Term Western blots, sera from women with a history of RPL exhibited greater immunoreactivities compared to controls, with a total antibody reactivity 3.6-fold greater with nuclear antigens (p=0.0044), a 4.1-fold greater reactivity with membrane-derived antigens (p=0.0001), and a 1.8-fold greater recognition of cytosolic antigens (p=0.0113).
Figure 3A:
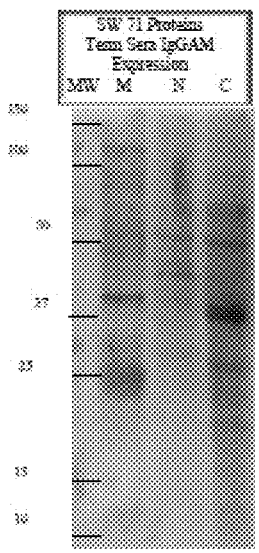
FIGS. 3A-F are a set of six Western blots showing the results of experiments performed as diagramed in FIG. 1 in Term samples (3A-3C) and RPL samples (3D-3F), showing levels of IgGAM (3A and 3D), IgG2 (3B and 3E); and IgG3 (3C and 3F). MW, molecular weight; M, membrane protein fractions; N, nuclear protein fractions; and C, Cytosolic protein fractions.
Figure 3B:
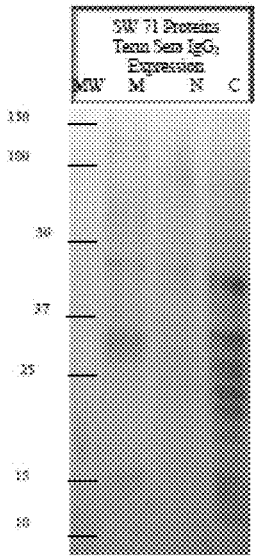
Figure 3C:
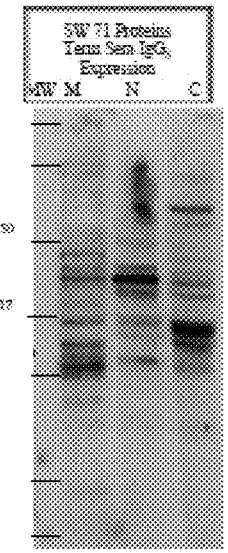
Figure 3D:
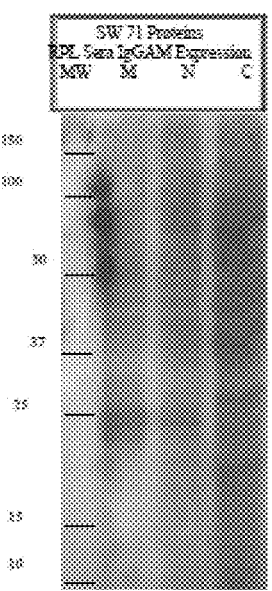
Figure 3E:
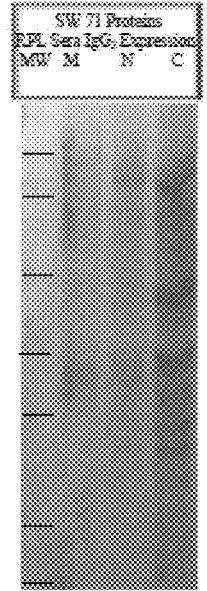
Figure 3F:
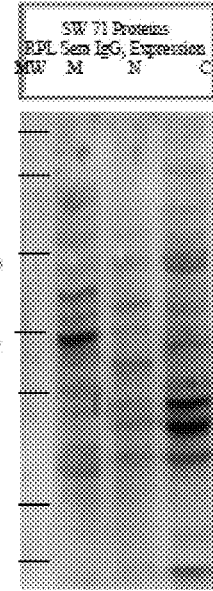

While survival of the fetal allograft in the maternal alloreactive environment remains unexplained, suppression of cellular immunity appears to be one manifestation of pregnancy that may be a critical factor in its success. The pathophysiology of recurrent pregnancy loss (RPL) is complex with many unknown contributing factors and mechanisms. Suggested causes currently applicable to clinical evaluation include anatomical uterine or pelvic defects, genetic, or molecular abnormalities, endocrine disorders, thrombophilias and anti-phospholipid antibody syndrome. However, in up to 50% of cases, no etiology can be identified (Szekeres-Bartho et al., *Hum. Reprod. Update* 14:27-35, 2008). Increasing evidence supports the involvement of various aberrant maternal-fetal immunoregulatory mechanisms and, while survival of the fetal allograft in the maternal allo-reactive environment remains unexplained, suppression of cellular immunity appears to be one manifestation of pregnancy that may be a critical factor in its success. The etiology of pregnancy loss varies and is often controversial, with multiple factors potentially involved, including genetic, anatomic, infectious, environmental, immunologic, endocrine, and hematologic causes.

Several pathways have been postulated regarding the normal pregnancy suppression of maternal immune responses, including the presence of asymmetric, protective antibodies, the induction of suppressor cells, the lack of specific classic major histocompatibility (MHC) antigens, production and release of suppression factors, Fas ligand (FasL)-mediated induction of T-cell apoptosis, and alteration in the T-helper 2 type (Th2) to T-helper 1 type (Th1) ratio (Choudhury et al., *Hum. Reprod. Update* 7:113-134, 2001; Giacomini et al., *Hum. Immunol.* 39:281-289, 1994; Gill et al., *Am. J. Reprod. Immunol.* 41:23-33, 1999; Guller et al., *Semin. Reprod. Endocrinol.* 17:39-44, 1999; Mellor et al., *Ann. Rev. Immunol.* 18:367-391, 2000; Zavazava et al., *Mol. Med. Today* 4:116-121, 1998; Jenkins et al., *Fertil. Steril.* 73:1206-1208, 2000; Wilson et al., *Fertil. Steril.* 76:915-917, 2001). The failure to effectively modulate these complex and likely intertwined maternal immune responses can lead to failure of placentation. Some studies, for example, have suggested that the binding of altered auto-antibodies to the endometrium may impair embryo implantation. Aberrant implantation and subsequent placentation may play a critical role in the pathogenesis of partial or total rejection of the fetal allograft, leading to complications, such as spontaneous miscarriage.

Successful pregnancy is linked with a shift to a Th2 immune response (e.g., an elevated Th2/Th1 immune response ratio), characterized by an increased rate of antibody production (e.g., the production of fetal reactive IgG antibodies) and decreased cell-mediated responses. The theory of immunodystrophism has been proposed to account for the dichotomous Th1- and Th2-cytokine profile associated with human pregnancy loss and success, respectively. Endometrial lymphocytes of recurrent spontaneous aborters express distinct immune-phenotypic profiles that antedate implantation and suggest that endometrial immunologic conditions are intrinsically altered in recurrent aborters.

Activation of T-lymphocytes during pregnancy can result in one of two different cytokine profiles: Th2-secreted cytokines (e.g., IL-4, IL-5, and IL-10) that suppress cellular immunity and Th1-secreted cytokines (e.g., IFN-γ, IL-2, and TNF-α) that induce cellular immunity (e.g., T-cell activation). Failure to suppress T-cell activation may allow the generation of cellular fetal-reactive immune responses, a potential key causative factor in infertility and adverse pregnancy outcomes. An increase in the ratio of Th2 cytokines to Th1 cytokines is associated with successful pregnancy and a decrease in this ratio is associated with recurrent pregnancy loss (Jenkins et al., *Fertil. Steril.* 73:1206-1208, 2000; Hill et al., *JAMA* 273:1933-1936, 1995). Clinical studies have demonstrated the predominance of Th1-type cytokine production in patients with pregnancy complications, such as pre-eclampsia (Hill et al., *JAMA* 273:1933-1936, 1995). There is no conclusive evidence as to whether some or all of these mechanisms are functional; however, it appears that mechanisms crucial for immunosuppression would be pivotal in early pregnancy.

A failure to suppress T-cell activation may allow the generation of cellular fetal-reactive immune responses, which may represent a key causative factor in infertility and adverse pregnancy outcomes. The data also indicate that the induction of IgG in normal pregnant patients is linked with a shift to a predominant IgG2 subclass, which does not appear to occur in women with recurrent pregnancy loss. One hypothesis is that, in women who suffer from recurrent pregnancy loss, the shift to anti-fetal immune responses lacking or exhibiting weak effector function fails to occur.

As demonstrated herein, women with a history of recurrent pregnancy loss demonstrate aberrant presence or absence of antibodies to three proteins: Apolipoprotein B-100, alpha2macrogloblin, and fibronectin. Thus, the presence, a detectable level, or an increase of maternal IgG antibodies to trophoblast-derived fibronectin (protein or nucleic acid) and/or ApoB-100 (protein or nucleic acid), and/or the presence, a detectable level, or a increase of antibodies that specifically bind to α2M (protein or nucleic acid) is associated with a history of RPL and in increased risk of future pregnancy loss.

Apolipoprotein B-100

Pregnancy is associated with a marked hyperlipidemia, mainly elevated plasma triglycerides and lipoproteins (Sarandol et al., *Clin. Biochem.* 37:990-996, 2004; Cekmen et al., *Clin. Biochem.* 36:575-578, 2003). Lipoproteins play a direct role on endothelial function and are highly susceptible to oxidation (Sarandol et al., *Arch. Gynecol. Obstet.* 270:157-160, 2004). Apolipoprotein B (ApoB-100 and ApoB-48) provides a framework for packaging neutral lipids, such as triglycerides and cholesterol esters, into lipoproteins for transportation in circulation (Farese et al., *J. Lipid Res.* 37:347-360, 1996). Low density lipoprotein (LDL)-receptors mediate ApoB uptake into cells and protect against oxidation. Trophoblast cells express high levels of LDL-receptor and related proteins. Elevated serum levels of ApoB noted in intrauterine growth restriction (IUGR) fetuses suggest overproduction, lack of utilization, and/or aberrant intracellular uptake.

Lipoprotein oxidation has been proposed as a key player in the pathogenesis of pregnancy complications, such as preeclampsia and IUGR (Sarandol et al., *Arch. Gynecol. Obstet.* 270:157-160, 2004). In normal pregnancies, physiologic hyperlipidemia is believed to be controlled by anti-oxidative defense mechanisms, hormonal, or other biochemical influences (Cekmen et al., *Clin. Biochem.* 36:575-578, 2003; Sarandol et al., *Arch. Gynecol. Obstet.* 270:157-160, 2004). Aberrances in these control mechanisms may lead to lipid peroxidation products that mediate oxidative damage and result in disseminated endothelial dysfunction (Sarandol et al., *Clin. Biochem.* 37:990-996, 2004). Perhaps, in normal pregnancy, an enzyme or other substrate/protein/molecule stabilizes and/or utilizes lipoproteins, inhibiting the common pathway of oxidation.

Some researchers have proposed a role for antioxidants such as vitamin E and/or estrogen to inhibit oxidation of lipoproteins (Sarandol et al., *Arch. Gynecol. Obstet.* 270:157-160, 2004). Conversely, the absence of an endogenous protection mechanism may also lead to aberrant lipoprotein oxidative damage at the uteroplacental interface.

ApoB activity has been detected in the maternal corpus luteum during early pregnancy (Yamada et al., *Human Reprod.* 13:944-952, 1998). Corpus luteal cells produce and secrete abundant progesterone, synthesized from serum-derived cholesterol compounds. Studies show that ApoB represents uptake of LDL in to the luteal steroid producing cells. Human chorionic gonadotropin (HCG) administration enhanced levels of mRNA for the LDL receptor in luteal cells (Yamada et al., *Human Reprod.* 13:944-952, 1998; Benyo et al., *Endocrinology* 133:699-704, 1993). Endogenous or exogenous HCG may play a role in preserving and/or augmenting the presence of LDL-receptors, thereby maintaining the uptake of cholesterol compounds required for substantial progesterone production. Perhaps antibody recognition of ApoB in normal pregnant patients permits or supports its utilization in the luteal production and secretion of progesterone required in early pregnancy support and development. Conversely, perhaps patients who do not display this IgG recognition are subject to dysfunctional corpus luteum and subsequent recurrent pregnancy loss.

Expression of ApoB mRNA has been localized in the human embryo yolk endodermal cells (Cekmen et al., *Clin. Biochem.* 36:575-578, 2003). Detection of ApoB in the yolk sac of mice has lead to a probable model for transport and packaging of maternally-derived, nutrient rich ApoB-containing lipoproteins into the yolk sac of developing embryo (Cekmen et al., *Clin. Biochem.* 36:575-578, 2003). Perhaps, humoral recognition of ApoB in normal pregnancies plays a potential role in the nutrient support of the maturing embryo, and a lack of antibody recognition results in failure of continued embryo development.

The sequence of human Apolipoprotein B 100 can be found at NM_000384.2 (nucleic acid; SEQ ID NO: 1) and NP_000375.2 (protein; SEQ ID NO: 2).

Some embodiments of all of the methods described herein include the detection or determination of the presence, a detectable level, or an increase in the level of antibodies that specifically bind to apopolipoprotein B-100 or an antigenic fragment thereof. The detected antibodies may be antibodies that specifically bind to an apolipoprotein B-100 protein, or an antigenic fragment thereof, or an apolipoprotein B-100 nucleic acid (e.g., mRNA), or an antigenic fragment thereof. For example, an antibody may specifically bind to at least 5 (e.g., at least 6, 7, 8, 9, 10, 11, 12, 13, 14, 15, 16, 17, 18, 19, or 20) contiguous amino acids in the sequence of SEQ ID NO: 2. The at least 5 (e.g., at least 6, 7, 8, 9, 10, 11, 12, 13, 14, 15, 16, 17, 18, 19, or 20) contiguous amino acids within the sequence of SEQ ID NO: 2 may be located anywhere within the sequence, for example, the contiguous amino acid sequence may begin at the N-terminus, may end at the C-terminus, or may begin at any amino acid within the sequence of SEQ ID NO: 2 (except for the last four C-terminal amino acids). In some embodiments, the detected antibody may specifically bind to polypeptide containing the sequence of SEQ ID NO: 2.

The detected antibodies may be antibodies that specifically bind to an apolipoprotein nucleic acid (e.g., mRNA) or an antigenic fragment thereof. For example, the detected antibody may specifically bind to at least 5 (e.g., at least 6, 7, 8, 9, 10, 11, 12, 13, 14, 15, 16, 17, 18, 19, or 20) contiguous nucleotides present within the sequence of SEQ ID NO: 1. The at least 5 (e.g., at least 6, 7, 8, 9, 10, 11, 12, 13, 14, 15, 16, 17, 18, 19, or 20) contiguous nucleotides within the sequence of SEQ ID NO: 1 may be located anywhere within the sequence, for example, the contiguous nucleotide sequence may begin at the 5'-terminus, may end at the 3'-terminus, or may begin at any nucleotide within the sequence of SEQ ID NO: 1 (except for the last four 3'-terminal nucleotides). In some embodiments, the detected antibody may specifically bind to a nucleic acid containing the sequence of SEQ ID NO: 1.

Additional embodiments of all of the methods described herein (e.g., methods for determining the risk of pregnancy loss in a subject, for identifying a subject at risk of pregnancy loss, for selecting a subject for participation in a clinical study, and for decreasing the risk of pregnancy loss in a subject) involve the detection or determination of the presence, a detectable level, or an increased level of Apolipoprotein B-100 protein or nucleic acid (e.g., mRNA), or an antigenic fragment thereof, in a sample from the subject (e.g., in the serum of the subject). In these methods, the Apolipoprotein B-100 protein that is detected may be, for example, a protein containing the sequence of SEQ ID NO: 2, or any antigenic fragment thereof. For example, an antigenic fragment of Apolipoprotein B-100 protein that may be detected can contain at least 5 (e.g., at least 6, 7, 8, 9, 10, 11, 12, 13, 14, 15, 16, 17, 18, 19, or 20) contiguous amino acids within the sequence of SEQ ID NO: 2. The at least 5 (e.g., at least 6, 7, 8, 9, 10, 11, 12, 13, 14, 15, 16, 17, 18, 19, or 20) contiguous amino acids within the sequence of SEQ ID NO: 2 may be located anywhere within the sequence, for example, the contiguous amino acid sequence may begin at the N-terminus, may end at the C-terminus, or may begin at any amino acid within the sequence of SEQ ID NO: 2 (except for the last four C-terminal amino acids).

In additional examples of these methods, the Apolipoprotein nucleic acid (e.g., mRNA) that is detected may be, for example, a nucleic acid containing the sequence of SEQ ID NO: 1, or any antigenic fragment thereof. For example, an antigenic fragment of Apolipoprotein B-100 nucleic acid that may be detected can contain at least 5 (e.g., at least 6, 7, 8, 9, 10, 11, 12, 13, 14, 15, 16, 17, 18, 19, or 20) contiguous nucleotides within the sequence of SEQ ID NO: 1. The at least 5 (e.g., at least 6, 7, 8, 9, 10, 11, 12, 13, 14, 15, 16, 17, 18, 19, or 20) contiguous nucleotides within the sequence of SEQ ID NO: 1 may be located anywhere within the sequence, for example, the contiguous nucleotide sequence may begin at the 5'-terminus, may end at the 3'-terminus, or may begin at any nucleotide within the sequence of SEQ ID NO: 1 (except for the last four 3'-terminal nucleotides).

Fibronectin

The maternal extracellular matrix and maternal-fetal interface have been suggested to play a pivotal role in conditions of early recurrent abortions, intrauterine growth restriction, and pre-eclampsia. Fetal fibronectin is one extracellular matrix protein that may act as "trophoblast glue," with increased concentrations at the chorionic-decidual margin and surrounding the extravillous trophoblasts (Mercorio et al., *Eur. J. Gynecol. Reprod. Biol.* 126:165-169, 2006; Guller et al., *Up-To-Date*, version 17.3, 2009). Integrin receptors for fibronectin with strong binding activity have been observed on the surface of blastocysts (Mercorio et al., *Eur. J. Gynecol. Reprod. Biol.* 126:165-169, 2006). Derangement in the signals and receptivity between cellular matrix proteins, e.g., fibronectin, and cell adhesion molecules may be responsible for pregnancy failure.

The fibronectin gene has three regions subject to alternative splicing, with the potential to produce 20 different transcript variants. The human reference sequences are as follows: NM_002026.2 (nucleic acid; SEQ ID NO: 3) and NP_002017.1 (protein; SEQ ID NO: 4) for fibronectin 1 isoform 3 preproprotein; NM_054034.2 (nucleic acid; SEQ ID NO: 5) and NP_473375.2 (protein; SEQ ID NO: 6) for fibronectin 1 isoform 7 preproprotein; NM_212474.1 (nucleic acid; SEQ ID NO: 7) and NP_997639.1 (protein; SEQ ID NO: 8) for fibronectin 1 isoform 6 preproprotein; NM_212475.1 (nucleic acid; SEQ ID NO: 9) and NP_997640.1 (protein; SEQ ID NO: 10) for fibronectin 1 isoform 2 preproprotein; NM_212476.1 (nucleic acid; SEQ ID NO: 11) and NP_997641.1 (protein; SEQ ID NO: 12) for fibronectin 1 isoform 5 preproprotein; NM_212478.1 (nucleic acid; SEQ ID NO: 13) and NP_997643.1 (protein; SEQ ID NO: 14) for fibronectin 1 isoform 4 preproprotein; and NM_212482.1 (nucleic acid; SEQ ID NO: 15) and NP_997647.1 (protein; SEQ ID NO: 16) for fibronectin 1 isoform 1 preproprotein (the longest transcript that encodes the longest isoform).

Some embodiments of all of the methods described herein include the determination of the presence, a detectable level, or an increase in the level of antibodies that specifically bind to fibronectin or an antigenic fragment thereof. The detected antibodies may be antibodies that specifically bind to a fibronectin protein or an antigenic fragment thereof, or a fibronectin nucleic acid (e.g., mRNA), or an antigenic fragment thereof. For example, an antibody may specifically bind to at least 5 (e.g., at least 6, 7, 8, 9, 10, 11, 12, 13, 14, 15, 16, 17, 18, 19, or 20) contiguous amino acids in the sequence of SEQ ID NO: 4, 6, 8, 10, 12, 14, or 16. The at least 5 (e.g., at least 6, 7, 8, 9, 10, 11, 12, 13, 14, 15, 16, 17, 18, 19, or 20) contiguous amino acids within the sequence of SEQ ID NOS: 4, 6, 8, 10, 12, 14, or 16 may be located anywhere within the sequence, for example, the contiguous amino acid sequence may begin at the N-terminus, may end at the C-terminus, or may begin at any amino acid within the sequence of SEQ ID NO: 4, 6, 8, 10, 12, 14, or 16 (except for the last four C-terminal amino acids in any one of these sequences). In some embodiments, the detected antibody may specifically bind to polypeptide containing the sequence of SEQ ID NO: 4, 6, 8, 10, 12, 14, or 16.

The detected antibodies may be antibodies that specifically bind to a fibronectin nucleic acid (e.g., mRNA). For example, the detected antibody may specifically bind to at least 5 (e.g., at least 6, 7, 8, 9, 10, 11, 12, 13, 14, 15, 16, 17, 18, 19, or 20) contiguous nucleotides present within the sequence of SEQ ID NO: 3, 5, 7, 9, 11, 13, or 15. The at least 5 (e.g., at least 6, 7, 8, 9, 10, 11, 12, 13, 14, 15, 16, 17, 18, 19, or 20) contiguous nucleotides within the sequence of SEQ ID NO: 3, 5, 7, 9, 11, 13, or 15 may be located anywhere within the sequence, for example, the contiguous nucleotide sequence may begin at the 5'-terminus, may end at the 3'-terminus, or may begin at any nucleotide within the sequence of SEQ ID NO: 3, 5, 7, 9, 11, 13, or 15 (except for the last four 3'-terminal nucleotides of any one of these sequences). In some embodiments, the detected antibody may specifically bind to a nucleic acid containing the sequence of SEQ ID NO: 3, 5, 7, 9, 11, 13, or 15.

In additional embodiments of the methods described herein (e.g., methods for determining the risk of pregnancy loss in a subject, for identifying a subject at risk of pregnancy loss, for selecting a subject for participation in a clinical study, and for decreasing the risk of pregnancy loss in a subject) involve the detection of the presence, a detectable level, or an increased level of fibronectin protein or nucleic acid (e.g., mRNA), or an antigenic fragment thereof, in a sample from the subject (e.g., in the serum of the subject). In these methods, the fibronectin protein that is detected may be, for example, a protein containing the sequence of SEQ ID NO: 4, 6, 8, 10, 12, 14, or 16, or any antigenic fragment thereof. For example, an antigenic fragment of a fibronectin protein that may be detected can contain at least 5 (e.g., at least 6, 7, 8, 9, 10, 11, 12, 13, 14, 15, 16, 17, 18, 19, or 20) contiguous amino acids within the sequence of SEQ ID NO: 4, 6, 8, 10, 12, 14, or 16. The at least 5 (e.g., at least 6, 7, 8, 9, 10, 11, 12, 13, 14, 15, 16, 17, 18, 19, or 20) contiguous amino acids within the sequence of SEQ ID NO: 4, 6, 8, 10, 12, 14, or 16 may be located anywhere within the sequence, for example, the contiguous amino acid sequence may begin at the N-terminus, may end at the C-terminus, or may begin at any amino acid within the sequence of SEQ ID NO: 4, 6, 8, 10, 12, 14, or 16 (except for the last four C-terminal amino acids of any one of the sequences).

In additional examples of these methods, the fibronectin nucleic acid (e.g., mRNA) that is detected may be, for example, a nucleic acid containing the sequence of SEQ ID NO: 3, 5, 7, 9, 11, 13, or 15, or any antigenic fragment thereof. For example, an antigenic fragment of a fibronectin nucleic acid that may be detected can contain at least 5 (e.g., at least 6, 7, 8, 9, 10, 11, 12, 13, 14, 15, 16, 17, 18, 19, or 20) contiguous nucleotides within the sequence of SEQ ID NO: 3, 5, 7, 9, 11, 13, or 15. The at least 5 (e.g., at least 6, 7, 8, 9, 10, 11, 12, 13, 14, 15, 16, 17, 18, 19, or 20) contiguous nucleotides within the sequence of SEQ ID NO: 3, 5, 7, 9, 11, 13, or 15 may be located anywhere within the sequence, for example, the contiguous nucleotide sequence may begin at the 5'-terminus, may end at the 3'-terminus, or may begin at any nucleotide within the sequence of SEQ ID NO: 3, 5, 7, 9, 11, 13, or 15 (except for the last four 3'-terminal nucleotides).

Alpha2-macroglobulin

Alpha2-macroglobulin ($\alpha 2M$) is a major inhibitor of endoproteinases and carries a regulatory role in the protection, transport, and clearance of cytokines and growth factors (Esadeg et al., *Placenta* 24:912-921, 2003). $\alpha 2M$ has a potential means of immunosuppression in the human uteroplacental interface and may be subject to transplacental transport to the neonate (Benyo et al., *Endocrinology* 133:699-704, 1993). $\alpha 2M$ targets cytokines to cells expressing the $\alpha 2M$-receptor or lipoprotein-receptor related protein (Esadeg et al., *Placenta* 24:912-921, 2003; Shimizu et al., *Exp. Anim.* 51:361-365, 2002). Uterine $\alpha 2M$ is thought to originate from endothelial cells lining the endometrial vessels. Small serum concentrations of $\alpha 2M$ are found in normal healthy adults, and its concentration has been reported to double or triple during the secretory phase of the menstrual cycle suggesting a role as a decidualization protein (Esadeg et al., *Placenta* 24:912-921, 2003). During pregnancy, a receptor for the $\alpha 2M$-proteinase complex has been demonstrated on the human placental syncytiotrophoblasts (Thomas et al., *Placenta* 11:413-430, 1990; Jensen et al., *Placenta* 9:463-477, 1988). In addition, synthesis and secretion of $\alpha 2M$ has also been detected in the visceral yolk sac of fetal rats. The sequence of human $\alpha 2M$ can be found at NM_000014.4 (nucleic acid; SEQ ID NO: 17) and NP_000005.2 (amino acid; SEQ ID NO: 18).

Some embodiments of the methods described herein include the determination or detection of the presence, a detectable level, or a increased level of antibodies that specifically bind to $\alpha 2M$ or an antigenic fragment thereof. The detected antibodies may be antibodies that specifically bind to an $\alpha 2M$ protein, or an antigenic fragment thereof, or an $\alpha 2M$ nucleic acid (e.g., mRNA), or an antigenic fragment thereof. For example, an antibody may specifically bind to at least 5 (e.g., at least 6, 7, 8, 9, 10, 11, 12, 13, 14, 15, 16, 17, 18, 19, or 20) contiguous amino acids in the sequence of SEQ ID NO: 18. The at least 5 (e.g., at least 6, 7, 8, 9, 10, 11, 12, 13, 14, 15, 16, 17, 18, 19, or 20) contiguous amino acids within the sequence of SEQ ID NO: 18 may be located anywhere within the sequence, for example, the contiguous amino acid sequence may begin at the N-terminus, may end at the C-terminus, or may begin at any amino acid within the sequence of SEQ ID NO: 18 (except for the last four C-terminal amino acids). In some embodiments, the detected antibody may specifically bind to polypeptide containing the sequence of SEQ ID NO: 18.

The detected antibodies may be antibodies that specifically bind to an $\alpha 2M$ nucleic acid (e.g., mRNA). For example, the detected antibody may specifically bind to at least 5 (e.g., at least 6, 7, 8, 9, 10, 11, 12, 13, 14, 15, 16, 17, 18, 19, or 20) contiguous nucleotides present within the sequence of SEQ ID NO: 17. The at least 5 (e.g., at least 6, 7, 8, 9, 10, 11, 12, 13, 14, 15, 16, 17, 18, 19, or 20) contiguous nucleotides within the sequence of SEQ ID NO: 17 may be located anywhere within the sequence, for example, the contiguous nucleotide sequence may begin at the 5'-terminus, may end at the 3'-terminus, or may begin at any nucleotide within the sequence of SEQ ID NO: 17 (except for the last four 3'-terminal nucleotides). In some embodiments, the detected antibody may specifically bind to a nucleic acid containing the sequence of SEQ ID NO: 17.

In additional embodiments of all of the methods described herein (e.g., methods for determining the risk of pregnancy loss in a subject, for identifying a subject at risk of pregnancy loss, for selecting a subject for participation in a clinical study, and for decreasing the risk of pregnancy loss in a subject) involve the detection of the presence, a detectable level, or a increased level of $\alpha 2M$ protein or nucleic acid (e.g., mRNA), or an antigenic fragment thereof, in a sample from the subject (e.g., in the serum of the subject). In these methods, the $\alpha 2M$ protein that is detected may be, for example, a protein containing the sequence of SEQ ID NO: 18, or any antigenic fragment thereof. For example, an antigenic fragment of α2M protein that may be detected can contain at least 5 (e.g., at least 6, 7, 8, 9, 10, 11, 12, 13, 14, 15, 16, 17, 18, 19, or 20) contiguous amino acids within the sequence of SEQ ID NO: 18. The at least 5 (e.g., at least 6, 7, 8, 9, 10, 11, 12, 13, 14, 15, 16, 17, 18, 19, or 20) contiguous amino acids within the sequence of SEQ ID NO: 18 may be located anywhere within the sequence, for example, the contiguous amino acid sequence may begin at the N-terminus, may end at the C-terminus, or may begin at any amino acid within the sequence of SEQ ID NO: 18 (except for the last four C-terminal amino acids).

In additional examples of these methods, the α2M nucleic acid (e.g., mRNA) that is detected may be, for example, a nucleic acid containing the sequence of SEQ ID NO: 17, or any antigenic fragment thereof. For example, an antigenic fragment of an α2M nucleic acid that may be detected can contain at least 5 (e.g., at least 6, 7, 8, 9, 10, 11, 12, 13, 14, 15, 16, 17, 18, 19, or 20) contiguous nucleotides within the sequence of SEQ ID NO: 17. The at least 5 (e.g., at least 6, 7, 8, 9, 10, 11, 12, 13, 14, 15, 16, 17, 18, 19, or 20) contiguous nucleotides within the sequence of SEQ ID NO: 17 may be located anywhere within the sequence, for example, the contiguous nucleotide sequence may begin at the 5'-terminus, may end at the 3'-terminus, or may begin at any nucleotide within the sequence of SEQ ID NO: 17 (except for the last four 3'-terminal nucleotides).

Methods of Predicting Pregnancy Loss

Provided herein are methods of predicting the risk of pregnancy loss in a subject that include providing a sample containing serum from the subject and detecting the presence, absence, or level of antibodies that specifically bind to one or more (e.g., one, two, or three) of a fibronectin (protein or nucleic acid), an α2M (protein or nucleic acid), and an Apolipoprotein B-100 (protein or nucleic acid), or an antigenic fragment thereof, in the sample, wherein the presence, a detectable level, or an increased level of antibodies to a fibronectin (protein or nucleic acid) and/or ApoB-100 (protein or nucleic acid), or antigenic fragment thereof, and/or the presence, a detectable level, or a increased level of antibodies to an α2M (protein or nucleic acid), or an antigenic fragment thereof, in the sample, indicate that the subject has an increased (e.g., a statistically significant increase, such as an increase of at least 5%, 10%, 15%, 20%, 25%, 30%, 35%, 40%, 45%, 50%, 55%, 60%, 65%, 70%, 75%, 80%, 85%, 90%, 95%, or 100%) risk of pregnancy loss. Additional methods for predicting the risk of pregnancy loss in a subject may include providing a sample (e.g., a sample containing serum) from the subject and detecting the presence, absence, or level of one or more (e.g., one, two, or three) of a fibronectin (protein or nucleic acid), an α2M (protein or nucleic acid), and an Apolipoprotein B-100 (protein or nucleic acid), or an antigenic fragment thereof, in the sample, wherein the presence, a detectable level, or an increased level of a fibronectin (protein or nucleic acid) and/or an ApoB-100 (protein or nucleic acid), or antigenic fragment thereof, and/or the presence, a detectable level, or a increased level of an α2M (protein or nucleic acid), or antigenic fragment thereof, in the sample, indicate that the subject has an increased (e.g., a statistically significant increase, such as an increase of at least 5%, 10%, 15%, 20%, 25%, 30%, 35%, 40%, 45%, 50%, 55%, 60%, 65%, 70%, 75%, 80%, 85%, 90%, 95%, or 100%) risk of pregnancy loss.

In some embodiments of all of the methods described herein, the subject may be a pregnant woman in the first (weeks 0-12) or second (weeks 13-27) trimester of pregnancy (e.g., any time between 0 to 20 weeks, 6 to 20 weeks, 6 to 12 weeks, or 24 weeks after conception). In some embodiments of all of the methods described herein, the subject may be a pregnant subject within the first 20 weeks of pregnancy (e.g., within 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, or 19 weeks of pregnancy). Early pregnancy loss is defined as the termination of pregnancy before 20 weeks gestation or with a fetal weight of <500 g.

The subject (e.g., a pregnant subject or a non-pregnant subject) may also have had at least one (e.g., two, three, four, five, or six) pregnancy loss or may be suspected of having had at least one (e.g., two, three, four, five, or six) previous pregnancy loss. In some embodiments, the subject is within the first 20 weeks of pregnancy (e.g., within 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, or 19 weeks of pregnancy) and has had at least one (e.g., two, three, four, five, or six) pregnancy loss or is suspected of having had at least one (e.g., two, three, four, five, or six) pregnancy loss.

A sample (e.g., serum) from the subject may be collected from the subject prior to pregnancy, following a miscarriage or a suspected miscarriage, or at any time during pregnancy (e.g., within 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, or 20 weeks). Samples may be frozen or stored for a period of time (e.g., at least one day, two days, three days, four days, five days, six days, or 1 week) prior to detecting/determining the presence, absence, or level of antibodies to one or more (e.g., one, two, or three) of a fibronectin (protein or nucleic acid), an Apolipoprotein B-100 (protein or nucleic acid), and an α2M (protein or nucleic acid), and/or the presence, absence, or level of one or more (e.g., one, two, or three) of a fibronectin (protein or nucleic acid), an Apolipoprotein B-100 (protein or nucleic acid), and an α2M (protein or nucleic acid), or an antigenic portion thereof.

Any method known in the art can be used for detecting the presence of antibodies in a sample (e.g., antibodies that specifically bind to fibronectin (protein or mRNA), Apolipoprotein B-100 (protein or mRNA), or α2M (protein or mRNA), or an antigenic portion thereof). For example, a sample from a subject (e.g., a sample containing serum, such as, serum, plasma, or blood), from a subject (e.g., any of the subjects described herein, such as a pregnant subject) can be contacted with all or an antigenic fragment of a protein or nucleic acid described herein (e.g., a fibronectin protein or nucleic acid, an α2M protein or nucleic acid, and/or an ApoB-100 protein or nucleic acid, or an antigenic fragment thereof), and binding of any antibodies in the sample to these antigen(s) can be detected using methods known in the art.

For example, an array (e.g., any array, microarray, biochip, or point-of-care test as is known in the art) can be provided that comprises one or more of the proteins, nucleic acids, or antigenic fragments thereof, and the array can be contacted with the sample containing serum from the subject, and the binding of any antibodies present in the sample can be detected.

Methods for detecting binding of the antibodies are known in the art, and can include the use of secondary antibodies; alternatively, any other antibody-specific ligand can be used. The secondary antibodies are generally modified to be detectable, e.g., labeled. The term "labeled" is intended to encompass direct labeling by coupling (i.e., physically linking) a detectable substance to the secondary antibody, as well as indirect labeling of the multimeric antigen by reactivity with a detectable substance. Examples of detectable substances include various enzymes, prosthetic groups, fluorescent materials, luminescent materials, bioluminescent materials, and radioactive materials. Examples of suitable enzymes include horseradish peroxidase (HRP), alkaline phosphatase, β-galactosidase, and acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, and quantum dots, dichlorotriazinylamine fluorescein, dansyl chloride, and phycoerythrin; an example of a luminescent material includes luminol; examples of bioluminescent materials include green fluorescent protein and variants thereof, luciferase, luciferin, and aequorin; and examples of suitable radioactive material include $^{125}I$, $^{131}I$, $^{35}S$, or $^{3}H$. Methods for producing such labeled antibodies are known in the art, and many are commercially available.

In some embodiments, the methods further include determining the subtype of the antibodies that bind to the antigens, e.g., detecting the presence of IgG3 antibodies, which as described herein are associated with an increased humoral response and increased risk of pregnancy loss. Antibodies that bind to the Fc region of IgG3 are commercially available and may be used to determine the presence, level, or absence of IgG3 antibodies in the sample.

Any method of detecting the antibodies can be used, including but not limited to radioimmunoassays (RIA), enzyme-linked immunosorbent assays (ELISA), Western blotting, surface plasmon resonance, microfluidic devices, protein array, mass spectrometry, or other assays as known in the art. In some embodiments, the antigens can be produced in tetrameric form as described in US-2009-005425-A1.

As described herein, the invention provides methods for predicting pregnancy loss by detecting the presence of aberrant humoral response; as noted above, these methods can include the use of an array. The invention provides an array (i.e., "biochip" or "microarray") that includes immobilized antigens that facilitate the detection of a particular antibody or antibodies in a biological sample. Antigens that identify the antibodies as described herein can be included in a custom array for detecting subjects predisposed to pregnancy loss, e.g., RPL. For example, a custom array can include antigens that specifically bind antibodies to one or more (e.g., one, two, or three) of a fibronectin, an α2M, and an ApoB-100. The antigens can be a full-length protein, a full-length nucleic acid (e.g., an mRNA), or a fragment thereof (as described herein). The array can also include biomolecules that identify additional antibodies. The arrays can be used to develop a database of information using data obtained using the methods described herein.

The term "array," as used herein, generally refers to a predetermined spatial arrangement of binding ligands, antigens, or spatial arrangements of binding ligands or antigens. Arrays according to the present invention that include antigens immobilized on a surface may also be referred to as "antigen arrays." Arrays according to the present invention that comprise surfaces activated, adapted, prepared, or modified to facilitate the binding of antigens to the surface may also be referred to as "binding arrays." Further, the term "array" may be used herein to refer to multiple arrays arranged on a surface, such as would be the case where a surface bore multiple copies of an array. Such surfaces bearing multiple arrays may also be referred to as "multiple arrays" or "repeating arrays." The use of the term "array" herein may encompass antigen arrays, binding arrays, multiple arrays, and any combination thereof; the appropriate meaning will be apparent from context. An array can include antigens that detect antibodies and other proteins altered in a subject who is likely to experience pregnancy loss. The array can be contacted with one or more biological samples from a subject; the samples can include fluid or solid samples from any tissue of the body including excretory fluids such as urine. Non-urine samples include, but are not limited to serum, plasma, amniotic fluid, and placental tissue.

An array of the invention comprises a substrate. By "substrate" or "solid support" or other grammatical equivalents, herein is meant any material appropriate for the attachment of antigens and is amenable to at least one detection method. As will be appreciated by those in the art, the number of possible substrates is very large. Possible substrates include, but are not limited to, glass and modified or functionalized glass, plastics (including acrylics, polystyrene, and copolymers of styrene and other materials, polypropylene, polyethylene, polybutylene, polyurethanes, TEFLON®, etc.), polysaccharides, nylon or nitrocellulose, resins, silica or silica-based materials including silicon and modified silicon, carbon, metals, inorganic glasses, plastics, ceramics, and a variety of other polymers. In addition, as is known the art, the substrate may be coated with any number of materials, including polymers, such as dextrans, acrylamides, gelatins, or agarose. Such coatings can facilitate the use of the array with a biological sample derived from urine or serum.

A planar array of the invention will generally contain addressable locations (e.g., "pads," "addresses," or "microlocations") of antigens in an array format. The size of the array will depend on the composition and end use of the array. The arrays can contain 1, 2, or more different antigens; in some embodiments, different portions of the same protein are also included, to detect antibodies that bind to different epitopes on the protein. Generally, the array will comprise from two to as many as 100,000 or more antigens, depending on the end use of the array. A microarray of the invention will generally comprise at least one antigen that identifies or "captures" an antibody present in a biological sample. In some embodiments, the compositions of the invention may not be in an array format; that is, for some embodiments, compositions comprising a single antigen may be made as well. In addition, in some arrays, multiple substrates may be used, either of different or identical compositions. Thus, for example, large planar arrays may comprise a plurality of smaller substrates.

As an alternative to planar arrays, bead-based assays in combination with flow cytometry have been developed to perform multiparametric immunoassays. In bead-based assay systems the antigens can be immobilized on addressable microspheres. Each antigen for each individual immunoassay is coupled to a distinct type of microsphere (i.e., "microbead") and the immunoassay reaction takes place on the surface of the microspheres. Dyed microspheres with discrete fluorescence intensities are loaded separately with their appropriate biomolecules. The different bead sets carrying different capture probes can be pooled as necessary to generate custom bead arrays. Bead arrays are then incubated with the sample in a single reaction vessel to perform the immunoassay.

In some embodiments, product formation of the antibody with their immobilized antigens can be detected with a fluorescence-based reporter system. The antibodies can be labeled directly by a fluorogen or detected by a second fluorescently-labeled capture biomolecule. The signal intensities derived from captured antibodies are measured in a flow cytometer. The flow cytometer first identifies each microsphere by its individual color code. Second the amount of captured antibody on each individual bead is measured by the second color fluorescence specific for the bound target. This allows multiplexed quantitation of multiple targets from a single sample within the same experiment. Sensitivity, reliability, and accuracy are comparable to standard microtiter ELISA procedures. With bead-based immunoassay systems antibodies can be simultaneously quantified from biological samples. An advantage of bead-based systems is the individual coupling of the antibody to distinct microspheres.

Thus, microbead array technology can be used to sort antibodies bound to specific antigens using a plurality of microbeads, each of which can carry about 100,000 identical molecules of a specific antigen on its surface. Once captured, the antibody can be handled as fluid, referred to herein as a "fluid microarray."

An array can encompass any means for detecting an antibody. For example, microarrays can be biochips that provide high-density immobilized arrays of antigens, where antibody binding is monitored indirectly (e.g., via fluorescence). In addition, an array can be of a format that involves the capture of antibodies by biochemical or intermolecular interaction, coupled with direct detection by mass spectrometry (MS).

Arrays and microarrays that can be used with the methods described herein can be made according to the methods described in U.S. Pat. Nos. 6,329,209; 6,365,418; 6,406,921; 6,475,808; and 6,475,809, which are incorporated herein in their entirety. New arrays, to detect specific selections or sets of biomarkers described herein can also be made using the methods described in these patents.

The antigens can be immobilized on the surface using methods and materials that minimize the denaturing of the antigens, that minimize alterations in the structure of the antigens, or that minimize interactions between the antigens and the surface on which they are immobilized.

Surfaces useful in the arrays may be of any desired shape (form) and size. Non-limiting examples of surfaces include chips, continuous surfaces, curved surfaces, flexible surfaces, films, plates, sheets, tubes, and the like. Surfaces preferably have areas ranging from approximately a square micron to approximately 500 cm$^2$. The area, length, and width of surfaces according to the present invention may be varied according to the requirements of the assay to be performed. Considerations may include, for example, ease of handling, limitations of the material(s) of which the surface is formed, requirements of detection systems, requirements of deposition systems (e.g., arrayers), and the like.

In certain embodiments, it is desirable to employ a physical means for separating groups or arrays of binding islands or immobilized antigens: such physical separation facilitates exposure of different groups or arrays to different solutions of interest. Therefore, in certain embodiments, arrays are situated within wells of 96, 384, 1536, or 3456 microwell plates. In such embodiments, the bottoms of the wells may serve as surfaces for the formation of arrays, or arrays may be formed on other surfaces and then placed into wells. In certain embodiments, such as where a surface without wells is used, binding islands may be formed or antigens may be immobilized on a surface and a gasket having holes spatially arranged so that they correspond to the islands or antigens may be placed on the surface. Such a gasket is preferably liquid-tight. A gasket may be placed on a surface at any time during the process of making the array and may be removed if separation of groups or arrays is no longer necessary.

The immobilized antigens can bind to antibodies present in a biological sample overlying the immobilized antigens. For example, an antibody present in a biological sample can contact an immobilized antigen and bind to it, thereby facilitating detection of the antibody.

Modifications or binding of antibodies to antigens in solution or immobilized on an array may be detected using detection techniques known in the art. Examples of such techniques include immunological techniques such as competitive binding assays and sandwich assays; fluorescence detection using instruments such as confocal scanners, confocal microscopes, or CCD-based systems, and techniques such as fluorescence, fluorescence polarization (FP), fluorescence resonant energy transfer (FRET), total internal reflection fluorescence (TIRF), fluorescence correlation spectroscopy (FCS); colorimetric/spectrometric techniques; surface plasmon resonance, by which changes in mass of materials adsorbed at surfaces may be measured; techniques using radioisotopes, including conventional radioisotope binding and scintillation proximity assays so (SPA); mass spectroscopy, such as matrix-assisted laser desorption/ionization mass spectroscopy (MALDI) and MALDI-time of flight (TOF) mass spectroscopy; ellipsometry, which is an optical method of measuring thickness of protein films; quartz crystal microbalance (QCM), a very sensitive method for measuring mass of materials adsorbing to surfaces; scanning probe microscopies, such as AFM and SEM; and techniques such as electrochemical, impedance, acoustic, microwave, and IR/Raman detection. See, e.g., Mere L, et al., "Miniaturized FRET assays and microfluidics: key components for ultra-high-throughput screening," *Drug Discovery Today* 4(8):363-369 (1999), and references cited therein; Lakowicz, J. R., Principles of Fluorescence Spectroscopy, 2nd Edition, Plenum Press, 1999.

Arrays as described herein can be included in kits. Such kits may also include, as non-limiting examples, one or more of reagents useful for preparing antigens for immobilization onto binding islands or areas of an array, reagents useful in preparing a sample, or reagents useful for detecting binding of antibodies in a sample to immobilized antigens, control samples that include known antibodies and instructions for use.

For example, kits provided by the invention may essentially include one or more (e.g., one, two, three, four, five, or six) of a fibronectin (protein and/or nucleic acid), an α2M (protein and/or nucleic acid), and an Apolipoprotein B-100 (protein and/or nucleic acid), or antigenic fragments thereof. Kits may also contain one or more (e.g., one, two, three, four, five, or six) antibodies that specifically bind to a fibronectin (protein or nucleic acid), an α2M (protein or nucleic acid), and an Apolipoprotein B-100 (protein or nucleic acid), or an antigenic fragment thereof. For example, the one or more antigens or the one or more antibodies provided in the kits may be immobilized on a surface (e.g., in the form of a ELISA assay).

In some embodiments of all the methods described herein, the presence, absence, or levels of one or more (e.g., one, two, or three) of fibronectin protein or mRNA, Apolipoprotein B-100 protein or mRNA, and α2M protein or mRNA, or an antigenic fragment thereof, present in a sample (e.g., a sample containing serum) from the subject is determined. A variety of examples of fibronectin protein and nucleic acid (e.g., mRNA), Apolipoprotein B-100 protein and nucleic acid (e.g., mRNA), and α2M protein and nucleic acid (e.g., mRNA), and antigenic fragments thereof are described herein. Methods for measuring the presence, absence, or levels of an antigenic protein or peptide in a biological sample using antibodies are known in the art, including, for example, radioimmunoassays (RIA), enzyme-linked immunosorbent assays (ELISA), Western blotting, surface plasmon resonance, microfluidic devices, protein array, and mass spectrometry. Methods for measuring the presence, absence, or levels of a nucleic acid in a biological sample are known in the art, for example, polymerase chain reaction (PCR)-based techniques (e.g., real-time quantitative PCR and gene array). Primers for use in the methods of measuring the presence, absence, or levels of a nucleic acid may be designed based on the sequence of SEQ ID NO: 1, 3, 5, 7, 9, 11, 13, 15, or 17 using methods known in the art.

In any of the methods described herein, one or more (e.g., one, two, three, four, five, six, seven, or eight) of any combination of the following, in a sample from the subject, indicate that the subject has an increased (e.g., a statistically significant increase, such at an increase of 5%, 10%, 15%, 20%, 25%, 30%, 35%, 40%, 45%, 50%, 55%, 60%, 65%, 70%, 75%, 80%, 85%, 90%, 95%, or 100%) risk of pregnancy loss: the or a detectable level of antibodies that specifically bind to an α2M protein or nucleic acid (e.g., mRNA), or an antigenic fragment thereof (as described herein); a increase in the level of antibodies that specifically bind to an α2M protein or nucleic acid (e.g., mRNA), or an antigenic fragment thereof (as described herein) (e.g., as compared to a control subject of the same age or a control subject that has had one or more successful pregnancies, or a subject that has not had a miscarriage or is not suspected of having had a miscarriage); the presence or a detectable level of α2M protein or nucleic acid (e.g., mRNA), or an antigenic fragment thereof (as described herein); a decreased increased level of α2M protein or nucleic acid (e.g., mRNA), or an antigenic fragment thereof (as described herein) (e.g., as compared to a control subject of the same age, a control subject that has had one or more successful pregnancies, and/or a control subject that has not had a miscarriage or is not suspected of having had a miscarriage); the presence or a detectable level of antibodies that specifically bind to a fibronectin protein or nucleic acid (e.g., mRNA), or an antigenic fragment thereof (as described herein); an increase in the level of antibodies that specifically bind to a fibronectin protein or nucleic acid (e.g., mRNA), or an antigenic fragment thereof (as described herein) (e.g., as compared to a control subject of the same age, a control subject that has had one or more successful pregnancies, and/or a control subject that has not had a miscarriage or is not suspected of having had a miscarriage); the presence or detectable level of a fibronectin protein or nucleic acid (e.g., mRNA), or an antigenic fragment thereof (as described herein); an increased level of a fibronectin protein or nucleic acid (e.g., mRNA), or an antigenic fragment thereof (as described herein) (e.g., as compared to a control subject of the same age, a control subject that has had one or more successful pregnancies, and/or a control subject that has not had a miscarriage or is not suspected of having had a miscarriage); the presence or a detectable level of antibodies that specifically bind to an Apolipoprotein B-100 protein or nucleic acid (e.g., mRNA), or an antigenic fragment thereof (as described herein); and an increase in the levels of antibodies that specifically bind to an Apolipoprotein B-100 protein or nucleic acid (e.g., mRNA), or an antigenic fragment thereof (as described herein) (e.g., as compared to a control subject of the same age, a control subject that has had one or more successful pregnancies, and/or a control subject that has not had a miscarriage or is not suspected of having had a miscarriage); the presence or a detectable level of an Apolipoprotein B-100 protein or nucleic acid (e.g., mRNA), or an antigenic fragment thereof (as described herein); and an increased level of an Apolipoprotein B-100 protein or nucleic acid (e.g., mRNA), or an antigenic fragment thereof (as described herein) (e.g., as compared to a control subject of the same age, a control subject that has had one or more successful pregnancies, and/or a control subject that has not had a miscarriage or is not suspected of having had a miscarriage). In any of methods described herein, the term "decrease" is meant a statistically significant decrease (e.g., by at least 5%, 10%, 15%, 20%, 25%, 30%, 35%, 40%, 45%, 50%, 55%, 60%, 65%, 70%, 75%, 80%, 85%, 90%, or 95%). In any of the methods described herein, the term "increase" is meant a statistically significant increase (e.g., by at least 5%, 10%, 15%, 20%, 25%, 30%, 35%, 40%, 45%, 50%, 55%, 60%, 65%, 70%, 75%, 80%, 85%, 90%, or 95%). By the term "non-detectable level" is meant a level of a protein, nucleic acid, or antibody that cannot be detected by the method used to perform the measurement in a given experiment. The non-detectable level of a protein, nucleic acid, or antibody will vary depending on the particular assay used to perform the measurement. By the term "detectable level" is meant a level of a protein, nucleic, or antibody that may be detected by the method used to perform the measurement in a given experiment.

Methods of Identifying a Subject at Risk of Pregnancy Loss

Also provided are methods of identifying a subject at risk (e.g., having an increased risk or pregnancy loss relative to a control population) of pregnancy loss that include providing a sample (e.g., a sample containing serum) from the subject and detecting the presence, absence, or level of antibodies that specifically bind to one or more (e.g., one, two, or three) of a fibronectin (protein or nucleic acid), an α2M (protein or nucleic acid), and an Apolipoprotein B-100, or an antigenic fragment thereof, in the sample, wherein the presence, a detectable level, or an increased level of antibodies to a fibronectin (protein or nucleic acid) and/or an ApoB-100 (protein or nucleic acid), or an antigenic fragment thereof, and/or the presence, a detectable level, or a increased level of antibodies to an α2M (protein or nucleic acid), or antigenic fragment thereof, in the sample, identifies the subject as having an increased (e.g., a statistically significant increase, such as an increase of at least 5%, 10%, 15%, 20%, 25%, 30%, 35%, 40%, 45%, 50%, 55%, 60%, 65%, 70%, 75%, 80%, 85%, 90%, 95%, or 100%) risk of pregnancy loss. Additional methods for identifying a subject at risk of pregnancy loss may include providing a sample (e.g., a sample containing serum) from the subject and detecting the presence, absence, or level of one or more (e.g., one, two, or three) of a fibronectin (protein or nucleic acid), an α2M (protein or nucleic acid), and an Apolipoprotein B-100 (protein or nucleic acid), or an antigenic fragment thereof, in the sample, wherein the presence, a detectable level, or an increased level of a fibronectin (protein or nucleic acid) and/or an ApoB-100 (protein or nucleic acid), or antigenic fragment thereof, and/or the presence, a detectable level, or a increased-level of an α2M (protein or nucleic acid), or antigenic fragment thereof, in the sample, identifies the subject as having an increased risk of pregnancy loss.

These methods may be performed on any of the subjects described herein. The method may be also be performed at any of the time points described herein.

The presence, absence, or levels of antibodies that specifically bind to a fibronectin (protein or nucleic acid), an α2M (protein or nucleic acid), or an Apolipoprotein B-100 (protein or nucleic acid), or an antigenic fragment thereof, may be determined using any of the methods described herein or those known in the art. The presence, absence, or levels of a fibronectin (protein or nucleic acid), an α2M (protein or nucleic acid), or a Apolipoprotein B-100 (protein or nucleic acid), or an antigenic fragment thereof, may be determined using any of the methods described herein or those known in the art.

In any of the methods described herein, one or more (e.g., one, two, three, four, five, six, seven, or eight) of any combination of the following, in a sample from the subject, identify the subject as being at risk (e.g., having an increased risk) of pregnancy loss: the presence or a detectable level of antibodies that specifically bind to an ApoB-100 protein or nucleic acid (e.g., mRNA), or an antigenic fragment thereof (as described herein); an increase in the level of antibodies that specifically bind to an ApoB-100 protein or nucleic acid (e.g., mRNA), or an antigenic fragment thereof (as described herein) (e.g., as compared to a control subject of the same age, a control subject that has had one or more successful pregnancies, and/or a control subject that has not had a miscarriage or is not suspected of having had a miscarriage); the presence or a detectable level of ApoB-100 protein or nucleic acid (e.g., mRNA), or an antigenic fragment thereof (as described herein); an increased level of ApoB-100 protein or nucleic acid (e.g., mRNA), or an antigenic fragment thereof (as described herein) (e.g., as compared to a control subject of the same age, a control subject that has had one or more successful pregnancies, and/or a control subject that has not had a miscarriage or is not suspected of having had a miscarriage); the presence or a detectable level of antibodies that specifically bind to a fibronectin protein or nucleic acid (e.g., mRNA), or an antigenic fragment thereof (as described herein); an increase in the level of antibodies that specifically bind to a fibronectin protein or nucleic acid (e.g., mRNA), or an antigenic fragment thereof (as described herein) (e.g., as compared to a control subject of the same age, a control subject that has had one or more successful pregnancies, and/or a control subject that has not had a miscarriage or is not suspected of having had a miscarriage); the presence or a detectable level of a fibronectin protein or nucleic acid (e.g., mRNA), or an antigenic fragment thereof (as described herein); an increased level of a fibronectin protein or nucleic acid (e.g., mRNA), or an antigenic fragment thereof (as described herein) (e.g., as compared to a control subject of the same age, a control subject that has had one or more successful pregnancies, and/or control subject that has not had a miscarriage or is not suspected of having had a miscarriage); the presence or a detectable level of antibodies that specifically bind to an $\alpha 2M$ protein or nucleic acid (e.g., mRNA), or an antigenic fragment thereof (as described herein); and a increase in the levels of antibodies that specifically bind to an $\alpha 2M$ protein or nucleic acid (e.g., mRNA), or an antigenic fragment thereof (as described herein) (e.g., as compared to a control subject of the same age, a control subject that has had one or more successful pregnancies, and/or a control subject that has not had a miscarriage or is not suspected of having had a miscarriage); the presence or a detectable level of an $\alpha 2M$ protein or nucleic acid (e.g., mRNA), or an antigenic fragment thereof (as described herein); and a increased level of an $\alpha 2M$ protein or nucleic acid (e.g., mRNA), or an antigenic fragment thereof (as described herein) (e.g., as compared to a control subject of the same age, a control subject that has had one or more successful pregnancies, and/or a subject that has not had a miscarriage or is not suspected of having had a miscarriage).

Methods of Selecting a Subject for Participation in a Clinical Study

Also provided are methods of selecting a subject for participation in a clinical study that include providing a sample (e.g., a sample containing serum) from the subject and detecting the presence, absence, or level of antibodies that specifically bind to one or more (e.g., one, two, or three) of a fibronectin (protein or nucleic acid), an $\alpha 2M$ (protein or nucleic acid), and an Apolipoprotein B-100 (protein or nucleic acid), or an antigenic fragment thereof, in the sample, wherein the presence, a detectable level, or an increased level of one or more antibodies that specifically bind to a fibronectin (protein or nucleic acid) and/or an ApoB-100 (protein or nucleic acid), or an antigenic fragment thereof, and/or the presence, a detectable level, or a increased level of antibodies that specifically bind to an $\alpha 2M$ (protein or nucleic acid), or antigenic fragment thereof, in the sample, indicates that the subject should be selected for participation in a clinical study. Additional methods for selecting a subject for participation in a clinical study may include providing a sample (e.g., a sample containing serum) from the subject and detecting the presence, absence, or level of one or more (e.g., one, two, or three) of a fibronectin (protein or nucleic acid), an $\alpha 2M$ (protein or nucleic acid), and an Apolipoprotein B-100 (protein or nucleic acid), or an antigenic fragment thereof, in the sample, wherein the presence, a detectable level, or an increased level of a fibronectin (protein or nucleic acid) and/or an ApoB-100 (protein or nucleic acid), or antigenic fragment thereof, and/or the presence, a detectable level, or a increased level of an $\alpha 2M$ (protein or nucleic acid), or antigenic fragment thereof, in the sample indicates that the subject should be selected for participation in a clinical study.

These methods may be performed on any of the subjects described herein. The method may be also be performed at any of the time points described herein.

The presence, absence, or levels of antibodies that specifically bind to a fibronectin (protein or nucleic acid), an $\alpha 2M$ (protein or nucleic acid), or a Apolipoprotein B-100 (protein or nucleic acid), or an antigenic fragment thereof, may be determined using any of the methods described herein or those known in the art. The presence, absence, or levels of a fibronectin (protein or nucleic acid), an $\alpha 2M$ (protein or nucleic acid), or a Apolipoprotein B-100 (protein or nucleic acid), or an antigenic fragment thereof, may be determined using any of the methods described herein or those known in the art.

In any of the methods described herein, one or more (e.g., one, two, three, four, five, six, seven, or eight) of any combination of the following, in a sample from the subject, indicate that the subject should be selected for participation in a clinical study: the presence or a detectable level of antibodies that specifically bind to an ApoB-100 protein or nucleic acid (e.g., mRNA), or an antigenic fragment thereof (as described herein); an increase in the level of antibodies that specifically bind to an ApoB-100 protein or nucleic acid (e.g., mRNA), or an antigenic fragment thereof (as described herein) (e.g., as compared to a control subject of the same age, a control subject that has had one or more successful pregnancies, and/or a control subject that has not had a miscarriage or is not suspected of having had a miscarriage); the presence or a detectable level of ApoB-100 protein or nucleic acid (e.g., mRNA), or an antigenic fragment thereof (as described herein); an increased level of ApoB-100 protein or nucleic acid (e.g., mRNA), or an antigenic fragment thereof (as described herein) (e.g., as compared to a control subject of the same age, a control subject that has had one or more successful pregnancies, and/or a control subject that has not had a miscarriage or is not suspected of having had a miscarriage); the presence or a detectable level of antibodies that specifically bind to a fibronectin protein or nucleic acid (e.g., mRNA), or an antigenic fragment thereof (as described herein); an increase in the level of antibodies that specifically bind to a fibronectin protein or nucleic acid (e.g., mRNA), or an antigenic fragment thereof (as described herein) (e.g., as compared to a control subject of the same age, a control subject that has had one or more successful pregnancies, and/or a control subject that has not had a miscarriage or is not suspected of having had a miscarriage); the presence or a detectable level of a fibronectin protein or nucleic acid (e.g., mRNA), or an antigenic fragment thereof (as described herein); an increased level of a fibronectin protein or nucleic acid (e.g., mRNA), or an antigenic fragment thereof (as described herein) (e.g., as compared to a control subject of the same age, a control subject that has had one or more successful pregnancies, and/or a control subject that has not had a miscarriage or is not suspected of having had a miscarriage); the presence or a detectable level of antibodies that specifically bind to an α2M protein or nucleic acid (e.g., mRNA), or an antigenic fragment thereof (as described herein); and a decrease increase in the levels of antibodies that specifically bind to an α2M protein or nucleic acid (e.g., mRNA), or an antigenic fragment thereof (as described herein) (e.g., as compared to a control subject of the same age, a control subject that has had one or more successful pregnancies, and/or a control subject that has not had a miscarriage or is not suspected of having had a miscarriage); the presence or a detectable level of an α2M protein or nucleic acid (e.g., mRNA), or an antigenic fragment thereof (as described herein); and a increased level of an α2M protein or nucleic acid (e.g., mRNA), or an antigenic fragment thereof (as described herein) (e.g., as compared to a control subject of the same age, a control subject that has had one or more successful pregnancies, and/or a control subject that has not had a miscarriage or is not suspected of having had a miscarriage).

Methods for Decreasing the Risk of Pregnancy Loss

Also provided are methods of decreasing the risk of pregnancy loss in a subject that include providing a sample (e.g., a sample containing serum) from the subject; determining the presence, absence, or level of antibodies that specifically bind to one or more (e.g., one, two, or three) of a fibronectin (protein or nucleic acid), an α2M (protein or nucleic acid), and an Apolipoprotein B-100 (protein or nucleic acid), or an antigenic fragment thereof, in the sample; and administering to the subject a therapeutic treatment if subject has, has a detectable level, or has an increased level of antibodies that specifically bind to a fibronectin (protein or nucleic acid) and/or an ApoB-100 (protein or nucleic acid), or an antigenic fragment thereof, and/or have, has a detectable level, or a increased level of antibodies that specifically bind to an α2M (protein or nucleic acid), or antigenic fragment thereof in the sample. Additional methods of decreasing the risk of pregnancy loss in a subject include providing a sample (e.g., a sample containing serum) from the subject; determining the presence, absence, or level of one or more (e.g., one, two, or three) of a fibronectin (protein or nucleic acid), an α2M (protein or nucleic acid), and an Apolipoprotein B-100 (protein or nucleic acid), or an antigenic fragment thereof, in the sample; and administering to the subject a therapeutic treatment if subject has, has a detectable level, or has an increased level of a fibronectin (protein or nucleic acid) and/or an ApoB-100 (protein or nucleic acid), or antigenic fragment thereof, and/or have, has a detectable level, or a decreased increased level of an α2M (protein or nucleic acid), or antigenic fragment thereof in the sample.

These methods may be performed on any of the subjects described herein. The method may be also be performed at any of the time points described herein. The methods may be used to select a subject for administration of a treatment to reduce the risk of a pregnancy loss.

The presence, absence, or levels of antibodies that specifically bind to a fibronectin (protein or nucleic acid), an α2M (protein or nucleic acid), or a Apolipoprotein B-100 (protein or nucleic acid), or an antigenic fragment thereof, may be determined using any of the methods described herein or those known in the art. The presence, absence, or levels of a fibronectin (protein or nucleic acid), an α2M (protein or nucleic acid), or an Apolipoprotein B-100 (protein or nucleic acid), or an antigenic fragment thereof, may be determined using any of the methods described herein or those known in the art.

In any of the methods described herein, at least one therapeutic treatment should be administered to a subject having one or more (e.g., one, two, three, four, five, six, seven, or eight) of any combination of the following features: the presence or a detectable level of antibodies that specifically bind to an ApoB-100 protein or nucleic acid (e.g., mRNA), or an antigenic fragment thereof (as described herein), in the sample; an increase in the level of antibodies that specifically bind to an ApoB-100 protein or nucleic acid (e.g., mRNA), or an antigenic fragment thereof (as described herein), in the sample (e.g., as compared to a control subject of the same age, a control subject that has had one or more successful pregnancies, and/or a control subject that has not had a miscarriage or is not suspected of having had a miscarriage); the presence or a detectable level of ApoB-100 protein or nucleic acid (e.g., mRNA), or an antigenic fragment thereof (as described herein), in the sample; an increased level of ApoB-100 protein or nucleic acid (e.g., mRNA), or an antigenic fragment thereof (as described herein), in the sample (e.g., as compared to a control subject of the same age, a control subject that has had one or more successful pregnancies, and/or a control subject that has not had a miscarriage or is not suspected of having had a miscarriage); the presence or a detectable level of antibodies that specifically bind to a fibronectin protein or nucleic acid (e.g., mRNA), or an antigenic fragment thereof (as described herein), in the sample; an increase in the level of antibodies that specifically bind to a fibronectin protein or nucleic acid (e.g., mRNA), or an antigenic fragment thereof (as described herein), in the sample (e.g., as compared to a control subject of the same age, a control subject that has had one or more successful pregnancies, and/or a control subject that has not had a miscarriage or is not suspected of having had a miscarriage); the presence or a detectable level of a fibronectin protein or nucleic acid (e.g., mRNA), or an antigenic fragment thereof (as described herein), in the sample; an increased level of a fibronectin protein or nucleic acid (e.g., mRNA), or an antigenic fragment thereof (as described herein), in the sample (e.g., as compared to a control subject of the same age, a control subject that has had one or more successful pregnancies, and/or a control subject that has not had a miscarriage or is not suspected of having had a miscarriage); the presence or a detectable level of antibodies that specifically bind to an α2M protein or nucleic acid (e.g., mRNA), or an antigenic fragment thereof (as described herein), in the sample; and a increase in the levels of antibodies that specifically bind to an α2M protein or nucleic acid (e.g., mRNA), or an antigenic fragment thereof (as described herein), in the sample (e.g., as compared to a control subject of the same age, a control subject that has had one or more successful pregnancies, and/or a subject that has not had a miscarriage or is not suspected of having had a miscarriage); the presence or a detectable level of an α2M protein or nucleic acid (e.g., mRNA), or an antigenic fragment thereof (as described herein), in the sample; and a increased level of an α2M protein or nucleic acid (e.g., mRNA), or an antigenic fragment thereof (as described herein), in the sample (e.g., as compared to a control subject of the same age, a control subject that has had one or more successful pregnancies, and/or a control subject that has not had a miscarriage or is not suspected of having had a miscarriage).

The therapeutic treatment may be administered by a health care professional (e.g., a physician, a nurse, or a physician's assistant). The treatment may be administered in a patient's home or in a heath care facility (e.g., a hospital or a clinic). In some embodiments, the therapeutic treatment is a treatment that decreases or suppresses a immune response, e.g., that decreases inflammation, or decreases a Th1-type immune response, and/or enhances a Th2-type immune response.

Non-limiting examples of therapeutic treatment include complement inhibitors (e.g., antibodies that bind to complement components, such as C1, C3, and C5 (e.g., 5G1.1SC and 5G1.1 (Alexion), eculizumab, and pex-elizumab); soluble complement receptor 1, C1-inhibitor (C1-Inh), C1 esterase inhibitor, C3 inhibitor (POT-4), C5 complement inhibitor (Alexion), compstatin, heparin, and the complement inhibitors described in U.S. Pat. Nos. 4,146,640; 4,007,270; 4,241,301; and 5,847,082; and U.S. Patent Application Publications Nos. 2007/0141573; 2009/0117098; and 2009/0214538), hormones (e.g., progesterone), steroids (e.g., prednisone), passive immunotherapy with intravenous immunoglobulin, aspirin (e.g., low-dose aspirin), and TNF antagonists (e.g., soluble fragments of TNF-$\alpha$ receptors (e.g., etanercept) and antibodies that specifically bind to TNF-$\alpha$ (e.g., adalimumab and infliximab), and small molecule inhibitors of TNF-$\alpha$ (e.g., pentoxyfyllene)). One or more (e.g., two, three, four, or five) therapeutic treatments may be administered to the subject. In some methods, the subject may be pregnant (e.g., within the first 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, or 20 weeks of pregnancy) or may be planning on becoming pregnant in the future (e.g., the therapeutic treatment is administered at least one month, at least 3 weeks, at least 2 weeks, at least 1 week prior to conception).

The dosage (e.g., 0.1 to 100 mg, 0.1 mg to 80 mg, 0.1 mg to 70 mg, 0.1 to 60 mg, 0.1 mg to 50 mg, 1 mg to 40 mg, 1 mg to 30 mg, 1 mg to 20 mg, and 1 mg to 10 mg) and administration regime (e.g., once a day, twice a day, three times a day, four times a day, once a week, twice a week, three times a week, four times a week, once every two weeks, once a month, twice a month, three times a month, or four times a month) of the therapeutic treatment may be determined by a health care professional based on the physical condition of the subject (e.g., age, health, pregnant or non-pregnant, and other health conditions) and based on the dosing and administration schedules known in the art (for a general review of exemplary treatments, see, Tincani et al., *Clinic Rev. Allerg. Immunol.* 39:153-159, 2010; Stephenson et al., *Human Reproduction* 25:2203-2209, 2010; and Dukhovny et al., *Curr. Opin. Endocrinol. Diabetes Obes.* 16:451-458, 2009). For example, a subject identified for the administration of a therapeutic treatment using the provided methods, may be intravenously administered passive immunoglobulin one or more times (e.g., two, three, four, or five times) during and/or prior to pregnancy (as described herein). A physician may monitor the subject (e.g., using the methods to determine the risk of pregnancy loss described herein) to determine whether the dosage or the frequency of therapeutic treatment should be altered (e.g., increase in the dosage and/or frequency of administration of a therapeutic treatment for those subjects indicated as having an increased risk of pregnancy loss) during a given time frame (e.g., during the term of the pregnancy (e.g., anywhere from between conception to 9 months of pregnancy, between conception and up to 8 months of pregnancy, between conception and up to 7 months of pregnancy, between conception up to 6 months of pregnancy, between conception up to 5 months of pregnancy, between conception up to 4 months of pregnancy, between conception up to 3 months of pregnancy, between conception and up to 2 months of pregnancy, between 3 and 20 weeks of pregnancy, between 5 and 20 weeks or pregnancy, or between 10 and 20 weeks of pregnancy), a period of time prior to conception (e.g., within 6 months of conception, within 5 months of conception, within 4 months of conception, within 3 months of conception, within 2 months of conception, within 1 month of conception, within 3 weeks of conception, within 2 weeks of conception, within 1 week of conception, or within 3 days of conception), or a period of time beginning prior to conception (e.g., within 6 months of conception, within 5 months of conception, within 4 months of conception, within 3 months of conception, within 2 months of conception, within 1 month of conception, within 3 weeks of conception, within 2 weeks of conception, within 1 week of conception, or within 3 days of conception) to the end of the term or a time point during the term of the pregnancy (e.g., anywhere from between conception to 9 months of pregnancy, between conception and up to 8 months of pregnancy, between conception up to 7 months of pregnancy, between conception up to 6 months of pregnancy, between conception up to 5 months of pregnancy, between conception up to 4 months of pregnancy, between conception up to 3 months or pregnancy, between conception and up to 2 months of pregnancy, between 3 and 20 weeks of pregnancy, between 5 and 20 weeks or pregnancy, or between 10 and 20 weeks of pregnancy).

EXAMPLES

The invention is further described in the following examples, which do not limit the scope of the invention described in the claims.

Example 1

Alterations in Immune Responses in Women with Recurrent Pregnancy Loss

Current literature supports the concept that failure to suppress maternal lymphoid activation pathways and aberrant auto-antibody production is associated with pregnancy complications, from infertility to spontaneous recurrent pregnancy loss (RPL). These experiments were designed to enhance understanding of the human immunologic responses and antigen recognition patterns that develop during the first trimester in women with a history of RPL compared to first-trimester, multi-parous women with an uncomplicated obstetrical history.

Western immunoblotting using human serum-derived antibodies from RPL and healthy subjects and trophoblast-derived antigens was used to characterize a distinct difference in the total IgG recognition profiles among healthy pregnant controls and RPL patients (see, schematic diagram of the experimental method in FIG. 1). These antigens were obtained from the first trimester trophoblast-derived cell line, SW.71 (Yale University, New Haven, Conn., USA), which was maintained in DMEM/F12 (Gibco Invitrogen) media supplemented with 2 mL L-glutamine, 10% fetal bovine serum, 1 mM sodium pyruvate, 0.1 mM non-essential amino acids, 100 units/mL penicillin-streptomycin at 37° C. and 5% $CO_2$ in 75-$cm^2$ tissue culture flasks. This cell line was isolated from a seven-week placenta immortalized by ectopic expression of the catalytic subunit of human telomerase.

Nuclear, cellular, and cytoplasmic proteins were extracted from the Sw.71 cell-line derived using a cell fraction kit (BioVision, Mountain View, Calif., USA) using the manufacturer's instructions. The protein concentrations of each fraction were determined using Bio-Rad DC protein quantification assay (Bio-Rad Laboratories, Hercules, Calif., USA).

To visualize subject autoantibody reactivity patterns, these extracted, solubilized nuclear, cytosolic, and cellular membrane proteins (40 μg/lane) were applied to 10% SDS-PAGE gels and electrophoretically separated by the method of Laemili (Nature 227:680-685, 1970). The reactive proteins were analyzed by Western immunoblotting (Brown et al., Int. J. Cancer 55:678-684, 1993). Nitrocellulose membranes were probed overnight at 4° C. with patient serum (diluted 1:100) and then washed three times in Tris-buffered saline (TBS). Western blotting was completed using peroxidase-conjugated anti-human IgG2, IgG3, and whole IgG (AbD Sertotec, Raleigh, N.C.). Bound antibody-antigen complexes were visualized using enhanced chemiluminescence (Immun-Star, Bio-Rad, Hercules, Calif.). The resulting x-ray film was scanned as a 16-bit grayscale JPEG image. This grayscale image was digitized and converted into pixel density using Un-scan-it software (Silk Scientific Corp., Orem, Utah). On each gel image, the number of pixels for all visualized bands was quantitated using Un-Scan-It and the total number of pixels for all bands within each lane was calculated. This total number of pixels for all bands in specific lanes was determined and the mean (average) total pixels for the specific lane for patients within each population (controls versus RPL) were calculated for antigens derived from the nuclear and membrane fractions.

The serum samples used in the experiments described herein were obtained from first trimester pregnant women who either had had ≥2 recurrent spontaneous abortions without a successful pregnancy (n=8) or had had two or more term, uncomplicated deliveries (n=2). Patients with histories of RPL were in their first trimester of pregnancy with a history of two or more recurrent consecutive miscarriages of unknown etiology (i.e., with documented normal maternal and paternal karyotypes, normal uterine cavity imaging and/or assessment, and normal thrombophilia profile). Venous blood samples were obtained, allowed to clot, and sera isolated. These samples were obtained from volunteers in the private gynecology offices and clinics of the Department of Obstetrics, Gynecology and Women's Health at the University of Louisville School of Medicine, under an informed consent protocol approved by the Institutional Review Board at the University. For this proteomics study, eight patients with a history of recurrent spontaneous abortions were enrolled in the study (Table 1). All patients were in good general health and were not taking any medications, except for one patient (subject #8), who was euthyroid while receiving replacement medication. All were Caucasian except for one (subject #6), who was Chinese. None patients with a history of RPL had anticardiolipin antibodies or lupus anticoagulant. Seven women had a normal uterine contour by evaluation with either hysterosalpingography or saline infusion sonohysterography. Seven women had either a normal serum progesterone level (10 ng/mL) or an in-phase luteal biopsy result.

The data from these experiments demonstrate a distinct difference in the total IgG recognition profiles among healthy pregnant controls and RPL patients (FIGS. 2 and 3A-F). The data in FIGS. 2 and 3A-3F, indicate that sera from women with a history of RPL exhibited greater immunoreactivities compared to controls, with a total antibody reactivity 3.6-fold greater with nuclear antigens (p=0.0044), a 4.1-fold greater reactivity with membrane-derived antigens (p=0.0001), and a 1.8-fold greater recognition of cytosolic antigens (p=0.0113). Among IgG subclasses, a notably enhanced recognition pattern was observed in IgG3, which revealed an increase of 1.8-fold greater immunoreactivity than controls. This increase was consistently noted across all three antigen sources (nuclear, membrane, and cytosolic antigens), with antigens ranging from 15 to 250 kDa.

Western blots of antibody-antigen complexes, resulting from the use of patient serum as the source of primary antibodies, were scanned, digitized, and converted to pixel density. The pixel densities for these two groups of patients were compared for total IgG reactivity for antigens derived from the membrane, nuclear, and cytoplasmic

TABLE 1

Figure 4:
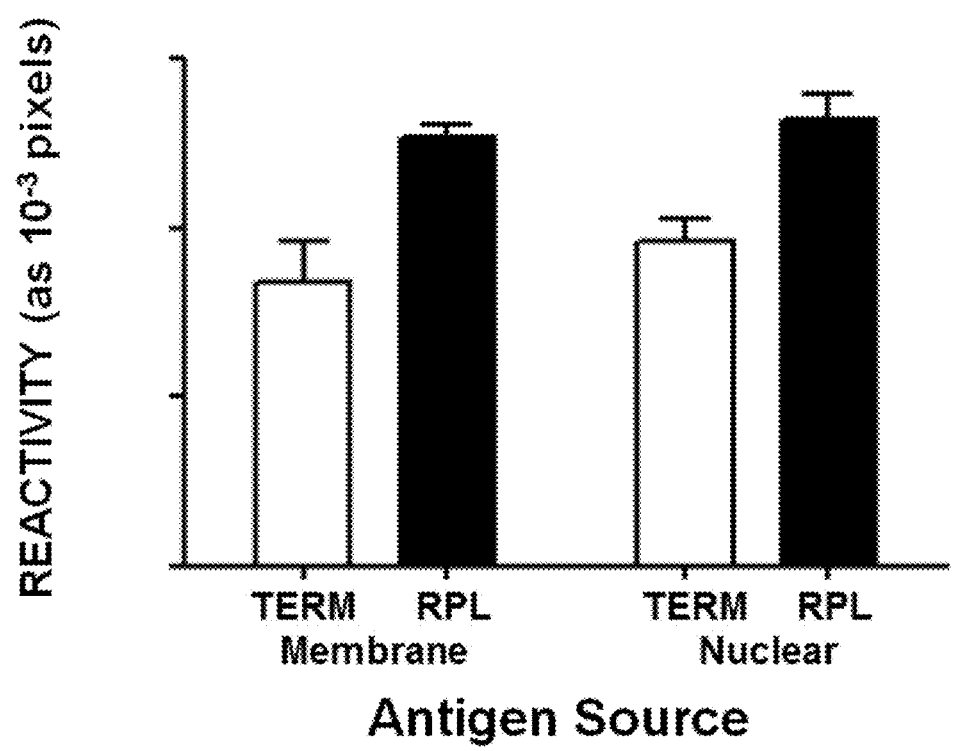
FIG. 4 is a bar graph showing the reactivity of antibodies from control (Term) and RPL subjects to antigens derived from the membrane or nucleus of SW-71 cells. In these experiments, the Western blot x-ray films with antibody-antigen complexes were scanned, digitized, and then converted to pixel density. Immunoreactivities for antigens from nuclear, membrane, or cytoslic compartments were standardized and the mean values and standard deviations were calculated.

| | | | | | Subjects | | | | | |
|---|---|---|---|---|---|---|---|---|---|---|
| Subject | Age (yrs) | Gravidity | Parity | No of abortions | ACA | LAC | HSG/SIS | Karyotype | EB/P4 | TSH |
| #1 | 32 | 3 | 0 | 3 | X | X | X | F | | X |
| #2 | 29 | 5 | 0 | 5 | X | X | | | | X |
| #3 | 26 | 3 | 0 | 3 | X | X | X | | | |
| #4 | 36 | 3 | 0 | 3 | X | X | X | F | | X |
| #5 | 32 | 3 | 0 | 3 | X | X | | | X | X |
| #6 | 35 | 5 | 0 | 5 | X | X | X | F | X | |
| #7 | 25 | 3 | 0 | 3 | X | X | X | M, F | | X |
| #8 | 30 | 3 | 0 | 3 | X | X | | M | X | X | fractions (FIG. 4). Immunoreactivities for antigens from each cellular compartment were standardized using the pixel values of control standard (HRP-anti-mouse IgG) included in each gel. Duplicate gels were run for each subject and the resulting ratios from the gels were averaged. The mean values and standard deviations were calculated using InStat Graph Pad. Sera from women with a history of RPL exhibited greater immunoreactivities compared to controls, with a total antibody reactivity 1.48-fold greater with nuclear antigens (p=0.0190), a 1.57-fold greater reactivity with membrane-derived antigens (p=0.0056), and a 1.90-fold greater recognition of cytosolic antigens (p=0.0162).

Figure 5:
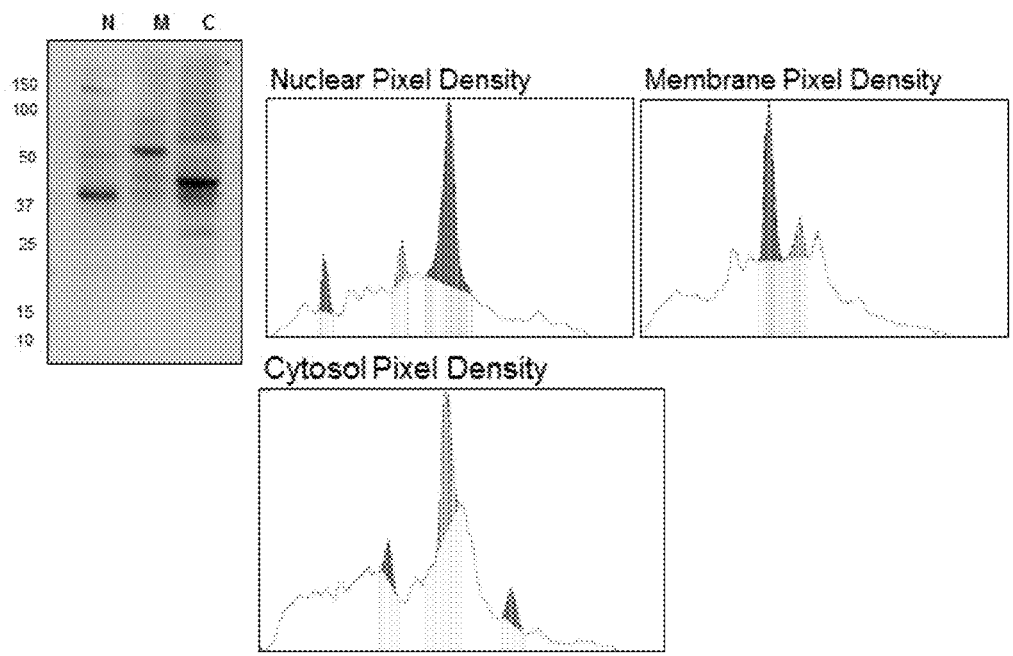
FIG. 5 is two Western blots and a set of six pixel density graphs correlated for each lane of Western blot antibody reactivity to trophoblast antigens: nuclear, membrane, and cytosolic. A representative Term Western blot and three correlated graphs for Term subjects are shown (top half) and a representative RPL Western blot and three correlated graphs for RPL subjects are depicted (bottom half). The RPL Western blot has 1.80-fold increased reactivity relative to the representative Term Western blot and its pixel density graphs.
Figure 5:
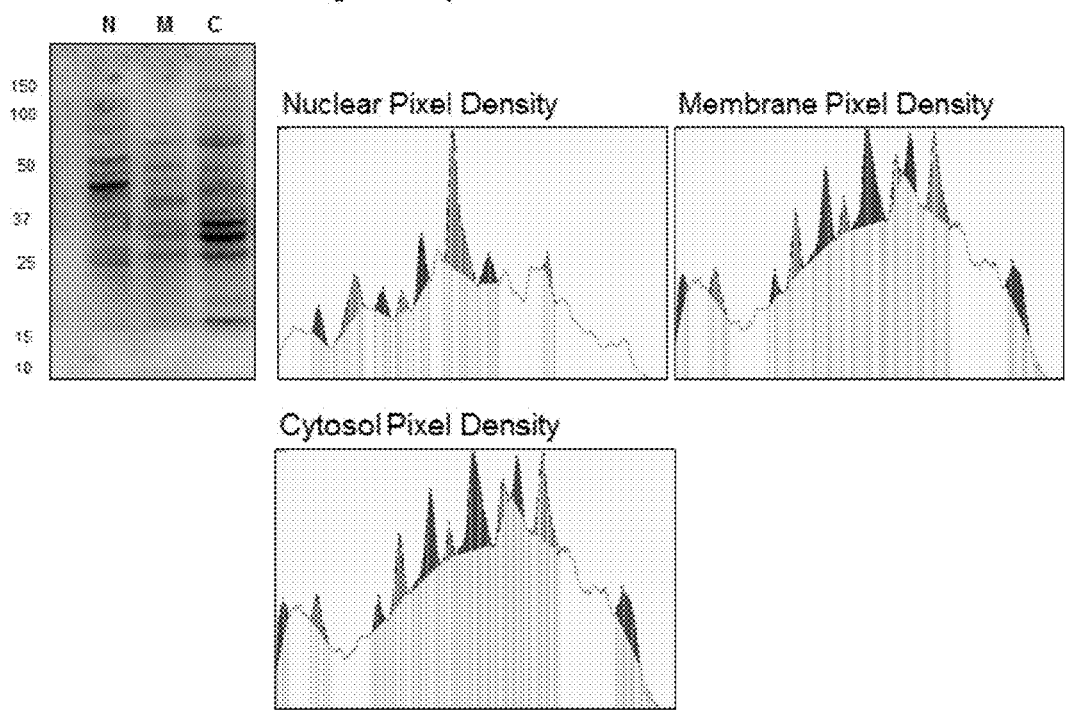

Among IgG subclasses, a notable enhanced recognition pattern was observed in IgG3 with an increase of 1.8-fold greater immunoreactivity compared to controls (FIG. 5). Digitization of the reactive bands demonstrated that this increase was consistently noted across all three antigen sources (nuclear, membrane, and cytosolic antigens), with antigens ranging from 15 to 250 kDa. The enhanced reactivity was linked with the recognition of additional antigenic proteins and not simply greater reactivity with the same components.

Figure 6:
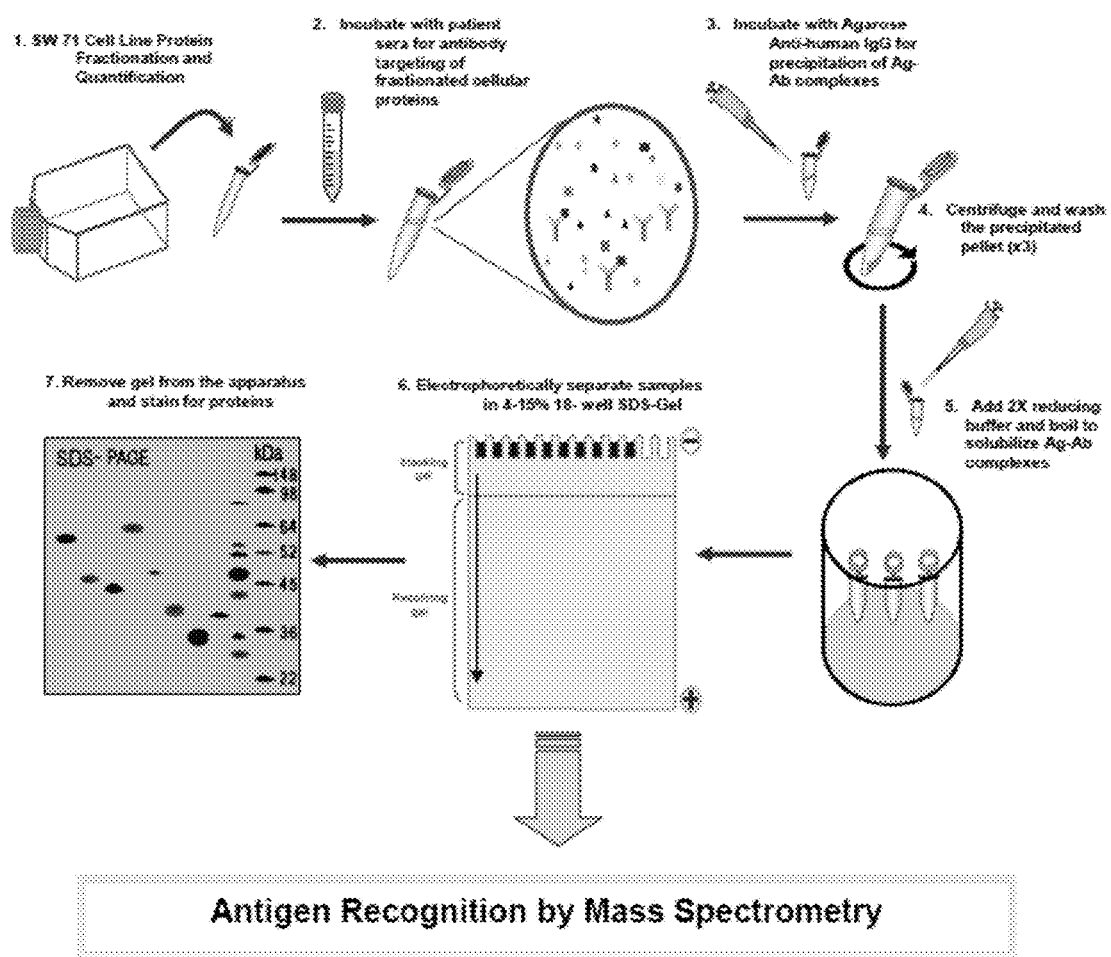
FIG. 6 is a schematic illustration of exemplary methods for protein expression profiling with immunoprecipitation.

Antigen recognition was also determined by immunoprecipitation and protein separation by gel electrophoresis, followed by mass spectrometry, substantially as shown in FIG. 6. In these experiments, Sw.71 cell-line derived nuclear and cellular solubilized proteins (50 µg) were individually sonicated in RIPA buffer (260 µL, containing protease and phosphatase inhibitor cocktails, Sigma Chemical) and incubated with serum-derived immunoglobulins (100 µL) from control (n=2) and test subjects (n=5). The individual samples were then incubated in agarose-bound anti-human IgG (40 µL), centrifuged, and washed to obtain a pellet of immunoaffinity-isolated cellular and nuclear proteins. This was done for each control and test subject. The antigen-antibody complexes were reduced and solubilized using 2× Laemili buffer. Samples were then applied to an 18-well 4-15% Tris-HCL, 1.0 mm, Criterion™ Precast Gel (Bio-Rad, Hercules, Calif.), and separated by electrophoresis. Each gel was then stained using Imperial™ Protein Stain and scanned using PharosFX™ Molecular Imager System (Bio-Rad, Hercules, Calif.).

Specific trophoblast cellular antigens recognized in antibody-antigen binding complexes were defined by mass spectrometry sequencing. The incongruent control and test immunoprecipitation gel spots were removed, washed to remove staining of dye and inhibitory chemicals, and dried to absorb maximum volume of digestion buffer. The dried gel spots were rehydrated in digestion buffer containing sequencing grade modified trypsin (1:30 by mass) and proteins were digested in-gel at 37° C. Digested peptides were extracted from the gel with trifluoroacetic acid extraction buffer and digested tryptic peptides were desalted using C-18 Zip-tips (Millipore). The desalted peptides were mixed with α-cyano-4-hydroxycinnamic acid matrix (CHCA) and spotted into wells of a MALDI plate. Mass spectra (MS) of the peptides in each sample were obtained using Applied Biosystems 4700 Proteomics Analyzer. A minimum of 10 of the most abundant peptides for each sample were further subjected to fragmentation and tandem mass spectrometry (MS/MS) analysis. Protein identification were based on peptide fingerprint mass mapping and peptide fragmentation mapping (using MS/MS spectra). Combined MS and MS/MS spectra were submitted for database search using GPS Explorer software equipped with MASCOT search engine to identify proteins from primary sequence databases.

Figure 7:
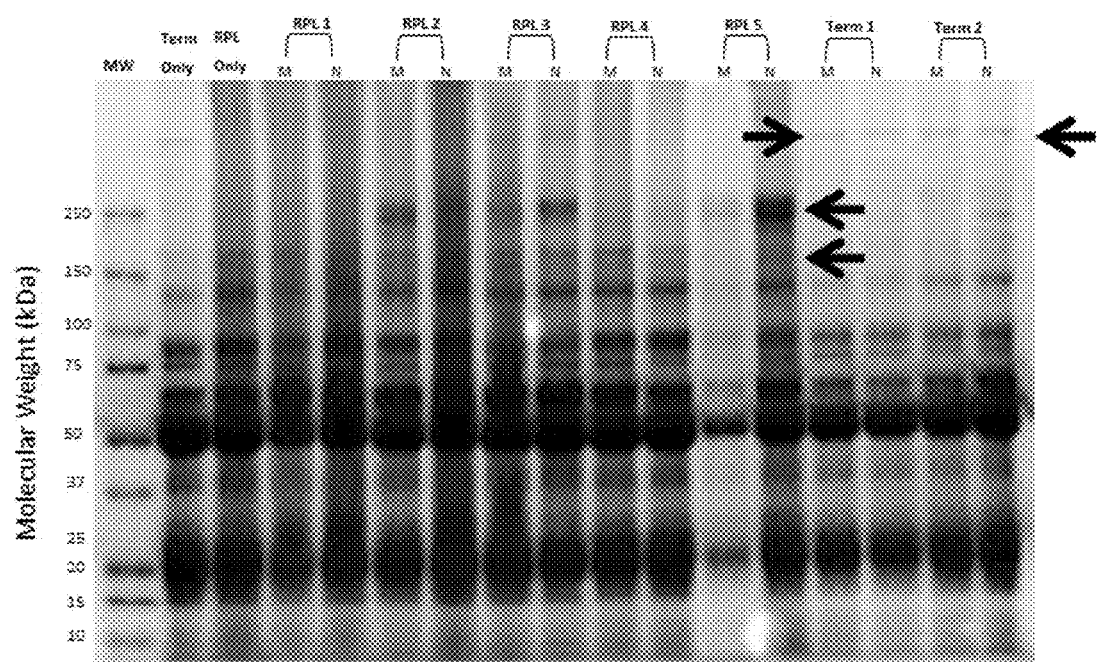
FIG. 7 depicts the incongruent antigen antibody complexes between the control (Term) and RPL subjects. The arrows indicate α2-macroglobulin, fibronectin, and Apolipoprotein B-100.

Specific trophoblast cellular antigens recognized in antibody-antigen binding complexes were defined by immunoprecipitation (FIG. 7) and subsequent mass spectrometry sequencing (Table 2). SDS-PAGE of the immunoprecipitated proteins derived from membrane and nuclear fractions derived from Sw.71 trophoblast cells revealed numerous qualitative and quantitative differences, as defined by the presence of specific bands (FIG. 7). Subsequent analyses focused on three major bands exhibiting unique association with RPL. Mass spectra (MS) of the peptides in each sample were obtained using Applied Biosystems 4700 Proteomics Analyzer. Protein identification was based on peptide fingerprint mass mapping and peptide fragmentation mapping (using MS/MS spectra). Combined MS+MS/MS analysis was performed using Mascot v 2.1.04 from Matrix Science Ltd and proteins were identified using SwissProt database. Each matched peptide was characterized by an ion score; a high confidence in peptide to protein match was reached when two or more ion scores indicated identity (Table 2). The results include three differently recognized trophoblast antigens: Apolipoprotein B-100 (ApoB-100), fibronectin, and α2-macroglobulin (α2-M). Specifically, recognition of maternal IgG antibodies to trophoblast-derived fibronectin and ApoB-100 were noted when serum was obtained from women who suffer RPL. This antibody recognition was when serum was obtained from pregnant, multiparous women with an uncomplicated obstetrical history. Notably, serum from these same control, multiparous subjects did not revealed antibody recognition to α2M, a pattern that was contrarily absent present in serum from RPL subjects. These findings suggest that perhaps an aberrant maternal antibody recognition of fibronectin and α2M leads to dysfunctional development of the maternal-fetal interface with possible subsequent pregnancy loss or other advanced-gestation obstetrical complications. Concurrently, a combination of the three previously-described functions and mechanisms of action of ApoB may play a vital role in the sustainability of early pregnancy. Perhaps this lack of antibody-ApoB binding, as demonstrated from the serum of healthy controls, alters the intended function of ApoB at the level of the uterine endothelium, the steroid-producing corpus luteal cells, and/or the nutrient-rich embryo yolk sac.

Since paternal genetic material determines at least half the antigenic array of the fetus, expression of these components are capable of eliciting an immune response that can result in the spontaneous loss (abortion) of the fetus. Antibodies that recognize the fetus have been demonstrated in the maternal circulation, and IgG that is reactive with paternal antigens can be eluted from the placenta (Creus et al., *Humn. Reprod.* 13:39-43, 1998; Wilson et al., *Fertil. Steril.* 76:915-917, 2001). In this study, we investigated the antigenic recognition patterns of circulating IgG obtained from women with RPL

TABLE 2

Mass Spectrometry (MS) Protein Identification.

| Serum Source | Protein Identification | Molecular Weight (Da) | Protein Score | Confidence Interval (100%) | Ion Score Notes[1] |
|---|---|---|---|---|---|
| Term | α2-Macroglobulin | 164614 | 514 | 100 | 7 ion scores indicated identity |
|  |  |  | 353 | 100 | 5 ion scores indicated identity |
|  | Apolipoprotein |  | 239 | 100 | 3 ion scores indicated identity |
| RPL | B100 | 516666 | 409 | 100 | 5 ion scores indicated identity |
| RPL | Fibronectin | 266034 | 593 | 100 | 7 ion scores indicated identity |
|  |  |  | 647 | 100 | 7 ion scores indicated identity |
|  |  |  | 652 | 100 | 8 ion scores indicated identity |
|  |  |  | 621 | 100 | 7 ion scores indicated identity |

TABLE 2-continued

Mass Spectrometry (MS) Protein Identification.

| Serum Source | Protein Identification | Molecular Weight (Da) | Protein Score | Confidence Interval (100%) | Ion Score Notes[1] |
|---|---|---|---|---|---|
| | | | 583 | 100 | 6 ion scores indicated identity |
| | | | 694 | 100 | 8 ion scores indicated identity |

[1]Combined MS + MS/MS analysis performed using Mascot v 2.1.04 from Matrix Science Ltd. Proteins were identified using SwissProt database. Protein significance level was 56 by Mascot (p < 0.05). The Ion Score Notes refers to matched peptides using Mascot. High confidence in peptide to protein match when two or more ion scores indicate identity.
* = MS also detected serum albumin by 2 ion scores;
+ = MS also detected Ig gamma-2 chain C region & Ig gamma 3 chain C region by 1 ion score.
compared with those of pregnant women in the first trimester of uncomplicated pregnancies.

Pregnancy has been shown to produce significant changes within the immune system, generally noted as a shift to a Th2-biased (humoral) immune response. Many of these alterations are not observed in women experiencing RPL. Pregnancy has been associated with the production of Th2 type cytokines (such as IL-10 and IL-4), while RPL has been linked with the production of Th1 type cytokines (such as IFN γ, IL-12). Previous studies have shown that normal uncomplicated pregnancy is associated with significant changes in IgG subclasses (Wilson et al., *Fertil. Steril.* 76:915-917, 2001). Normal pregnancy-associated IL-4 production can induce peripheral blood mononuclear cells to become activated and increase total IgG production, as well as enhanced IgG4. In contrast, RPL-associated IFN-γ production can inhibit these events. RPL is generally associated with reduced levels of IL-10 and these patients exhibit diminished levels of total IgG (Eblen et al., *Fertil. Steril.* 73:305-313, 2000; Wilson et al., *Fertil. Steril.* 76:915-917, 2001).

The present data show that uncomplicated pregnancy is linked with changes in the production of IgG reactive with trophoblast-derived antigens. Pregnant women who subsequently abort exhibited a different IgG subset patterns compared with healthy pregnant women, e.g., increased levels of IgG3. The IgG class of antibody predominates in the blood and interstitial fluids and is the most multi-functional of the all antibody classes. The IgG molecule consists of two antigen binding regions (Fab) and one ligand binding region (Fc) through which various effector activities are initiated (e.g., activation of the classical complement pathway, phagocytosis, and antibody-dependent cellular cytotoxicity) (Jefferis et al., *Ann. Biol. Clin.* 52:57-65, 1994). While generally representing only 7% of total circulating IgG, the IgG3 subclass exhibits the highest complement activation and high affinity for Fc receptors on immune effector cells. Results from this study demonstrate an overall increase in antibody recognition of trophoblastic antigens, as well as distinct antigen-antibody binding patterns (FIGS. 2, 3A-3F, and 4), particularly for IgG3 subclasses (FIG. 5), in women experiencing RPL compared to controls. This increase in IgG3 immunoreactivity, recognized in sera obtained from RPL subjects compared to controls, suggests a higher degree of Th2 immune cell activation and subsequent fetal allograft rejection. Perhaps an atypical ratio of the IgG subclasses in RPL patients, favoring the more immunoreactive IgG3, is a potential link to the mechanism and etiology of recurrent aborters.

In addition to the enhanced recognition of trophoblast-derived antigens by IgG3, patients experiencing RPL, exhibited the recognition of distinct antigenic proteins. Of the trophoblast-derived proteins, we isolated and defined two proteins exhibiting unique antibody recognition in RPL patients: fibronectin and Apolipoprotein B-100, while RPL patients have antibodies that recognize alpha2-macroglobulin. Additional trophoblast-derived antigens recognized in patients experiencing RPL are listed in Table 2.

Alpha2-macroglobulin (α2M) is homo-tetramer of 180 kDa subunits. It is a major inhibitor of endoproteinases and plays a regulatory role in the transport and clearance of cytokines and growth factors. It also may protect against the cytotoxic effects of various cytokines while inhibiting the degradation of other cytokines (Esadeg et al., *Placenta* 24:912-921, 2003). It exists in low serum concentrations in normal healthy adults and, in mammalian blood, it targets cytokines to cells expressing the α2M-receptor or lipoprotein-receptor related protein (Esadeg et al., Placenta 24:912-921, 2003; Shimizu et al., *Exp. Anim.* 51:361-365, 2002). In humans, uterine α2M is thought to originate from endothelial cells lining the endometrial vessels. Its concentration has been reported to double or triple during the secretory phase of the menstrual cycle suggesting a role as a decidualization protein (Esadeg et al., *Placenta* 24:912-921, 2003). During pregnancy, a receptor for the α2M-proteinase complex has been demonstrated on the human placental syncytiotrophoblasts (Jensen et al., *Placenta* 9:463-477, 1988; Thomas et al., *Placenta* 11:413-430, 1990). Exhibiting immuno-suppressive activity, α2M is believed to be a potential means of immunosuppression in the human uteroplacental interface and may be subject to transplacental transport to the neonate (Benyo et al., *Endocrinology* 133:699-704, 1993). In this study, serum obtained from healthy control subjects revealed no antibody recognition to the α2M tetramer; whereas, serum obtained from pregnant women afflicted with RPL did (FIG. 7, Table 2). With its regulatory role in the activities of leukocytic and non-leukocytic derived cytokines, α2M may be a key component in the anomalous processes resulting in RPL. The antibody recognition and binding to this protein, as demonstrated from the serum of healthy subjects with RPL, may influence α2-M activities from various involved sites, including uterine decidualization, endothelial structure, trophoblast invasion and growth, and transplacental transport.

Apolipoprotein B is a core protein of LDL, which mediates the interaction between low density lipoproteins (LDL) and its receptor (Yamada et al., *Hum. Reprod.* 13:944-952, 1998). The principal function of Apolipoprotein B (ApoB-100 and ApoB-48) is to provide a structural framework for packaging neutral lipids, such as triglycerides and cholesterol esters, into lipoproteins for their transportation in an aqueous circulation (Farese et al., *J. Lipid Res.* 37:347-360, 1996). It, furthermore, contains ligands for the receptor-mediated endocytosis of various lipoproteins. Mutations in the LDL-receptor and related proteins have been shown to result in aberrant uptake of ApoB and other lipoproteins into cells. A lack of appropriate lipoprotein control mechanisms ultimately leads to lipoprotein oxidation products that mediate oxidative damage and result in endothelial dysfunction and premature atherosclerosis (Cekmen et al., *Clin. Biochem.* 36:575-578, 2003; Sarandol et al., *Clin. Biochem.* 37:990-996, 2004; Sarandol et al., *Arch. Gynecol. Obstet.* 270:157-160, 2004). In normal pregnancies, there appears to be factors that promote ApoB utilization via receptor mediated endocytosis while protecting it from oxidation and subsequent destructive effects. Trophoblast cells, in particular, express high levels of LDL-receptor and related proteins giving rise to the idea that growth restriction or other vascular obstetrical complications may be associated with a chronic pattern of atherogenic or aberrant lipoprotein metabolism. Perhaps, in normal pregnancy, a specific enzyme or other substrate, protein, or molecule plays a role in stabilizing lipoproteins, inhibiting the common pathway of oxidation. Some researchers have proposed a role for antioxidants such as vitamin E and/or estrogen to inhibit oxidation of lipoproteins (Sarandol et al., *Arch. Gynecol. Obstet.* 270:157-160, 2004). Conversely, the absence of an endogenous protection mechanism may also lead to aberrant lipoprotein oxidative damage at the uteroplacental interface. Such a process may be involved in the circumstances of complicated pregnancies (i.e., RPL, pre-eclampsia, IUGR, etc.).

The expression of ApoB mRNA has been localized in the human embryo yolk endodermal cells by in situ hybridization (Cekmen et al., *Clin. Biochem.* 36:575-578, 2003). While its physiologic purpose in the human yolk sac remains unclear, detection of ApoB in the yolk sac of mice and rats has led to a probable model for transport and packaging of maternally-derived, nutrient rich ApoB-containing lipoproteins into the yolk sac of developing embryo (Cekmen et al., *Clin. Biochem.* 36:575-578, 2003). The humoral recognition of ApoB in affected RPL subjects may play a hostile role in the nutrition of the maturing embryo, hindering normal embryo development.

This study observed maternal IgG antibody recognition of trophoblast-derived ApoB-100 when serum was obtained from pregnant women with history of RPL. This same antibody recognition was not observed when serum was obtained from healthy pregnant controls (FIG. 7). These data suggests that the recognition pattern from test subjects, and lack of recognition by control subjects, may play an aberrant role in lipoprotein metabolism, oxidative destruction, and impairment of endovascular function at the uteroplacental interface. The data show serum antibody recognition of trophoblast-derived ApoB-100 from early pregnancy subjects experiencing RPL. A lack of this recognition was noted when serum was obtained from subjects with a normal obstetrical history. The antibody-ApoB recognition may alter the intended function of ApoB whether at the level of the uterine endothelium, the steroid-producing corpus luteal cells, or the nutrient-rich embryo yolk sac.

Fetal fibronectin is an extracellular matrix protein that is thought of as "trophoblast glue" and is found in increased concentrations at the chorionic-decidual margin and surrounding the extravillous trophoblasts (Guller et al., *Up-to-Date* 17.3, 2009; Mercorio et al., *Eur. J. Obstet. Gynecol. Reprod. Biol.* 126:165-169, 2006). A tightly-regulated balance exists between the activity of the receptive maternal decidua, the invading trophoblast, and developing chorion. Indeed, the maternal extracellular matrix and maternal-fetal interface are thought to play a pivotal role in conditions of early recurrent abortions, intrauterine growth restriction, and pre-eclampsia. Furthermore, derangement in the autocrine and paracrine signals and receptivity between cellular matrix proteins, such as fibronectin, and cell adhesion molecules may be responsible for pregnancy failure. Acquisition of adhesion-competent invading trophoblast cells is characterized by apical accumulation of integrin receptors for fibronectin and strong fibronectin binding activity on the surface of blastocysts (Mecorio et al., *Eur. J. Obstet. Reprod. Biol.* 126:165-169, 2006). The data herein show the recognition of maternal IgG antibodies to trophoblast-derived fibronectin when serum was obtained from women who suffer a history of RPL (FIG. 7, Table 1). This recognition was absent in healthy, multiparous control subjects. These findings suggest that perhaps aberrant maternal antibody recognition of fibronectin leads to dysfunctional development of the maternal-fetal interface with possible subsequent pregnancy loss or other advanced-gestation obstetrical complications. A growing bulk of evidence suggests an active role of fetal fibronectin in implantation. The autocrine/paracrine control mechanism operating within the decidua has been implicated in the regulation of trophoblast invasion, possibly via modulations of extracellular matrix proteins as fibronectin and its specific integrin trophoblast receptor.

Of particular immunologic importance, fibronectin can regulate production and release of IL-1β. Due to the profound effects of IL-1β on immune cell function during inflammation, investigations have focused on the factors that regulate IL-1β expression. Extracellular matrix components (ECM) can induce the expression of IL-1β (Roman et al., *Cytokine* 12:1581-1596, 2000). One component well-studied is fibronectin (FN) and this high molecular weight adhesive molecule is expressed by tissue macrophages and fibroblasts. Thus, FN appears to be well positioned to affect the expression of IL-1β. In vitro studies have demonstrated that FN can stimulate the expression of IL-1β mRNA, and its translation into the 31 kDa intracellular precursor protein, as well as the secretion of the 17 kDa active form in human mononuclear cells (Roman et al., *Cytokine* 12:1581-1596, 2000). Thus, the production of effector IgG3 reactive with fibronection may block the FN-induced IL-1β production. Since IL-1β serves as a "master" pro-inflammatory regulator associated with early pregnancy, its blockage may prevent the induction of pro-inflammatory environment.

It is likely that these specific trophoblast cellular responses activate various pro-inflammatory or other immunoregulatory activities that inhibit proper implantation and ultimately inhibit growth and survival of the invading trophoblast and developing embryonic cells. This data is clinically useful for screening for women afflicted with RPL and, more importantly, for developing treatment strategies during pre-conceptual and prenatal care.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for predicting risk of pregnancy loss in a subject, the method comprising:
   (a) providing a sample comprising serum from the subject; and
   (b) performing an assay to detect the presence of antibodies to fibronectin and antibodies to alpha2-macroglobulin (α2M) in the sample;
   (c) identifying the subject as having an increased risk of pregnancy loss based on the presence of antibodies to fibronectin and α2M in the sample.

2. The method of any claim 1, wherein detecting the presence or absence of antibodies comprises contacting the sample with one fibronectin and α2M, or antigenic fragments thereof, and detecting binding of antibodies in the sample to the fibronectin and α2M.

3. A method of selecting a subject for participation in a clinical study of recurrent pregnancy loss comprising:
   (a) providing a sample comprising serum from the subject; and
   (b) detecting the presence or absence of antibodies to fibronectin and α2M in the sample, and
   (c) selecting a subject having antibodies to fibronectin and α2M present in the sample of (a) is selected for participation in said clinical study.

4. The method of claim 3, wherein detecting the presence or absence of antibodies comprises contacting the sample with fibronectin and α2M, or antigenic fragments thereof, and detecting binding of antibodies in the sample to the fibronectin and α2M.

5. A method of decreasing the risk of pregnancy loss in a subject comprising:
   (a) providing a sample comprising serum from the subject;
   (b) detecting the presence of antibodies to fibronectin and α2M in the sample; and
   (c) administering a therapeutic treatment to a subject having antibodies to fibronectin and α2M present in the sample of (a).

6. The method of claim 1, wherein the subject has had at least one previous pregnancy loss or is suspected of having had at least one previous pregnancy loss.

7. The method of claim 1, wherein the subject is not pregnant, but is planning or considering a future pregnancy.

8. The method of claim 1, wherein the subject is pregnant.

9. The method of claim 1, wherein the sample in (a) is obtained from the subject within the first 20 weeks, within the first 13 weeks, or within the first 12 weeks of pregnancy.

10. The method of claim 5, wherein detecting the presence of antibodies comprises contacting the sample with fibronectin and α2M, or antigenic fragments thereof, and detecting binding of antibodies in the sample to the fibronectin and α2M.

11. The method of claim 1, wherein the subject is human.

12. The method of claim 5, wherein said therapeutic treatment is selected from the group consisting of: complement inhibitors, hormone treatment, steroid treatment, passive immunotherapy with intravenous immunoglobulins, aspirin, and tumor necrosis factor (TNF)-α antagonists.

13. The method of claim 5, wherein the subject has had at least one previous pregnancy loss or is suspected of having had at least one previous pregnancy loss.

14. The method of claim 5, wherein the subject is not pregnant, but is planning or considering a future pregnancy.

15. The method of claim 5, wherein the subject is pregnant.

16. The method of claim 5, wherein the sample in (a) is obtained from the subject within the first 20 weeks, within the first 13 weeks, or within the first 12 weeks of pregnancy.

17. The method of claim 5, wherein the subject is human.

* * * * *

UNITED STATES PATENT AND TRADEMARK OFFICE
CERTIFICATE OF CORRECTION

PATENT NO.      : 9,068,990 B2                                                           Page 1 of 1
APPLICATION NO. : 14/276601
DATED           : June 30, 2015
INVENTOR(S)     : Douglas D. Taylor, Cicek Gercel-Taylor and Rhiana Dawn Saunders It is certified that error appears in the above-identified patent and that said Letters Patent is hereby corrected as shown below:

On the title page

Item (72) Inventors, line 6, delete "Louisville, KY" and insert -- Monmouth Junction --;

Item (72) Inventors, line 7, delete "Louisville, KY" and insert -- Monmouth Junction --;

Item (72) Inventors, after line 7, insert -- Rhiana Dawn Saunders, San Antonio, TX (US) --;

In the claims

In column 197, line 52, in Claim 2, delete "of any" and insert -- of --;

In column 197, line 53, in Claim 2, delete "presence or absence" and insert -- presence --;

In column 197, line 54, in Claim 2, delete "with one" and insert -- with --;

In column 197, line 64, in Claim 3, delete "(a) is selected" and insert -- (a) --;

In column 197, line 67, in Claim 4, delete "presence or absence" and insert -- presence --.

Signed and Sealed this
Second Day of February, 2016

Michelle K. Lee
*Director of the United States Patent and Trademark Office*